(12) United States Patent
Brugiere

(10) Patent No.: US 8,916,749 B2
(45) Date of Patent: Dec. 23, 2014

(54) ISOPENTENYL TRANSFERASE SEQUENCES AND METHODS OF USE

(75) Inventor: Norbert Brugiere, Johnston, IA (US)

(73) Assignee: Pioneer Hi Bred International Inc, Johnston, IA (US)

(*) Notice: Subject to any disclaimer, the term of this patent is extended or adjusted under 35 U.S.C. 154(b) by 872 days.

(21) Appl. No.: 12/388,113

(22) Filed: Feb. 18, 2009

(65) Prior Publication Data
US 2009/0165177 A1    Jun. 25, 2009

Related U.S. Application Data

(63) Continuation of application No. 11/228,659, filed on Sep. 16, 2005, now abandoned.

(60) Provisional application No. 60/610,656, filed on Sep. 17, 2004, provisional application No. 60/637,230, filed on Dec. 17, 2004, provisional application No. 60/696,405, filed on Jul. 1, 2005.

(51) Int. Cl.
| | | |
|---|---|---|
| *A01H 5/00* | (2006.01) | |
| *A01H 1/00* | (2006.01) | |
| *C12N 15/82* | (2006.01) | |
| *A01H 5/10* | (2006.01) | |
| *C12N 9/10* | (2006.01) | |

(52) U.S. Cl.
CPC ........ *C12N 15/8295* (2013.01); *C12N 15/8216* (2013.01); *C12N 15/8261* (2013.01); *C12N 9/1085* (2013.01)
USPC ........ 800/298; 435/320.1; 435/468; 800/278; 800/290; 800/320.1

(58) Field of Classification Search
None
See application file for complete search history.

(56) References Cited

U.S. PATENT DOCUMENTS 6,310,271 B1 * 10/2001 Hanson et al. ................ 800/278

FOREIGN PATENT DOCUMENTS

| EP | 1 384 776 A1 | 1/2004 |
|---|---|---|
| WO | 0063401 A1 | 10/2000 |
| WO | 2004074442 A2 | 9/2004 |

OTHER PUBLICATIONS

Roeckel et al (1997, Transgenic Research 6(2):133-141).*
Sa et al (2002, Transgenic Research 11(3):269-278).*
Takei et al (2001, Journal of Biological Chemistry 276(28):26405-26410).*
Kakimoto, T.; "Biosynthesis of cytokinins"; J Plant Res (2003) 116:233-239; Springer-Verlag; Tokyo, Japan.
Whitelaw, C.A., et al.; "Accession No. OGWGF17TV" Aug. 2003 (XP-002378666); European Bioinformatics Institute, Cambridge, UK.
Whitelaw, C.A., et al.; "Accession No. OGWAE68TV" Aug. 2003 (XP-002378668); European Bioinformatics Institute, Cambridge, UK.
Whitelaw, C.A., et al.; "Accession No. OGAOS76TM" Jan. 2003 (XP-002394041); European Bioinformatics Institute, Cambridge, UK.
Whitelaw, C.A., et al.; "Accession No. OG5AC21TV" Nov. 2003 (XP-00239402); European Bioinformatics Institute, Cambridge, UK.
Whitelaw, C.A., et al.; "Accession No. PUEHV63TD" May 2003 (XP-002394043); European Bioinformatics Institute, Cambridge, UK.
Whitelaw, C.A., et al.; "Accession No. OGWAE68TH" Aug. 2003 (XP-002378667); European Bioinformatics Institute, Cambridge, UK.

* cited by examiner

*Primary Examiner* — Stuart F Baum
(74) *Attorney, Agent, or Firm* — Pioneer Hi-Bred Int't Inc.

(57) ABSTRACT

Methods and compositions for modulating plant development are provided. Polynucleotide sequences and amino acid sequences encoding isopentenyl transferase (IPT) polypeptides are provided. The sequences can be used in a variety of methods including modulating root development, modulating floral development, modulating leaf and/or shoot development, modulating senescence, modulating seed size and/or weight, and modulating tolerance of plants to abiotic stress. Polynucleotides comprising an IPT promoter are also provided. The promoter can be used to regulate expression of a sequence of interest. Transformed plants, plant cell, tissues, and seed are also provided.

12 Claims, 25 Drawing Sheets

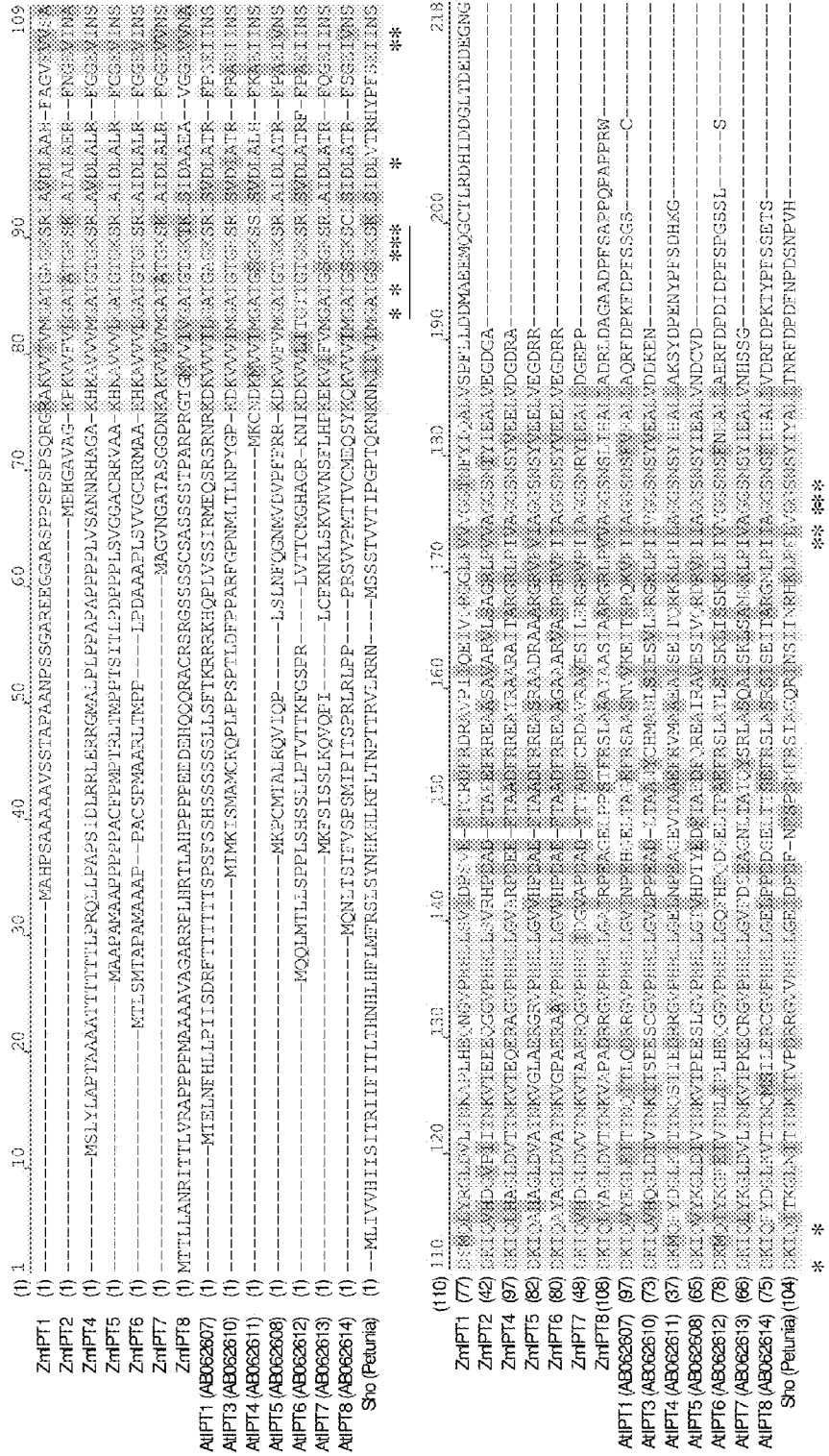

Figure 1: Alignment of the amino acid sequences corresponding to Arabidopsis IPT proteins (AtIPT), the petunia IPT protein (Sho) and corn putative IPT proteins (ZmIPT). Asterisks indicate the positions of amino acid conserved in most IPT proteins and following the consensus sequence GxTxxGK[ST]xxxx[VLI][VLI]xxxxxx[VLI][VLI]xxDxx Qx{57,60}[VLI][VLI]xGG[ST] (where x denotes any amino acid residue, [ ] anyone of the amino acids shown in [ ], and x{m,n} m to n amino acid residues in number; SEQ ID NO: 32) (Takei et al., 2001; Kakimoto 2001). The presence of putative ATP/GTP-binding site (P-loop) motif (prosite PS00017: consensus [AG]-x(4)-G-K-[ST]; SEQ ID NO: 68), is underlined.

Figure 2. Structure of ZmIPT1
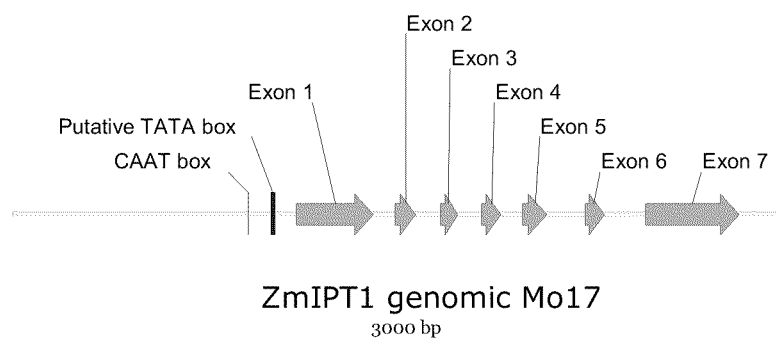

Figure 3. Alignment of ZmIPT1 polypeptides from B73 and Mo17.

```
                         1                                                50
ZmIPT1-B73     (1)  MAHPSAAAAVSSTAPAANPSSGAREEGGARSPPSPSPS--QRGRAKVVI
ZmIPT1-Mo17    (1)  MAHP-SSAAAVSSTAPAANPSYGAREEGGARSPPSPSPSPSQRGRAKVVI
Consensus      (1)  MAHP AAAAVSSTAPAANPS GAREEGGARSPPSPSPS   QRGRAKVVI
                         51                                               100
ZmIPT1-B73    (49)  VMGATGAGKSRLAVDLAAHFAGVEVVSADSMQLYRGLDVLTNKAPLHEQN
ZmIPT1-Mo17   (50)  VMGATGAGKSRLAVDLAAHFAGVEVVSADSMQLYRGLDVLTNKAPLHEQN
Consensus     (51)  VMGATGAGKSRLAVDLAAHFAGVEVVSADSMQLYRGLDVLTNKAPLHEQN
                        101                                               150
ZmIPT1-B73    (99)  GVPHHLLSVIDPSVEFTCRDFRDRAVPIIQEIVDRGGLPVVVGGTNFYIQ
ZmIPT1-Mo17  (100)  GVPHHLLSVIDPSVEFTCRDFRDRALPIIQEIVDRGGLPVVVGGTNFYIQ
Consensus    (101)  GVPHHLLSVIDPSVEFTCRDFRDRALPIIQEIVDRGGLPVVVGGTNFYIQ
                        151                                               200
ZmIPT1-B73   (149)  ALVSPFLLDDMAEEMQGCTLRDHIDDGLTDEDEGNGFERLKEIDPVAAQR
ZmIPT1-Mo17  (150)  ALVSPFLLDDMAEEMQGCTLRDHIDDGLTDEDEGNGFERLKEIDPVAAQR
Consensus    (151)  ALVSPFLLDDMAEEMQGCTLRDHIDDGLTDEDEGNGFERLKEIDPVAAQR
                        201                                               250
ZmIPT1-B73   (199)  IHPNDHRKIKRYLELYATTGALPSDLFQGEAAKKWGRPSNSRLDCCFLWV
ZmIPT1-Mo17  (200)  IHPNDHRKIKRYLELYATTGALPSDLFQGEAAKKWGRPSNSRLDCCFLWV
Consensus    (201)  IHPNDHRKIKRYLELYATTGALPSDLFQGEAAKKWGRPSNSRLDCCFLWV
                        251                                               300
ZmIPT1-B73   (249)  DADLQVLDSYVNKRVDCMMDGGLLDEVCSIYDADAVYTQGLRQAIGVREF
ZmIPT1-Mo17  (250)  DADLQVLDSYVNKRVDCMMDGGLLDEVCSIYDADAVYTQGLRQAIGVREF
Consensus    (251)  DADLQVLDSYVNKRVDCMMDGGLLDEVCSIYDADAVYTQGLRQAIGVREF
                        301                                               350
ZmIPT1-B73   (299)  DEFFRAYLPRKESGEGSCASLLGMHDDQLKSLLDEAVSQLKANTRRLVRR
ZmIPT1-Mo17  (300)  DEFFRAYLPRKESGEGSCASLLGMHDDQLKSLLDEAVSQLKANTRRLVRR
Consensus    (301)  DEFFRAYLPRKESGEGSCASLLGMHDDQLKSLLDEAVSQLKANTRRLVRR
                        351
ZmIPT1-B73   (349)  QVST-
ZmIPT1-Mo17  (350)  QVST-
Consensus    (351)  QVST
```

Figure 4. Lynx analysis of ZmIPT1 expression in embryos
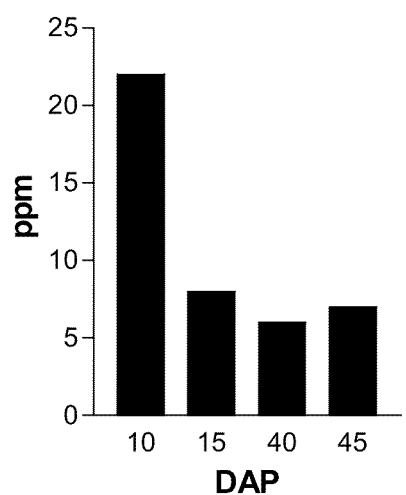

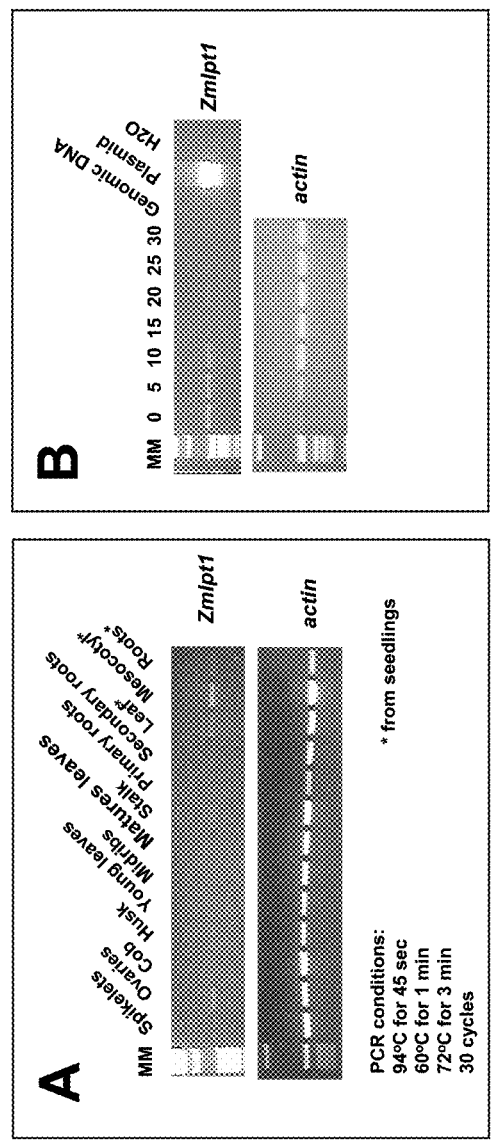
Figure 5. Characterization of ZmIPT1 expression. A. RT-PCR of variouis maize organs and tissues from B73. B. RT-PCR of developing kernels from B73.

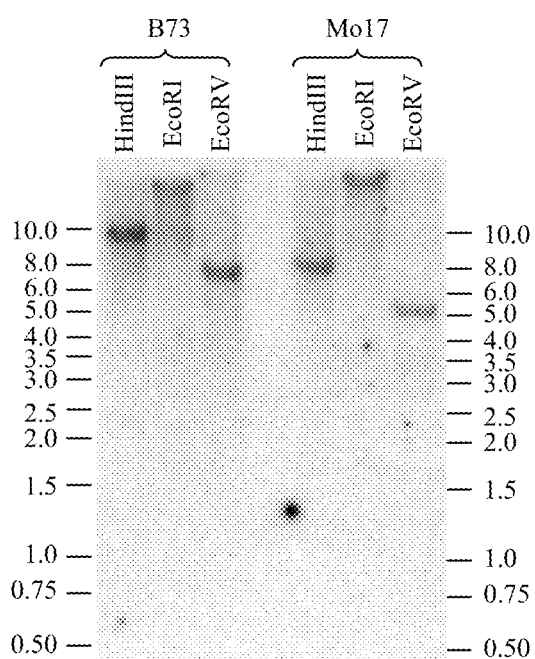
Figure 6. Hybridization of digested genomic DNA with ZmIPT2 probe

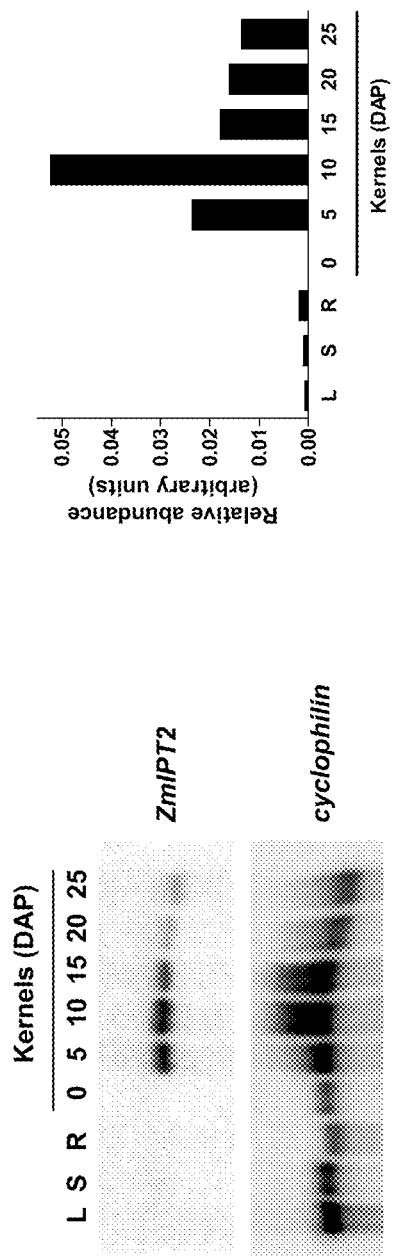
Figure 7. ZmIPT1 expression quantified relative to cyclophilin.

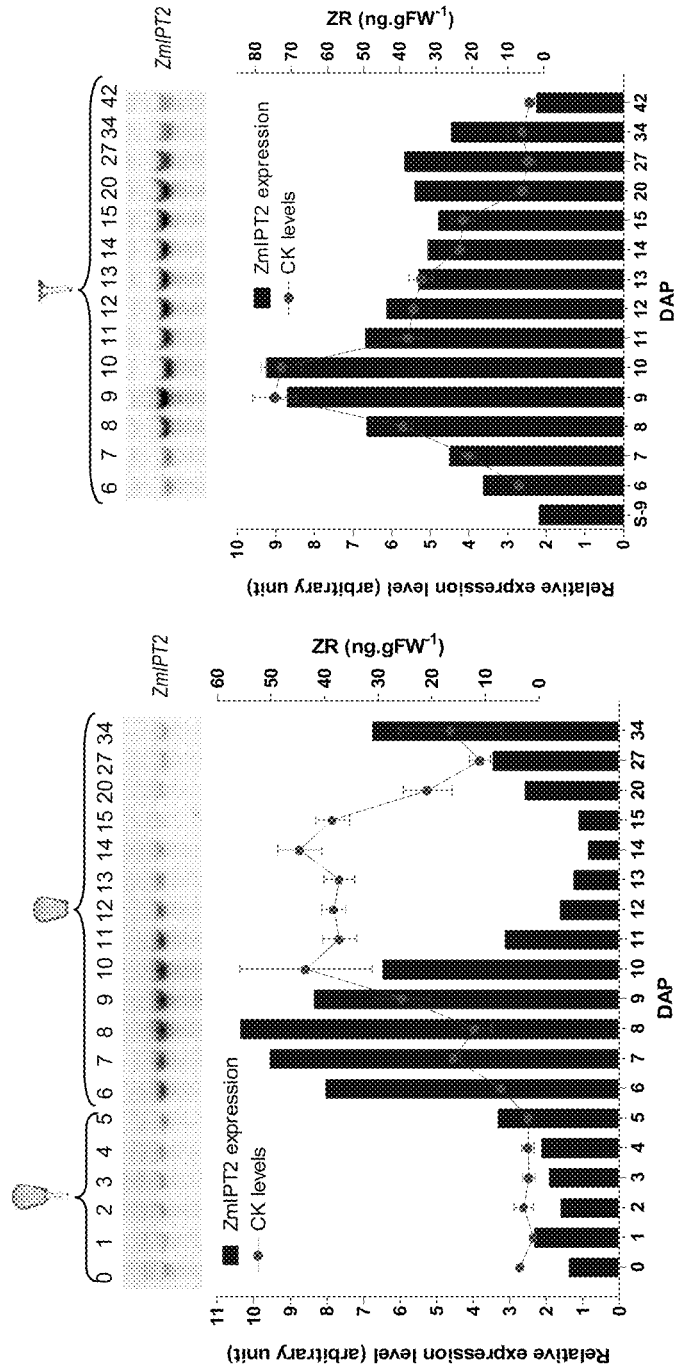
Figure 8. ZmIPT2 expression and cytokinin levels.

FIG. 10A

```
                              1                                                50
        OsIPT6    (1)  --------------------------------------------------
        OsIPT8    (1)  --------------------------------------------------
        OsIPT10   (1)  --------------------------------------------------
        OsIPT11   (1)  MENSSKKTQEFFPKGGNGGYAEQLELLLKQLRFPNKPIHHAEQVIKGFRK
        OsIPT9    (1)  --------------------------------------------------
        OsIPT3    (1)  --------------------------------------------------
        OsIPT2    (1)  --------------------------------------------------
        OsIPT1    (1)  --------------------------------------------------
        OsIPT8    (1)  --------------------------------------------------
        OsIPT4    (1)  --------------------------------------------------
        OsIPT7    (1)  --------------------------------------------------
           IPT    (1)  --------------------------------------------------
AtIPT1 (AB062607) (1)  --------------------------------------------------
AtIPT3 (AB062610) (1)  --------------------------------------------------
AtIPT4 (AB062611) (1)  --------------------------------------------------
AtIPT5 (AB062608) (1)  --------------------------------------------------
AtIPT6 (AB062612) (1)  --------------------------------------------------
AtIPT7 (AB062613) (1)  --------------------------------------------------
AtIPT8 (AB062614) (1)  --------------------------------------------------
    Sho (Petunia) (1)  --------------------------------------------------
        Consensus (1)

51                                              100
        OsIPT6    (1)  --------------------------------------------------
        OsIPT8    (1)  --------------------------------------------------
        OsIPT10   (1)  ---MKIYIQAREEKCQGHVFKSRHLRANKEAALQDASREAFMRLCKIYSI
        OsIPT11  (51)  DWTMKIYIQAREEKCQGHVFKSRHLRANKEAALQDASREAFMRLCKIYSI
        OsIPT9    (1)  --------------------------------------------------
        OsIPT3    (1)  --------------------------------------------------
        OsIPT2    (1)  --------------------------------------------------
        OsIPT1    (1)  --------------------------------------------------
        OsIPT8    (1)  --------------------------------------------------
        OsIPT4    (1)  --------------------------------------------------
        OsIPT7    (1)  --------------------------------------------------
           IPT    (1)  --------------------------------------------------
AtIPT1 (AB062607) (1)  --------------------------------------------------
AtIPT3 (AB062610) (1)  --------------------------------------------------
AtIPT4 (AB062611) (1)  --------------------------------------------------
AtIPT5 (AB062608) (1)  --------------------------------------------------
AtIPT6 (AB062612) (1)  --------------------------------------------------
AtIPT7 (AB062613) (1)  --------------------------------------------------
AtIPT8 (AB062614) (1)  --------------------------------------------------
    Sho (Petunia) (1)  --------------------------------------------------
        Consensus (51)

101                                             150
        OsIPT6    (1)  --------------------------------------------------
        OsIPT8    (1)  --------------------------------------------------
        OsIPT10  (48)  EVASTPFFLHPFRECGDRRCHIRKFRGFEEHSPIHFSMWMWAADEAYEEA
        OsIPT11 (101)  EVASTPFFLHPFRECGDRRCHIRKFRGFEEQSPIHFSMWMWAADEAYEEA
        OsIPT9    (1)  --------------------------------------------------
        OsIPT3    (1)  --------------------------------------------------
        OsIPT2    (1)  --------------------------------------------------
        OsIPT1    (1)  --------------------------------------------------
        OsIPT8    (1)  --------------------------------------------------
        OsIPT4    (1)  --------------------------------------------------
        OsIPT7    (1)  --------------------------------------------------
           IPT    (1)  --------------------------------------------------
AtIPT1 (AB062607) (1)  --------------------------------------------------
AtIPT3 (AB062610) (1)  --------------------------------------------------
```

FIG. 10B

```
AtIPT4 (AB062611)   (1) ----------------------------------------------------
AtIPT5 (AB062608)   (1) ----------------------------------------------------
AtIPT6 (AB062612)   (1) ----------------------------------------------------
AtIPT7 (AB062613)   (1) ----------------------------------------------------
AtIPT8 (AB062614)   (1) ----------------------------------------------------
    Sho (Petunia)   (1) ----------------------------------------------------
        Consensus (101)

151                                                200
         OsIPT6    (1) ----------------------------------------------------
         OsIPT8    (1) ----------------------------------------------------
         OsIPT10  (98) LEELDMLRSKIAGWEERYNHLAKEHTTRGQLLEAIKLRLQWYFRTPSQAQ
         OsIPT11 (151) LEELDMLRSKIAGWEERYNHLAKEHTTRGQLLEAIKLRLQWYFRTPSQAH
         OsIPT9    (1) ----------------------------------------------------
         OsIPT3    (1) ----------------------------------------------------
         OsIPT2    (1) ----------------------------------------------------
         OsIPT1    (1) ----------------------------------------------------
         OsIPT8    (1) ----------------------------------------------------
         OsIPT4    (1) ----------------------------------------------------
         OsIPT7    (1) ----------------------------------------------------
            IPT    (1) ----------------------------------------------------
AtIPT1 (AB062607)   (1) ----------------------------------------------------
AtIPT3 (AB062610)   (1) ----------------------------------------------------
AtIPT4 (AB062611)   (1) ----------------------------------------------------
AtIPT5 (AB062608)   (1) ----------------------------------------------------
AtIPT6 (AB062612)   (1) ----------------------------------------------------
AtIPT7 (AB062613)   (1) ----------------------------------------------------
AtIPT8 (AB062614)   (1) ----------------------------------------------------
    Sho (Petunia)   (1) ----------------------------------------------------
        Consensus (151)

201                                                250
         OsIPT6    (1) ----------------------------------------------------
         OsIPT8    (1) ----------------------------------------------------
         OsIPT10 (148) IQRTLSPPPQRVTRSDGEDYSQINAQQACLERSEVKLDRATSQDYLQGYK
         OsIPT11 (201) IQRTLPPPPQRVTRSDGEDYSQINAHQACLERSEVKLDRATSQDYLQGYK
         OsIPT9    (1) ----------------------------------------------------
         OsIPT3    (1) ----------------------------------------------------
         OsIPT2    (1) ----------------------------------------------------
         OsIPT1    (1) ----------------------------------------------------
         OsIPT8    (1) ----------------------------------------------------
         OsIPT4    (1) ----------------------------------------------------
         OsIPT7    (1) ------------------------------------------MAATGRNAAAA
            IPT    (1) ----------------------------------------------------
AtIPT1 (AB062607)   (1) -------------------------------------------MTELNFHL
AtIPT3 (AB062610)   (1) ----------------------------------------------------
AtIPT4 (AB062611)   (1) ----------------------------------------------------
AtIPT5 (AB062608)   (1) ----------------------------------------------------
AtIPT6 (AB062612)   (1) ----------------------------------------------------
AtIPT7 (AB062613)   (1) ----------------------------------------------------
AtIPT8 (AB062614)   (1) ----------------------------------------------------
    Sho (Petunia)   (1) ---------------------------------------------MLIVVHI
        Consensus (201)

251                                                300
         OsIPT6    (1) ----------------------------------------------------
         OsIPT8    (1) ------------------MAHLAASAAPLPSADPDAGE---------------
         OsIPT10 (198) PPSESLDAIVWPLVEGKHDNTSSGRRNEKAWEMAKQVPRGRIYALVYKHQ
         OsIPT11 (251) PPSESLDAIVWPLVEGKHDNTSSGRRNEKAWEMAKQV
         OsIPT9    (1) ------------------MTSVATRIATLVRAAAAA--------------
         OsIPT3    (1) -------MQAYMAVAAAPAPPASLTLLPRTTTVIRDR--------------
         OsIPT2    (1) ----------------------------------------------------
```

FIG. 10C

```
         OsIPT1      (1) -------------------------------------------
         OsIPT8      (1) -----------------MERSRVGDGCCCSCSGRG--------
         OsIPT4      (1) -------MATSLSLAPKPAAVAVAAAAIPRLVPPPSI------
         OsIPT7     (11) RRTRRSIPRAAAVLPLSSGSPAAVLRRLGLGECFGWAGFMSSLGLKIRTV
           IPT      (1) -------------------------------------------
AtIPT1 (AB062607)    (9) LPIISDRFTTTTTTSPSFSSHSSSSSSLLSFTKRRRK------
AtIPT3 (AB062610)    (1) -----------------MIMKISMAMCKQPLPPSPTL------
AtIPT4 (AB062611)    (1) -------------------------------------------
AtIPT5 (AB062608)    (1) ------------------MKPCMTALRQVIQP-----------
AtIPT6 (AB062612)    (1) ------MQQLMTLLSPPLSHSSLLPTVTTKFGSPR--------
AtIPT7 (AB062613)    (1) -----------------MKFSISSLKQVQPI------------
AtIPT8 (AB062614)    (1) ---------MQNLTSTFVSPSMIPITSPRLRLPP---------
   Sho (Petunia)     (8) ISITRIIFITLTHNHLHFLMFRSLSYNHKHLKFLTNP------
       Consensus   (251)                       SS 301                                      350
         OsIPT6      (1) ---------------------------------MQYGCRRPAVWKRS
         OsIPT8     (21) ---------------------------------------ESS-HSPPP
        OsIPT10    (248) DNIGLVLEKRVGPAAHLGDRYVSDRVISHLGDLYVIRTLSYFPFMLNFHP
        OsIPT11    (288) -----------------------------------IRTLSYFPFMLNFHP
         OsIPT9     (19) ----------------------------------------SRPLRLHRRP
         OsIPT3     (31) ----------------------------------------ERFDAAVPVAP
         OsIPT2      (1) ---------------------------------------MEHCNGI
         OsIPT1      (1) ---------------------------------------MEYHVGGV
         OsIPT8     (19) ----------------------------------------GVASTTAVRP
         OsIPT4     (31) ----------------------------------------DMSALSPPPPL
         OsIPT7     (61) VRSPMAAAAVAGVGRDGSFASQKRPRRVSVRMERSRVGDGCCCSCSGRGG
           IPT      (1) ---------------------------------------------------
AtIPT1 (AB062607)   (46) ----------------------------------------HQPLVSSIRMEQ
AtIPT3 (AB062610)   (21) ----------------------------------------DFPPARFGPNM
AtIPT4 (AB062611)    (1) ---------------------------------------------------
AtIPT5 (AB062608)   (15) ----------------------------------------LSLNFQGNM
AtIPT6 (AB062612)   (30) ----------------------------------------LVTTCMGHA
AtIPT7 (AB062613)   (15) ----------------------------------------LCFKNKLSK
AtIPT8 (AB062614)   (26) ----------------------------------------PRSVVPMTTV
   Sho (Petunia)    (45) ---------------------------------TTRVLRRNMSSSTVV
       Consensus   (301)

351                                      400
         OsIPT6     (15) WSPAAAAATKNKVIVISGPTGAGKTRLALDLAKR--LSGEIISADSVQVY
         OsIPT8     (29) PEKG-----LRKVVVVMCATGTGKSRLAVDLASHF-AGVEVVSADSMQVY
        OsIPT10    (298) SCDCFLNMLGNKLVVIIGATGTGKTRLSIEIAKA--IGGEVVNGDKMQIY
        OsIPT11    (303) SCDCFLNMLGNKLVVIIGATGTGKTRLSIEIAKA--IGGEVVNADKMQIY
         OsIPT9     (29) GGE------DTRMVVIVGATGTGKTKLSIDAAKV--IGGEVVNADKIQLY
         OsIPT3     (42) LVLRHGAGVKHKAVVVMCATGTGKSRLAVDLALR--FGGEVINSDKMQIH
         OsIPT2      (8) AAVGRWLSTKPKVIFVLGATATGKSKLAIRLAAR--FDGEVINSDKIQAH
         OsIPT1      (9) IGQ----SPKPKVVFVLGATATGKSKLAISIAER--FGGEVINSDKIQVY
         OsIPT8     (29) ---------STGMVVIVGATGTGKTKLSIDAAQE--LAGEVVNADKIQLY
         OsIPT4     (42) VSVSRSMVAKHKAVVVMCATGTGKTRLAVDLALQ--FGGEVINADKLQLH
         OsIPT7    (111) VASTTAVRPSTGMVVIVGATGTGKTKLSIDAAQE--LAGEVVNADKIQLY
           IPT      (1) ---------MDLRLIFGPTCTGKTSTAIALAQQ--TGLPVLSLDRVQCC
AtIPT1 (AB062607)   (58) SRS---RNRKDKVVVLGATGAGKSRLSVDLATR--FPSEIINSDKIQVY
AtIPT3 (AB062610)   (32) LTLNPYGP-KDKVVVMCATGTGKSRLSVDIATR--FRAEIINSDKIQVH
AtIPT4 (AB062611)    (1) ------MKCNDKMVVIMCATGSGKSSLSVDLALH--FKAEIINSDKMQFY
AtIPT5 (AB062608)   (24) VDVPFFRR-KDKVVFVMCATGTGKSRLAIDLATR--FPAEIVNSDKIQVY
AtIPT6 (AB062612)   (39) GR----KNIKDKVIITGTTGTGKSRLSVDLATRF-FPAEIINSDKMQIY
AtIPT7 (AB062613)   (24) VNVNSFLHPKEKVIFVMCATGSGKSRLAIDLATR--FQGEIINSDKIQLY
AtIPT8 (AB062614)   (36) CME---QSYKQKVVVIMCATGSGKSCLSIDLATR--FSGEIVNSDKIQFY
   Sho (Petunia)    (60) TIPGPTQKNKNKIIVIMCATGSGKSKLSIDLVTRHYPFSEIINSDKIQIT
       Consensus   (351)            K KVVVIMGATGTGKSRLSIDLA R  FGGEVINSDKIQVY
                                     *  *  ***      *       **  *   *
```

FIG. 10D

```
                       401                                               450
       OsIPT6    (63)  RGLDVGSAKPSSSDRAAVPHHLIDILHASDD-YSAGDFFHDARAATDHLL
       OsIPT8    (73)  GGLDVLTNKVPLHEQKGVPHHLLSVIDPSVE-FTCRDFRDHAVPIIEGIL
       OsIPT10  (346)  DGLDITTNKVSLQDRCGIPHHLIASIPHNAGDFPVSFFRYAAKTTINCIA
       OsIPT11  (351)  DGLDITTNKVSLQDRCGIPHHLIASIPRNAGDFPVSFFRSAAKTTINCIA
       OsIPT9    (71)  DGLDVTTNKVSLADRRGVPHHLLGAIRPEAGELPPSSFRSLAAATAASIA
       OsIPT3    (90)  SGLDVVTNKVTEEECAGVPHHLIGVARPDDE-FTAADFRREAARAAAGAV
       OsIPT2    (56)  DGFPVITNKVTDEERAGVAHHLLGGVSPDAD-FTAEDFRREAAAAVARVH
       OsIPT1    (53)  DGFPIITNKVTEEERAGVPHHLLGVLHPDAD-FTAEDFRREAAAAVARVL
       OsIPT8    (68)  DGLDVTTNKVSLADRRGVPHHLLGAIRAEAGELPPSSFRSLAAAAAGIA
       OsIPT4    (90)  RGLDVATNKATADERAGVPHHLIGVAHPDEE-FTAADFRRAASRAAAAVA
       OsIPT7   (159)  DGLDVTTNKVSLADRRGVPHHLLGAIRAEAGELPPSSFRSLAAAAAGIA
          IPT    (39)  PQLSTGSGRPTVEELKGTTRLYLDDRPLVKGIITAKQAHERLIAEVHNHE
AtIPT1 (AB062607) (103) EGLEITTNQITLQDRRGVPHHLGVINPEHGELTAGEFRSAASNVVKEIT
AtIPT3 (AB062610)  (79) QGLDIVTNKITSEESCGVPHHLGVLPPEAD-LTAANYCHMANLSIESVL
AtIPT4 (AB062611)  (43) DGLKITTNQSTIEDRRGVPHHLGELNPEAGEVTAAEFRVMAAEAISEIT
AtIPT5 (AB062608)  (71) KGLDIVTNKVTPEESLGVPHHLGTVHDTYEDFTAEDFQREAIRAVESIV
AtIPT6 (AB062612)  (84) KGFEIVTNLIPLHEQGGVPHHLGQFHPQDGELTPAEFRSLATLSISKLI
AtIPT7 (AB062613)  (72) KGLDVLTNKVTPKECRGVPHHLGVFDSEAGNLTATQYSRLASQAISKLS
AtIPT8 (AB062614)  (81) DGLKVTTNQMSILERCGVPHHLGELPPDDSELTTSEFRSLASRSISEIT
    Sho (Petunia) (110) KGLNITTNKITVPDRRGVVHHLGEIDPDFN-FSPSHFRSIAGQRINSII
        Consensus (401) DGLDV TNKVTL ER GVPHHLLG I PEAGELTASDFR  AA AIA I
                       *

451                                               500
       OsIPT6   (112)  ARARVPIVAGGTGLYLRWYIYGKPSVPQSSMDVTSAVWSELSRFRDTGRW
       OsIPT8   (122)  DRGGLPVIVGGTNFYIQALVSPFLFDDMAQDIEGLTLNDHLDEIGLDNDD
       OsIPT10  (396)  RRGHTPIVVGGSNSLIHGLLVDNFDLSIVDPFG-----------------
       OsIPT11  (401)  RRGHTPIVVGGSNSLIHGLLVDNFDSSIVDPFG-----------------
       OsIPT9   (121)  ARRLVPVIAGGSNSLIHALLADHFDASAGDPFS-----------------
       OsIPT3   (139)  ERGRLPIIAGGSNSYVEELVEGDGRA------------------------
       OsIPT2   (105)  AAGRLPVVAGGSNIYVEALVAGGGGA------------------------
       OsIPT1   (102)  AAGRLPVVAGGSNTYVEALVEGGGGA------------------------
       OsIPT8   (118)  SRGRVPVVAGGSNSLIHALLADPIDAAPRDPFA-----------------
       OsIPT4   (139)  ARGALPIIAGGSNSYIEELVDGDRRA------------------------
       OsIPT7   (209)  SRGRVPVVAGGSNSLIHALLADPIDAAPRDPFA-----------------
          IPT    (89)  AKG-GLILEGGSISLLRCMAQSRYWN------------------------
AtIPT1 (AB062607) (153) SRQKVPIIAGGSNSFVHALLAQRFDP-KFDPFS-----------------
AtIPT3 (AB062610) (128) NRGKLPILVGGSNSYVEALVDDKENK------------------------
AtIPT4 (AB062611)  (93) QRKKLPILAGGSNSIHALLAKSYDP-ENYPFS-----------------
AtIPT5 (AB062608) (121) QRDRVPIIAGGSNSYIEALVNDCVDF------------------------
AtIPT6 (AB062612) (134) SSKKLPIVVGGSNSFNHALLAERFDP-DIDPFS-----------------
AtIPT7 (AB062613) (122) ANNKLPIVAGGSNSYIEALVNHSSGF------------------------
AtIPT8 (AB062614) (131) ARGNLPIIAGGSNSFIHALLVDRFDP-KTYPFS-----------------
    Sho (Petunia) (159) NRHKLPFLVGGSNSYIYALLTNRFDPDFNPDSN-----------------
        Consensus (451) ARGRLPIVAGGSNSYIHALL       D
                             *  ** **
                             *

501                                               550
       OsIPT6   (162)  EEAVDLVANAGDPKARDLSVNNWSRLRRSLEIIRSSGSPPSAFSLPYNAY
       OsIPT8   (172)  EAGLYEHLKKIDPVAAQRIHPNNHRKIKRYLEL-------------YEST
       OsIPT10  (429)  --------------------------------------------------
       OsIPT11  (434)  --------------------------------------------------
       OsIPT9   (154)  --------------------------------------------------
       OsIPT3   (165)  --------------------------------------------------
       OsIPT2   (131)  --------------------------------------------------
       OsIPT1   (128)  --------------------------------------------------
       OsIPT8   (151)  --------------------------------------------------
       OsIPT4   (165)  --------------------------------------------------
       OsIPT7   (242)  --------------------------------------------------
          IPT   (114)  --------------------------------------------------
AtIPT1 (AB062607) (185) --------------------------------------------------
```

FIG. 10E

```
AtIPT3 (AB062610)   (154) ----------------------------------------------------
AtIPT4 (AB062611)   (125) ----------------------------------------------------
AtIPT5 (AB062608)   (147) ----------------------------------------------------
AtIPT6 (AB062612)   (166) ----------------------------------------------------
AtIPT7 (AB062613)   (148) ----------------------------------------------------
AtIPT8 (AB062614)   (163) ----------------------------------------------------
     Sho (Petunia)  (192) ----------------------------------------------------
         Consensus  (501)

551                                               600
           OsIPT6   (212) NLNHHRRLSLTNQADQPTELELDYDFLCIFLACPRVELYRSIDLRCEEML
           OsIPT8   (209) GALPSDLFQGQATEDRSGVDLVTPDLTVVSCDADLHVLDRYVNERVDCMI
           OsIPT10  (429) ----------QLEVS--YQPTPQWQCCFLWVHVNEVILNEYLKRRVDGMV
           OsIPT11  (434) ----------QLEVS--YRPTPRSQCCFLWVHVNEVILNEYLKRRVDNMV
           OsIPT9   (154) ----------PAAAFRHYRPALRFPCCLLWVHVDEALLDEYLDRRVDDMV
           OsIPT3   (165) -------------------FRERCSAVSSPAASTRCAGEASSGR------
           OsIPT2   (131) -------------------FLAAYDCLFLWTDVAPDLLRWYTAARVDDMV
           OsIPT1   (128) -------------------FRAAHDCLFLWTDVAPGLLRWYTAARVDDMV
           OsIPT8   (151) ----------DADVG--YRPALRFPCCLLWVDVDDDVLDEYLDRRVDDMV
           OsIPT4   (165) -------------------FRDRYDCCLFLWVDVQLPVLHGFVGRRVDDMC
           OsIPT7   (242) ----------DADVGYRPALRFPCCLLWVDVDDDVLDEYLDRRVDDMV
             IPT    (114) -------------------ADFRWHIIRNELADEESFMSVAKTRVKQM
AtIPT1 (AB062607)   (185) ----------SGS--CLISSDLRYECCFIWVDVSETVLYEYLLRRVDEMM
AtIPT3 (AB062610)   (154) -------------------FRSRYDCCFLWVDVALPVLHGFVSERVDKMV
AtIPT4 (AB062611)   (125) ----------DHKG--SICSELKYDCCFIWIDVDQSVLFEYLSLRLDLMM
AtIPT5 (AB062608)   (147) -------------------RLR-YNCCFLWVDVSRPVLHSFVSERVDKMV
AtIPT6 (AB062612)   (166) ----------PGSSLSTICSDLRYKCCILWVDVLEPVLFQHLCNRVDQMI
AtIPT7 (AB062613)   (148) -------------------LLNNYDCCFIWVDVSLPVLNSFVSKRVDRMM
AtIPT8 (AB062614)   (163) ----------SETS---ISSGLRYECCFLWVDVSVSVLFEYLSKRVDQMM
     Sho (Petunia)  (192) ------------PVHFISNELRYNCCFIWVDVLNPVLNEYLDKRVDEMM
         Consensus  (551)                       LRYDCCFLWVDV   VL   YL RRVD MV 601                                               650
           OsIPT6   (262) ADTGGLLSEASWLLDIGLSPG-------MNSATCAIGYRQAMEYLLQCRH
           OsIPT8   (259) DD--GLLDEVCNIYDREAT--------YTQGLRQAIGVREFDEFFRFYFA
           OsIPT10  (467) DA--GLVEEIEEYFDTLSVNGH----VPYVGLGKAIGVPELSEYFTGR--
           OsIPT11  (472) DA--GLVEEIEEYFDTLSVNGH----VPYVGLGKAIGVPELSEYFTGR--
           OsIPT9   (194) DA--GMVEELREYFATTTAAER----AAHSGLGKAIGVPELGDYFAGR--
           OsIPT3   (190) ---------WPQRSTRAAP-------TTPRGIWRAIGVPELDAYLRSRGD
           OsIPT2   (162) RR--GLVGEARAGFDAGA--------DYTRGVRRAIGLPEMHGYLLAERE
           OsIPT1   (159) RR--GLVGEARAGFVDGAGAAD----YYTRGVRRAIGIPEMHGYLLAERS
           OsIPT8   (189) GE--GMVEELEEYFATTSASER----ASHAGLGKAIGVPELGDYFAGR--
           OsIPT4   (196) GR--GMVAEIEAAFDPDRT-------DYSRGVWRAIGVPELDAYLRSCAA
           OsIPT7   (280) GE--GMVEELEEYFATTSASER----ASHAGLGKAIGVPELGDYFAGRK-
             IPT    (143) LRPSAGLSIIQELVQLWREP-------RLRPILEGIDGYRYALLFATQN-
AtIPT1 (AB062607)   (223) DS--GMFEELSRFYDPVKSGLE----T-RFGIRKAIGVPEFDGYFKEYPP
AtIPT3 (AB062610)   (185) ES--GMVEEVREFFDFSNS-------DYSRGIKKAIGFPEFDREFRNEQ-
AtIPT4 (AB062611)   (163) KS--GMFEEIAEFHRSKKAPKE----PLGIWKAIGVQEFDDYLKMYKW
AtIPT5 (AB062608)   (177) DM--GLVDEVRRIFDPSSS-------DYSAGIRRAIGVPELDEFLRSEMR
AtIPT6 (AB062612)   (206) ES--GLVEQLAELYDPVVDSGR----RLGVRKTIGVEEFDRYFRVYPK
AtIPT7 (AB062613)   (179) EA--GLIEEVREVFNP-KA-------NYSVGIRRAIGVPELHEYLRNES-
AtIPT8 (AB062614)   (200) ES--GMFEELAGFYDPRYSGSA----IRAHGIHKTIGIPEFDRYFSLYPP
     Sho (Petunia)  (229) NS--GMYEELEQFFKENRFSDPGLEPGRATGLRKAIGVPEMERYFKKSC-
         Consensus  (601) DS   GLVEEL EFFD   A         GI KAIGVPELDEYFR 651                                               700
           OsIPT6   (305) N-------GGSSSPQEFLEFLTKFQTASRNFSKRQ-MTWFRNEKIYQWVD
           OsIPT8   (299) R--KETGLHDDNLKGLLDEAVSQLKANTRRLVRRQRRRLHRLNKYFEWNL
           OsIPT10  (509) ------V--------SCSDALSMMKTNTQILARSQVTKIHRMVDVWGWHV
           OsIPT11  (514) ------V--------SCSDALSMMKTNTQILARSQVTKIHRMVDVWGWPI
           OsIPT9   (236) ------K--------TFSEAIDDIKANTRVLAAAQVSKIRRMSDAWGWPI
           OsIPT3   (224) GA------DEEERARMLAAAVAEIKSNTFRLACRQHRKIERLDRM-WRA
```

FIG. 10F

```
         OsIPT2  (202) GG-AGAEDDDDLLAGMLEAAVREIKDNTFRLTVSQVAKIRRLSALPGWDV
         OsIPT1  (203) G---GEAADDGELAAMLDGAVREIKANTYRLAATQVAKIRRLSALDGWDV
         OsIPT8  (231) ------K--------SLDAAIDEIKANTRVLAGRQ---------------
         OsIPT4  (237) AG------GEEERARLLANAIEDIKANTRWLSCRQRAKIVRLDRL--WRI
         OsIPT7  (323) ---------------SLDAAIDEIKANTRVLAARQVGKIRRMADVWGWPI
            IPT  (185) -----------QITPDMLLQLDADMENKLIHGIAQEFLIHARRQEQKFPL
AtIPT1 (AB062607) (266) E--KKMIKWDALRKAAYDKAVDDIKRNTWTLAKRQVKKIEMLKDA-GWEI
AtIPT3 (AB062610) (225) ------FLNVEDREELLSKVLEEIKRNTFELACRQREKIERLRKVKKWSI
AtIPT4 (AB062611) (205) DN--DMDKWDPMRKEAYEKAVRAIKENTFQLTKDQITKINKLRNA-GWDI
AtIPT5 (AB062608) (218) ------NYPAETTERLLETAIEKIKENTCLLACRQLQKIQRLYKQWKWNM
AtIPT6 (AB062612) (248) E--MDKGIWDLARKAAYEETVKGMKERTCRLVKKQKEKIMKLIRG-GWEI
AtIPT7 (AB062613) (218) ------LVDRATKSKMLDVAVKNIKKNTEILACRQLKKIQRLHKKWKMSM
AtIPT8 (AB062614) (244) ERKQKMSEWDQARKGAYDEAVQEIKENTWRLAKKQIERIMKLKSS-GWDI
    Sho (Petunia) (276) ---------------TYEEAVREIKENTWRLAKKQMWKIQRLREA-GWDL
      Consensus  (651)                 LD AV EIK NT  LA RQV KI RL    GW I 701                                             750
         OsIPT6  (347) ASQPFDAIAQFICDAYHDRAARLVPDSLEMKRESCRHESRDLKTYRSENR
         OsIPT8  (347) RHIDATEAFYG-----------ATADSWNMKVVKPCVDIVRDFLSDDT
        OsIPT10  (545) HALDCTETILAHLTGSN-----KYMEDLVWKRDVSDSGLAAIQDFL----
        OsIPT11  (550) HALDCTETILAHLTGSN-----KYMEDLVWKRDVSDPGLAAIQDFL----
         OsIPT9  (272) HRIDASDTVRARLTRAG-----SAAESASWERDVRGPGLATIRSFLADQS
         OsIPT3  (266) RRVDATEVFRRRGH----------AADDAWQRLVAAPCIDAVRSFLFEDQ
         OsIPT2  (251) RRVDATAVVARMAEG--------APHGETWREVVWEPCEEMVSRFLETPA
         OsIPT1  (250) RRVDATVVVARMAEG--------APHRETWEAVVWKPCEEMVGRFLEASA
         OsIPT8  (252) --------------------------------------------------
         OsIPT4  (279) RRVDATEAFRRRGG----------AANEAWERHVAAPSIDTVRSFLHGEF
         OsIPT7  (358) RRLDATATIRARLSGAG-----RAAEAAAWERDVRGPGLAAMRQFVGRAD
            IPT  (224) VGATAVEAFEGPPFRM----------------------------------
AtIPT1 (AB062607) (313) ERVDATASFKAVMMKSS-SE---KKWRENWEEQVLEPSVKIVKRHLVQN-
AtIPT3 (AB062610) (269) QRVDATPVFTKRRSK--------MDANVAWERLVAGPSTDTVSRFLLDIA
AtIPT4 (AB062611) (252) KKVDATASFREAIRAAKEGEGVAEMQRKIWNKEVLEPCVKIVRSHLDQPI
AtIPT5 (AB062608) (262) HRVDATEVFLRR--G--------EEADEAWDNSVAHPSALAVEKFLSYSD
AtIPT6 (AB062612) (295) KRLDATAAIMAELNQST-AKGEGKNGREIWEKHIVDESVEIVKKFLLEV-
AtIPT7 (AB062613) (262) HRVDATEVFLKRN-V--------EEQDEAWENLVARPSERIVDKFYNNNN
AtIPT8 (AB062614) (293) QRLDATPSFG-------------RSSREIWDNTVLDESIKVVKRFLVKDK
    Sho (Petunia) (310) QRVDATEAFVEAMSNKK-------EKGIIWEKQVVEPSVKIVNRFLLD--
      Consensus  (701)   RVDATE F                E WER V  P V  VR FL 751                                             800
         OsIPT6  (397) VFRGDDDCCHVLDWITRTQRK-----------------------------
         OsIPT8  (384) ILASRDGSSVTGSPRMSSRELWTQYVCEACDNRVLRGTHEWEQHKQGRCH
        OsIPT10  (586) --------------------------------------------------
        OsIPT11  (591) --------------------------------------------------
         OsIPT9  (317) PPPRSEGTNDYLYAMETEPEPPPPPTLPPRLLRLPRMQYCDMVGRICVLF
         OsIPT3  (306) ERSSIAAGKPPLFAAGKATSGNISVFASAAAAMAAAAAI-----------
         OsIPT2  (293) AAAAVVANGKVDVNVGDAAAGLPEAAAAAVVAAGVV---------------
         OsIPT1  (292) AVDDDDN-----AASGSPAALAPMTAACRLRAQLVQLQY-----------
         OsIPT8  (252) --------------------------------------------------
         OsIPT4  (319) TTAAETTAAP------VPPPPFLPMFALAAAGAGV---------------
         OsIPT7  (403) FNAAAVDQLAARSRRQCLRGGMVAG-------------------------
            IPT  (240) --------------------------------------------------
AtIPT1 (AB062607) (358) --------------------------------------------------
AtIPT3 (AB062610) (311) SRRPLVEASTAVAAAMERELSRCLVA------------------------
AtIPT4 (AB062611) (302) NYYYYYFYLLKRFLSLN---------------------------------
AtIPT5 (AB062608) (302) DHHLEGANILLPEISAVPPLPAAVAAISR---------------------
AtIPT6 (AB062612) (343) --------------------------------------------------
AtIPT7 (AB062613) (303) QLKNDDVEHCLAASYGGGSGSRAHNMI-----------------------
AtIPT8 (AB062614) (330) V-------------------------------------------------
    Sho (Petunia) (351) --------------------------------------------------
      Consensus  (751)
```

FIG. 10G

```
                        801                                              850
        OsIPT6   (418) ----------------------------------------------
        OsIPT8   (434) RKRVQRLKQKASTVISL-----------------------------
        OsIPT10  (586) ----------------------------------------------
        OsIPT11  (591) ----------------------------------------------
        OsIPT9   (367) LGEVVIHHIALLLTAALILQSSTFACTIAAVYECQVSWIIASFASGLFCR
        OsIPT3   (345) ----------------------------------------------
        OsIPT2   (329) ----------------------------------------------
        OsIPT1   (326) ----------------------------------------------
        OsIPT8   (252) ----------------------------------------------
        OsIPT4   (348) ----------------------------------------------
        OsIPT7   (428) ----------------------------------------------
           IPT   (240) ----------------------------------------------
AtIPT1 (AB062607) (358) ----------------------------------------------
AtIPT3 (AB062610) (337) ----------------------------------------------
AtIPT4 (AB062611) (319) ----------------------------------------------
AtIPT5 (AB062608) (331) ----------------------------------------------
AtIPT6 (AB062612) (343) ----------------------------------------------
AtIPT7 (AB062613) (330) ----------------------------------------------
AtIPT8 (AB062614) (331) ----------------------------------------------
    Sho (Petunia) (351) ----------------------------------------------
        Consensus (801)

851                                  889
        OsIPT6   (418) ---------------------------------------
        OsIPT8   (451) ---------------------------------------
        OsIPT10  (586) ---------------------------------------
        OsIPT11  (591) ---------------------------------------
        OsIPT9   (417) IAVLDETVKELDIWKLKIANGFLKITMCLKDWSGYPLGV
        OsIPT3   (345) ---------------------------------------
        OsIPT2   (329) ---------------------------------------
        OsIPT1   (326) ---------------------------------------
        OsIPT8   (252) ---------------------------------------
        OsIPT4   (348) ---------------------------------------
        OsIPT7   (428) ---------------------------------------
           IPT   (240) ---------------------------------------
AtIPT1 (AB062607) (358) ---------------------------------------
AtIPT3 (AB062610) (337) ---------------------------------------
AtIPT4 (AB062611) (319) ---------------------------------------
AtIPT5 (AB062608) (331) ---------------------------------------
AtIPT6 (AB062612) (343) ---------------------------------------
AtIPT7 (AB062613) (330) ---------------------------------------
AtIPT8 (AB062614) (331) ---------------------------------------
    Sho (Petunia) (351) ---------------------------------------
        Consensus (851)
```

Figure 11. Relative expression of ZmIPT2 at various DAP in several kernel tissues.
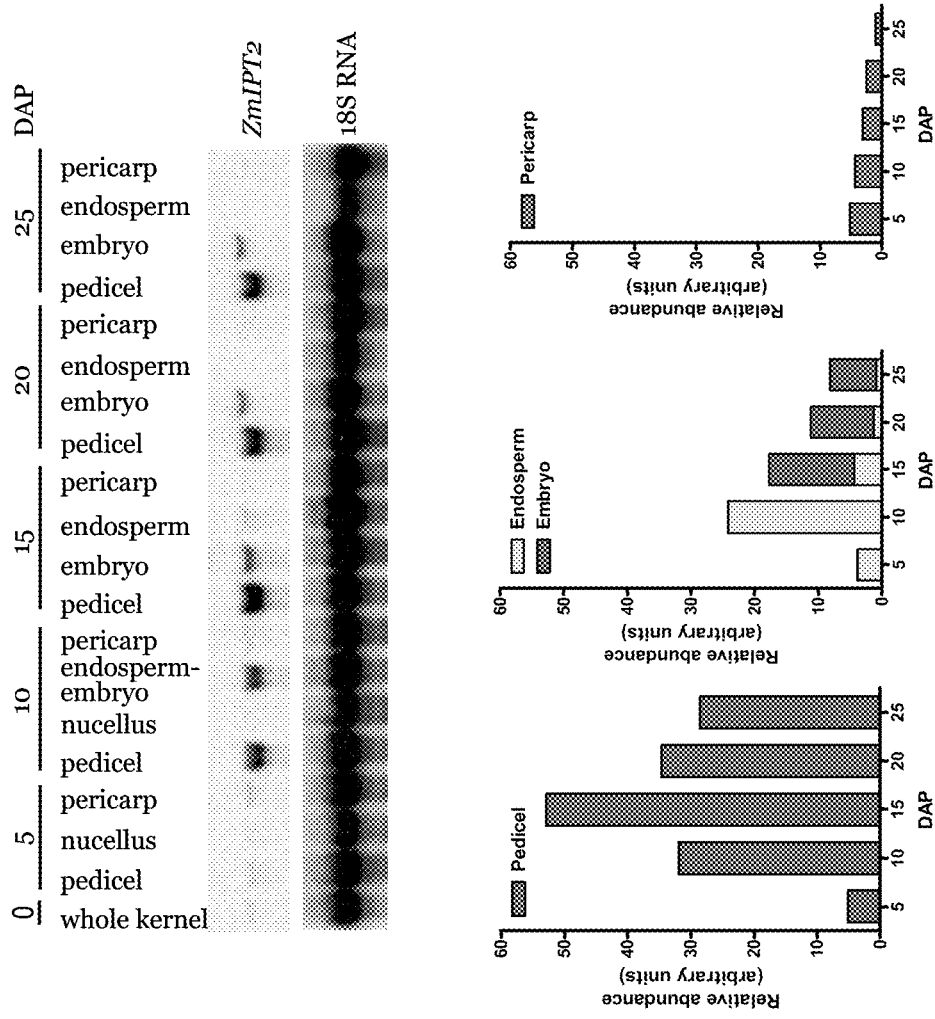

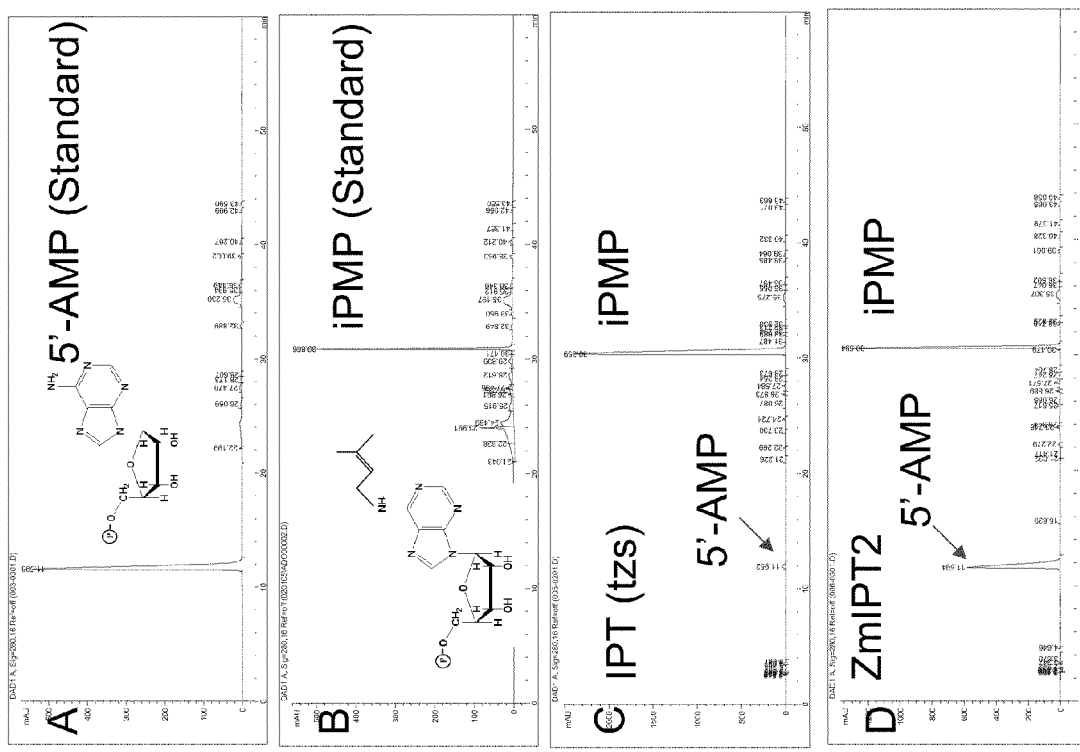
Figure 12: Reversed phase HPLC chromatography.
(A) Chromatogram of 5'-AMP.
(B) Chromatogram of iPMP standard.
(C) Chromatogram of reaction products after incubation of purified IPT (tzs) protein with DMAPP and 5'-AMP for 2h at 30°C.
(D) Chromatogram of reaction products after incubation of purified ZmIPT2 protein with DMAPP and 5'-AMP for 2h at 30°C.

Figure 13: Reversed phase HPLC chromatography (A) Chromatogram of iPAR standard.

(B) Chromatogram of Adenosine standard.

(C) Chromatogram of reaction products after incubation of purified IPT (tzs) protein with DMAPP and 5'-AMP for 2h at 30°C and treatment with calf intestine alkaline phosphatase (CAIP).

(D) Chromatogram of reaction products after incubation of ZmIPT2 purified protein with DMAPP and 5'-AMP for 2h at 30°C and treatment with CAIP.

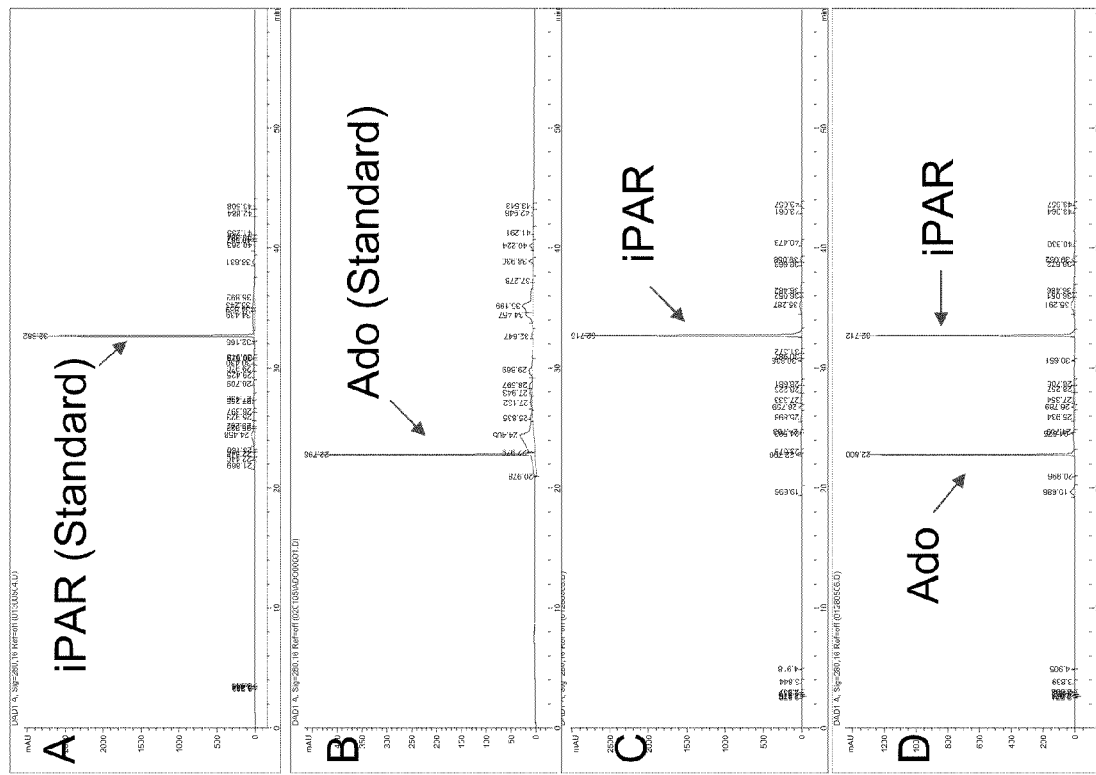

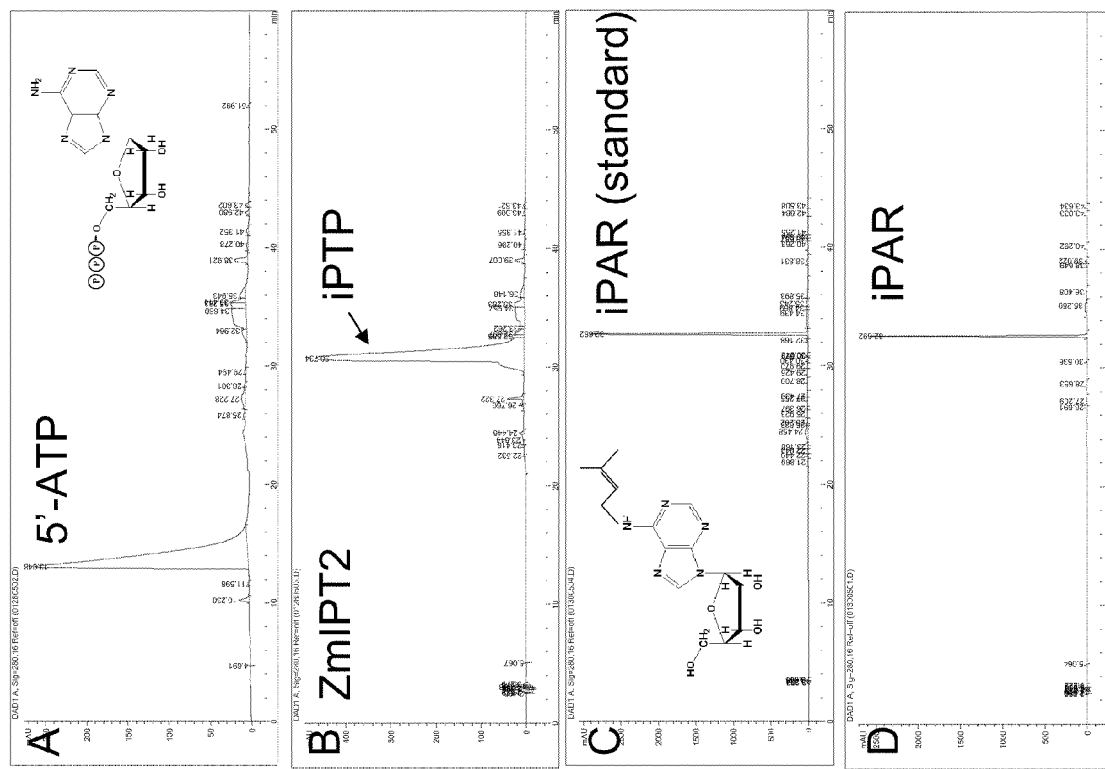

Figure 14: Reversed phase HPLC chromatography.

(A) Chromatogram of 5'-ATP.

(B) Chromatogram of reaction products after incubation of ZmIPT2 purified protein with DMAPP and 5'-ATP for 2h at 30°C. The reaction was stopped using 1/10 volume of a 20% acetic acid solution. Isopentenyl transferase activity should create iPTP. If the product of the reaction identified in the chromatogram is iPTP, it should be converted to iPAR using treatment with a calf intestine alkaline phosphatase.

(C) Chromatogram of iPAR standard.

(D) Chromatogram of the reaction product from (B) after incubation with calf-intestine alkaline phosphatase for 1h at 37°C.

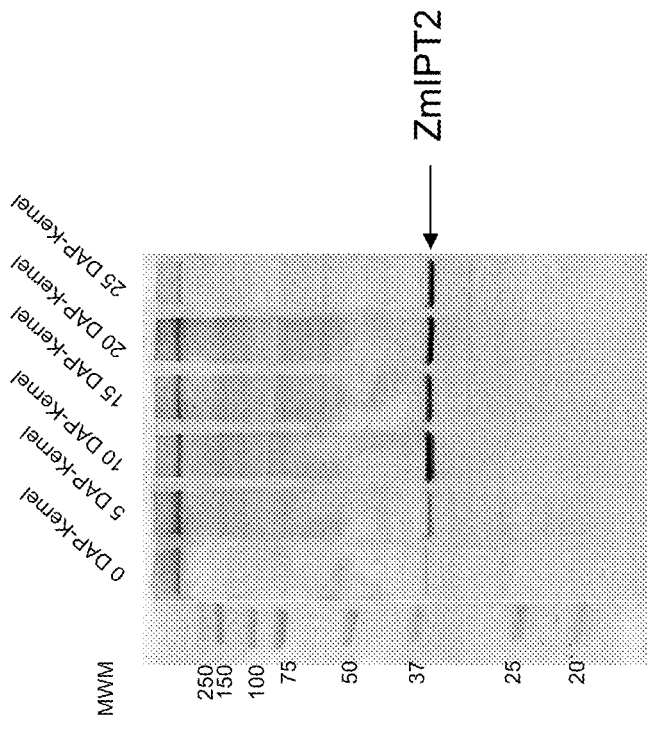
Figure 15. ZmIPT2 protein detection in whole kernel extracts

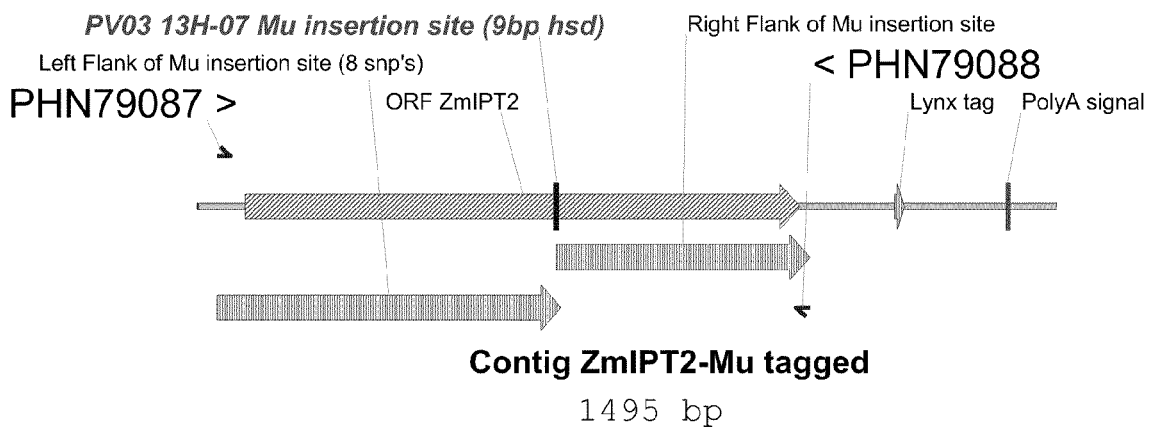
Figure 16: Graphical description of the TUSC project results for ZmIPT2. ORF (upward diagonal lines); ZmIPT2 primers (>, <); PCR product sequences (vertical lines); Mu insertion site (italics).

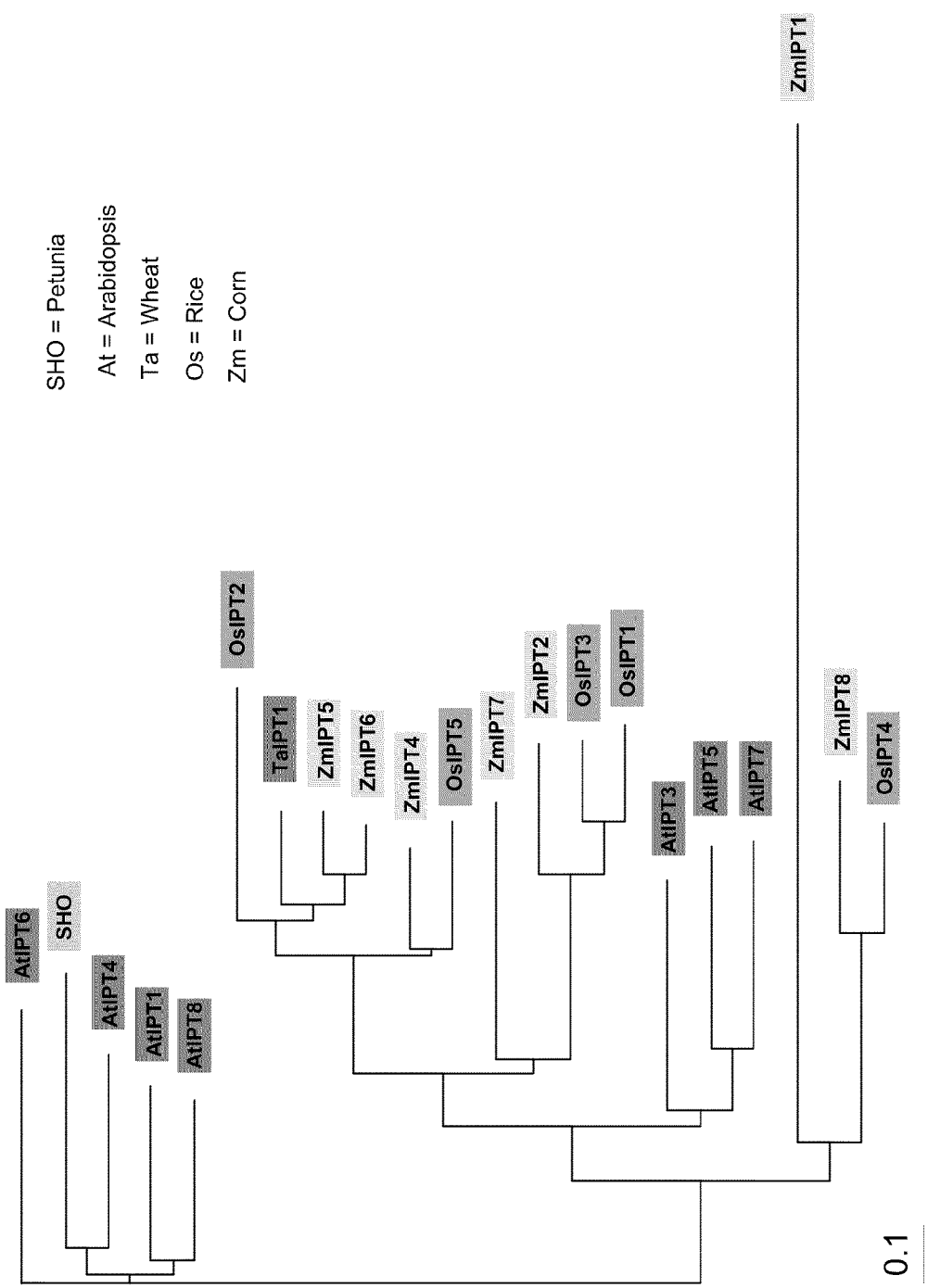
Figure 17. Phylogenetic tree of plant IPT proteins

ISOPENTENYL TRANSFERASE SEQUENCES AND METHODS OF USE

CROSS-REFERENCE

This application claims priority to, and hereby incorporates by reference, U.S. patent application Ser. No. 11/228,659 filed Sep. 16, 2005, U.S. Provisional Patent Application Ser. Nos. 60/610,656 filed Sep. 17, 2004; 60/637,230 filed Dec. 17, 2004; and 60/696,405 filed Jul. 1, 2005.

FIELD OF THE INVENTION

The invention relates to the field of genetic manipulation of plants, particularly the modulation of gene activity to affect plant development and growth.

BACKGROUND OF THE INVENTION

Cytokinins are a class of $N^6$ substituted purine derivative plant hormones that regulate cell division and influence a large number of developmental events, such as shoot development, sink strength, root branching, control of apical dominance in the shoot, leaf development, chloroplast development, and leaf senescence (Mok, et al., (1994) *Cytokinins. Chemistry, Action and Function*. CRC Press, Boca Raton, Fla., pp. 155-166; Horgan, (1984) *Advanced Plant Physiology ed.* M B., Pitman, London, UK, pp. 53-75; and Letham, (1994) *Annual Review of Plant Physiol* 34:163-197). In maize, cytokinins (CK) play an important role in establishing seed size, decreasing tip kernel abortion, and increasing seed set during unfavorable environmental conditions (Cheikh, et al., (1994) *Plant Physiol.* 106:45-51; Dietrich, et al., (1995) *Plant Physiol Biochem* 33:327-36). Active cytokinin pools are regulated by rates of synthesis and degradation.

Until recently, roots were believed to be the major site of cytokinin biosynthesis but evidence indicates that others tissues, such as shoot meristems and developing seeds, also have high cytokinin biosynthetic activity. It has been suggested that cytokinins are synthesized in restricted sites where cell proliferation is active. The presence of several AtIPT genes in *Arabidopsis* and their differential pattern of expression might serve this purpose.

The catabolic enzyme isopentenyl transferase (IPT) directs the synthesis of cytokinins and plays a major role in controlling cytokinin levels in plant tissues. Multiple routes have been proposed for cytokinin biosynthesis. Transfer RNA degradation has been suggested to be a source of cytokinin, because some tRNA molecules contain an isopentenyladenosine (iPA) residue at the site adjacent to the anticodon (Swaminathan, et al., (1977) *Biochemistry* 16:1355-1360). The modification is catalyzed by tRNA isopentenyl transferase (tRNA IPT; EC 2.5.1.8), which has been identified in various organisms such as *Escherichia coli, Saccharomyces cerevisiae, Lactobacillus acidophilus, Homo sapiens*, and *Zea mays* (Bartz, et al., (1972) *Biochemie* 54:31-39; Kline, et al., (1969) *Biochemistry* 8:4361-4371; Holtz, et al., (1975) *Hoppe-Seyler's Z. Physiol. Chem.* 356:1459-1464; Golovko, et al., (2000) *Gene* 258:85-93; and, Holtz, et al., (1979) *Hoppe-Seyler's Z. Physiol. Chem.* 359:89-101). However, this pathway is not considered to be the main route for cytokinin synthesis (Chen, et al., (1997) *Physiol. Plant* 101:665-673 and McGraw, et al., (1995) *Plant Hormones, Physiology, Biochemistry and Molecular Biology*. Ed. Davies, 98-117, Kluwer Academic Publishers, Dordrecht).

Another possible route of cytokinin formation is de novo biosynthesis of iPMP by adenylate isopentenyl transferase (IPT; EC 2.5.1.27) with dimethylallyl-diphosphate (DMAPP), AMP, ATP, and ADP as substrates. Our current knowledge of cytokinin biosynthesis in plants is largely deduced from studies on a possible analogous system in *Agrobacterium tumefaciens*. Cells of *A. tumefaciens* are able to infect certain plant species by inducing tumor formation in host plant tissues (Van Montagu, et al., (1982) *Curr Top Microbiol Immunol* 96:237-254; Hansen, et al., (1999). *Curr Top Microbiol Immunol* 240:21-57). To do so, the *A. tumefaciens* cells synthesize and secrete cytokinins which mediate the transformation of normal host plant tissues into tumors or calli. This process is facilitated by the *A. tumefaciens* tumor-inducing plasmid which contains genes encoding the necessary enzyme and regulators for cytokinin biosynthesis. Biochemical and genetic studies revealed that Gene 4 of the tumor-inducing plasmid encodes an isopentenyl transferase (IPT), which converts AMP and DMAPP into isopentenyladenosine-5'-monophosphate (iPMP), the active form of cytokinins (Akiyoshi, et al., (1984) *Proc. Natl. Acad. Sci. USA* 81:5994-5998). Overexpression of the *Agrobacterium* ipt gene in a variety of transgenic plants has been shown to cause an increased level of cytokinins and elicit typical cytokinin responses in the host plant (Hansen, et al., (1999) *Curr Top Microbiol Immunol* 240:21-57). Therefore, it has been postulated that plant cells use machinery similar to that of *A. tumefaciens* cells for cytokinin biosynthesis. *Arabidopsis* IPT homologs have recently been identified in *Arabidopsis* and Petunia (Takei, et al., (2001) *J. Biol. Chem.* 276:26405-26410 and Kakimoto, (2001) *Plant Cell Physiol.* 42:677-685). Overexpression of the *Arabidopsis* IPT homologs in plants elevated cytokinin levels and elicited typical cytokinin responses in planta and under tissue culture conditions (Kakimoto, (2001) *Plant Cell Physiol.* 42:677-685).

*Arabidopsis* ipt genes are members of a small multigene family of nine different genes, two of which code for tRNA isopentenyl transferases, and seven of which encode a gene product with a cytokinin biosynthetic function. Biochemical analysis of the recombinant AtIPT4 protein showed that, in contrast to the bacterial enzyme, the *Arabidopsis* enzyme uses ATP as a substrate instead of AMP. Another plant IPT gene (Sho) was identified in *Petunia hybrida* using an activation tagging strategy (Zubko, et al., (2002) *The Plant Journal* 29:797-808).

In view of the influence of cytokinins on a wide variety of plant developmental processes, including root architecture, shoot and leaf development, and seed set, the ability to manipulate cytokinin levels in higher plant cells, and thereby drastically effect plant growth and productivity, offers significant commercial value (Mok, et al., (1994) *Cytokinins. Chemistry, Action and Function*. CRC Press, Boca Raton, Fla., pp. 155-166).

BRIEF SUMMARY OF THE INVENTION

Compositions and methods of the invention comprise and employ isopentenyl transferase (IPT) polypeptides and polynucleotides that are involved in modulating plant development, morphology and physiology.

Compositions further include expression cassettes, plants, plant cells and seeds having the IPT sequences of the invention. The plants, plant cells and seeds of the invention may exhibit phenotypic changes, such as modulated (increased or decreased) cytokinin levels; modulated floral development; modulated root development; altered shoot to root ratio; increased seed size or an increased seed weight; increased plant yield or plant vigor; maintained or improved stress tolerance (e.g., increased or maintained size of the plant, minimized tip kernel abortion, increased or maintained seed set); decreased shoot growth; delayed senescence or an enhanced vegetative growth, all relative to a plant, plant cell, or seed not modified per the invention.

Compositions of the invention also include IPT promoters, DNA constructs comprising the IPT promoter operably linked to a nucleotide sequence of interest, expression vectors, plants, plant cells and seeds comprising these DNA constructs.

Methods are provided for reducing or eliminating the activity of an IPT polypeptide in a plant, comprising introducing into the plant a selected polynucleotide. In specific methods, providing the polynucleotide decreases the level of cytokinin in the plant and/or modulates root development of the plant.

Methods are also provided for increasing the level of an IPT polypeptide in a plant comprising introducing into the plant a selected polynucleotide. In specific methods, expression of the IPT polynucleotide increases the level of a cytokinin in the plant; maintains or improves the stress tolerance of the plant; maintains or increases the size of the plant; minimizes seed abortion; increases or maintains seed set; increases shoot growth; increases seed size or seed weight; increases plant yield or plant vigor; modulates floral development; delays senescence; or increases leaf growth.

Methods are also provided for regulating the expression of a nucleotide sequence of interest. The method comprises introducing into a plant a DNA construct comprising a heterologous nucleotide sequence of interest operably linked to an IPT promoter of the invention.

BRIEF DESCRIPTION OF THE DRAWINGS

Figure 1C:
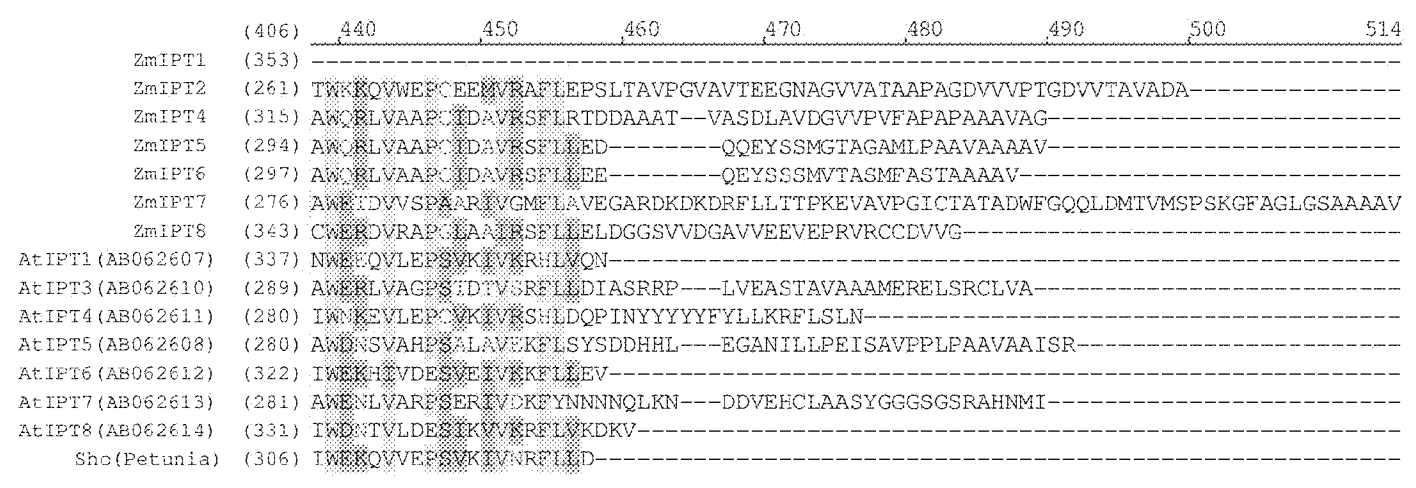

FIG. 1 (A-C) provides an alignment of cytokinin biosynthetic enzymes from maize, petunia, and *Arabidopsis*. The amino acid sequences present in the alignment include ZmIPT1 (SEQ ID NO: 23), ZmIPT2 (SEQ ID NO: 2), ZmIPT4 (SEQ ID NO: 6), ZmIPT5 (SEQ ID NO: 9), ZmIPT6 (SEQ ID NO: 12), ZmIPT7 (SEQ ID NO: 15), ZmIPT8 (SEQ ID NO: 18), AtIPT1 (SEQ ID NO: 29), AtIPT3 (SEQ ID NO: 34), AtIPT4 (SEQ ID NO: 30), AtIPT5 (SEQ ID NO: 35), AtIPT6 (SEQ ID NO: 36), AtIPT7 (SEQ ID NO: 37), AtIPT8 (SEQ ID NO: 38) and Sho (SEQ ID NO: 31). Asterisks indicate amino acids conserved in many IPT proteins and the underlined amino acids represent a putative ATP/GTP binding site.

FIG. 2 provides a schematic of the structure of the ZmIPT1 gene from Mo17 (SEQ ID NO: 21). Coding regions are indicated by the thick arrows and the CAAT and a putative TATA box are shown.

FIG. 3 provides an amino acid sequence alignment of ZmIPT1 (SEQ ID NO: 23, referred to as ZmIPT-Mo17) and a variant of ZmIPT1 (SEQ ID NO: 27, referred to as ZmIPT-B73). The sequences have 98% amino acid sequence identity. The consensus sequence for the ZmIPT1 polypeptide is found in SEQ ID NO: 39.

FIG. 4 provides ppm values for ZmIPT1 in Lynx embryo libraries at various days after pollination (DAP).

FIG. 5A shows the detection of ZmIPT1 in different maize organs using RT-PCR.

FIG. 5B shows the detection of ZmIPT1 in developing kernels using RT-PCR.

FIG. 6 shows a Southern blot with B73 or Mo17 genomic DNA digested by 3 different restriction enzymes. 40 µg of genomic DNA was digested and run on a 0.8% agarose gel and transferred to a nylon membrane. The ZmIPT2-B73 gene coding sequence was used as a probe.

FIG. 7 shows a Northern blot and relative expression of the ZmIPT2 gene in different vegetative organs and in whole kernels at different days after pollination (DAP). Transcript levels were measured in leaves (L), stalks (S), roots (R), and in whole kernels at 0, 5, 10, 15, 20 and 25 days after pollination, and quantified relative to abundance of cyclophilin transcripts.

FIG. 8 provides a Northern blots and relative expression of the ZmIPT2 gene in kernels at different days after pollination. Transcript levels were measured in 0- to 5-DAP whole kernels and in 6- to 34-DAP kernels without pedicels, and quantified relative to abundance of cyclophilin transcripts. Zeatin riboside levels (the most abundant CK in corn kernels) were previously measured in the same samples and are indicated by the solid line (Brugière, et al., (2003) *Plant Physiol* 132:1228-1240).

FIG. 10 provides an alignment of the amino acid sequences corresponding to *Arabidopsis* IPT proteins (AtIPT), the petunia IPT protein (Sho) and rice putative IPT proteins (OsIPT). The sequences in the alignment are as follows: OsIPT6 (SEQ ID NO: 57); OsIPT8 (SEQ ID NO: 41); OsIPT10 (SEQ ID NO: 59); OsIPT11 (SEQ ID NO: 43); OsIPT9 (SEQ ID NO: 61); OsIPT3 (SEQ ID NO: 63); OsIPT2 (SEQ ID NO: 46); OsIPT1 (SEQ ID NO: 49); OsIPT5 (SEQ ID NO: 52); OsIPT4 (34394150) (SEQ ID NO: 66); OsIPT7 (SEQ ID NO: 54); AtIPT1 (AB062607) (SEQ ID NO: 29); AtIPT3 (AB062610) (SEQ ID NO: 34); AtIPT4 (AB062611) (SEQ ID NO: 30); AtIPT5 (AB062608) (SEQ ID NO: 35); AtIPT6 (AB062612) (SEQ ID NO: 36); AtIPT7 (AB062613) (SEQ ID NO: 37); AtIPT8 (AB062614) (SEQ ID NO: 38); Sho (Petunia) (SEQ ID NO: 31); and, consensus (SEQ ID NO: 67).

FIG. 11 is a Northern blot that shows the relative expression of the ZmIPT2 gene at different days after pollination in different parts of the kernels. Transcript levels were measured in 0- to 25-DAP dissected kernels and quantified relative to abundance of 18S RNA transcripts.

FIG. 12 shows chromatograms related to the DMAPP:: AMP isopentenyl transferase activity of *Agrobacterium* and maize purified recombinant protein.

FIG. 13 shows chromatograms related to further treatment of the reaction products of FIG. 12.

FIG. 14 shows chromatograms related to the DMAPP:: ATP isopentenyl transferase activity of the maize purified recombinant protein.

FIG. 15 is a Western blot of whole maize kernels at various days after pollinations.

FIG. 16 is a graphic representation of the TUSC results.

FIG. 17 is a phylogenetic tree of plant IPT sequences.

DETAILED DESCRIPTION OF THE INVENTION

Figure 9:
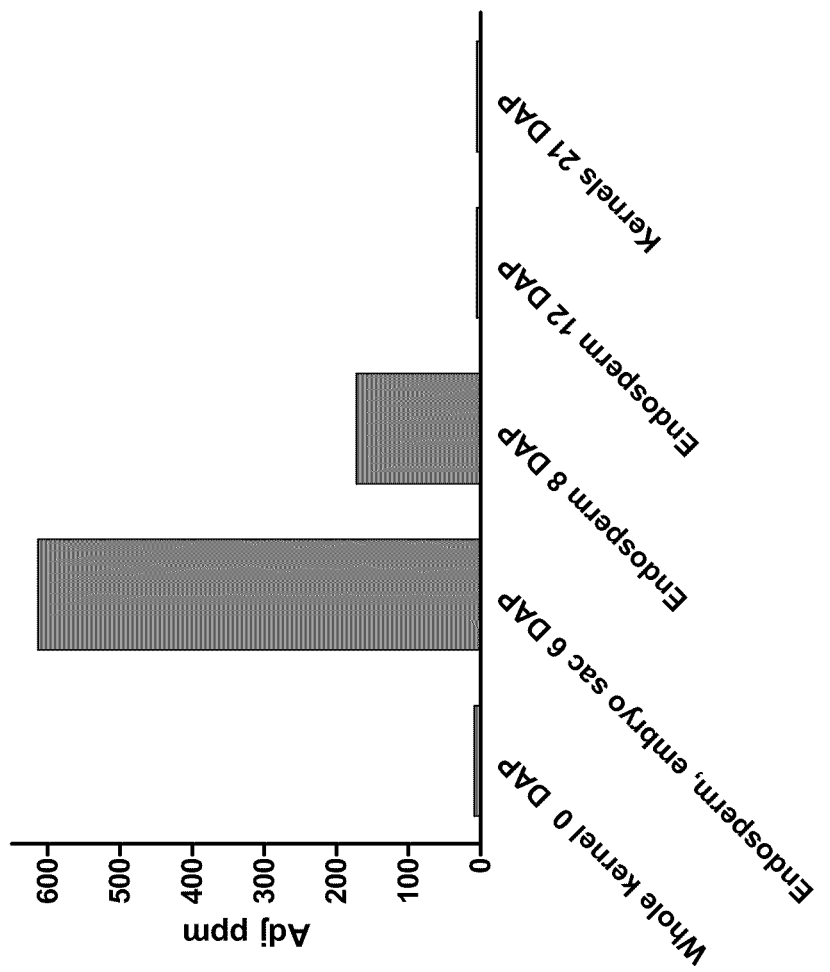
FIG. 9 provides ppm values in Lynx embryo libraries for ZmIPT2.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

COMPOSITIONS

Compositions of the invention include isopentenyl transferase (IPT) polypeptides and polynucleotides that are involved in modulating plant development, morphology, and physiology. Compositions of the invention further include IPT promoters that are capable of regulating transcription. In particular, the present invention provides for isolated polynucleotides comprising nucleotide sequences encoding the amino acid sequences shown in SEQ ID NO: 2, 6, 9, 12, 15, 18, 23, 27, 41, 43, 46, 49, 52, 54, 57, 59, 61, 63, 66 and 77. Further provided are isolated polypeptides having an amino acid sequence encoded by a polynucleotide described herein, for example those set forth in SEQ ID NO: 1, 3, 4, 5, 7, 8, 10, 11, 13, 14, 16, 17, 19, 20, 21, 22, 24, 26, 28, 40, 42, 44, 47, 50, 53, 55, 58, 60, 62, 64, 45, 48, 51, 56, 65, 69, 70, 71, 72, 73, 74 or 77. Additional compositions include the IPT promoter sequences set forth in SEQ ID NO: 25 or 75, and promoter sequences as further isolated and characterized from the 5' regions provided herein for ZmIPT4 (SEQ ID NO: 5), ZmIPT5 (SEQ ID NO: 8), ZmIPT6 (SEQ ID NO: 11), ZmIPT7 (SEQ ID NO: 14), ZmIPT8 (SEQ ID NO: 17), ZmIPT9 (SEQ ID NO: 20), OsIPT1 (SEQ ID NO: 47), OsIPT2 (SEQ ID NO: 44), OsIPT3 (SEQ ID NO: 62), OsIPT4 (SEQ ID NO: 64), OsIPT5 (SEQ ID NO: 50), OsIPT6 (SEQ ID NO: 55), OsIPT7 (SEQ ID NO: 53), OsIPT8 (SEQ ID NO: 40), OsIPT9 (SEQ ID NO: 60), OsIPT10 (SEQ ID NO: 58), and OsIPT11 (SEQ ID NO: 42).

Figure 1B:
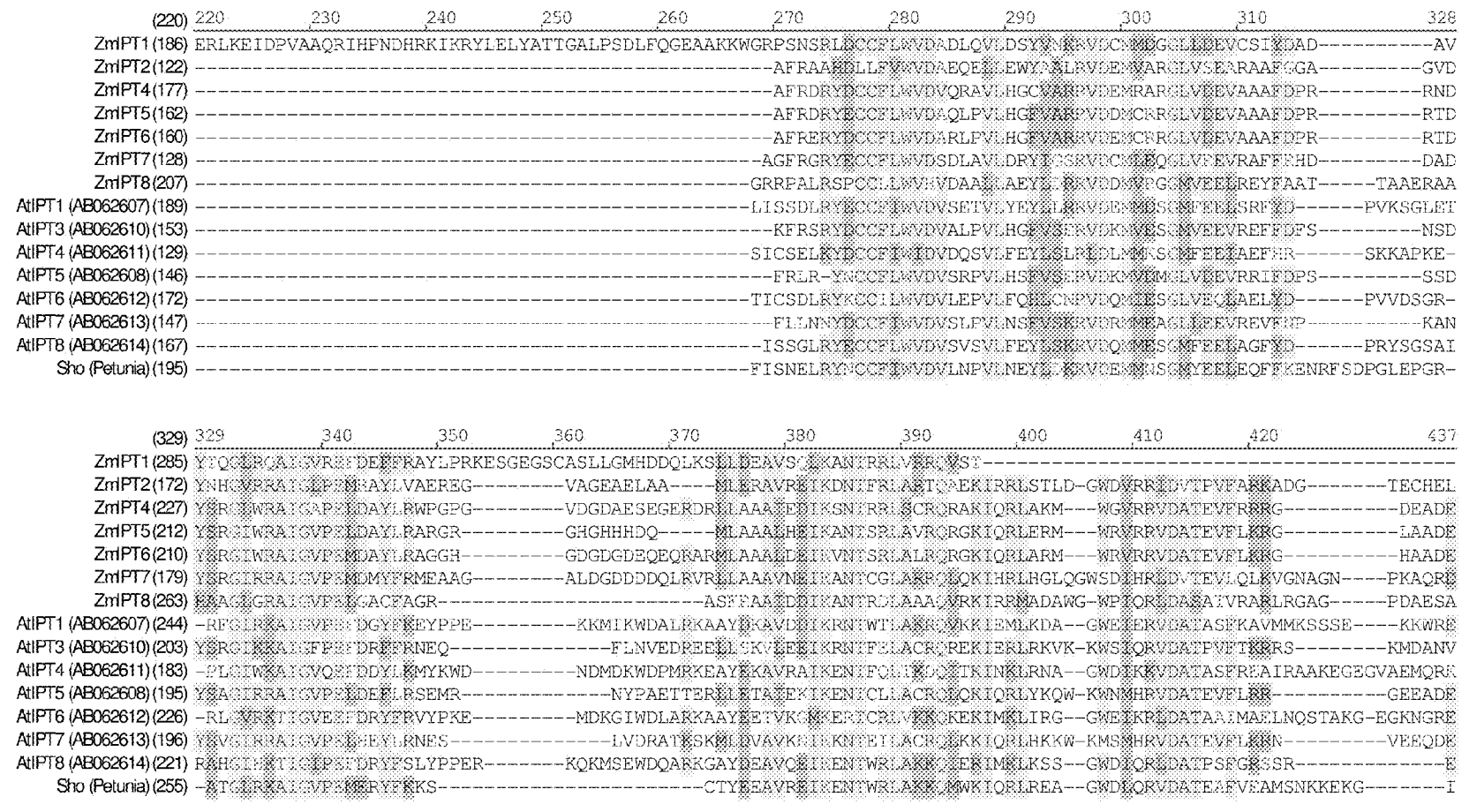

The isopentenyl transferase polypeptides of the invention share sequence identity with members of the isopentenyl transferase family of proteins. Polypeptides in the IPT family have been identified in various bacteria and in *Arabidopsis* and Petunia. See, for example, (Kakimoto, (2001) *Plant Cell Physiol* 42:677-658); Takei, et al., (2001) *The Journal of Biological Chemistry* 276:26405-26410 and Zubko, et al., (2002) *The Plant Journal* 29:797-808). Members of the IPT family are characterized by having the consensus sequence GxTxxGK[ST]xxxxx[VLI]xxxxxxx[VLI][VLI] xxDxxQx{57,60}[VLI][VLI]xGG[ST] (SEQ ID NO: 32) (where x denotes any amino acid residue, [ ] any one of the amino acids shown in [ ], and x{m,n} m to n amino acid residues in number). See, Kakimoto, et al., (2001) *Plant Cell Physiol.* 42:677-85 and Kakimoto, et al., (2003) *J. Plant Res.* 116:233-9, both of which are herein incorporated by reference. IPT family members may also have ATP/GTP binding sites. An amino acid alignment of the maize IPT proteins along with *Arabidopsis* and petunia cytokinin biosynthetic enzymes is provided in FIG. 1, and an amino acid alignment of the rice IPT proteins with *Arabidopsis* and petunia cytokinin biosynthetic enzymes is provided in FIG. 10. Asterisks indicate a consensus sequences found in many cytokinin biosynthetic enzymes. The underlined amino acids indicate a putative ATP/GTP binding domains.

Isopentenyl transferase enzymes are involved in cytokinin biosynthesis, therefore the IPT polypeptides of the invention have "cytokinin synthesis activity." By "cytokinin synthesis activity" is intended enzymatic activity that generates cytokinins, derivatives thereof, or any intermediates in the cytokinin synthesis pathway. Cytokinin synthesis activity therefore includes, but is not limited to, DMAPP:AMP isopentenyltransferase activity (the conversion of AMP (adenosine-5'-monophosphate) and DMAPP into iPMP (isopentenyladenosine-5'-monophosphate)), DMAPP:ADP isopentenyltransferase activity (the conversion of ADP (adenosine-5'-diphosphate) and DMAPP into iPDP (isopentenyladenosine-5'-diphosphate)); DMAPP:ATP isopentenyltransferase activity (the conversion of ATP (adenosine-5'-triphosphate) and DMAPP into iPTP (isopentenyladenosine-5'-triphosphate)), and DMAPP:tRNA isopentenyltransferase activity (the modification of cytoplasmic and/or mitrochondrial tRNAs to give isopentenyl). Cytokinin synthesis activity can further include a substrate comprising a second side chain precursor, other than DMAPP. Examples of side chain donors include compounds of terpenoid origin. For example, the substrate could be hydroxymethylbutenyl diphosphate (HMBPP) which would allow trans-zeatin riboside monophosphate (ZMP) synthesis. See, for example, Åstot, et al., (2000) *Proc Natl Acad Sci* 97:14778-14783 and Takei, et al., (2003) *J Plant Res.* 116(3): 265-9.

Cytokinin synthesis activity further includes the synthesis of intermediates involved in formation of ZMP. Methods to assay for the production of various cytokinins and their intermediates can be found, for example, in Takei, et al., (2001) *The Journal of Biological Chemistry* 276:26405-26410, Zubo, et al., (2002) *The Plant Journal* 29:797-808; Kakimoto, et al., (2001) *Plant Cell Physio.* 42:677-658, and Sun, et al., (2003) *Plant Physiology* 131:167-176, each of which is herein incorporated by reference. "Cytokinin synthesis activity" also includes any alteration in a plant or plant cell phenotype that is characteristic of an increase in cytokinin concentration. Such cytokinin specific effects are discussed elsewhere herein and include, but are not limited to, enhanced shoot formation, reduced apical dominance, delayed senescence, delayed flowering, increased leaf growth, increased cytokinin levels in the plant, increased tolerance under stress, minimization of tip kernel abortion, increased or maintained seed set under stress conditions and a decrease in root growth. Assays to measure or detect such phenotypes are known. See, for example, Miyawaki, et al., (2004) *The Plant Journal* 37:128-138, Takei, et al., (2001) *The Journal of Biological Chemistry* 276:26405-26410, Zubo, et al., (2002) *The Plant Journal* 29:797-808; Kakimoto, et al., (2001) *Plant Cell Physio.* 42:677-658 and Sun, et al., (2003) *Plant Physiology* 131:167-176, each of which is herein incorporated by reference. Additional phenotypes resulting from an increase in cytokinin synthesis activity in a plant are discussed herein.

Compositions of the invention include IPT sequences that are involved in cytokinin biosynthesis. In particular, the present invention provides for isolated polynucleotides comprising nucleotide sequences encoding the amino acid sequences shown in SEQ ID NO: 2, 6, 9, 12, 15, 18, 23, 27, 41, 43, 46, 49, 52, 54, 57, 59, 61, 63, 66 and 77. Further provided are polypeptides having an amino acid sequence encoded by a polynucleotide described herein, for example those set forth in SEQ ID NOS: 1, 3, 4, 5, 7, 8, 10, 11, 13, 14, 16, 17, 19, 20, 21, 22, 24, 26, 28, 40, 42, 44, 47, 50, 53, 55, 58, 60, 62, 64, 45, 48, 51, 56, 65, 69, 70, 71, 72, 73 or 74 and fragments and variants thereof. In addition, further provided are promoter sequences, for example, the sequence set forth in SEQ ID NO: 25 or 75, variants and fragments thereof.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of the native protein and hence have cytokinin synthesis activity. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotide encoding the proteins of the invention.

A fragment of an IPT polynucleotide that encodes a biologically active portion of an IPT protein of the invention will encode at least 15, 25, 30, 50, 100, 150, 200, 225, 250, 275, 300, 310, 315 or 320 contiguous amino acids, or up to the total number of amino acids present in a full-length IPT protein of the invention (for example, 322, 364, 337, 338, 352, 388, 353, 352, 450, 590, 328, 325, 251, 427, 417, 585, 455, 344 and 347 amino acids for SEQ ID NO: 2, 6, 9, 12, 15, 18, 23, 27, 41, 43, 46, 49, 52, 54, 57, 59, 61, 63 and 66, respectively). Fragments of an IPT polynucleotide that are useful as hybridization probes or PCR primers generally need not encode a biologically active portion of an IPT protein.

Thus, a fragment of an IPT polynucleotide may encode a biologically active portion of an IPT protein, or it may be a fragment that can be used as a hybridization probe or PCR primer using methods disclosed below. A biologically active portion of an IPT protein can be prepared by isolating a portion of one of the IPT polynucleotides of the invention, expressing the encoded portion of the IPT protein (e.g., by recombinant expression in vitro), and assessing the activity of the encoded portion of the IPT protein. Polynucleotides that are fragments of an IPT nucleotide sequence comprise at least 16, 20, 50, 75, 100, 150, 200, 250, 300, 350, 400, 450, 500, 550, 600, 650, 700, 800, 900, 950 or 965 contiguous nucleotides, or up to the number of nucleotides present in a full-length IPT polynucleotide disclosed herein (for example, 1495, 969, 2901, 2654, 1095, 4595, 1014, 1955, 1017, 1652, 1059, 3419, 1167, 1535, 3000, 1209, 1062, 1299, 1056, 4682, 8463, 4470, 4114, 2599, 1284, 5030, 8306, 7608, 5075, 4777, 984, 975, 753, 1254, 1044, 1035, 1284, 1353, 1368, 1758 and 1773 nucleotides for SEQ ID NO: 1, 3, 4, 5, 7, 8, 10, 11, 13, 14, 16, 17, 19, 20, 21, 22, 24, 26, 28, 40, 42, 44, 47, 50, 53, 55, 58, 60, 62, 64, 45, 48, 51, 56, 65, 69, 70, 71, 72, 73 and 74, respectively).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the IPT polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an IPT protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 2, 6, 9, 12, 15, 18, 23, 27, 41, 43, 46, 49, 52, 54, 57, 59, 61, 63, 66 or 77 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Certain variant proteins encompassed by the present invention are biologically active, that is they continue to possess the desired biological activity of the native protein, that is, cytokinin synthesis activity, as described herein. Such variants may result from, for example, genetic polymorphism or from human manipulation. Biologically active variants of a native IPT protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The proteins of the invention may be altered in various ways including amino acid substitutions, deletions, truncations, and insertions. Methods for such manipulations are generally known in the art. For example, amino acid sequence variants and fragments of the IPT proteins can be prepared by mutations in the DNA. Methods for mutagenesis and polynucleotide alterations are well known in the art. See, for example, Kunkel, (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired IPT activity. Obviously, the mutations that will be made in the DNA encoding the variant must not place the sequence out of reading frame and optimally will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for cytokinin synthesis activity. See, for example, Takei, et al., (2001) *The Journal of Biological Chemistry* 276:26405-26410; Zubo, et al., (2002) *The Plant Journal* 29:797-808; Kakimoto, et al., (2001) *Plant Cell Physio.* 42:677-658; Sun, et al., (2003) *Plant Physiology* 131:167-176; and Miyawaki, et al., (2004) *The Plant Journal* 37:128-138, all of which are herein incorporated by reference.

Variant polynucleotides and proteins also encompass sequences and proteins derived from a mutagenic and recombinogenic procedure such as DNA shuffling. With such a procedure, one or more different IPT coding sequences can be manipulated to create a new IPT polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the IPT gene of the invention and other known IPT genes to obtain a new gene coding for a protein with an improved property of interest, such as an increased $K_m$ in the case of an enzyme. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

The compositions of the invention also include isolated polynucleotides comprising an IPT promoter nucleotide sequence as set forth in SEQ ID NO: 25 or 75, and promoter sequences as further isolated and characterized from the regions 5' to the coding sequence provided as a part of SEQ ID NO: 5 (ZmIPT4), SEQ ID NO: 8 (ZmIPT5), SEQ ID NO: 11 (ZmIPT6), SEQ ID NO: 14 (ZmIPT7), SEQ ID NO: 17 (ZmIPT8), SEQ ID NO: 20 (ZmIPT9), SEQ ID NO: 47 (OsIPT1), SEQ ID NO: 44 (OsIPT2), SEQ ID NO: 62 (OsIPT3), SEQ ID NO: 64 (OsIPT4), SEQ ID NO: 50 (OsIPT5), SEQ ID NO: 55 (OsIPT6), SEQ ID NO: 53 (OsIPT7), SEQ ID NO: 40 (OsIPT8), SEQ ID NO: 60 (OsIPT9), SEQ ID NO: 58 (OsIPT10) and SEQ ID NO: 42 (OsIPT11).

By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences of the present invention regulate (i.e., repress or activate) transcription.

It is recognized that additional domains can be added to the promoter sequences of the invention and thereby modulate the level of expression, the developmental timing of expression, or tissue type that expression occurs in. See particularly, Australian Patent Number AU-A-77751/94 and U.S. Pat. Nos. 5,466,785 and 5,635,618.

Fragments and variants of the disclosed IPT promoter polynucleotides are also encompassed by the present invention. Fragments of a promoter polynucleotide may retain biological activity and hence retain transcriptional regulatory activity. Alternatively, fragments of a polynucleotide that are useful as hybridization probes generally do not retain biological activity. Thus, fragments of a promoter nucleotide sequence may range from at least about 20 nucleotides, about 50 nucleotides, about 100 nucleotides and up to the full-length polynucleotide of the invention.

Thus, a fragment of an IPT promoter polynucleotide may encode a biologically active portion of an IPT promoter, or it may be a fragment that can be used as a hybridization probe or PCR primer using methods disclosed below. A biologically active portion of the IPT promoter polynucleotides can be prepared by isolating a portion of one of the IPT promoter polynucleotide of the invention, and assessing the activity of the portion of the IPT promoter. Polynucleotides that are fragments of an IPT promoter comprise at least 16, 20, 50, 75, 100, 150, 200, 250, 300, 350, 400, 450, 500, 550, 600, 650, 700, 800, 900, 1,000, 1,050 or 1,080 contiguous nucleotides, or up to the number of nucleotides present in a full-length IPT promoter polynucleotide disclosed herein (for example, 1082 and 1920 nucleotides for SEQ ID NOS: 25 and 75, respectfully).

For a promoter polynucleotide, a variant comprises a deletion and/or addition of one or more nucleotides at one or more internal sites within the native polynucleotide and/or a substitution of one or more nucleotides at one or more sites in the native polynucleotide. Generally, variants of a particular promoter polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variant polynucleotides also encompass sequences derived from a mutagenic and recombinogenic procedure such as DNA shuffling. With such a procedure, one or more different promoter sequences can be manipulated to create a new IPT promoter possessing the desired properties. Strategies for such DNA shuffling are described elsewhere herein.

Methods are available in the art for determining if a promoter sequence retains the ability to regulate transcription. Such activity can be measured by Northern blot analysis. See, for example, Sambrook, et al., (1989) *Molecular Cloning: A Laboratory Manual* (2d ed., Cold Spring Harbor Laboratory Press, Plainview, N.Y.), herein incorporated by reference. Alternatively, biological activity of the promoter can be measured using assays specifically designed for measuring the activity and/or level of the polypeptide being expressed from the promoter. Such assays are known in the art. Also, known promoter elements can be identified within a putative promoter sequence. For example, the IPT1 promoter (SEQ ID NO: 25) of the invention has a TATA-box at bp 688. A TATA-box like sequence can be found 48 bp upstream of the transcription start site (between bp 1035 and 1042). A potential CAAT box can be found between bp 929 and 932.

The polynucleotides of the invention (i.e., the IPT sequences and the IPT promoter sequences) can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire IPT sequences or the IPT promoter sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode for an IPT protein or comprise an IPT promoter sequence and which hybridize under stringent conditions to the IPT sequences or the IPT promoter sequences disclosed herein, or to variants or fragments or complements thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the IPT polynucleotides or the IPT promoter sequences of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, the entire IPT polynucleotide or the IPT promoter sequence disclosed herein, or one or more portions thereof, may be used as a probe capable of specifically hybridizing to corresponding IPT polynucleotides, messenger RNAs, or promoter sequences. To achieve specific hybridization under a variety of conditions, such probes include sequences that are unique among IPT polynucleotide sequences or IPT promoter sequences and are optimally at least about 10 nucleotides in length, and most optimally at least about 20 nucleotides in length. Such probes may be used to amplify corresponding IPT polynucleotides or IPT promoters from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen, (1993) *Laboratory Techniques in Biochemistry and Molecular Biology-Hybridization with Nucleic Acid Probes*, Part I, Chapter 2 (Elsevier, N.Y.); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 87:2264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff, (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The invention further provides plants having altered levels and/or activities of the IPT polypeptides of the invention. In some embodiments, the plants of the invention have stably incorporated into their genome the IPT sequences of the invention. In other embodiments, plants that are genetically modified at a genomic locus encoding an IPT polypeptide of the invention are provided. By "native genomic locus" is intended a naturally occurring genomic sequence. For some embodiments, the genomic locus is set forth in SEQ ID NO: 21, 40, 42, 44, 47, 50, 53, 55, 58, 60, 62 or 64. The genomic locus may be modified to reduce or eliminate the activity of the IPT polypeptide. The term "genetically modified" as used herein refers to a plant or plant part that is modified in its genetic information by the introduction of one or more foreign polynucleotides, and the insertion of the foreign polynucleotide leads to a phenotypic change in the plant. By "phenotypic change" is intended a measurable change in one or more cell functions. For example, plants having a genetic modification at the genomic locus encoding the IPT polypeptide can show reduced or eliminated expression or activity of the IPT polypeptide. Various methods to generate such a genetically modified genomic locus are described elsewhere herein, as are the variety of phenotypes that can result from the modulation of the level/activity of the IPT sequences of the invention.

The invention further provides plants having at least one DNA construct comprising a heterologous nucleotide sequence of interest operably linked to the IPT promoter of the invention. In further embodiments, the DNA construct is stably integrated into the genome of the plant.

As used herein, the term plant includes reference to whole plants, plant parts or organs (e.g. leaves, stems, roots), plant cells, and seeds and progeny of same. Plant cell, as used herein, includes, without limitation, cells obtained from or found in seeds, suspension cultures, embryos, meristematic regions, callus tissue, leaves, roots, shoots, gametophytes, sporophytes, pollen and microspores, as well as plant protoplasts and plant cell tissue cultures, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, "grain" refers to the mature seed produced by commercial growers for purposes other than growing or reproducing the species. Progeny, variants, and mutants of the regenerated plants are also included within the scope of the invention, provided that these parts comprise the introduced nucleic acid sequences.

Methods

I. Providing Sequences

The sequences of the present invention can be introduced/expressed in a host cell such as bacteria, yeast, insect, mammalian or optimally plant cells. It is expected that those of skill in the art are knowledgeable in the numerous systems available for the introduction of a polypeptide or a nucleotide sequence of the present invention into a host cell. No attempt to describe in detail the various methods known for providing proteins in prokaryotes or eukaryotes will be made.

By "host cell" is meant a cell which comprises a heterologous nucleic acid sequence of the invention. Host cells may be prokaryotic cells such as *E. coli*, or eukaryotic cells such as yeast, insect, amphibian or mammalian cells. Host cells can also be monocotyledonous or dicotyledonous plant cells. In certain embodiments, the monocotyledonous host cell is a maize host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures and the like.

The IPT polynucleotides or the IPT promoters of the invention can be provided in expression cassettes for expression in the plant of interest. The cassette will include 5' and 3' regulatory sequences operably linked to an IPT polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. An expression cassette may be provided with a plurality of restriction sites and/or recombination sites for insertion of the IPT polynucleotide to be under the transcriptional regulation of the regulatory regions. The expression cassette may additionally contain selectable marker genes.

In certain embodiments, the expression cassette will include in the 5'-3' direction of transcription, a transcriptional and translational initiation region (i.e., a promoter), an IPT polynucleotide of the invention, and a transcriptional and translational termination region (i.e., termination region) functional in plants. The regulatory regions (i.e., promoters, transcriptional regulatory regions and translational termination regions) and/or the IPT polynucleotide of the invention may be native/analogous to the host cell or to each other. Alternatively, the regulatory regions and/or the IPT polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably-linked polynucleotide. As used herein, a chimeric gene comprises a coding sequence operably linked to a transcription initiation region that is heterologous to the coding sequence.

While heterologous promoters can be used to express the IPT sequences, the native promoter sequences or other IPT promoters (e.g., SEQ ID NO: 25 or 75) may also be used. Such constructs can change expression levels of IPT sequences in the plant or plant cell. Thus, the phenotype of the plant or plant cell can be altered.

The termination region may be native with the transcriptional initiation region, may be native with the operably-linked IPT polynucleotide of interest, may be native with the plant host, or may be derived from another source (i.e., foreign or heterologous with reference to the promoter), the IPT polynucleotide of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831 and 5,436,391, and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968. Other methods known to enhance translation can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-28), cyan fluorescent protein (CYP) (Bolte, et al., (2004) *J. Cell Science* 117:943-54 and Kato, et al., (2002) *Plant Physiol* 129:913-42), and yellow fluorescent protein (PhiYFP™ from Evrogen, see, Bolte, et al., (2004) *J. Cell Science* 117:943-54). For additional selectable markers, see generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. The nucleic acids can be combined with constitutive, inducible, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

Tissue-preferred promoters can be utilized to target enhanced IPT expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol. Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression. See, also, US Patent Application Publication Number 2003/0074698, herein incorporated by reference.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:4732; Mitra, et al., (1994) *Plant Molecular Biology* 26:35-93; Kayaya, et al., (1995) *Molecular and General Genetics* 248:668-674; and Matsuoka, et al., (1993) *Proc. Natl. Acad. Sci. USA* 90(20):9586-9590. Senecence regulated promoters are also of use, such as, SAM22 (Crowell, et al., (1992) *Plant Mol. Biol.* 18:459-466). See, also, U.S. Pat. No. 5,589,052 herein incorporated by reference.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*); and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772); rolB promoter (Capana, et al., (1994) *Plant Mol. Biol.* 25(4):681-691; and the CRWAQ81 root-preferred promoter with the ADH first intron (US Patent Application Publication Number 2005/0097633). See also, U.S. Pat. Nos. 5,837,876; 5,750,386; 5,633,363; 5,459,252; 5,401,836; 5,110,732 and 5,023,179.

"Seed-preferred" promoters refers to those promoters active during seed development and may include expression in seed initials or related maternal tissue. Such seed-preferred promoters include, but are not limited to, Cim1 (cytokinin-induced message); cZ19B1 (maize 19 kDa zein); milps (myo-inositol-1-phosphate synthase) (see, WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733, where seed-preferred promoters from end1 and end2 genes are disclosed; herein incorporated by reference. Additional embryo specific promoters are disclosed in Sato, et al., (1996) *Proc. Natl. Acad. Sci.* 93:8117-8122; Nakase, et al., (1997) *Plant J* 12:235-46; and Postma-Haarsma, et al., (1999) *Plant Mol. Biol.* 39:257-71. Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 and Wu, et al., (1998) *Plant Cell Physiology* 39:885-889.

Also of interest are promoters active in meristem regions, such as developing inflorescence tissues, and promoters which drive expression at or about the time of anthesis or early kernel development. This may include, for example, the maize Zag promoters, including Zag1 and Zag2 (see, Schmidt. et al., (1993) *The Plant Cell* 5:729-37; GenBank X80206; Theissen, et al., (1995) *Gene* 156:155-166 and U.S. patent application Ser. No. 10/817,483); maize Zap promoter (also known as ZmMADS; U.S. patent application Ser. No. 10/387,937; WO 03/078590); maize ckx1-2 promoter (US Patent Application Publication Number 2002/0152500 A1; WO 02/0078438); maize eep1 promoter (U.S. patent application Ser. No. 10/817,483); maize end2 promoter (U.S. Pat. No. 6,528,704 and U.S. patent application Ser. No. 10/310, 191); maize lec1 promoter (U.S. patent application Ser. No. 09/718,754); maize F3.7 promoter (Baszczynski, et al., (1997) *Maydica* 42:189-201); maize tb1 promoter (Hubbarda, et al., (2002) *Genetics* 162:1927-1935 and Wang, et al., (1999) *Nature* 398:236-239); maize eep2 promoter (US Patent Application Ser. No. 10/817,483); maize thioredoxinH promoter (U.S. Provisional Patent Application Ser. No. 60/514,123); maize Zm40 promoter (U.S. Pat. No. 6,403,862 and WO 01/2178); maize mLIP15 promoter (U.S. Pat. No. 6,479,734); maize ESR promoter (U.S. patent application Ser. No. 10/786,679); maize PCNA2 promoter (U.S. patent application Ser. No. 10/388,359); maize cytokinin oxidase promoters (U.S. patent application Ser. No. 11/094,917); promoters disclosed in Weigal, et al., (1992) *Cell* 69:843-859; Accession No. AJ131822; Accession No. Z71981; Accession No. AF049870; and shoot-preferred promoters disclosed in McAvoy, et al., (2003) *Acta Hort.* (ISHS) 625:379-385. Other dividing cell or meristematic tissue-preferred promoters that may be of interest have been disclosed in Ito, et al., (1994) *Plant Mol. Biol.* 24:863-878; Regad, et al., (1995) *Mo. Gen. Genet.* 248:703-711; Shaul, et al., (1996) *Proc. Natl. Acad. Sci.* 93:4868-4872; Ito, et al., (1997) *Plant J.* 11:983-992; and Trehin, et al., (1997) *Plant Mol. Biol.* 35:667-672, all of which are hereby incorporated by reference herein.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:240-245), pollen specific genes (Albani, et al., (1990) *Plant Mol. Biol.* 15:605, Zm13 (Buerrero, et al., (1993) *Mol. Gen. Genet.* 224:161-168), maize pollen-specific gene (Hamilton, et al., (1992) *Plant Mol. Biol.* 18:211-218), sunflower pollen expressed gene (Baltz, et al., (1992) *The Plant Journal* 2:713-721), and *B. napus* pollen specific genes (Arnoldo, et al., (1992) *J. Cell. Biochem, Abstract No. Y101204*).

Stress-inducible promoters include salt/water stress-inducible promoters such as P5CS (Zang, et al., (1997) *Plant Sciences* 129:81-89); cold-inducible promoters, such as, cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423-324-328), ci7 (Kirch, et al., (1997) *Plant Mol. Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57); osmotic inducible promoters, such as, Rab17 (Vilardell, et al., (1991) *Plant Mol. Biol.* 17:985-93) and osmotin (Raghothama, et al., (1993) *Plant Mol Biol* 23:1117-28); and, heat inducible promoters, such as, heat shock proteins (Barros, et al., (1992) *Plant Mol.* 19:665-75; Marrs, et al., (1993) *Dev. Genet.* 14:27-41), and smHSP (Waters, et al., (1996) *J. Experimental Botany* 47:325-338). Other stress-inducible promoters include rip2 (U.S. Pat. No. 5,332,808 and US Patent Application Publication Number 2003/0217393) and rd29a (Yamaguchi-Shinozaki, et al., (1993) *Mol. Gen. Genetics* 236:331-340).

Stress-insensitive promoters can also be used in the methods of the invention. This class of promoters, as well as representative examples, are further described elsewhere herein.

Nitrogen-responsive promoters can also be used in the methods of the invention. Such promoters include, but are not limited to, the 22 kDa Zein promoter (Spena, et al., (1982) *EMBO J* 1:1589-1594 and Muller, et al., (1995) *J. Plant Physiol* 145:606-613); the 19 kDa zein promoter (Pedersen, et al., (1982) *Cell* 29:1019-1025); the 14 kDa zein promoter (Pedersen, et al., (1986) *J. Biol. Chem.* 261:6279-6284), the b-32 promoter (Lohmer, et al., (1991) *EMBO J.* 10:617-624); and the nitrite reductase (NiR) promoter (Rastogi, et al., (1997) *Plant Mol. Biol.* 34(3):465-76 and Sander, et al., (1995) *Plant Mol. Biol.* 27(1):165-77). For a review of consensus sequences found in nitrogen-induced promoters, see for example, Muller, et al., (1997) *The Plant Journal* 12:281-291.

Chemically-regulated promoters can be used to modulate the expression of a gene in a plant through the application of an exogenous chemical regulator. Depending upon the objective, the promoter may be a chemically-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad.*

Sci. USA 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237, and U.S. Pat. Nos. 5,814,618 and 5,789,156), herein incorporated by reference.

A promoter induced by cytokinin, such as the ZmCkx1-2 promoter (U.S. Pat. No. 6,921,815, and pending U.S. patent application Ser. No. 11/074,144), may also be used in the methods and compositions of the invention. Such a construct would amplify biosynthesis of cytokinin occurring in developmental stages and/or tissues of interest. Other cytokinin-inducible promoters are described in pending U.S. patent application Ser. Nos. 11/094,917 and 60/627,394, all hereby incorporated by reference.

Additional inducible promoters include heat shock promoters, such as Gmhsp17.5-E (soybean) (Czarnecka, et al., (1989) *Mol Cell Biol.* 9(8):3457-3463); APX1 gene promoter (*Arabidopsis*) (Storozhenko, et al., (1998) *Plant Physiol.* 118 (3):1005-1014): Ha hsp17.7 G4 (*Helianthus annuus*) (Almoguera, et al., (2002) *Plant Physiol.* 129(1):333-341; and Maize Hsp70 (Rochester, et al., (1986) *EMBO J.* 5:451-8.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides or polypeptides into plants are known in the art and include, but are not limited to, stable transformation methods, transient transformation methods, and virus-mediated methods.

"Stable transformation" is intended to mean that the nucleotide construct of interest introduced into a plant integrates into the genome of the plant and is capable of being inherited by the progeny thereof. "Transient transformation" is intended to mean that a sequence is introduced into the plant and is only temporarily expressed or present in the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. No. 5,563,055 and U.S. Pat. No. 5,981,840), direct gene transfer (Paszkowski, et al., (1984) *EMBO J.* 3:2717-2722), and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips (Springer-Verlag, Berlin); McCabe, et al., (1988) *Biotechnology* 6:923-926); and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Hoque, et al., (2005) *Plant Cell Tissue & Organ Culture* 82(1):45-55 (rice); Sreekala, et al., (2005) *Plant Cell Reports* 24(2):86-94 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the IPT sequences or the IPT promoter sequences of the invention can be provided to a plant using a variety of transient transformation methods. Such transient transformation methods include, but are not limited to, the introduction of the IPT protein or IPT promoter or variants and fragments thereof directly into the plant or the introduction of an IPT transcript into the plant. Such methods include, for example, microinjection or particle bombardment. See, for example, Crossway, et al., (1986) *Mol. Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the IPT polynucleotide or the IPT promoter can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethyenlimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that an IPT polynucleotide of the invention may be initially synthesized as part of a viral polyprotein, which later may be processed by proteolysis in vivo or in vitro to produce the desired recombinant protein. Further, it is recognized that promoters useful for the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta, et al., (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, and U.S. Pat. Nos. 6,187,994; 6,552,248; 6,624,297; 6,331,661; 6,262,341; 6,541,231; 6,664,108; 6,300,545; 6,528,700 and 6,911,575, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and pollinated with either the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Pedigree breeding starts with the crossing of two genotypes, such as an elite line of interest and one other inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F4; F4→F5, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. Backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of a maize inbred line of interest, comprising the steps of crossing a plant of a maize inbred line of interest with a donor plant comprising a mutant gene or transgene conferring a desired trait (i.e., a modulation in the level of cytokinin (an increase or a decrease) or any plant phenotype resulting from the modulated cytokinin level (such plant phenotypes are discussed elsewhere herein)), selecting an F1 progeny plant comprising the mutant gene or transgene conferring the desired trait, and backcrossing the selected F1 progeny plant to a plant of the maize inbred line of interest. This method may further comprise the step of obtaining a molecular marker profile of the maize inbred line of interest and using the molecular marker profile to select for a progeny plant with the desired trait and the molecular marker profile of the inbred line of interest. In the same manner, this method may be used to produce F1 hybrid seed by adding a final step of crossing the desired trait conversion of the maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development," Fehr, 1993 Macmillan Publishing Company, the disclosure of which is incorporated herein by reference. In addition, mutations created in other lines may be used to produce a backcross conversion of elite lines that comprises such mutations.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as maize, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235); Mosbach, et al., (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman, et al., (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired. A protein of the present invention, once expressed, can be isolated from yeast by lysing the cells and applying standard protein isolation techniques to the lists. The monitoring of the purification process can be accomplished by using Western blot techniques or radioimmunoassay or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler, (1997) *Biochemical Methods in Cell Culture and Virology*, Dowden, Hutchinson and Ross, Inc.).

II. Modulating the Concentration and/or Activity of an Isopentenyl Transferase Polypeptide A method for modulating the concentration and/or activity of the polypeptide of the present invention in a plant is provided. In general, concentration and/or activity of the IPT polypeptide is increased or reduced by at least 1%, 5%, 10%, 20%, 30%, 40%, 50%, 60%, 70%, 80% or 90% or more, relative to a native control plant, plant part or cell which does not comprise the introduced sequence. Modulation of the concentration and/or activity may occur at one or more stages of development. In specific embodiments, the polypeptides of the present invention are modulated in monocots, such as maize.

The expression level of the IPT polypeptide may be measured directly, for example, by assaying for the level of the IPT polypeptide in the plant, or indirectly, for example, by measuring the cytokinin synthesis activity in the plant. Methods for assaying for cytokinin synthesis activity are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; all of which are herein incorporated by reference. See also, WO 98/49350, WO 99/07865, WO 99/25821, and Beetham, et al., (1999) *Proc. Natl. Acad. Sci. USA* 96:8774-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of a polynucleotide into a cell. For example, the polynucleotide, or any part thereof, may incorporate into the genome of the plant. Alterations to the genome include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprise at least one nucleotide.

It is further recognized that modulating the level and/or activity of the IPT sequence can be performed to elicit the effects of the sequence only during certain developmental stages and to switch the effect off in other stages where expression is no longer desirable. Control of the IPT expression can be obtained via the use of inducible or tissue-preferred promoters. Alternatively, the gene could be inverted or deleted using site-specific recombinases, transposons or recombination systems, which would also turn on or off expression of the IPT sequence.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

In the present case, for example, changes in cytokinin levels, including changes in absolute amounts of cytokinin, cytokinin ratios, cytokinin activity, or cytokinin distribution, or changes in plant or plant cell phenotype, such as flowering time, seed set, branching, senescence, stress tolerance or root mass, could be measured by comparing a subject plant or plant cell to a control plant or plant cell.

A. Increasing the Activity and/or Concentration of an Isopentenyl Transferase Polypeptide Methods are provided to increase the activity and/or concentration of the IPT polypeptide of the invention. An increase in the concentration and/or activity of the IPT polypeptide of the invention can be achieved by providing to the plant an IPT polypeptide. As discussed elsewhere herein, many methods are known in the art for providing a polypeptide to a plant including, but not limited to, direct introduction of the polypeptide into the plant, and introducing into the plant (transiently or stably) a polynucleotide construct encoding a polypeptide having cytokinin synthesis activity. It is also recognized that the methods of the invention may employ a polynucleotide that is not capable of directing, in the transformed plant, the expression of a protein or an RNA. Thus, the level and/or activity of an IPT polypeptide may be increased by altering the gene encoding the IPT polypeptide or its promoter. See, e.g., Kmiec, U.S. Pat. No. 5,565,350; Zarling, et al., PCT/US93/03868. Therefore mutagenized plants that carry mutations in IPT genes, where the mutations increase expression of the IPT gene or increase the cytokinin synthesis activity of the encoded IPT polypeptide are provided. As described elsewhere herein, methods to assay for an increase in protein concentration or an increase in cytokinin synthesis activity are known.

B. Reducing the Activity and/or Concentration of an Isopentenyl Transferase Polypeptide Methods are provided to reduce or eliminate the activity and/or concentration of the IPT polypeptide by transforming a plant cell with an expression cassette that expresses a polynucleotide that inhibits the expression of the IPT polypeptide. The polynucleotide may inhibit the expression of an IPT polypeptide directly, by preventing translation of the IPT polypeptide messenger RNA, or indirectly, by encoding a molecule that inhibits the transcription or translation of an IPT polypeptide gene encoding an IPT polypeptide. Methods for inhibiting or eliminating the expression of a gene in a plant are well known in the art, and any such method may be used in the present invention to inhibit the expression of the IPT polypeptides.

In accordance with the present invention, the expression of an IPT polypeptide is inhibited if the level of the IPT polypeptide is statistically lower than the level of the same IPT polypeptide in a plant that has not been genetically modified or mutagenized to inhibit the expression of that IPT polypeptide. In particular embodiments of the invention, the protein level of the IPT polypeptide in a modified plant according to the invention is less than 95%, less than 90%, less than 80%, less than 70%, less than 60%, less than 50%, less than 40%, less than 30%, less than 20%, less than 10% or less than 5% of the protein level of the same IPT polypeptide in a plant that is not a mutant or that has not been genetically modified to inhibit the expression of that IPT polypeptide. The expression level of the IPT polypeptide may be measured directly, for example, by assaying for the level of the IPT polypeptide expressed in the cell or plant or indirectly, for example, by measuring the cytokinin synthesis activity in the cell or plant. Methods for determining the cytokinin synthesis activity of the IPT polypeptide are described elsewhere herein.

In other embodiments of the invention, the activity of one or more IPT polypeptides is reduced or eliminated by transforming a plant cell with an expression cassette comprising a polynucleotide encoding a polypeptide that inhibits the activity of one or more IPT polypeptides. The cytokinin synthesis activity of an IPT polypeptide is inhibited according to the present invention if the cytokinin synthesis activity of the IPT polypeptide is statistically lower than the cytokinin synthesis activity of the same IPT polypeptide in a plant that has not been genetically modified to inhibit the cytokinin synthesis activity of that IPT polypeptide. In particular embodiments of the invention, the cytokinin synthesis activity of the IPT polypeptide in a modified plant according to the invention is less than 95%, less than 90%, less than 80%, less than 70%, less than 60%, less than 50%, less than 40%, less than 30%, less than 20%, less than 10% or less than 5% of the cytokinin synthesis activity of the same IPT polypeptide in a plant that that has not been genetically modified to inhibit the expression of that IPT polypeptide. The cytokinin synthesis activity of an IPT polypeptide is "eliminated" according to the invention when it is not detectable by the assay methods described elsewhere herein. Methods of determining the cytokinin synthesis activity of an IPT polypeptide are described elsewhere herein.

In other embodiments, the activity of an IPT polypeptide may be reduced or eliminated by disrupting the gene encoding the IPT polypeptide. The invention encompasses mutagenized plants that carry mutations in IPT genes, where the mutations reduce expression of the IPT gene or inhibit the cytokinin synthesis activity of the encoded IPT polypeptide.

Thus, many methods may be used to reduce or eliminate the activity of an IPT polypeptide. More than one method may be used to reduce the activity of a single IPT polypeptide. In addition, combinations of methods may be employed to reduce or eliminate the activity of two or more different IPT polypeptides.

Non-limiting examples of methods of reducing or eliminating the expression of an IPT polypeptide are given below.

1. Polynucleotide-Based Methods

In some embodiments of the present invention, a plant cell is transformed with an expression cassette that is capable of expressing a polynucleotide that inhibits the expression of an IPT sequence. The term "expression" as used herein refers to the biosynthesis of a gene product, including the transcription and/or translation of said gene product. For example, for the purposes of the present invention, an expression cassette capable of expressing a polynucleotide that inhibits the expression of at least one IPT sequence is an expression cassette capable of producing an RNA molecule that inhibits the transcription and/or translation of at least one IPT polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an IPT sequence are given below.

i. Sense Suppression/Cosuppression

In some embodiments of the invention, inhibition of the expression of an IPT polypeptide may be obtained by sense suppression or cosuppression. For cosuppression, an expression cassette is designed to express an RNA molecule corresponding to all or part of a messenger RNA encoding an IPT polypeptide in the "sense" orientation. Over expression of the RNA molecule can result in reduced expression of the native gene. Accordingly, multiple plant lines transformed with the cosuppression expression cassette are screened to identify those that show the greatest inhibition of IPT polypeptide expression.

The polynucleotide used for cosuppression may correspond to all or part of the sequence encoding the IPT polypeptide, all or part of the 5' and/or 3' untranslated region of an IPT polypeptide transcript, or all or part of both the coding sequence and the untranslated regions of a transcript encoding an IPT polypeptide. In some embodiments where the polynucleotide comprises all or part of the coding region for the IPT polypeptide, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657; each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

ii. Antisense Suppression

In some embodiments of the invention, inhibition of the expression of the IPT polypeptide may be obtained by antisense suppression. For antisense suppression, the expression cassette is designed to express an RNA molecule complementary to all or part of a messenger RNA encoding the IPT polypeptide. Over expression of the antisense RNA molecule can result in reduced expression of the native gene. Accordingly, multiple plant lines transformed with the antisense suppression expression cassette are screened to identify those that show the greatest inhibition of IPT polypeptide expression.

The polynucleotide for use in antisense suppression may correspond to all or part of the complement of the sequence encoding the IPT polypeptide, all or part of the complement of the 5' and/or 3' untranslated region of the IPT polypeptide transcript, or all or part of the complement of both the coding sequence and the untranslated regions of a transcript encoding the IPT polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of an IPT polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of IPT polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of one or more IPT polypeptides may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731; and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

Alternatively, the base-paired stem region may correspond to a portion of a promoter sequence controlling expression of the gene to be inhibited. Transcriptional gene silencing (TGS) may be accomplished through use of hpRNA constructs wherein the inverted repeat of the hairpin shares sequence identity with the promoter region driving expression of a gene to be silenced. Processing of the hpRNA into short RNAs which can interact with the homologous promoter region may trigger degradation or methylation to result in silencing (Aufsatz, et al., (2002) *PNAS* 99(4):16499-16506; Mette, et al., (2000) *EMBO J.* 19(19):5194-5201).

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295, and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for an IPT polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of an IPT polypeptide. Thus, the polynucleotide causes the degradation of the endogenous messenger RNA, resulting in reduced expression of the IPT polypeptide. This method is described, for example, in U.S. Pat. No. 4,987,071, herein incorporated by reference.

vii. Small Interfering RNA or Micro RNA

In some embodiments of the invention, inhibition of the expression of one or more IPT polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of IPT polypeptide expression, the 22-nucleotide sequence is selected from an IPT polypeptide transcript sequence and contains 22 nucleotides encoding said IPT polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding an IPT polypeptide, resulting in reduced expression of the gene. In particular embodiments, the zinc finger protein binds to a regulatory region of an IPT polypeptide gene. In other embodiments, the zinc finger protein binds to a messenger RNA encoding an IPT polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355; each of which is herein incorporated by reference.

3. Polypeptide-Based Inhibition of Protein Activity

In some embodiments of the invention, the polynucleotide encodes an antibody that binds to at least one IPT polypeptide, and reduces the cytokinin synthesis activity of the IPT polypeptide. In another embodiment, the binding of the antibody results in increased turnover of the antibody-IPT polypeptide complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an IPT polypeptide is reduced or eliminated by disrupting the gene encoding the IPT polypeptide. The gene encoding the IPT polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced IPT activity.

i. Transposon Tagging

In one embodiment of the invention, transposon tagging is used to reduce or eliminate the cytokinin synthesis activity of one or more IPT polypeptides. Transposon tagging comprises inserting a transposon within an endogenous IPT gene to reduce or eliminate expression of the IPT polypeptide. "IPT gene" is intended to mean the gene that encodes an IPT polypeptide according to the invention.

In this embodiment, the expression of one or more IPT polypeptides is reduced or eliminated by inserting a transposon within a regulatory region or coding region of the gene encoding the IPT polypeptide. A transposon that is within an exon, intron, 5' or 3' untranslated sequence, a promoter, or any other regulatory sequence of an IPT polypeptide gene may be used to reduce or eliminate the expression and/or activity of the encoded IPT polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima, et al., (1998) *Virology* 243: 472-481; Okubara, et al., (1994) *Genetics* 137:867-874 and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (IPT activity) of the encoded protein are well known in the art. Insertional mutations in gene exons usually result in null-mutants. Mutations in conserved residues are particularly effective in inhibiting the cytokinin synthesis activity of the encoded protein. Conserved residues of plant IPT polypeptides suitable for mutagenesis with the goal to eliminate IPT activity have been described. See, for example, FIG. 1. Such mutants can be isolated according to well-known procedures, and mutations in different IPT loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more IPT polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731, 181; 5,756,325; 5,760,012; 5,795,972 and 5,871,984; each of which are herein incorporated by reference. See also, WO 98/49350, WO 99/07865, WO 99/25821 and Beetham, et al., (1999) *Proc. Natl. Acad. Sci. USA* 96:8774-8778; each of which is herein incorporated by reference.

III. Modulating Cytokinin Level and/or Activity

As used herein, "cytokinin" refers to a class, or member of the class, of plant-specific hormones that play a central role during the cell cycle and influence numerous developmental programs. Cytokinins comprise an $N^6$-substituted purine derivative. Representative cytokinins include isopentenyladenine ($N^6$-($\Delta^2$-isopentenyl)adenine (hereinafter, iP), zeatin (6-(4-hydroxy-3-methylbut-trans-2-enylamino) purine) (hereinafter, Z), and dihydrozeatin (DZ). The free bases and their ribosides (iPR, ZR, and DZR) are believed to be the active compounds. Additional cytokinins are known. See, for example, U.S. Pat. No. 5,211,738 and Keiber, et al., (2002) *Cytokinins, The Arabidopsis Book*, American Society of Plant Biologists, both of which are herein incorporated by reference.

"Modulating the cytokinin level" includes any statistically significant decrease or increase in cytokinin level and/or activity in the plant when compared to a control plant. For example, modulating the level and/or activity can comprise either an increase or a decrease in overall cytokinin content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95%, or greater when compared to a control plant or plant part. Alternatively, the modulated level and/or activity of the cytokinin can include about a 0.2 fold, 0.5 fold, 2 fold, 4 fold, 8 fold, 16 fold, 32 fold or greater overall increase or decrease in cytokinin level/activity in the plant or a plant part when compared to a control plant or plant part.

It is further recognized that the modulation of the cytokinin level/activity need not be an overall increase/decrease in cytokinin level and/or activity, but also includes a change in tissue distribution of the cytokinin. Moreover, the modulation of the cytokinin level/activity need not be an overall increase/decrease in cytokinins, but also includes a change in the ratio of various cytokinin derivatives. For example, the ratio of various cytokinin derivatives such as isopentenyladenine-type, zeatin-type, or dihydrozeatin-type cytokinins, and the like, could be altered and thereby modulate the level/activity of the cytokinin of the plant or plant part when compared to a control plant.

Methods for assaying for a modulation in cytokinin level and/or activity are known in the art. For example, representative methods for cytokinin extraction, immunopurification, HPLC separation, and quantification by ELISA methods can be found, for example, in Faiss, et al., (1997) *Plant J.* 12:401-415. See, also, Werner, et al., (2001) *PNAS* 98:10487-10492) and Dewitte, et al., (1999) *Plant Physiol.* 119:111-121. Each of these references are herein incorporated by reference. As discussed elsewhere herein, modulation in cytokinin level and/or activity can further be detected by monitoring for particular plant phenotypes. Such phenotypes are described elsewhere herein.

In specific methods, the level and/or activity of a cytokinin in a plant is increased by increasing the level or activity of the IPT polypeptide in the plant. Methods for increasing the level and/or activity of IPT polypeptides in a plant are discussed elsewhere herein. Briefly, such methods comprise providing an IPT polypeptide of the invention to a plant and thereby increasing the level and/or activity of the IPT polypeptide. In other embodiments, an IPT nucleotide sequence encoding an IPT polypeptide can be provided by introducing into the plant a polynucleotide comprising an IPT nucleotide sequence of the invention, expressing the IPT sequence, and thereby increasing the level and/or activity of a cytokinin in the plant or plant part when compared to a control plant. In some embodiments, the IPT nucleotide construct introduced into the plant is stably incorporated into the genome of the plant.

In other methods, the level and/or activity of cytokinin in a plant is decreased by decreasing the level and/or activity of one or more of the IPT polypeptides in the plant. Such methods are disclosed in detail elsewhere herein. In one such method, an IPT nucleotide sequence is introduced into the plant and expression of the IPT nucleotide sequence decreases the activity of the IPT polypeptide, and thereby decreases the level and/or activity of a cytokinin in the plant or plant part when compared to a control plant or plant part. In other embodiments, the IPT nucleotide construct introduced into the plant is stably incorporated into the genome of the plant.

As discussed above, one of skill will recognize the appropriate promoter to use to modulate the level/activity of a cytokinin in the plant. Exemplary promoters for this embodiment have been disclosed elsewhere herein.

Accordingly, the present invention further provides plants having a modulated level/activity of a cytokinin when compared to the cytokinin level/activity of a control plant. In one embodiment, the plant of the invention has an increased level/activity of the IPT polypeptide of the invention, and thus has an increased level/activity of cytokinin. In other embodiments, the plant of the invention has a reduced or eliminated level of the IPT polypeptide of the invention, and thus has a decreased level/activity of a cytokinin. In certain embodiments, such plants have stably incorporated into their genome a nucleic acid molecule comprising an IPT nucleotide sequence of the invention operably linked to a promoter that drives expression in the plant cell.

IV. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the IPT polypeptide in the plant. In one method, an IPT sequence of the invention is provided to the plant. In another method, the IPT nucleotide sequence is provided by introducing into the plant a polynucleotide comprising an IPT nucleotide sequence of the invention (which may be a fragment of a full-length IPT sequence provided), expressing said IPT sequence, and thereby modifying root development. In still other methods, the IPT nucleotide construct introduced into the plant is stably incorporated into the genome of the plant.

In other methods, root development is modulated by decreasing the level or activity of the IPT polypeptide in the plant. Such methods can comprise introducing an IPT nucleotide sequence into the plant and decreasing the activity of the IPT polypeptide. In some methods, the IPT nucleotide construct introduced into the plant is stably incorporated into the genome of the plant. A decrease in cytokinin synthesis activity can result in at least one or more of the following alterations to root development, including, but not limited to, larger root meristems, increased root growth, enhanced radial expansion, an enhanced vasculature system, increased root branching, more adventitious roots and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc. Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the IPT polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse environmental conditions. This trait relates to the size, depth and morphology of the root system. In addition, stimulating root growth and increasing root mass by decreasing the level and/or activity of the IPT polypeptide at appropriate developmental stages also finds use in promoting in vitro propagation of explants.

Increased root biomass and/or altered root architecture may also find use in improving nitrogen-use efficiency of the plant. Such improved efficiency may lead to, for example, an increase in plant biomass and/or seed yield at an existing level of available nitrogen, or maintenance of plant biomass and/or seed yield when available nitrogen is limited. Thus, agronomic and/or environmental benefits may ensue.

Furthermore, higher root biomass production due to a decreased level and/or activity of an IPT polypeptide has an indirect effect on production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has a decreased level/activity of an IPT polypeptide of the invention and has enhanced root growth and/or root biomass. In certain embodiments, such plants have stably incorporated into their genome a nucleic acid molecule comprising an IPT nucleotide sequence of the invention operably linked to a promoter that drives expression in the plant cell.

V. Modulating Shoot and Leaf Development

Methods are also provided for modulating vegetative tissue growth in plants. In one embodiment, shoot and leaf development in a plant is modulated. By "modulating shoot and/or leaf development" is intended any alteration in the development of the plant shoot and/or leaf when compared to a control plant or plant part. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of an IPT polypeptide of the invention. In one embodiment, an IPT sequence of the invention is provided. In other embodiments, the IPT nucleotide sequence can be provided by introducing into the plant a polynucleotide comprising an IPT nucleotide sequence of the invention, expressing the IPT sequence, and thereby modifying shoot and/or leaf development. In other embodiments, the IPT nucleotide construct introduced into the plant is stably incorporated into the genome of the plant.

In specific embodiments, shoot or leaf development is modulated by decreasing the level and/or activity of the IPT polypeptide in the plant. A decrease in IPT activity can result in one or more alterations in shoot and/or leaf development, including, but not limited to, smaller apical meristems, reduced leaf number, reduced leaf surface, reduced vascular tissues, shorter internodes and stunted growth, and accelerated leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, senescence-activated promoters, stress-induced promoters, root-preferred promoters, nitrogen-induced promoters and leaf-preferred promoters. Exemplary promoters have been disclosed elsewhere herein.

Decreasing cytokinin synthesis activity in a plant generally results in shorter internodes and stunted growth. Thus, the methods of the invention find use in producing dwarf plants. In addition, as discussed above, modulation of cytokinin synthesis activity in the plant modulates both root and shoot growth. Thus, the present invention further provides methods for altering the root/shoot ratio.

Shoot or leaf development can further be modulated by increasing the level and/or activity of the IPT polypeptide in the plant. An increase in IPT activity can result in one or more alterations in shoot and/or leaf development including, but not limited to, increased leaf number, increased leaf surface, increased vascular tissue, increased shoot formation, longer internodes, improved growth, improved plant yield and vigor, and retarded leaf senescence when compared to a control plant.

In one embodiment, the tolerance of a plant to flooding is improved. Flooding is a serious environmental stress that affects plant growth and productivity. Flooding causes premature senescence which results in leaf chlorosis, necrosis, defoliation, cessation of growth and reduced yield. Cytokinins can regulate senescence, and by increasing the level/activity of the IPT polypeptide in the plant, the present invention improves the tolerance of the plant to a variety of environmental stresses, including flooding. Delayed senescence may also advantageously expand the maturity adaptation of crops, improve the shelf-life of potted plants, and extend the vase-life of cut flowers.

In still other embodiments, methods for modulating shoot regeneration in a callus are provided. In this method, increasing the level and/or activity of the IPT polypeptide will increase the level of cytokinins in the plant. Accordingly, lower concentrations of exogenous growth regulators (i.e., cytokinins) or no exogenous cytokinins in the culture medium will be needed to enhance shoot regeneration in callus. Thus, in one embodiment of the invention, the increased level and/or activity of the IPT sequence can be used to overcome the poor shooting potential of certain species that has limited the success and speed of transgene technology for those species. Moreover, multiple shoot induction can be induced for crops where it is economically desirable to produce as many shoots as possible. Accordingly, methods are provided to increase the rate of regeneration for transformation. In specific embodiments, the IPT sequence will be under the control of an inducible promoter (e.g., heat shock promoter, chemically inducible promoter). Additional inducible promotors are known in the art and are discussed elsewhere herein.

Methods for establishing callus from explants are known. For example, roots, stems, buds, and aseptically germinated seedlings are just a few of the sources of tissue that can be used to induce callus formation. Generally, young and actively growing tissues (i.e., young leaves, roots, meristems or other tissues) are used, but are not required. Callus formation is controlled by growth regulating substances present in the medium (auxins and cytokinins). The specific concentrations of plant regulators needed to induce callus formation vary from species to species and can even depend on the source of explant. In some instances, it is advised to use different growth substances (e.g. 2,4-D or NAA) or a combination of them during tests, since some species may not respond to a specific growth regulator. In addition, culture conditions (i.e., light, temperature, etc.) can also influence the establishment of callus. Once established, callus cultures can be used to initiate shoot regeneration. See, for example, Gurel, et al., (2001) *Turk J. Bot.* 25:25-33; Dodds, et al., (1995). Experiments in Plant Tissue Culture, Cambridge University Press; Gamborg (1995) *Plant Cell, Tissue and Organ Culture*, eds. G. Phillips; and, US Patent Application Publication Number 2003/0180952, all of which are herein incorporated by reference.

It is further recognized that increasing seed size and/or weight can be accompanied by an increase in the rate of growth of seedlings or an increase in vigor. In addition, modulating the plant's tolerance to stress, as discussed below, along with modulation of root, shoot and leaf development can increase plant yield and vigor. As used herein, the term "vigor" refers to the relative health, productivity, and rate of growth of the plant and/or of certain plant parts, and may be reflected in various developmental attributes, including, but not limited to, concentration of chlorophyll, photosynthetic rate, total biomass, root biomass, grain quality, and/or grain yield. In *Zea mays* in particular, vigor may also be reflected in ear growth rate, ear size, and/or expansiveness of silk exsertion. Vigor may relate to the ability of a plant to grow rapidly during early development and to the successful establishment, after germination, of a well-developed root system and a well-developed photosynthetic apparatus. Vigor may be determined with reference to different genotypes under similar environmental conditions, or with reference to the same or different genotypes under different environmental conditions.

Accordingly, the present invention further provides plants having modulated shoot and/or leaf development when compared to a control plant. In some embodiments, the plant of the invention has an increased level/activity of the IPT polypeptide of the invention. In other embodiments, the plant of the invention has a decreased level/activity of the IPT polypeptide of the invention.

VI. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant or plant part. "Modulating floral development" further includes any alteration in the timing of the development of a plant's reproductive tissue (i.e., delayed or accelerated floral development) when compared to a control plant or plant part. Macroscopic alterations may include changes in size, shape, number, or location of reproductive organs, the developmental time period during which these structures form, or the ability to maintain or proceed through the flowering process in times of environmental stress. Microscopic alterations may include changes to the types or shapes of cells that make up the reproductive organs.

The method for modulating floral development in a plant comprises modulating (either increasing or decreasing) the level and/or activity of the IPT polypeptide in a plant. In one method, an IPT sequence of the invention is provided. An IPT nucleotide sequence can be provided by introducing into the plant a polynucleotide comprising an IPT nucleotide sequence of the invention, expressing the IPT sequence, and thereby modifying floral development. In some embodiments, the IPT nucleotide construct introduced into the plant is stably incorporated into the genome of the plant.

As discussed above, one of skill will recognize the appropriate promoter to use to modulate floral development in the plant. Exemplary promoters for this embodiment include constitutive promoters, inducible promoters, shoot-preferred promoters, and inflorescence-preferred promoters (including developing-female-inflorescence-preferred promoters), including those listed elsewhere herein.

In specific methods, floral development is modulated by increasing the level and/or activity of the IPT sequence of the invention. Such methods can comprise introducing an IPT nucleotide sequence into the plant and increasing the activity of the IPT polypeptide. In some methods, the IPT nucleotide construct introduced into the plant is stably incorporated into the genome of the plant. An increase in the level and/or activity of the IPT sequences can result in one or more alterations in floral development including, but not limited to, accelerated flowering, increased number of flowers, and improved seed set when compared to a control plant. In addition, an increase in the level or activity of the IPT sequences can result in the prevention of flower senescence and an alteration in embryo number per kernel. See, Young, et al., (2004) *Plant J.* 38:910-22. Methods for measuring such developmental alterations in floral development are known in the art. See, for example, Mouradov, et al., (2002) *The Plant Cell S*111-S130, herein incorporated by reference.

In other methods, floral development is modulated by decreasing the level and/or activity of the IPT sequence of the invention. A decrease in the level and/or activity of the IPT sequence can result in kernel abortion and infertile female inflorescence. Inducing delayed flowering or inhibiting flowering can be used to enhance yield in forage crops such as alfalfa.

Accordingly, the present invention further provides plants having modulated floral development when compared to the floral development of a control plant. Compositions include plants having a decreased level/activity of the IPT polypeptide of the invention and having an altered floral development. Compositions also include plants having an increased level/activity of the IPT polypeptide of the invention wherein the plant maintains or proceeds through the flowering process in times of stress.

VII. Modulating the Stress Tolerance of a Plant

Methods are provided for the use of the IPT sequences of the invention to modify the tolerance of a plant to abiotic stress. Increases in the growth of seedlings or early vigor is often associated with an increase in stress tolerance. For example, faster development of seedlings, including the root system of seedlings upon germination, is critical for survival particularly under adverse conditions such as drought. Promoters that can be used in this method are described elsewhere herein, including low-level constitutive, inducible, or root-preferred promoters, such as root-preferred promoters derived from ZmIPT4 and ZmIPT5 regulatory sequences. Accordingly, in one method of the invention, a plant's tolerance to stress is increased or maintained when compared to a control plant by decreasing the level of IPT activity in the germinating seedling. In other methods, an IPT nucleotide sequence is provided by introducing into the plant a polynucleotide comprising a IPT nucleotide sequence of the invention, expressing the IPT sequence, and thereby increasing the plant's tolerance to stress. In other embodiments, the IPT nucleotide construct introduced into the plant is stably incorporated into the genome of the plant.

Methods are also provided to increase or maintain seed set during abiotic stress episodes. During periods of stress (i.e., drought, salt, heavy metals, temperature, etc.) embryo development is often aborted. In maize, halted embryo development results in aborted kernels on the ear (Cheikh and Jones, (1994) *Plant Physiol.* 106:45-51; Dietrich, et al., (1995) *Plant Physiol Biochem* 33:327-336). Preventing this kernel loss will maintain yield. Accordingly, methods are provided to increase the stress resistance in a plant (e.g., during flowering and seed development). Increasing expression of the IPT sequence of the invention can also modulate floral development during periods of stress, and thus methods are provided to maintain or improve the flowering process in plants under stress. The method comprises increasing the level and/or activity of the IPT sequence of the invention. In one method, an IPT nucleotide sequence is introduced into the plant and the level and/or activity of the IPT polypeptide is increased, thereby maintaining or improving the tolerance of the plant under stress conditions. In other methods, the IPT nucleotide construct introduced into the plant is stably incorporated into the genome of the plant. See, for example, WO 00/63401.

Significant yield instability can occur as a result of unfavorable environments during the lag phase of seed development. During this period, seeds undergo dramatic changes in ultra structure, biochemistry, and sensitivity to environmental perturbation, yet demonstrate little change in dry mass accumulation. Two important events that occur during the lag phase are initiation and division of endosperm cells and amyloplasts (which are the sites for starch deposition). It has been demonstrated that during the lag phase (around 10-12 days after pollination (DAP) in maize) a dramatic increase in cytokinin concentration immediately precedes maximum rates of endosperm cell division and amyloplast formation, indicating that this hormone plays a central role in these processes and in what is called the 'sink strength' of the developing seed. Cytokinins have been demonstrated to play an important role in establishing seed size, decreasing tip kernel abortion, and increasing seed set during unfavorable environmental conditions. For example, elevated temperatures affect seed formation. Elevated temperatures can inhibit the accumulation of cytokinin, decrease endosperm cell division and amyloplast number, and as a consequence, increase kernel abortion.

Kernel sink capacity in maize is principally a function of the number of endosperm cells and starch granules established during the first 6 to 12 DAP. The final number of endosperm cells and amyloplasts formed is highly correlated with final kernel weight. (Capitanio, et al., (1983); Reddy and Daynard, (1983); Jones, et al., (1985), Engelen-Eigles, et al., (2000)). Hormones, especially cytokinins, have been shown to stimulate cell division, plastid initiation and other processes important in the establishment of kernel sink capacity (Davies, (1987)). Cytokinin levels could for example be manipulated using the ZmIPT2 promoter to drive the expression of the *Agrobacterium* IPT gene. Similarly, endosperm- and/or pedicel-preferred promoters could be used to increase the level and/or duration of expression of ZmIPT2, which would result in an increase of cytokinin levels which would in turn increase sink strength and kernel yield. Capitano, et al., (1983). Grain weight and its components in maize inbred lines. *Maydica* 23:365-379. Jones, et al., (1985). Thermal environment during endosperm cell division in maize: effects on number of endosperm cells and starch granules. *Crop Science* 25:830-834. Jones, et al., (1996). Kernel sink strength capacity in maize: Genotypic and maternal regulation. *Crop Science* 36:301-306. Davies, (1987). The plant hormones: their nature, occurrences and function. P 1-12. In Davies and Nijhoff (ed.). Plant hormones and their role in plant growth and development. Dordrecht, the Netherlands. Engelen-Eigles, et al., (2000). DNA endoreduplication in maize endosperm cells: the effect of exposure to short-term high temperature. *Plant, Cell and Environment* 23:657-663.

Methods are therefore provided to increase the activity and/or level of IPT polypeptides in the developing inflorescence, thereby elevating cytokinin levels and allowing developing seed to achieve their full genetic potential for size, minimize seed abortion, and buffer seed set during unfavorable environments. The methods further allow the plant to maintain and/or improve the flowering process during unfavorable environments.

In this embodiment, a variety of promoters could be used to direct the expression of a sequence capable of increasing the level and/or activity of the IPT polypeptide, including but not limited to, constitutive promoters, seed-preferred promoters, developing seed or kernel promoters, meristem-preferred promoters, stress-induced promoters, and inflorescence-preferred (such as developing female inflorescence promoters). In one method, a promoter that is stress insensitive and is expressed in a tissue of the developing seed during the lag phase of development is used. By "insensitive to stress" is intended that the expression level of a sequence operably linked to the promoter is not altered or only minimally altered under stress conditions. By "lag phase" promoter is intended a promoter that is active in the lag phase of seed development. A description of this developmental phase is found elsewhere herein. By "developing seed-preferred" is intended a promoter that allows for enhanced IPT expression within a developing seed. Such promoters that are stress insensitive and are expressed in a tissue of the developing seed during the lag phase of development are known in the art and include Zag2.1 (Theissen, et al., (1995) *Gene* 156:155-166, Genbank Accession No. X80206), and mzE40 (Zm40) (U.S. Pat. No. 6,403, 862 and WO01/2178).

An expression construct may further comprise nucleotide sequences encoding peptide signal sequences in order to effect changes in cytokinin level and/or activity in the mitochondria or chloroplasts. See, for example, Neupert, (1997) *Annual Rev. Biochem.* 66:863-917; Glaser, et al., (1998) *Plant Molecular Biology* 38:311-338; Duby, et al., (2001) *The Plant J* 27(6):539-549.

Methods to assay for an increase in seed set during abiotic stress are known in the art. For example, plants having the increased IPT activity can be monitored under various stress conditions and compared to control plants. For instance, the plant having the increased cytokinin synthesis activity can be subjected to various degrees of stress during flowering and seed set. Under identical conditions, the genetically modified plant having the increased cytokinin synthesis activity will have a higher number of developing kernels than a control plant.

Accordingly, the present invention further provides plants having increased yield or a maintained yield and/or an increased or maintained flowering process during periods of abiotic stress (drought, salt, heavy metals, temperature extremes, etc.). In some embodiments, the plants having an increased or maintained yield during abiotic stress have an increased level/activity of the IPT polypeptide of the invention. In some embodiments, the plant comprises an IPT nucleotide sequence of the invention operably linked to a promoter that drives expression in the plant cell. In some embodiments, such plants have stably incorporated into their genome a nucleic acid molecule comprising an IPT nucleotide sequence of the invention operably linked to a promoter that drives expression in the plant cell.

VIII. Methods of Use for IPT Promoter Polynucleotides

The polynucleotides comprising the IPT promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the IPT promoter polynucleotides of the invention are provided in expression cassettes along with a heterologous polynucleotide sequence of interest for expression in the host cell of interest. As discussed in Example 2 below, the IPT promoter sequences of the invention are expressed in a variety of tissues and thus the promoter sequences can find use in regulating the temporal and/or the spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the IPT promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic IPT promoter sequence may comprise duplications of the upstream promoter elements found within the IPT promoter sequences.

It is recognized that a promoter sequence of the invention may be used with its native IPT coding sequence. A DNA construct comprising an IPT promoter operably linked with its native IPT gene may be used to transform any plant of interest to bring about a desired phenotypic change, such as modulating cytokinin levels, modulating root, shoot, leaf, floral and embryo development, stress tolerance, and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In one embodiment, sequences of interest improve plant growth and/or crop yields. In more specific embodiments, expression of the nucleotide sequence of interest improves the plant's response to stress induced under high density growth conditions. For example, sequences of interest include agronomically important genes that result in improved primary or lateral root systems. Such genes include, but are not limited to, nutrient/water transporters and growth inducers. Examples of such genes, include but are not limited to, maize plasma membrane H$^+$-ATPase (MHA2) (Frias, et al., (1996) *Plant Cell* 8:1533-44); AKT1, a component of the potassium uptake apparatus in *Arabidopisis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that negatively affect root development.

Additional, agronomically important traits such as oil, starch, and protein content can be genetically altered in addition to using traditional breeding methods. Modifications include increasing content of oleic acid, changing the proportions of saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Illinois), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109); and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical emasculation. Examples of genes used in such ways include male tissue-preferred genes and genes with male sterility phenotypes such as DAM, described in U.S. Pat. Nos. 5,750,868; 5,689,051 and 6,281,348. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

IX. Antibody Creation and Use

Antibodies can be raised to a protein of the present invention, including variants and fragments thereof, in both their naturally-occurring and recombinant forms. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., Janin, (1979) *Nature* 277:491-492; Wolfenden, et al., (1981) *Biochemistry* 20:849-855; Kyte and Doolite, (1982) *J. Mol Biol.* 157:105-132; Rose, et al., (1985) *Science* 229:834-838. The antibodies can be used to screen expression libraries for particular expression products such as normal or abnormal protein, or altered levels of the same, which may be useful for detecting or diagnosing various conditions related to the presence of the respective antigens. Assays indicating high levels of an IPT protein of the invention, for example, could be useful in detecting plants, or specific plant parts, with elevated cytokinin levels. Usually the antibodies in such a procedure are labeled with a moiety which allows easy detection of presence of antigen/antibody binding.

The following discussion is presented as a general overview of the techniques available; however, one of skill will recognize that many variations upon the following methods are known.

A number of immunogens are used to produce antibodies specifically reactive with a protein of the present invention. Polypeptides encoded by isolated recombinant, synthetic, or native polynucleotides of the present invention are the preferred antigens for the production of monoclonal or polyclonal antibodies. Polypeptides of the present invention are optionally denatured, and optionally reduced, prior to injection into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Specific monoclonal and polyclonal antibodies will usually have an antibody binding site with an affinity constant for its cognate monovalent antigen at least between $10^6$-$10^7$, usually at least $10^8$, $10^9$, $10^{10}$ and up to about $10^{11}$ liters/mole. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, often 15 to 20 amino acids in length, and may be longer. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from hybrid cells secreting the desired antibody. Monoclonal antibodies are screened for binding to a protein from which the antigen was derived. Description of techniques for preparing such monoclonal antibodies are found in, e.g., *Basic and Clinical Immunology*, 4th ed., Stites, et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986) and Kohler and Milstein, (1975) *Nature* 256:495-497. Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secretes a single antibody species to the antigen. In this manner, the individual antibody species obtained are the products of immortalized and cloned single B cells generated by the animal in response to a specific site recognized on the antigenic substance.

Other suitable techniques involve selection of libraries of recombinant antibodies in phage or similar vectors (see, e.g., Huse, et al., (1989) *Science* 246:1275-1281; and Ward, et al., (1989) *Nature* 341:544-546; and Vaughan, et al., (1996) *Nature Biotechnology* 14:309-314). Also, recombinant immunoglobulins may be produced. See, Cabilly, U.S. Pat. No. 4,816,567 and Queen, et al., (1989) *Proc. Nat'l. Acad. Sci.* 86:10029-10033.

Antibodies to the polypeptides of the invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed, and treated with increasing concentrations of a mild denaturant, whereby purified proteins are released.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles and the like.

Protein Immunoassays

Means of detecting the proteins of the present invention are not critical aspects of the present invention. In certain examples, the proteins are detected and/or quantified using any of a number of well-recognized immunological binding assays (see, e.g., U.S. Pat. Nos. 4,366,241; 4,376,110; 4,517,288 and 4,837,168). For a general review of immunoassays, see also, Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassaysm*, Price and Newman Eds., Stockton Press, NY (1991); and *Non-isotopic Immunoassays*, Ngo, Ed., Plenum Press, NY (1988).

Immunological binding assays (or immunoassays) typically utilize a "capture agent" to specifically bind to and often immobilize the analyte (in this case, a protein of the present invention). The capture agent is a moiety that specifically binds to the analyte. In certain embodiments, the capture agent is an antibody that specifically binds a protein of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

Throughout the assays, incubation and/or washing steps may be required after each combination of reagents. Incubation steps can vary from about 5 seconds to several hours, often from about 5 minutes to about 24 hours. However, the incubation time will depend upon the assay format, analyte, volume of solution, concentrations and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one example, the "sandwich" assay, the capture agent (e.g., an antibody specifically reactive, under immunoreactive conditions, to a protein of the present invention) can be bound directly to a solid substrate where it is immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In one embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another competitive assay. In this assay a known analyte, such as a protein of the present invention, is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be determined by detecting either the immobilized fraction of antibody or the fraction of the antibody that remains in solution. Detection may be direct, where the antibody is labeled, or indirect, by the subsequent addition of a labeled moiety that specifically binds to the antibody, as described above.

C. Generation of Pooled Antisera for Use in Immunoassays

A protein that specifically binds to, or that is specifically immunoreactive with, an antibody generated against a defined antigen is determined in an immunoassay. The immunoassay uses a polyclonal antiserum which is raised to a polypeptide of the present invention (i.e., the antigenic polypeptide). This antiserum is selected to have low cross-reactivity against other proteins, and any such cross-reactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide of the present invention is isolated as described herein. For example, recombinant protein can be produced in a mammalian or other eukaryotic cell line. An inbred strain of mice is immunized with the protein using a standard adjuvant, such as Freund's adjuvant, and a standard mouse immunization protocol (see, Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of 104 or greater are selected and tested for their cross reactivity against polypeptides of different forms or substrate specificity, using a competitive binding immunoassay such as the one described in Harlow and Lane, supra, at pages 570-573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for cross-reactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent cross-reactivity for the above proteins is calculated, using standard methods. Those antisera with less than 10% cross-reactivity for a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In certain embodiments, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled, or may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, Western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property, including magnetic beads, fluorescent dyes, radiolabels, enzymes, and colorimetric labels or colored glass or plastic beads, as discussed for nucleic acid labels, supra. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions. Means of detecting labels are well known to those of skill in the art.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used.

The molecules can also be conjugated directly to signal-generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal-producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

A catalytically active polypeptide of the present invention may be contacted with a compound in order to determine whether said compound binds to and/or modulates the enzymatic activity of such polypeptide. The polypeptide employed will have at least 20%, 30%, 40%, 50% 60%, 70% or 80% of the specific activity of the native, full-length enzyme of the present invention. Generally, the polypeptide will be present in a range sufficient to determine the effect of the compound, typically about 1 nM to 10 µM. Likewise, the compound being tested will be present in a concentration of from about 1 nM to 10 µM. Those of skill will understand that such factors as enzyme concentration, ligand concentrations (i.e., substrates, products, inhibitors, activators), pH, ionic strength, and temperature will be controlled so as to obtain useful kinetic data and determine the presence or absence of a compound that binds or modulates polypeptide activity. Methods of measuring enzyme kinetics are well known in the art. See, e.g., Segel, Biochemical Calculations, $2^{nd}$ ed., John Wiley and Sons, New York (1976).

Embodiments of the invention include, but are not limited to, an isolated polypeptide comprising an amino acid sequence of SEQ ID NO:2, 6, 9, 12, 15, 18, 23, 27, 41, 43, 46, 49, 52, 54, 57, 59, 61, 63, 66 or 77; an isolated polynucleotide comprising a nucleotide sequence of SEQ ID NO:1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 or 76; and expression cassettes, vectors and transformed plants comprising same. Further embodiments include, but are not limited to, a plant that is genetically modified at a native genomic locus, said genomic locus encoding a polypeptide of SEQ ID NO: 2, 6, 9, 12, 15, 18, 23, 27, 41, 43, 46, 49, 52, 54, 57, 59, 61, 63, 66 or 77; and methods for modulating expression of a polynucleotide of SEQ ID NO: 1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 or 76. Further embodiments include, but are not limited to, an isolated polynucleotide comprising a nucleotide sequence of SEQ ID NO: 25 or 75; and compositions and methods of use comprising a nucleotide sequence of SEQ ID NO: 25 or 75.

The following examples are offered by way of illustration and not by way of limitation.

EXPERIMENTAL

Example 1

Cloning and Gene Characterization of ZmIPT1

Below we describe the identification and characterization of an IPT polypeptide from maize designated ZmIPT1.

Material and methods: A Mo17 BAC library was screened using a 3'-end fragment of the ZmIPT1 cDNA from B73, identified by sequence similarity to Agrobacterium ipt. One of the positive clones was digested by HindIII, and subcloned into pBluescript. Recombinant plasmids were screened using colony screening and a 3'-end fragment as a probe. One positive clone was sequenced. Samples used for RT-PCR were harvested in the field from three individual plants. Five µg of total RNA was used for RT-PCR using ThermoScript RT-PCR System from Invitrogen. The reverse transcribed mixture for PCR used primers designed across an intron-exon-intron junction in order to avoid amplification of genomic DNA.

Results:

A. Deduced Protein Sequence:

Two putative maize ipt ESTs were identified whose deduced amino acid sequences show similarity to the Agrobacterium (data not shown), Arabidopsis and Petunia IPT proteins (FIG. 1). Full-insert sequencing of these two ESTs revealed that they were identical and the corresponding cDNA sequence was called ZmIPT1 (SEQ ID NO: 22).

FIG. 1 provides an amino acid alignment of the ZmIPT1, Arabidopsis, and Petunia cytokinin biosynthetic enzymes. Asterisks indicate amino acids conserved in many cytokinin biosynthetic enzymes. The amino acids designated by the underline indicate a putative ATP/GTP binding site (at about amino acids 84-90). As shown in FIG. 1, the deduced protein sequence of ZmIPT1 contains the exact consensus sequence GxTxxGK[ST]xxxxx[VLI]xxxxxxx[VLI][VLI] xxDxxQx{57,60}[VLI][VLI]xGG[ST] (SEQ ID NO: 32) (where x denotes any amino acid residue, [ ] any one of the amino acids shown in [ ], and x{m,n} m to n amino acid residues in number) that was used by Takei, et al., (2001) J. Biol. Chem. 276:26405-26410 to isolate the Arabidopsis genes. Note that ZmIPT1 also has a putative ATP/GTP binding site at about amino acids 51-58. In addition, the length of ZmIPT1 is very similar to the AtIPT4 and Sho genes. In addition, the specific zinc-finger like motif (CxxCx{12,18}HxxxxxH) (SEQ ID NO:33) found in all tRNA IPTs of eukaryotes (which is necessary to bind tRNA molecules) is absent from ZmIPT1.

The ZmIPT1 sequence shares 21.9% amino acid sequence identity (34.1% similarity) across the full length to Sho (cytokinin biosynthetic protein from Petunia); 10.8% identity (21.2% similarity) across its full length to ipt (Agrobacterium); 24.7% identity (34.8% similarity) across its full length to AtIPT1 (Arabidopsis); 35.6% identity (45.3% similarity) across its full length to AtIPT2 (Arabidopsis); 22.4% identity (34.6% similarity) across its full length to AtIPT3 (Arabidopsis); 20.7% identity (31.6% similarity) across its full length to AtIPT4 (Arabidopsis); 22.7% identity (35.7% similarity) across its full length to AtIPT5 (Arabidopsis); 21.8% identity (36.4% similarity) across its full length to AtIPT6 (Arabidopsis); 23.4% identity (33.1% similarity) across its full length to AtIPT7 (Arabidopsis); 26.3% identity (35.9% similarity) across its full length to AtIPT8 (Arabidopsis); and, 18.9% identity (31.2% similarity) across its full length to AtIPT9 (Arabidopsis).

A variant of the ZmIPT1 sequence is also provided. SEQ ID NOS: 22, 23 and 24 correspond to the nucleotide and amino acid sequence of ZmIPT1 derived from the spliced sequence of the Mo17 genomic clone. SEQ ID NOS: 26, 27 and 28 are variants of the ZmIPT1 sequence derived from sequencing the full-length EST from B73. An alignment of ZmIPT1 and its variant is shown in FIG. 3. These sequences share 98% overall amino acid sequence identity.

B. Gene Structure:

A Mo17 BAC library was screened using probes corresponding to the two ESTs and four identical clones were identified. An 11kb HindIII fragment from one of the clones was subcloned in pBluescript and sequenced. Alignment with the full-insert sequence of the EST clone revealed the presence of six introns. Interestingly neither the AtIPT4 gene from Arabidopsis nor the Sho gene from Petunia contain introns. The genomic sequence of ZmIPT1 is set forth in SEQ ID NO: 21.

Example 2

Gene Expression of ZmIPT1

One of the identified ZmIPT1 ESTs was from a B73 embryo library, the other one was from a developing root library. In order to gain an impression of the level of expression of ZmIPT1, a search of the Lynx database was performed. A perfect tag was found in the 3'-end of the gene, 231bp from the poly A tail start. Tissue types, number of library hits, and average ppm are presented in Table 1. Expression was found to be very low in most organs, but higher in seedling and embryo libraries. In embryo libraries, expression was higher at 10 DAP than at later development stages (FIG. 4).

TABLE 1

Number of Lynx libraries containing the ZmIPT1 tag and average ppm values.

| Tissue type | # of Lynx libraries | Average ppm |
|---|---|---|
| Seedling | 1 | 29 |
| Ear | 5 | 4 |
| Endosperm | 2 | 8 |
| Embryo | 4 | 10.75 |
| Stalk | 1 | 9 |
| Leaf | 2 | 3 |
| Root | 2 | 2.5 |

Using RT-PCR, the expression pattern of ZmIPT in various maize organs and on a kernel developmental series was tested. No amplification product could be detected after 20 cycles, confirming the very low expression of the gene. However, after 30 cycles, bands of the appropriate size were amplified (FIG. 5). FIG. 5A shows ZmIPT1 transcripts are present in ovaries of mature plants and leaf, mesocotyl, and roots of seedlings. This distribution indicates a bias in expression of this gene to meristematic-like and rapidly developing tissues. In developing B73 kernels (FIG. 5B), ZmIPT1 transcript is strongly present from 0 to 10 DAP, then decreases beyond 15 DAP. This pattern of expression of ZmIPT1 correlates with the known profile of cytokinin accumulation in developing kernels, which peaks during the lag phase. This accumulation of cytokinin is thought to drive early cell division in endosperm and embryo development.

In a similar manner, the ZmIPT1 tag could only be detected in the cell division zone of leaves, and in leaf discs treated with BA. This distribution of transcripts indicates a bias in expression of ZmIPT1 to meristematic-like and rapidly developing tissues, indicating that maize roots and developing kernels are strong sites for cytokinin synthesis.

Example 3

Isolation and Gene Characterization of ZmIPT2, ZmIPT4, ZmIPT5, ZmIPT6, ZmIPT7, ZmIPT8, and ZmIPT9

The AtIPT1 and AtIPT3 to AtIPT8 protein sequences were blasted against the six possible frames generated by the maize genomic sequences and searched for some degree of similarity. Because rice and maize genomes show a significant degree of synteny, the same method was used against rice genomic database to optimize this search. The rice sequences with an E-score of at least 200 were then used for an additional screen of the GSS maize database. Since at that time, the GSS database had not been assembled into contigs, the sequences obtained which had an E-score of at least 150 were pooled and aligned using Sequencher.

Using this method, eight maize contigs encoding putative CK biosynthetic enzymes were identified (ZmIPT2 to ZmIPT9), six of them showing an open reading frame without introns. The translated proteins corresponding to these putative genes contained 320 to 380 amino acids, which correlates with the expected size for plant IPT proteins. An alignment of the corresponding proteins is presented in FIG. 1. The deduced protein sequences of the new ZmIPT genes (except for ZmIPT8) contain the exact consensus sequence found in IPT proteins from different species. This sequence, GxTxxGK[ST]xxxxx[VLI]xxxxxxx[VLI][VLI] xxDxxQx{57,60}[VLI][VLI]xGG[ST] (where x denotes any amino acid residue, [ ] anyone of the amino acids shown in [ ], and x{m,n} m to n amino acid residues in number) (SEQ ID NO: 32) is also found in ZmIPT1 and was previously used by Kakimoto and Takei to isolate the *Arabidopsis* IPT genes. Homology with other plant IPT proteins was found to be around 40%.

The amino acid sequence identity and similarity to top BLAST hits across the full length of ZmIPT2, ZmIPT4, ZmIPT5, ZmIPT6, ZmIPT7, ZmIPT8 and ZmIPT9 are provided below in Table 2.

TABLE 2

| | 34394150 (rice) | | AtIPT5 (*Arabidopsis*) | |
|---|---|---|---|---|
| Gene | Similarity | Identity | Similarity | Identity |
| ZmIPT2 | 55.15 | 46.51 | 53.02 | 45.30 |
| ZmIPT4 | 74.05 | 69.68 | 58.70 | 53.73 |
| ZmIPT5 | 71.99 | 65.96 | 60.70 | 55.59 |
| ZmIPT6 | 71.86 | 64.67 | 59.62 | 53.53 |
| ZmIPT7 | 58.63 | 50.16 | 59.36 | 51.94 |
| ZmIPT8 | 54.71 | 47.72 | 46.73 | 38.89 |

The maize IPT sequences also have putative ATP/GTP binding sites at about amino acids 17-24 for ZmIPT2, about amino acids 72-79 for ZmIPT4, about amino acids 57-64 for ZmIPT5, about amino acids 55-62 for ZmIPT6, about amino acids 23-30 for ZmIPT7 and about amino acids 83-90 for ZmIPT8.

The polypeptides encoded by ZmIPT polynucleotides share sequence similarity to known proteins. For example, a polypeptide encoded by nucleotides 821 to 3 of ZmIPT9 shares 55% amino acid sequence identity to amino acids 48 to 327 of a tRNA isopentenyltransferase from *Arabidopsis thaliana* (GenBank Accession Number BAB59048.1). A polypeptide encoded by nucleotides 821 to 3 of ZmIPT9 shares 55% amino acid sequence identity to amino acids 48 to 327 of a putative IPP transferase from *Arabidopsis thaliana* (GenBank Accession Number AAK64114.1). A polypeptide encoded by nucleotides 821 to 3 of ZmIPT9 shares 55% amino acid sequence identity to amino acids 48 to 327 of a IPP transferase-like protein from *Arabidopsis thaliana* (GenBank Accession Number AAM63091.1). A polypeptide encoded by nucleotides 839 to 3 of ZmIPT9 shares 36% amino acid sequence identity to amino acids 28 to 278 of a putative tRNA delta-2-isopentenylpyrophosphate transferase from *Arabidopsis thaliana* (GenBank Accession Number YP_008242.1). A polypeptide encoded by nucleotides 824 to 3 of ZmIPT9 shares 35% amino acid sequence identity to amino acids 17 to 248 of a tRNA isopentenylpyrophosphate transferase from *Streptococcus pneumoniae* R6 (GenBank Accession Number NP_358182.1). A polypeptide encoded by nucleotides 818 to 3 of ZmIPT9 shares 34% amino acid sequence identity to amino acids 2 to 231 of a tRNA delta(2)-isopentenylpyrophosphate transferase (GenBank Accession Number Q8CWS7). A polypeptide encoded by nucleotides 818 to 3 of ZmIPT9 shares 34% amino acid sequence identity to amino acids 2 to 231 of a tRNA isopentenylpyrophosphate transferase from *Streptococcus pneumoniae* R6 (GenBank Accession Number NP_345176.1). A polypeptide encoded by nucleotides 818 to 3 of ZmIPT9 shares 34% amino acid sequence identity to amino acids 31 to 275 of a tRNA delta (2)-isopentenylpyrophosphate transferase from *Chlamydophila caviae* (GenBank Accession Number AAP05599.1). A polypeptide encoded by nucleotides 818 to 435 of ZmIPT9 shares 48% amino acid sequence identity to amino acids 6 to 133 of a tRNA delta(2)-isopentenylpyrophosphate transferase from *Xylella fastidiosa* 9a5c (GenBank Accession Number NP_297383.1). A polypeptide encoded by nucleotides 818 to 435 of ZmIPT9 shares 48% amino acid sequence identity to amino acids 6 to 133 of a tRNA delta(2)-isopentenylpyrophosphate transferase from *Xylella fastidiosa* Dixon (GenBank Accession Number *Xylella fastidiosa* Dixon).

Example 4

Isolation of ZmIPT2 from Mo17 and B73 Maize Lines and Molecular Characterization of the ZmIPT2 Gene Material and Methods:

Plant materials: Maize (*Zea mays*) varieties B73 and Mo17 were used in this study. Samples were harvested from field-grown plants at different stages of development and stored at −80° C. Kernel samples were harvested every five days from 0 to 25 DAP and dissected by isolating whole kernels (0 DAP), pedicel, nucellus and pericarp (5 DAP), pedicel, nucellus, endosperm/embryo sac and pericarp (10 DAP), or pedicel, embryo, endosperm and pericarp (15, 20 and 25 DAP). Tissues corresponding to 2 to 4 different ears were pooled. The series of sample harvested every DAP from 0 to 5 (whole kernels), from 6 to 15 and then 20, 27 and 34 DAP (seeds without pedicel) or 20, 25, 30 and 35 DAP (pedicels) were previously used to study the expression pattern of the cytokinin oxidase 1 gene (Ckx1) from corn (Brugière, et al., (2003) supra).

*Arabidopsis thaliana* ecotype Columbia was used for *Arabidopsis* transformation studies.

PCR: ZmIPT2 coding sequence was PCR amplified from B73 and Mo17 genomic DNA. Primers ZmIPT2-5' (5'-ATCATCAAGACAATGGAGCACGGTG-3') (SEQ ID NO: 78) and ZmIPT2-3' (5'-CGTCCGCTAGCTACTTATGCATCAG-3') (SEQ ID NO: 79) were designed based on the GSS contig sequence (coding sequence is underlined). As part of the Gateway cloning procedure, att-flanked ZmIPT2 fragment was amplified using primers ZmIPT2-5-Gateway (5'-GGGGACAAGTTTGTACAAAAAAGCAG-GCTCAATGG-AGCACGGTGCCGTCGCCG-3') (SEQ ID NO: 80) and ZmIPT2-3-Gateway (5'-GGGGACCACTTTG-TACAA-GAAAGCTGGGTCTTATGCATCAGCCACG-GCGGTG-3') (SEQ ID NO: 81).

In each case, a touchdown PCR was performed (GeneAmp PCR System 9700), using the following cycling parameters: 94° C. for 2 min (one cycle), 94° C. for 30 s, 65° C. for 45 s and 72° C. for 1 min 30 s (5 cycles, annealing temperature reduced by 1° C. per cycle), 94° C. for 30 s, 60° C. for 45 s and 72° C. for 1 min 30 s (30 cycles), 72° C. for 7 min, and termination at 4° C. Pfu Ultra Hotstart DNA polymerase (Stratagene) for its very low average error rate (less than 0.5% per 500-bp fragment amplified) was used.

PCR products were loaded on an agarose gel containing ethidium bromide (1:10000, v/v). Bands corresponding to ZmIPT2 gene and att-flanked ZmIPT2 gene were gel extracted using QIAquick PCR purification kit (QIAgen).

DNA and RNA extraction: Genomic DNA was extracted from B73 and Mo17 plant samples at V3-4 stage according to Dellaporta, et al., (1983) *Plant Mol Biol* 1:19-21 and stored at −20° C. Total RNA was prepared using a hot phenol extraction procedure according to Verwoerd, et al., (1989) *Nucleic Acid Res* 17:2362 and stored at −80° C. The kernel developmental series samples were purified using *RNeasy Mini Protocol for RNA Cleanup* (QIAgen) and eluted in 50 μl DEPC water. Optical Density (DO) at 260 and 280 nm was used to assess the purity of RNA preps and measure RNA and DNA concentrations.

Southern blots Northern blots and hybridization: For Southern blots, digested genomic or BAC clones DNA were run on 0.8% agarose gel at 110V, stained after migration in a 1:10000 (v/v) ethidium bromide solution in TAE buffer, and transferred as indicated below. For Northern blots, ethidium bromide was added to denatured RNA samples and run at 80 V on 1.5% denaturing agarose gel (Brugière, et al., (2003) *Plant Physiol*. 132:1228-1240). Blotting was performed using Turbo-blotter (Schleicher and Schuell) according to the manufacturer guidelines. After transfer, nylon membranes (Nytran plus, Schleicher and Schuell) were cross-linked with a Stratalinker (Stratagene) and baked at 80° C. for 30 min. Probes were labeled with [α-$^{32}$P]-dCTP using random priming (Rediprime II RandomPrime Labelling System, Amersham Biosciences) and purified with Quick Spin Columns (Roche). Hybridizations were carried out at 65° C. for 16 h using ExpressHyb hybridization solution (BD Biosciences) and membranes were washed under stringent conditions (0.1×SSC, 0.1% SDS) as previously described (Brugière, et al., (2003) *Plant Physiol*. 132:1228-1240). Relative transcript abundance was quantified using a phosphor imager (MD860, Molecular Dynamic) with imaging software (ImageQuant, Molecular Dynamics).

BAC subcloning: BAC clones were digested and subcloned in pBluescript SK+. This plasmid includes a multiple cloning site between the lacZ gene and its promoter. The lacZ gene is often used as a reporter gene because it encodes a β-galactosidase, which produces a dark blue precipitate on X-gal[1] enzymatic hydrolysis. The bacteria containing a plasmid in which the BAC fragment is inserted in the multiple cloning site and therefore do not synthesize this enzyme will appear white. This allows the selection of colonies containing BAC subclones that can be further screened by PCR or Southern blot.

Results:

Isolation of the ZmIPT2 gene from corn genomic DNA: Genomic DNA from two different varieties of corn, B73 and Mo17, was extracted and ZmIPT2 coding sequence was amplified by touch-down PCR. The ZmIPT2 gene amplification product was used as a probe for Southern and Northern blot experiments. The ZmIPT2 CDS was cloned in pDONR221 (Invitrogen) and sequenced. The Mo17 sequence was 100% homologous to the GSS contig sequence. The B73 and Mo17 genes were found to be 98.8% homologous at the nucleotide level. The differences between the two genes at the nucleotide level resulted in the modification of 3 amino acids at the protein level (96.1% identity). The nucleotide and amino acid sequences of ZmIPT2 are set forth in SEQ ID NO:3 and 2, and the nucleotide and amino acid sequences of a variant of ZmIPT2 are set forth in SEQ ID NO:76 and 77. An alignment of ZmIPT 2 and the variant of ZmIPT2 shows that the differences in the polypeptides occur at amino acid 125 (A→L), amino acid 138 (Q→R), and amino acid 193 R→H.

Mapping of the gene on the maize genome: To determine if ZmIPT2 was a single- or multi-copy gene in maize, B73 and Mo17 genomic DNA were digested with HindIII, EcoRI, and EcoRV and run on a gel, which was blotted as described in the *Materials and Methods* section. The membrane was hybridized with the previously extracted ZmIPT2 genomic fragment as a probe. The picture of the membrane autoradiography is presented in FIG. 6.

The single bands observed for each of these digestions show that ZmIPT2 is most likely a single-copy gene. The size of the corresponding HindIII fragment was later confirmed using BAC clones. To obtain additional information regarding the physical location of the ZmIPT2 gene in the maize genome, the Oat-Maize chromosome addition lines were used (Ananiev, et al., (1997) *Proc. Natl. Acad. Sci.* 94:3524-3529). A PCR was performed with the ZmIPT2-5' and ZmIPT2-3' primers as described in the *Materials and Methods* section (data not shown). The expected size of the amplification fragment was 995 bp. B73 genomic DNA samples were used as positive controls, while oat genomic DNA and water were used as negative ones.

The data shows that the amplification of the ZmIPT2 sequence could only be seen with the chromosome 2 oat-maize addition line. This finding was verified and the position on chromosome 2 refined using a bioinformatics approach. The ZmIPT2 sequence was first used to screen the B73 and Mo17 public and proprietary Bacterial Artificial Chromosomes (BAC) libraries. Positive clones were identified and used to identify a BAC contig using FPC Contig Viewer. Using this strategy, markers were identified including several MZA markers that were physically mapped on maize chromosome 2, bin 4 (data not shown), which confirmed the experimental mapping of ZmIPT2 gene using the OMA lines.

Example 5

Gene Expression of ZmIPT2, ZmIPT4, ZmIPT5, ZmIPT6, and ZmIPT8

In order to gain an impression of the level of expression of the various ZmIPT sequences, a search of the Lynx database was performed. Tissue types, number of library hits, and average ppm are presented in Tables 3-7.

As shown in table 3, expression of ZmIPT2 was found to be restricted to kernel tissue and to correlate with the start of cytokinin biosynthesis in the kernel as described in Brugière, et al., (2003) *Plant Physiol.* 132(3):1228-1240. FIG. 9 provides a graphical illustration of the ppm values for ZmIPT2 in the Lynx embryo libraries. Other ZmIPT genes have low expression, consistent with their possible function as cytokinin synthases in other tissues such as root, meristem and endosperm. See table 4-7 below.

TABLE 3

Lynx libraries containing the ZmIPT2 tag and average ppm values

| Tissue type | # of Lynx Libraries | Average ppm |
| --- | --- | --- |
| Endosperm <10 DAP | 2 | 393 |
| Corn Endosperm >10 DAP | 1 | 5 |
| Embryo | 2 | 17 |
| Whole Kernels <10 DAP | 2 | 10 |
| Whole Kernels >10 DAP | 4 | 11 |
| Ear | 2 | 20 |
| Pericarp | 1 | 5 |
| Pith | 1 | 5 |

TABLE 4

Lynx libraries containing the ZmIPT4 tag and average ppm values.

| Tissue type | # of Lynx libraries | Average PPM |
| --- | --- | --- |
| Embryos 15 DAP | 1 | 5 |
| Roots | 3 | 33 |

TABLE 5

Lynx libraries containing the ZmIPT5 tag and average ppm values.

| Tissue type | # of Lynx libraries | Average PPM |
| --- | --- | --- |
| Roots, V6 or less | 9 | 4.8 |
| Roots, V12-R1 | 1 | 91 |
| Seedling | 4 | 3.5 |
| Leaf | 5 | 5.2 |
| Embryo 11 DAP | 1 | 3 |
| Stalk | 4 | 33.25 |
| Sheath or husk | 2 | 1 |
| Tassel spikelet | 1 | 2 |
| Ear 0 DAP | 1 | 7 |
| Rind | 2 | 2.5 |
| Pulvinus | 1 | 7 |

TABLE 6

Lynx libraries containing the ZmIPT6 tag and average ppm values.

| Tissue type | # of Lynx libraries | PPM |
| --- | --- | --- |
| Roots, V6 or less | 7 | 6 |
| Roots, V12-R1 | 1 | 0 |
| Seedling mesocotyl | 1 | 5 |
| Silk or ear shoot | 5 | 6 |
| R1 apical meristem | 1 | 23 |
| V3 leaf base | 1 | 1 |
| Stalk | 4 | 19 |
| Root | 2 | 13 |

TABLE 7

Lynx libraries containing the ZmIPT8 tag and average ppm values.

| Tissue type | # of Lynx libraries | Average PPM |
| --- | --- | --- |
| Base of immature ear | 1 | 3 |
| Ear meristem | 1 | 9 |
| Endosperm | 1 | 7 |
| Stalk-rot-resistant inbred | 1 | 12 |
| Stalk-rot-susceptible inbred | 1 | 5 |

Example 6

Expression of the ZmIPT2 Gene in Corn Tissues

The expression pattern of ZmIPT2 in different organs at different stages of development was studied in order to provide information regarding its putative function in cytokinin biosynthesis. Based on Lynx data (discussed in Example 5), the expression of ZmIPT2 seemed to be restricted to developing kernels (FIG. 9). To get an overall view of ZmIPT2 expression in corn and verify Lynx data, RNA was extracted from different B73 tissues: leaf, stalk, roots, and whole kernels at 0, 5, 10, 15, 20 and 25 DAP. Forty µg of total RNA from each sample were stained with ethidium bromide and loaded on an agarose gel. The blot obtained was hybridized with a [$\alpha$-$^{32}$P]-dCTP labeled ZmIPT2 probe. In a second hybridization, a cyclophilin probe was used as a loading control. After quantification via a phosphor-imager, the ratio of the expression of ZmIPT2 compared to cyclophilin was calculated. Cyclophilin is considered to be constitutively expressed across different organs (Marivet, et al. (1995) *Mol Genet Gen* 247:222-228. Results are shown in FIG. 7. ZmIPT2 transcripts are detected at low levels in the leaf, stalk and roots, but at higher levels in kernels, where expression is low at 0 DAP, increases from 5 to 10 DAP and decreases from 15 to 25 DAP. This expression profile not only confirms the Lynx data but coincides with the appearance and disappearance of CK in the kernels (See, Example 5).

To obtain a more precise view of the expression pattern of ZmIPT2 in kernels, levels of ZmIPT2 transcripts were measured in 0- to 5-DAP kernels with pedicels; 6- to 34-DAP kernels without pedicels; and pedicels alone, 6 to 42 DAP. See FIG. 8. As previously done, the gel was loaded with 40 µg of total RNA, stained with ethidium bromide, and blotted on a nylon membrane. Membranes were hybridized with a 32P-dCTP labeled ZmIPT2 probe. The results of the Northern experiment with "seed without pedicel" samples indicate that low levels of ZmIPT2 expression are detected between 0 and 4 DAP. The expression increases from 5 to 8 DAP, peaks at 8 DAP, and decreases until 14 DAP. At later stages (15 to 34 DAP), transcript levels seem to increase again. However, it is not clear whether this is the result of diminution of cyclophilin expression. This phenomenon was also observed for Ckx1 expression (Brugière, et al., (2003) *Plant Physiol* 132:1228-1240). In the Northern experiment with pedicel samples, transcript levels drastically increase from 6 to 10 DAP, peak at 10 DAP, and slowly decrease until 15 DAP. In this experiment again, transcript levels seem to rise at later stages, but it is unclear whether this is due to the diminution of cyclophilin expression. In this experiment, the sample corresponding to "seed without pedicel at 9 DAP" was used as a control to allow the comparison with the other blot. The relative expression at 9 DAP is four times as high as in the control, showing that ZmIPT2 expression in the pedicel is much higher than in the rest of the seed. This difference is consistent with the fact that CK levels are nearly twice as abundant in the pedicel as in the rest of the seed (Brugière, et al., (2003) *Plant Physiol* 132:1228-1240).

The relative transcript levels were compared to ZR concentrations measured in the same samples (solid line in FIG. 8). Interestingly, ZmIPT2 expression nicely overlaid ZR accumulation in the pedicel, whereas in the rest of the seed, it slightly preceded the peak in ZR, including at later stages.

Taken together, these results indicate that ZmIPT2 is expressed transiently during kernel development both in the pedicel and the rest of the seed, and that its pattern of expression, which parallels ZR levels in the kernel, is consistent with ZmIPT2 role as a CK biosynthetic gene.

The expression of ZmIPT2 in different kernel tissue was also studied in different kernel tissues. In this study, dissected kernel samples from 0 to 25 DAP were used. Samples were collected from the field in Johnston, Iowa, USA. Kernels were dissected into different parts (pedicel, nucellus, endosperm/embryo sac, endosperm, embryo and pericarp) depending on the stage considered. The gel was loaded with 30 µg of purified total RNA, stained with ethidium bromide, and blotted onto a nylon membrane.

The results shown in FIG. 11 confirm that ZmIPT2 transcripts levels in pedicel are more abundant than in the rest of the seed. This is especially true at 15, 20 and 25 DAP where some expression is also seen in the embryo samples. At 10 DAP however, ZmIPT2 transcripts are found in similar amounts in developing endosperm/embryo sac and pedicel. Together with the fact that 1) cytokinins are more abundant in the pedicel than the rest of the seed and that 2) transcript and activity of cytokinin oxidase in this organ is also more abundant than the rest of the seed (Brugière, et al., (2003) *Plant Physiol.* 132:1228-1240), these results indicate that the pedicel is most likely a major site for CK biosynthesis. Recent data presented on the expression of *Arabidopsis* IPT genes allows us to hypothesize that the expression of ZmIPT2 could occur in phloem cells where it could be responsible for the synthesis of CK, which would be targeted to the vascular bundles for transport to developing kernels. The presence of ZmIPT2 transcripts in both developing endosperm and embryo is observed at times when cell division is the most active in these tissues. This again supports a role for ZmIPT2 as a CK biosynthetic protein, which catalyzes CK formation in fast dividing/developing tissues such as endosperm at 10 DAP and growing embryo, and could drive sink strength in the pedicel to support kernel growth.

Example 7

Expression and Purification of the ZmIPT2 Polypeptide from *E. coli*

Materials and Methods:

Recombinant protein purification, gel electrophoresis and Western blot: BL21-AI (Invitrogen) *E. coli* harboring the pDEST17-ZmIPT2 (Mo17) plasmid was grown overnight. A 1/200 dilution of this culture was used to inoculate fresh LB medium and bacteria were grown at 37° C. for 2 h before induction with 0.2% L-arabinose and then grown for 2 to 4 h. Bacterial protein extracts were prepared as described by the supplier and run on a 12.5% polyacrylamide gel in denaturing condition. The His-tagged protein was purified from crude protein extracts using a Ni-NTA agarose solution according to the provider's recommendations (Qiagen). After electrophoresis, proteins were either revealed by gel staining with GelCode (Pierce) or blotted onto a polyvinylidene difluoride (PVDF) membrane using an electro-transfer procedure. Western blot was carried out as described previously (Brugière, et al., (1999) *Plant Cell* 11:1995-2012) using an anti-poly histidine monoclonal antibody developed in mice (Sigma-Aldrich) and an anti-mice IgG antibody conjugated to alkaline phosphatase developed in goat.

Results:

Cloning of the ZmIPT2 coding sequence in a vector compatible with the Gateway system: In an effort to characterize the function of the ZmIPT2 protein both in vitro and in vivo, two approaches were used. The first aimed at expressing and purifying a tagged ZmIPT2 protein in *E. coli*, and the second at transforming *Arabidopsis* calli with a construct driving the over-expression of the ZmIPT2 gene under the control of the 35S promoter of the cauliflower mosaic virus. For this purpose the Gateway system for molecular cloning was used.

The Gateway technology was used to build both the protein expression vector (*E. coli Expression System with Gateway Technology* kit, Invitrogen) and *Arabidopsis* transformation vector (*Multisite Gateway Three-Fragment Vector Construc-*

*tion Kit*, Invitrogen). The first step was the addition of specific att sequences to the previously extracted ZmIPT2 fragment. This was achieved by amplifying this fragment by PCR with a pair of primers specially designed to flank the gene with the proper att sites.

Once flanked with these specific sites, the new gel-extracted fragment was inserted by recombination into a donor vector (pDONR221). Recombination was catalyzed in vitro by the BP clonase. The vector generated was checked by digestion with multiple restriction enzymes and migration on agarose gel electrophoresis. The sizes of digested fragments matched with the expected length of digestion products for each enzyme. Both Mo17 and B73 ZmIPT2 genes were cloned in individual donor vectors and the inserts sequenced using M13 forward and reverse primers. The Mo17 clone showed a homology of 100% with the GSS contig sequence and was therefore used to build the expression and transformation constructs.

In vitro study: expression of the ZmIPT2 protein in *E. coli*: A tagged recombinant ZmIPT2 protein was expressed in *E. coli*. Besides allowing the ZmIPT2 gene to be transcriptionally activated in *E. coli* via induction of the T7 promoter, this approach also permitted addition of a six-histidine-tag to the N-terminal end of the recombinant ZmIPT2 protein, which could be used for its purification. The expression vector was generated by recombination of the ZmIPT2 coding sequence between pDONR221-ZmIPT2 and pDEST17 (Invitrogen).

The transcriptional fusion of the 6×His-tag with ZmIPT2 was sequenced and the expression vector was used to transform the BL21-AI strain of *E. coli*. These cells contain an expression system modulated by L-arabinose, which induces the expression of T7 RNA polymerase. Protein extracts collected at different times (2 h and 4 h) after T7 RNA polymerase induction were tested on denaturing polyacrylamide gel electrophoresis (SDS-PAGE). Samples that had not been induced were collected and used as negative controls, as well as GUS protein expression with and without induction. The gel was stained with Coomassie blue, which reveals the presence of proteins.

After electrophoresis, induced and non-induced samples were blotted onto a PVDF membrane. A Western blot was performed to confirm that the induced protein contained a His-tag. For this purpose, we used mice antibodies raised against a poly histidine peptide. These antibodies would only recognize the tagged protein and would be in turn recognized by anti-mice IgG antibodies carrying alkaline phosphatase. The presence of the recombinant protein could therefore be characterized by a reaction transforming a colorless substrate in a purple product that precipitates on the membrane.

Two bands could be observed, one of expected size (approximately 37 kDa) and one of a slightly bigger size (approximately 40 kDa), both of which were induced by L-arabinose. The two bands could be due to the addition of extra-basic residues that would increase the positive charge of the protein therefore altering its migration. It could also be due to the presence of a covalently bound co-factor on the *E. coli* expressed protein. In order to decipher between these two possibilities trypsic digestions of each purified bands could be analyzed by mass spectrometry. In order to further characterize the two bands it was necessary to partially purify the protein.

Purification of the His-tagged ZmIPT2 protein: The presence of a 6×His tag allowed affinity purification of this protein using a Ni-NTA resin column. The crude extract was loaded on the column and the effluent collected. After several washes of the column, the protein was eluted using a solution containing imidazol that, because of its higher affinity to the column, is able to release the protein from the column. Samples were collected at each step of the purification and run on a gel, which was stained as previously.

The experiment indicated that the protein is expressed in a soluble form since it was shown to be present in both the supernatant and the effluent, but in smaller amounts in the pellet. The protein was eluted in the second and third elution fractions. The amount of ZmIPT2 protein in the fraction corresponding to the second volume of elution was visually estimated to represent 70 to 80% of the total protein.

A Western blot was carried out using the same samples. The result confirmed that although the protein is present in small amount in the pellet, most of it remains in solution (effluent). The strong signal with the effluent indicates that the amount of ZmIPT2 protein in the crude extract exceeded the column capacity.

In addition, the ZmIPT2 protein was expressed using a C-terminal tag which allowed the purification of ZmIPT2 as one single band on SDS-PAGE. The purity of the fractions was close to 100%. Fractions were found to provide DMAPP: ADP and DMAPP:ATP isopentenyltransferase activity.

Example 8

In Vivo Study of the Over-Expression of the ZmIPT2 Gene in *Arabidopsis* Calli

Materials and Methods:
In vitro culture: Different media were used for *Arabidopsis* germination, callus culture and regeneration (Kakimoto, (1998) *J. Plant Res.* 111:261-265). The media used were as follows:
  5000×CIM (callus-inducing medium) hormone mix: 2.5 mg/ml 2,4 dichlorophenoxyacetic acid (2,4-D), 0.25 mg/ml kinetin and 5 mg/ml biotin dissolved in dimethyl sulfoxide (DMSO).
  500× vitamin mix: 50 mg/ml myo-inositol, 10 mg/ml thiamine-HCl, 0.5 mg/ml pyridoxine-HCl, and 0.5 mg/ml nicotinic acid.
  GM (germination medium): 1 L of mixture comprising 4.3 g Murashige and Skoog's medium salt base (Sigma), 10 g sucrose, 2 ml 500× vitamin mix, 10 ml 5% 2-(N-morpholino)-ethanesulfonic acid (MES, adjusted to pH 5.7 with KOH), and 3 g Phytagel (Sigma), autoclaved.
  CIM (callus-inducing medium): 1 L of mixture comprising 3.08 g Gamborg's B5 medium salt base (Sigma), 20 g glucose, 2 ml 500× vitamin mix, 10 ml 5% MES (adjusted to pH 5.7 with KOH), and 3 g Phytagel, autoclaved and 200 µl 5000×CIM hormone mix added to it.
  AIM (Agrobacterium infection medium): CIM from which Phytagel is omitted.
  WASHM (washing medium): GM from which Phytagel is omitted, plus 100 mg/l sodium cefotaxime.
Selection media for transformed calli:
  GM+IBA (GIBA): GM plus 100 mg/l cefotaxime, 50 mg/l carbenicilin, 3 mg/l Bialaphos and 0.3 mg/l indolebutyric acid (IBA).
  GM+IBA+Z (GIBAZ): GM plus 100 mg/l cefotaxime, 50 mg/l carbenicilin, 3 mg/l Bialaphos, 0.3 mg/l indolebutyric acid (IBA), and 1 mg/l trans-zeatin (tZ).

In the experiment aimed at testing the effect of auxin to cytokinin ratio on root and shoot regeneration, GM was prepared and different amounts of hormones were added. Twenty-five media containing different combinations of tZ and IBA concentrations, which were set at 0, 100, 300, 1000 and 3000 ng/ml for each hormone, were prepared.

Sterilized *Arabidopsis thaliana* seeds were germinated on GM medium and grown on continuous light at 23° C. For the above experiment, hypocotyls from 15 day-old seedlings were cut with a scalpel and grown on each of the 25 media for 3 weeks at 23° C. under continuous light. For experiments requiring the use of callus tissue, hypocotyls were grown on CIM for 10 to 12 days in the same conditions.

*Arabidopsis* calli transformation: Induced calli were soaked in a suspension of *Agrobacterium* (0.2 $OD_{600}$) in AIM for 5 minutes. Most of the liquid was removed on filter paper, and calli were placed on CIM culture medium and grown in continuous light at 23° C. for 2 days. Calli were then washed thoroughly in WASHM medium and placed on GIBA or GIBAZ medium and cultured for about 3 weeks.

Cloning: In order to constitutively express ZmIPT2 in *Arabidopsis* using the Gateway system, a construct was built in which the gene was placed under the control of the 35S promoter of the cauliflower mosaic virus. A Gateway clone containing the 35S promoter was constructed using the pDONR-P4-P1R plasmid. Once these 3 elements were available, a multisite recombination was performed using the three donor vectors and a fourth vector called destination vector.

The LR clonase allows an organized "three-site" recombination to occur between the plasmids carrying the promoter, gene of interest and terminator, and a binary vector containing the left and right border of the Ti plasmid and the BAR resistance gene. The resulting construct was verified by digestion with restriction enzymes, migration on agarose gel, and comparison of digested fragment sizes with expected digestion products.

The final construct contained the 35S-ZmIPT2-PINII sequence and included the BAR gene. This gene is used as a selection marker for the herbicide resistance it confers to transformed plant cells.

Transformation in *Agrobacterium*: The next step was the transformation of a plasmid containing the 35S-ZmIPT2-PINII construct in *Agrobacterium tumefaciens* (LBA4044). This plasmid contains the genes required for infection and delivery of the T-DNA to *A. thaliana* cells (vir genes). After electroporation in the bacteria (Suzuki, (1999) *Plant Cell Physiol* 39:1258-1268), the two plasmids are able to recombine at their respective COS sites. The result of this recombination is a 48 kb plasmid called "co-integrate".

*Agrobacteria* containing this co-integrate were checked using a quality control process. This procedure consists of extracting the co-integrate plasmid and transforming it into *E. coli* in order to verify it by restriction digestions. This step is necessary to screen for "mis-recombinations" of the two plasmids at the COS sites, which would result in a non-functional construct.

Although many trials were attempted to transform *Agrobacterium* cells with the 35S-ZmIPT2-PINII construct, no colonies containing the right co-integrate plasmid could be identified. Since the 35S promoter is leaky in *Agrobacterium*, it was assumed that ZmIPT2 expression could be lethal for *Agrobacterium*. The lethality of the construct could be the result of an active degradation of an essential compound for *Agrobacterium*. Such a metabolite could for example be from the isoprenoid biosynthetic pathway, which includes potential substrates of CK biosynthesis, such as 4-hydroxy-3-methyl-2-(E)-butenyl diphosphate (HMBPP).

Analysis of microbial genomes combined with biochemical experiments established the existence of two pathways for isoprenoid synthesis, the mevalonate (MVA) and non-mevalonate (1-deoxyxylulose 5-phosphate, DXP or 2-C-methyl-D-erythritol-4-phosphate, MEP) pathways. The DXP pathway has been found to be present in some bacteria and the chloroplasts of plants. The genes encoding the non-mevalonate pathway are present mostly in Gram-positive bacteria. HMBPP is a precursor of the non-mevalonate (MEP) pathway of isoprenoid biosynthesis and was shown to be a possible substrate for AtIPT7 (Takei, et al., (2003) *J Plant Res* 116:265-9). Analysis of the genomic sequence of *A. tumefaciens* C58 showed that it encodes the enzymes of the MEP pathway but that those of the MVA pathway are absent (Wood, et al., (2001) *Science* 294:2317-2323; Goodner, et al., (2001) *Science* 294:232-2328). Based on these results we believe that HMBPP could be the substrate of the ZmIPT2 protein and that utilization of this compound by the enzyme could prevent the formation of isoprenoid, which would result in the incapacity of the bacteria to grow.

To elude this problem, the same construct was built but this time using the 35S promoter with the ADH1 intron to prevent the expression of ZmIPT2 gene in *Agrobacterium*. Using this construct, *Agrobacteria* carrying the right co-integrate were obtained.

Results:

*Arabidopsis* calli in culture regenerate roots or shoots depending on auxin and cytokinin levels present in the medium. As a proof of concept, *Arabidopsis* hypocotyls were cultured on media containing increasing levels of auxin and cytokinin. Twenty-five different combinations of tZ and IBA concentrations, at 0, 100, 300, 1000 and 3000 ng/ml for each hormone, were prepared and hypocotyls transferred to the media as described above. After 3 weeks in the culture room, pictures of 2 representative calli were taken for each hormone combination. Results indicated that a higher auxin:cytokinin ratio favored root formation, while a higher cytokinin:auxin ratio favored shoot formation.

This experiment confirmed that root or shoot formation is influenced by the auxin/cytokinin ratio. Auxins have a root-inducing effect whereas cytokinins induce shoot formation. Based on these results, *Arabidopsis* calli over-expressing a cytokinin biosynthetic gene should not be able to develop roots on a medium containing only auxin. The functionality of this assay to characterize putative cytokinin biosynthetic genes by using the *Agrobacterium tumefaciens* IPT (tmr) gene has been tested. Specifically, using the Gateway cloning system, two constructs were developed aimed at over-expressing either IPT as a cytokinin biosynthetic enzyme or GUS as a control. Three weeks after transformation of *Arabidopsis* calli, roots could be observed on calli transformed with the 35S-GUS-PINII construct but not on calli transformed with the 35S-IPT-PINII construct. In order to demonstrate that calli were efficiently transformed, in situ GUS staining was performed. Tissue transformed with 35S-GUS-PINII contained the GUS protein as revealed by the blue color observed after incubation in a solution containing the GUS substrate. These experiments validated the use of a high-throughput assay to test the putative corn CK biosynthetic genes.

The 35S-ADHI-ZmIPT2-PinII construct was transformed into 10 day-old *Arabidopsis* calli which were transferred onto GM medium containing either auxin or both auxin and cytokinin. Bialaphos was added to select for transformed calli. Clear phenotypes could be observed 3 weeks after transformation. Control and 35S-ADHI-ZmIPT2-PINII calli grew identically on medium containing both auxin and cytokinin. As expected, control calli transformed with the 35S-GUS-PINII construct were able to regenerate roots on medium containing only auxin. On the contrary, calli transformed with the 35S-ADH1-ZmIPT2-PINII construct, like calli transformed with the 35S-IPT-PINII construct, could not form any roots on this medium and some calli were even able to regenerate shoots. Given results of the preliminary experiment described above, this implies that these calli are synthesizing CK due to the expression of the ZmIPT2 gene. In turn this decreases the auxin:cytokinin ratio, which prevents root formation. These results support the conclusion that ZmIPT2 is a cytokinin biosynthetic gene.

Example 9

Isolation and Sequencing of the ZmIPT2 Promoter

To isolate the promoter of the ZmIPT2 gene, a high-throughput Bacterial Artificial Chromosomes (BAC) screening process was used. Five positive clones were isolated by PCR screening based on the ZmIPT2 sequence. To confirm that the gene of interest was present in the bacterial chromosome, the BAC clones were cultured and prepped. The BACs obtained were digested with HindIII and run on an agarose gel, which was used for a Southern blot. The blot was hybridized with a $[\alpha\text{-}^{32}P]$-dCTP labeled ZmIPT2 probe. Methods for the Southern blot are described above in Example 4.

The Southern blot confirmed the presence of the ZmIPT2 sequence on all BAC clones isolated. Once checked, the BACs were subcloned in pBluescript after digestion with BamHI and HindIII. After ligation, chemically competent E. coli were transformed and grown on ampicillin LB medium. Positive clones were then screened by a colony hybridization method. Colonies were transferred onto a nylon membrane, which was hybridized with a $[\alpha\text{-}^{32}P]$-dCTP ZmIPT2 probe to detect the clones containing the ZmIPT2 region on their plasmid. Finally, the colonies selected were prepped and the plasmid was sent for sequencing using 5'OH-oriented primers. This allowed the upstream region of ZmIPT2 up to 1354 bp to be sequenced. A BAC walking strategy was employed which gave 3280 bp of promoter sequence for this gene. The sequence for the ZmIPT2 promoter is set forth in SEQ ID NO: 75. A similar strategy was followed to identify the ZmIPT1 promoter set forth in SEQ ID NO: 25.

Promoter sequences for ZmIPT4 through ZmIPT9, and OsIPT 1 through OsIPT11, may be isolated in a similar manner. Sequences provided herein for ZmIPT4 (SEQ ID NO: 5), ZmIPT5 (SEQ ID NO: 8), ZmIPT6 (SEQ ID NO: 11), ZmIPT7 (SEQ ID NO: 14), ZmIPT8 (SEQ ID NO: 17), and ZmIPT9 (SEQ ID NO: 20), OsIPT1 (SEQ ID NO: 47), OsIPT2 (SEQ ID NO: 44), OsIPT3 (SEQ ID NO: 62), OsIPT4 (SEQ ID NO: 64), OsIPT5 (SEQ ID NO: 50), OsIPT6 (SEQ ID NO: 55), OsIPT7 (SEQ ID NO: 53), OsIPT8 (SEQ ID NO: 40), OsIPT9 (SEQ ID NO: 60), OsIPT10 (SEQ ID NO: 58), and OsIPT11 (SEQ ID NO: 42) include appropriate upstream regions useful for characterization of functional promoter sequence.

Example 10

Assaying for IPT Activity

A. Synthesis of Cytokinin by Maize or Rice IPT Sequences in Bacterial Culture Medium The ability of an IPT sequence of the invention to synthesize cytokinin is assayed in a bacterial culture medium in which cytokinin is known to be secreted. Enzyme activity in E. coli is measured.

E. coli strain BL21-AI (Invitrogen) containing a T7 promoter::IPT sequence (IPT cloned in pDEST17 (Invitrogen)) is cultured for 4 h at 37° C. and the accumulation of the protein is induced for 12 hours at 20° C. in the presence of 0.2% arabinose. The microorganisms are collected by centrifugation, and after Buffer A (25 mM Tris-HCl, 50 mM KCl, 5 mM β-mercaptoethanol, 1 mM PMSF and 20 μg/ml of leupeptin) is added to an OD600 of 100, the E. coli are disrupted by freezing and thawing. The disrupted E. coli are then centrifuged for 10 minutes at 300,000 g followed by recovery of the supernatants. 10 μl of these supernatants are mixed with Buffer A containing 60 μM DMAPP, 5 μM [3H] AMP (722 GBq/mmol) and 10 mM MgCl$_2$ followed by incubation for 30 minutes at 25° C. Subsequently, 50 mM of Tris-HCl (pH 9) is added to this reaction liquid followed by the addition of calf intestine alkaline phosphatase to a concentration of 2 units/30 μl and incubating for 30 minutes at 37° C. to carry out a dephosphatization reaction. As a result of developing the reaction liquid by C18 reversed-phase thin layer chromatography (mobile phase: 50% methanol) and detecting the reaction products by autoradiography, formation of isopentenyl adenosine is confirmed in the reaction liquids containing extracts of E. coli having T7::IPT sequence.

It is further recognized that 3H-HMBPP (4-hydroxyl-3-methyl-2-(E)-butenyl diphosphate) could also be used as a substrate in the assay described above. See, for example, Krall, et al., (2002) *FEBS Letters* 527:318-8, herein incorporated by reference.

B. Assay for DMAPP:ATP or ADP or AMP Isopentenyl Transferase Activity

DMAPP:ATP (or ADP or AMP) isopentenyl transferase activity is measured by the method described by Blackwell and Horgan, (1991) *FEBS Lett.* 16:10-12, with some modifications. The samples to be assayed are crude extracts and purified proteins of E. coli harboring the T7 promoter::IPT sequence. Purified proteins are diluted to appropriate concentrations with dilution buffer (25 mM Tris•HCl, pH 7.5; 5 mM 2-mercaptoethanol; 0.2 mg ml$^{-1}$ bovine serum albumin). Isopentenylation reactions are started by mixing samples with an equal volume of 2× assay mixture containing 25 mM Tris•HCl (pH 7.5), 10 mM MgCl$_2$, 5 mM 2-mercaptoethanol, 60 μM DMAPP, and 2 μM [2,8-$^3$H]ATP (120 GBq mmol-$^1$), [2,8-$^3$H]ADP (118 GBq mmol-$^1$), [2-$^3$H]AMP (72 GBq mmol-$^1$), or [2,8-$^3$H]adenosine (143 GBq mmol-$^1$). After incubation for an appropriate time, ½ volume of calf intestine alkaline phosphatase (CIAP) mix [0.5 Tris•HCl (pH 9.0), 10 mM MgCl$_2$, and 1,000 units ml-$^1$ of CIAP (Takara Shuzo Co. Ltd., Otsu, Shiga, Japan)] is added and the mixtures are incubated at 37° C. for 30 min. Then, 700 μl of ethyl acetate is added and the mixtures are vortexed. After centrifugation at 17,000×g for 2 min, the organic phase is recovered and washed twice with water. The organic phase is mixed with ten volumes of scintillant, ACSII (Amersham Pharmacia Biotech, Tokyo, Japan), and radioactivity levels are measured with a liquid scintillation counter. Recovery of [2,8-$^3$H]isopentenyladenosine (iPA) is measured and is used to calculate the amounts of the products formed. The [2,8-$^3$H]iPA is synthesized through isopentenylation of ATP by using purified IPT sequences, followed by CIAP treatment as described above. All assays are performed in duplicate and mean values are used for calculation.

To determine the $K_m$ for ATP, purified protein (2 ng ml$^{-1}$ in dilution buffer) is mixed with the same volume of a 2× assay mixture containing 25 mM Tris•HCl (pH 7.5), 10 mM MgCl$_2$, 5 mM 2-mercaptoethanol, 0.4 mM DMAPP, and ATP (2-502 μM [2,8-$^3$H]ATP, 1.22 MBq ml-$^1$). To determine the $K_m$ for DMAPP, purified protein (2 ng ml-$^1$) is mixed with the same volume of a 2× assay mixture containing 25 mM Tris•HCl (pH 7.5), 10 mM MgCl$_2$, 5 mM 2-mercaptoethanol, 0.25-200 μM DMAPP, and 200 μM [2,8-$^3$]ATP (7.07 GBq mmol-$^1$). After the mixture is incubated at 24° C. for 0 min or 4 min, the reaction mixtures are treated with CIAP, and then extracted with ethyl acetate as described above. Values obtained at 0 min are subtracted from those at 4 min, and the resulting differences are taken as enzyme activity.

To confirm that the IPT sequences catalyzed the transfer of the isopentenyl moiety to ATP, ADP or AMP, the reaction products are analyzed by HPLC and mass spectrometry. Briefly, crude extract prepared from IPTG-induced *E. coli* harboring the pDEST17-IPT plasmid is incubated with Ni-NTA agarose beads. After the beads have been washed thoroughly, they are re-suspended in a solution containing 25 mM Tris•HCl (pH 7.5), 100 mM KCl, and 5 mM 2-mercaptoethanol. The bead pellets are mixed with an equal volume of a 2× assay mixture that contains 1 mM unlabeled ATP and 1 mM DMAPP, and incubated at 25° C. for 1 h with shaking. After a brief spin, the supernatant is recovered and separated into two portions, and one portion is treated with CIAP as described before. The supernatant with or without treatment with CIAP is mixed with three volumes of acetone. The mixture is incubated at −80° C. for 30 min and centrifuged at 17,000×g for 30 min to remove the proteins. The supernatants are dried under vacuum, and the residues are dissolved in methanol. Aliquots are separated by HPLC with a Chemco-bond ODS-W column (Chemco, Osaka, Japan), by using the following program: 20 mM $KH_2PO_4$ for 15 min, followed by linear gradient of 0% acetonitrile and 20 mM $KH_2PO_4$ to 80% acetonitrile and 4 mM $KH_2PO_4$ over 30 min. The fractions are collected and dried under vacuum, and the residues are resuspended in ethanol. After centrifugation to remove any possible salt precipitates, the solutions are subjected to fast atom bombardment mass spectrometry (JMS-SX102 or JEOL MStation, JEOL DATUM LTD., Tokyo, Japan).

C. Assaying for Shoot and Root Regeneration

Transformation of *Arabidopsis* callus is performed as follows. Selection for transformants is made using 3 mg/L of bialaphos. *Arabidopsis* seeds are sterilized according to Koncz, et al., (1992) *Methods in Arabidopsis Research*, Sinapore, River Edge, N.J., World Scientific. Seeds are placed on GM medium and grown in continuous light at 23° C. for 11 days. Hypocotyl segments are cut and placed on CIM for 8 days. Calli are soaked in a suspension of *Agrobacterium* (0.2 $OD_{600}$) in AIM for 5 minutes. Most of the liquid is removed on the filter paper, and the *Arabidopsis* is placed on CIM culture medium and grown in continuous light at 23° C. for 2 days. The calli are washed thoroughly in WASHM medium and placed on GM+IBA or GM+Z+IBA medium and cultured for about 3 weeks. Selection for transformants is made on 3 mg/L of bialaphos.

Media recipes for the transformation protocol discussed above are as follows. 5000×CIM hormone mix comprises 2.5 mg/ml 2,4-D (Sigma Cat. No. D 6679); 0.25 mg/ml kinetin (Sigma Cat no. K 0753); and, 5 mg/ml biotin dissolved in DMSO (Sigma Cat. No. B 3399. 500× vitamin mix comprises 50 g/l myo-inositol (Sigma Cat. No. 13011); 10 g/l thiamine-HCl (Sigma Cat. No. T 3902); 0.5 g/l pyridoxine-HCl (Sigma Cat. No. P 8666); and, 0.5 g/l nicotinic acid (Sigma Cat. No. N0765). GM (germination medium) (for 1 liter) comprises 4.3 g MS medium salt base (Sigma Cat. No. M 5524); 10 g sucrose (Sigma Cat. No. S 8501); 2 ml 500× vitamin mix; 10 ml 5% MES (adjusted to pH 5.7 with KOH) (Sigma Cat. No. M 2933); and, 3 g Phytagel (Sigma Cat. No. P 8169). The mixture is autoclaved and poured in Petri dishes. CIM (callus inducing medium) comprises 3.08 g Gamborg's B5 medium salt base (Sigma Cat. No. G 5768); 20 g glucose (Sigma Cat. No. G7528); 2 ml 500× vitamin mix; 10 ml 5% MES (adjusted to pH 5.7 with KOH); and, 3 g Phytagel. The mixture is autoclaved, cooled and 200 μl of CIM hormone mix is added. The mixture is then poured into Petri dishes. AIM (Agrobacterium infection medium) comprises CIM without Phytagel. WASHM (washing medium) comprises GM from which Phytagel has been omitted, plus 100 mg/l of sodium cefotaxime. GM+(selection of transformed calli) comprises GM medium that was autoclaved with the following components add via filter: 1 ml of 100 mg/ml cefotaxime (Sigma Cat. No. C 7039); 1 ml of 50 mg/ml of carbenicilin (Sigma Cat. No. C 3416); and, 3 ml of 1 mg/ml Bialaphos. GM+IBA comprises the addition of 300 μl of 1 mg/ml indolebutyric acid (IBA) (Sigma Cat. No. 17512) to the GM media described above. GM+IBA+Z comprises the addition of 300 μl of 1 mg/ml IBA and 1 ml of 1 mg/ml trans-Zeatin (Z) (Sigma Cat. No. Z 2753) to the GM media described above.

In order to examine the function of IPT, the maize IPT sequences are first selected and introduced in *Arabidopsis* calli under the control of the 35S promoter. Calli transformed with a control vector will exhibit normal hormone responses: root formation in the presence of only an auxin and shoot formation in the presence of a cytokinin and an auxin. By contrast, calli transformed with 35S::IPT will regenerate shoots even in the absence of exogenously applied cytokinins or in the presence of a reduced concentration of exogenously applied cytokinins. In addition, modulation in cytokinin synthesis could be assayed for changes in either direction. Representative methods include cytokinin extraction, immunopurification, HPLC separation, and quantification by ELISA methods can be found, for example, in Faiss, et al., (1997) *Plant J.* 12:401-415. See, also, Werner, et al., (2001) *PNAS* 98:10487-10492) and Dewitte, et al., (1999) *Plant Physiol.* 119:111-121.

D. Assaying for DMAPP:tRNA Isopentenyltransferase Activity

Undermodified tRNA is prepared by permanganate-treatment of yeast tRNA (type X, Sigma-Aldrich Japan, Tokyo, Japan) according to the method of Kline, et al., (1969) *Biochemistry* 8:4361-4371. Twenty microliters of purified protein samples (20 ng (protein ml$^{-1}$) in dilution buffer is mixed with the same volume of 2× tRNA isopentenyltransferase assay mixture (25 mM Tris-HCl, pH 7.5; 10 mM $MgCl_2$; 5 mM 2-mercaptoethanol; 0.67 μM [1-$^3$H]DMAPP, 555 GBq mmol$^{-1}$; and 567 $A_{260}$ units ml$^{-1}$ undermodified tRNA), and incubated at 25° C. for 30 min. After 160μ of 0.4 M sodium acetate and 500 μl of ethanol is added and allowed to settle on ice for 10 minutes, the tRNA precipitates are recovered by centrifugation (17,000×g for 20 minutes), washed with 80% ETOH, and dissolved in 30 μl of distilled water. These are mixed with ten volumes of ACSII, and radioactivity levels are measured.

Example 11

Maintaining or Increasing Seed Set During Stress

Targeted overexpression of the IPT sequences of the invention to the developing female inflorescence will elevate cytokinin levels and allow developing maize seed to achieve their full genetic potential for size, minimize tip kernel abortion, and buffer seed set during unfavorable environments. Abiotic stress that occurs during kernel development in maize has been shown to cause reduction in cytokinin levels. Under stress conditions, it is likely that cytokinin biosynthesis activity is decreased and cytokinin degradation is increased (Brugière, et al., (2003) *Plant Physiol.* 132(3):1228-40). Consequently, in one non-limiting method, to maintain cytokinin levels in lag phase kernels, IPT genes could be ligated to control elements that: 1) are stress insensitive; 2) direct expression of structural genes predominantly to the developing kernels; and 3) preferentially drive expression of structural genes during the lag phase of kernel development. Promoters which target expression to related maternal tissues at or around anthesis may also be employed. Alternatively, a constitutive promoter could be employed.

For example, immature maize embryos from greenhouse donor plants are bombarded with a plasmid containing a sequence, chosen from ZmIPT1-9 or OsIPT1-11, operably linked to the Zag2.1 promoter (Schmidt, et al., (1993) *Plant Cell* 5:729-737) and containing the selectable marker gene BAR (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

The ears are husked and surface-sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the IPT sequence operably linked to a Zag2.1 promoter is made. This plasmid DNA plus plasmid DNA containing a BAR selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the maintenance or increase of seed set during an abiotic stress episode. In addition, transformants under stress will be monitored for cytokinin levels (as described in Example 5c) and maintenance of kernel growth.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature). Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 12

Modulating Root Development

For *Agrobacterium*-mediated transformation of maize with a plasmid designed to achieve post-transcriptional gene silencing (PTGS) with an appropriate promoter, the method of Zhao may be employed (U.S. Pat. No. 5,981,840, and PCT Patent Publication Number WO98/32326, the contents of which are hereby incorporated by reference). Briefly, immature embryos are isolated from maize and the embryos contacted with a suspension of *Agrobacterium* capable of transferring a DNA construct. Said construct may comprise the CRWAQ81 root-preferred promoter::ADH intron promoter operably linked to a hairpin structure made from the coding sequence of any one of the ZmIPT1-9 or OsIPT1-11 polynucleotides of the invention. Other useful constructs may comprise a hairpin construct targeting the promoter of any one of the ZmIPT1-9 or OsIPT1-11 polynucleotides of the invention. (Aufsatz, et al., (2002) *PNAS* 99(4):16499-16506; Mette, et al., (2000) *EMBO J* 19(19):5194-5201) The construct is transferred to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step); this may take place on solid medium. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Next, inoculated embryos are cultured on medium containing a selective agent; growing, transformed callus is recovered (step 4: the selection step). The callus is then regenerated into plants (step 5: the regeneration step).

Plants are monitored and scored for a modulation in root development. The modulation in root development includes monitoring for enhanced root growth of one or more root parts including the primary root, lateral roots, adventitious roots, etc. Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

Example 13

Modulating Senescence of a Plant

A DNA construct comprising any of the ZmIPT1-9 or OsIPT1-11 polynucleotides operably linked to a constitutive promoter, a root-preferred promoter, or a senescence-activated promoter, such as SAG12 (Gan, et al., (1995) *Science* 270:5244, Genbank Accession Number U37336) is introduced into maize plants as outlined in Zhao, et al., (1998) *Maize Genetics Corporation Newsletter* 72:34-37, herein incorporated by reference.

For example, maize plants comprising the IPT sequence operably linked to the SAG12 promoter are obtained. As a control, a non-cytokinin-related construct is also introduced into maize plants using the transformation method outlined above. The phenotypes of transgenic maize plants having an elevated level of the IPT polypeptide are studied. For example, plants can be monitored for an improved vitality, shelf and vase life, and improved tolerance against infection. Plants could also be monitored for delayed senescence under various environmental stresses including, for example, flooding which normally results in leaf chlorosis, necrosis, defoliation, cessation of growth and reduction in yield.

Example 14

Soybean Embryo Transformation

Soybean embryos are bombarded with a plasmid containing the IPT sequence operably linked to a ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188), and the 3' region of the nopaline synthase gene from the T-DNA of the Ti plasmid of *Agrobacterium tumefaciens*. The expression cassette comprising the IPT sequence operably linked to the ubiquitin can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 15

Sunflower Meristem Tissue Transformation

Sunflower meristem tissues are transformed with an expression cassette containing the IPT sequence operably linked to a ubiquitin promoter as follows (see also, European Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer, et al., (Schrammeijer, et al., (1990) Plant Cell Rep. 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.* 15:473-497), Shepard's vitamin additions (Shepard, (1980) in *Emergent Techniques for the Genetic Improvement of Crops* (University of Minnesota Press, St. Paul, Minn.), 40 mg/l adenine sulfate, 30 g/l sucrose, 0.5 mg/l6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the IPT gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for cytokinin synthesis activity. Such assays are described elsewhere herein.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by cytokinin synthesis activity analysis of leaf extracts while transgenic seeds harvested from NPTII-positive $T_0$ plants are identified by cytokinin synthesis activity analysis of small portions of dry seed cotyledon.

Example 16

Variants of IPT

A. Variant Nucleotide Sequences of ZmIPT1-9 and OsIPT1-11 (SEQ ID NO: 1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 or 76) That do not Alter the Encoded Amino Acid Sequence The ZmIPT1-9 or OsIPT1-11 nucleotide sequences set forth in SEQ ID NO: 1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 or 76 are used to generate variant nucleotide sequences having the nucleotide sequence of the open reading frame with about 70%, 75%, 80%, 85%, 90% and 95% nucleotide sequence identity when compared to the corresponding starting unaltered ORF nucleotide sequence. These functional variants are generated using a standard codon table. While the nucleotide sequence of the variant is altered, the amino acid sequence encoded by the open reading frame does not change.

B. Variant Amino Acid Sequences of ZmIPT1-9 and OsIPT1-11

Variant amino acid sequences of ZmIPT1-9 and OsIPT1-11 are generated. In this example, one or more amino acids are altered. Specifically, the open reading frame set forth in SEQ ID NO: 1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 or 76 is reviewed to determine the appropriate amino acid alteration. The selection of an amino acid to change is made by consulting a protein alignment with orthologs and other gene family members from various species. See FIG. 1 and/or FIG. 10. An amino acid is selected that is deemed not to be under high selection pressure (not highly conserved) and which is rather easily substituted by an amino acid with similar chemical characteristics (i.e., similar functional side-chain). Assays as outlined in Example 10 may be followed to confirm functionality. Variants having about 70%, 75%, 80%, 85%, 90%, or 95% nucleic acid sequence identity to each of SEQ ID NO: 1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 and 76 are generated using this method.

C. Additional Variant Amino Acid Sequences of ZmIPT1-9 and OsIPT1-11

In this example, artificial protein sequences are created having 80%, 85%, 90% and 95% identity relative to the reference protein sequence. This latter effort requires identifying conserved and variable regions from the alignment set forth in FIG. 1 and/or FIG. 10 and then the judicious application of an amino acid substitutions table. These parts will be discussed in more detail below.

Largely, the determination of which amino acid sequences are altered is made based on the conserved regions among the IPT proteins or among the other IPT polypeptides. See, FIGS. 1 and 10. Based on the sequence alignment, the various regions of the IPT polypeptides that can likely be altered can be determined. It is recognized that conservative substitutions can be made in the conserved regions without altering function. In addition, one of skill will understand that functional variants of the IPT sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 8.

TABLE 8

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed are identified and "marked off" for insulation from the substitution. The start methionine will of course be added to this list automatically. Next, the changes are made.

H, C and P are not changed. The changes will occur with isoleucine first, sweeping N-terminal to C-terminal. Then leucine, and so on down the list until the desired target is reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of ZmIPT1-9 and OsIPT1-11 are generating having about 82%, 87%, 92% and 97% amino acid identity to the starting unaltered ORF nucleotide sequence of SEQ ID NO: 1, 3, 4, 5, 7, 8, 10, 11, 13, 14, 16, 17, 19, 20, 21, 22, 24, 26, 28, 40, 42, 44, 45, 47, 48, 50, 51, 53, 55, 56, 58, 60, 62, 64, 65, 69, 70, 71, 72, 73, 74 or 76.

Example 17

Characterization of Rice IPT Sequences

Eleven putative rice ipt sequences were identified which comprise deduced amino acid sequences showing similarity to the *Arabidopsis* and Petunia IPT proteins. FIG. 10 provides an alignment of the amino acid sequences corresponding to *Arabidopsis* IPT proteins (AtIPT), the petunia IPT protein (Sho) and rice putative IPT proteins (OsIPT). Asterisks indicate the positions of amino acids conserved in most IPT proteins and following the consensus sequence GxTxxGK[ST]xxxxx[VLI]xxxxxxx[VLI][VLI]xxDxx Qx{57,60}[VLI][VLI]xGG[ST] (SEQ ID NO: 32) (where x denotes any amino acid residue, [ ] any one of the amino acids shown in [ ], and x{m,n} m to n amino acid residues in number) (Takei, et al., (2001) *J. Biol. Chem.* 276:26405-26410).

The presence of putative ATP/GTP-binding site (P-loop) motif (prosite PS00017: consensus [AG]-x(4)-G-K-[ST]), (SEQ ID NO: 68) is underlined. This domain is found at about amino acids 128-135 of SEQ ID NO: 54; at about amino acids 59-66 of SEQ ID NO: 66: at about amino acids 59-66 of SEQ ID NO: 63; at about amino acids 40-47 of SEQ ID NO: 61; at about amino acids 320-327 of SEQ ID NO: 43; at about amino acids 22-29 of SEQ ID NO: 49; at about amino acids 315-322 of SEQ ID NO: 59; at about amino acids 32-39 of SEQ ID NO: 57; at about amino acids 41-48 of SEQ ID NO: 41; at about amino acids 25-32 of SEQ ID NO: 46; and, at about amino acids 37-44 of SEQ ID NO: 52. The presence of a putative tRNA isopentenyltransferase domain (PF01715) was found at about amino acids 59-348 of SEQ ID NO: 57 and about amino acids 69-352 of SEQ ID NO: 41.

The Align X program was used on default settings to determine the overall amino acid sequence identity for the various rice IPT sequences compared with known *Arabidopsis* IPT sequences. Table 9 summarizes these results. Table 10 provides polypeptides that share homology to the rice IPT sequences. Such sequences were identified using BLASTP2.2.6

TABLE 9

| Rice protein | SEQ ID NO: | Best IPT hit | Similarity (%) | Identity (%) |
|---|---|---|---|---|
| OsIPT7 | 54 | AtIPT1 | 43.4 | 32.1 |
| OsIPT6 | 57 | AtIPT9 | 61 | 51.9 |
| OsIPT10 | 59 | AtIPT1 | 28 | 19.2 |
| OsIPT3 | 63 | AtIPT5 | 48.3 | 41.4 |
| OsIPT8 | 41 | AtIPT2 | 57.9 | 46.2 |
| OsIPT11 | 43 | AtIPT1 | 28.6 | 20.4 |
| OsIPT4 | 66 | AtIPT5 | 55.6 | 45.9 |
| OsIPT5 | 52 | AtIPT1 | 38.4 | 28.4 |
| OsIPT1 | 49 | AtIPT5 | 40.4 | 28.2 |
| OsIPT9 | 61 | AtIPT1 | 37.1 | 26.5 |
| OsIPT2 | 46 | AtIPT7 | 51.6 | 37.7 |

TABLE 10

| Rice IPT sequence | Sequence having homology to rice IPT sequence | Approximate region of rice IPT sequence sharing homology | % identity of homologous region. |
|---|---|---|---|
| SEQ ID NO: 54 | NP_917001.1 cytokinin synthase-like protein | 16-427 | 73% |

TABLE 10-continued

| Rice IPT sequence | Sequence having homology to rice IPT sequence | Approximate region of rice IPT sequence sharing homology | % identity of homologous region. |
|---|---|---|---|
| | XP_475862.1 putative tRNA delta(2)-isopentenylpyrophosphate transferase | 121-398 | 61% |
| | AAT85187.1|unknown protein [*Oryza sativa* (*japonica* cultivar-group)]|BACK| | 121-398 | 61% |
| | BAB59040.1|adenylate isopentenyltransferase [*Arabidopsis thaliana*] | 123-365 | 39% |
| | BAB59029.1|cytokinin synthase [*Arabidopsis thaliana*] | 123-365 | 39% |
| SEQ ID NO: 41 | NP_914320.1|similar to tRNA isopentenyltransferase [*Oryza sativa* (*japonica* cultivar-group)] | 1-450 | 80% |
| | BAB59042.1|tRNA isopentenyltransferase [*Arabidopsis thaliana*] | 35-441 | 35% |
| | F84676 hypothetical protein At2g27760 [imported] - *Arabidopsis thaliana* | 35-441 | 37% |
| | AAS79605.1|putative tRNA isopentenylpyrophosphatase [*Ipomoea trifida*] | 35-442 | 46% |
| | AAL87321.1|putative tRNA isopentenylpyrophosphate transferase [*Arabidopsis thaliana*] | 156-441 | 43% |
| SEQ ID NO: 43 | XP_476953.1|hypothetical protein [*Oryza sativa* (*japonica* cultivar-group)] | 1-252 | 93% |
| | XP_475862.1|putative tRNA delta(2)-isopentenylpyrophosphate transferase [*Oryza sativa* (*japonica* cultivar-group)] | 314-590 | 57% |
| | AAT85187.1|unknown protein [*Oryza sativa* (*japonica* cultivar-group)] | 314-590 | 57% |
| | NP_917001.1|cytokinin synthase-like protein [*Oryza sativa* (*japonica* cultivar-group)] | 315-590 | 56% |
| | BAB59029.1|cytokinin synthase [*Arabidopsis thaliana*] | 313-590 | 38% |
| SEQ ID NO: 46 | AAT77921.1|putative adenylate isopentenyltransferase [*Oryza sativa* (*japonica* cultivar-group)] | 17-288 | 42% |
| | XP_477138.1|putative cytokinin synthase [*Oryza sativa* (*japonica* cultivar-group)] | 7-288 | 39% |
| | AAN46854.1|At3g63110/T20O10_210 [*Arabidopsis thaliana*] | 17-288 | 37% |
| | emb|CAB87756.1|tRNA isopentenyl transferase-like protein [*Arabidopsis thaliana*] | 17-288 | 37% |
| | BAB02782.1|tRNA isopentenyl transferase-like protein [*Arabidopsis thaliana*] | 10-287 | 37% |
| SEQ ID NO: 49 | AAT77921.1|putative adenylate isopentenyltransferase [*Oryza sativa* (*japonica* cultivar-group)] | 10-287 | 43% |
| | XP_477138.1|putative cytokinin synthase [*Oryza sativa* (*japonica* cultivar-group)] | 14-312 | 39% |
| | AAN46854.1|At3g63110/T20O10_210 [*Arabidopsis thaliana*] | 13-287 | 40% |
| | CAB87756.1|tRNA isopentenyl transferase-like protein [*Arabidopsis thaliana*] | 13-287 | 40% |
| | BAB59032.1|cytokinin synthase [*Arabidopsis thaliana*] | 14-287 | 40% |
| SEQ ID NO: 52 | NP_917001.1|cytokinin synthase-like protein [*Oryza sativa* (*japonica* cultivar-group)] | 21-251 | 75% |
| | XP_475862.1|putative tRNA delta(2)-isopentenylpyrophosphate transferase [*Oryza sativa* (*japonica* cultivar-group)] | 30-251 | 63% |
| | AAT85187.1|unknown protein [*Oryza sativa* (*japonica* cultivar-group)] | 30-251 | 63% |
| | BAB59040.1|adenylate isopentenyltransferase [*Arabidopsis thaliana*] | 32-251 | 38% |
| | BAB59029.1|cytokinin synthase [*Arabidopsis thaliana*] | 32-251 | 38% |
| | BAB02956.1|tRNA isopentenyl transferase-like protein [*Arabidopsis thaliana*] | 32-251 | 36% |
| SEQ ID NO: 57 | BAD62118.1|putative tRNA isopentenyltransferase [*Oryza sativa* (*japonica* cultivar-group)] | 1-417 | 96% |
| | AAK64114.1|putative IPP transferase [*Arabidopsis thaliana*] | 24-411 | 58% |
| | AAM63091.1|IPP transferase-like protein [*Arabidopsis thaliana*] | 24-411 | 58% |
| | BAB59048.1|tRNA isopentenyltransferase [*Arabidopsis thaliana*] | 24-411 | 58% |
| | YP_008242.1|putative tRNA delta-2-isopentenylpyrophosphate transferase | 17-346 | 33% |

TABLE 10-continued

| Rice IPT sequence | Sequence having homology to rice IPT sequence | Approximate region of rice IPT sequence sharing homology | % identity of homologous region. |
|---|---|---|---|
| SEQ ID NO: 59 | XP_476953.1|hypothetical protein [*Oryza sativa* (*japonica* cultivar-group)] | 1-199 | 91% |
| | XP_475862.1|putative tRNA delta(2)-isopentenylpyrophosphate transferase [*Oryza sativa* (*japonica* cultivar-group)] | 309-585 | 55% |
| | AAT85187.1|unknown protein [*Oryza sativa* (*japonica* cultivar-group)] | 309-585 | 55% |
| | NP_917001.1|cytokinin synthase-like protein [*Oryza sativa* (*japonica* cultivar-group)] | 310-585 | 54% |
| | BAB59029.1|cytokinin synthase [*Arabidopsis thaliana*] | 308-585 | 37% |
| SEQ ID NO: 61 | XP_475862.1|putative tRNA delta(2)-isopentenylpyrophosphate transferase [*Oryza sativa* (*japonica* cultivar-group)] | 1-360 | 83% |
| | AAT85187.1|unknown protein [*Oryza sativa* (*japonica* cultivar-group)] | 1-360 | 83% |
| | NP_917001.1|cytokinin synthase-like protein [*Oryza sativa* (*japonica* cultivar-group)] | 33-312 | 74% |
| | BAB59040.1|adenylate isopentenyltransferase [*Arabidopsis thaliana*] | 34-312 | 43% |
| | BAB59029.1|cytokinin synthase [*Arabidopsis thaliana*] | 34-312 | 43% |
| SEQ ID NO: 63 | AAT77921.1|putative adenylate isopentenyltransferase [*Oryza sativa* (*japonica* cultivar-group)] | 1-344 | 71% |
| | XP_477138.1|putative cytokinin synthase [*Oryza sativa* (*japonica* cultivar-group)] | 35-326 | 53% |
| | AAN46854.1|At3g63110/T20O10_210 [*Arabidopsis thaliana*] | 49-320 | 43% |
| | CAB87756.1|tRNA isopentenyl transferase-like protein [*Arabidopsis thaliana*] | 49-320 | 43% |
| | BAB59041.1|adenylate isopentenyltransferase [*Arabidopsis thaliana*] | 51-325 | 44% |
| SEQ ID NO: 66 | XP_477138.1|putative cytokinin synthase [*Oryza sativa* (*japonica* cultivar-group)] | 1-316 | 78% |
| | AAT77921.1|putative adenylate isopentenyltransferase [*Oryza sativa* (*japonica* cultivar-group)] | 51-314 | 67% |
| | AAN46854.1|At3g63110|T20O10_210 [*Arabidopsis thaliana*] | 51-314 | 51% |
| | CAB87756.1|tRNA isopentenyl transferase-like protein [*Arabidopsis thaliana*] | 51-314 | 51% |
| | BAB59041.1|adenylate isopentenyltransferase [*Arabidopsis thaliana*] | 51-314 | 52% |

TABLE 11

Summary of Zm and Os IPT Sequences

| SEQ ID NO | Description | Type |
|---|---|---|
| 1 | ZmIPT2 full length | DNA |
| 2 | ZmIPT2 polypeptide | AA |
| 3 | ZmIPT2 coding sequence | DNA |
| 76 | ZmIPT2 variant coding sequence | DNA |
| 77 | ZmIPT2 variant polypeptide | AA |
| 4 | ZmIPT1 duplicate sequence | DNA |
| 5 | ZmIPT4 full length | DNA |
| 6 | ZmIPT4 polypeptide | AA |
| 7 | ZmIPT4 coding sequence | DNA |
| 8 | ZmIPT5 full length | DNA |
| 9 | ZmIPT5 polypeptide | AA |
| 10 | ZmIPT5 coding sequence | DNA |
| 11 | ZmIPT6 full length | DNA |
| 12 | ZmIPT6 polypeptide | AA |
| 13 | ZmIPT6 coding sequence | DNA |
| 14 | ZmIPT7 full length | DNA |
| 15 | ZmIPT7 polypeptide | AA |
| 16 | ZmIPT7 coding sequence | DNA |
| 17 | ZmIPT8 full length | DNA |
| 18 | ZmIPT8 polypeptide | AA |
| 19 | ZmIPT8 coding sequence | DNA |
| 20 | ZmIPT9 full length | DNA |
| 21 | ZmIPT1 genomic | DNA |
| 22 | ZmIPT1 full length | DNA |
| 23 | ZmIPT1 polypeptide | AA |
| 24 | ZmIPT1 coding sequence | DNA |
| 26 | Variant ZmIPT1 full length | DNA |
| 27 | Variant ZmIPT1 polypeptide | AA |
| 28 | Variant ZmIPT1 coding sequence | DNA |
| 25 | ZmIPT1 promoter | DNA |
| 40 | OsIPT8 genomic | DNA |
| 41 | OsIPT8 polypeptide | AA |
| 71 | OsIPT8 coding sequence | DNA |
| 42 | OsIPT11 genomic | DNA |
| 43 | OsIPT11 polypeptide | AA |
| 74 | OsIPT11 coding sequence | DNA |
| 44 | OsIPT2 genomic | DNA |
| 45 | OsIPT2 coding sequence | DNA |
| 46 | OsIPT2 polypeptide | AA |
| 47 | OsIPT1 genomic | DNA |
| 48 | OsIPT1 coding sequence | DNA |
| 49 | OsIPT polypeptide | AA |
| 50 | OsIPT5 genomic | DNA |
| 51 | OsIPT5 coding sequence | DNA |
| 52 | OsIPT5 polypeptide | AA |
| 53 | OsIPT7 genomic | DNA |
| 54 | OsIPT7 polypeptide | AA |
| 70 | OsIPT7 coding sequence | DNA |

TABLE 11-continued

Summary of Zm and Os IPT Sequences

| SEQ ID NO | Description | Type |
|---|---|---|
| 55 | OsIPT6 genomic | DNA |
| 56 | OsIPT6 coding sequence | DNA |
| 57 | OsIPT6 polypeptide | AA |
| 58 | OsIPT10 genomic | DNA |
| 59 | OsIPT10 polypeptide | AA |
| 73 | OsIPT10 coding sequence | DNA |
| 60 | OsIPT9 genomic | DNA |
| 61 | OsIPT9 polypeptide | AA |
| 72 | OsIPT9 coding sequence | DNA |
| 62 | OsIPT3 genomic | DNA |
| 63 | OsIPT3 polypeptide | AA |
| 69 | OsIPT3 coding sequence | DNA |
| 64 | OsIPT4 genomic | DNA |
| 65 | OsIPT4 coding sequence | DNA |
| 66 | OsIPT4 polypeptide | AA |
| 75 | ZmIPT2 promoter | DNA |

Example 18

IPT Activity Assay

Assays were conducted to test the ability of a protein encoded by a sequence of the invention to synthesize cytokinin in a bacterial culture medium. The results confirmed that sequences of the invention encode proteins with isopentenyltransferase activity. The reaction catalyzed by *Agrobacterium* ipt is shown in Akiyoshi, et al., (1984) *PNAS* 81(19):5994-5998.

The IPT assay protocol was adapted from the following references: Kakimoto, (2001) Identification of plant biosynthetic enzymes as dimethylallyl diphosphate: ATP/ADP isopentenyltransferases, *Plant Cell Physiol* 42:677-685. Sakakibara and Takei, (2002) Identification of Cytokinin Biosynthesis Genes in *Arabidopsis*: A Breakthrough for Understanding the Metabolic Pathway and the Regulation in Higher Plants, *J. Plant Growth Regul.* 21:17-23. Sakano, et al., (2004) Molecular cloning, expression, and characterization of adenylate isopentenyltransferase from hop (*Humulus lupulus* L.), *Phytochemistry* 65:2439-2446.

The ZmIPT2 gene was amplified using gene-specific primers with appropriate NdeI and NotI restriction site extensions and cloned into pET28a (N-terminal tag) or pET30b (C-terminal tag) digested by NdeI and NotI. The sequence of the resulting plasmid was verified by sequencing of the His-tag translational fusion with ZmIPT2, and BL21-Star™ *E. coli* competent cells (Invitrogen™) were transformed with pET28a-ZmIPT2 and pET30b-ZmIPT2. Similarly, The tzs IPT gene from *Agrobacterium tumefaciens* was cloned into pET28a to yield a plasmid for transformation of Rosetta2 (DE3)pLysS.

Recombinant his-tagged proteins were purified using a TALON™ column (BD Biosciences) according to the instructions provided by the manufacturer. Purified protein samples were used to determine Dimethylallyl diphosphate (DMAPP)::AMP and DMAPP::ATP isopentenyl transferase activities using the following protocol:

Each purified protein extract was incubated in a reaction mixture containing 12.5 mM Tris-HCl (pH 7.5), 37.5 mM KCl, 5 mM MgCl$_2$, 1 mM DMAPP and 1 mM AMP or ATP for 2 hours at 30° C. The reaction was stopped by boiling the samples for 5 minutes.

Half of the reaction mixture was treated with calf intestine alkaline phosphatase (CAIP) by adding one volume of 2×CAIP reaction buffer (0.45M Tris-HCl pH 9, 10 mM MgCl$_2$, 1000 unit of CAIP/ml) and incubating for 1 hour at 37° C.

The reaction products were separated using reversed phase HPLC (Agilent 1100 system with diode-array-detector) using a C18-ODS2 column (Phenomenex) and a separation protocol using 0.1 M acetic acid pH 3.3 (Buffer A) and acetonitrile (Buffer B) as follows:

100% buffer A for 15 minutes, linear gradient from 100% buffer A and 0% buffer B to 20% buffer A and 80% buffer B over 35 minutes.

UV absorbance was monitored at 280 nm. Product retention times were compared to standards obtained from Sigma or OIChemIm.

The recombinant Tzs and ZmIPT2 proteins were first used to determine DMAPP::AMP isopentenyl transferase activity. FIG. 12A and FIG. 12B show HPLC chromatograms obtained for one of the substrates of the reaction, 5'-AMP (Sigma), and the expected product isopentenyladenosine 5'-monophosphate (iPMP) (OIChemIm). The chromatogram obtained with the IPT (tzs) protein shows that almost all 5'-AMP substrate has been converted to iPMP (FIG. 12C). Similarly, the chromatogram obtained with ZmIPT2 purified protein shows that the enzyme is able to convert 5'-AMP to iPMP but with a lower efficiency than does *Agrobacterium* IPT since not all the 5'-AMP has been converted (FIG. 12D).

Treatment of reaction products with calf intestine alkaline phosphatase (CAIP) and chromatography using HPLC confirmed the identity of the reaction product iPMP. FIGS. 13A and 13B show chromatograms obtained with Adenosine (Ado) (Sigma) and isopentenyladenosine (iPAR) (Sigma). As expected, after dephosphorylation of the product of each reaction, iPMP was transformed to isopentenyladenosine (iPAR) (FIGS. 13C and 13D) whereas remaining 5'-AMP was transformed to Ado (FIG. 13D). This confirms that ZmIPT2 can metabolize 5'-AMP and DMAPP into iPMP.

Determination of DMAPP::ATP activity was carried out using the same reaction buffer but replacing 5'-AMP by 5'-ATP in the reaction mixture. FIG. 14A shows the chromatogram obtained with 5'-ATP. If ZmIPT2 is able to catalyze the transfer of DMAPP onto 5'-ATP, the resulting product should create iPTP. The chromatogram of FIG. 14B shows that all 5'-ATP was metabolized into iPTP by ZmIPT2, suggesting that ZmIPT2 uses 5'-ATP with higher efficiency than 5'-AMP. The reaction product was treated with CAIP to ascertain its identity. Such treatment should yield iPAR. After separation by HPLC, the chromatogram was compared to the chromatogram of an iPAR standard (FIG. 14C). After treatment, the reaction product was transformed to iPAR (FIG. 14D) therefore confirming that ZmIPT2 can metabolize 5'-ATP and DMAPP into iPTP. Altogether these results prove that ZmIPT2 is a cytokinin biosynthetic enzyme preferentially using 5'-ATP as a substrate.

Similar experiments established that 5'-ADP is also a suitable substrate for the encoded enzyme. Taken together, these results prove that ZmIPT2 is a cytokinin biosynthetic enzyme preferentially using 5'-ATP as a substrate. Future experiments will determine the kinetic properties for each substrate using a purified ZmIPT2 protein.

Example 19

Detection of the ZmIPT2 Protein in Developing Kernels

In order to study further the expression pattern of the ZmIPT2 protein, polyclonal antibodies were used for a Western blot experiment. Polyclonal antibodies were raised in rabbit against purified N-terminal His-tagged recombinant ZmIPT2 protein. Fifteen micrograms of proteins extracted from whole kernels harvested at different days after pollination (DAP) were run using SDS-PAGE and blotted on a PVDF membrane. ZmIPT2 proteins were detected using the method of Laemmli (*Nature* 227:680-685, 1970) with anti-ZmIPT2 polyclonal antibodies as primary antibodies and anti-rabbit IgG antibodies raised in goat conjugated to an alkaline phosphatase as secondary antibodies.

FIG. 15 shows that ZmIPT2 protein levels increase from 0 to 10 DAP, peak at 10 DAP, then decrease from 10 DAP to 15 DAP and stay approximately constant thereafter. This is in agreement with Northern blot results showing that expression of the gene peaks around 10 DAP where it is strong in the pedicel and the endosperm. Although total expression of the gene decreases thereafter, expression levels remain high in the pedicel at later stages. ZmIPT2 protein levels in kernels were very high compared to other organs. Results suggest that the cytokinin activity of ZmIPT2 protein in kernels is most likely controlled at the transcriptional level. The Western blot analysis of protein levels in kernels suggests that the antibodies are very specific to ZmIPT2. Antibodies, together with in situ hybridization, will be very useful in determining the precise site of expression of the gene during kernel development.

Example 20

Ectopic Overexpression of ZmIPT2 in Transgenic *Arabidopsis*

Previous examples describe the overexpression of ZmIPT2 in *Arabidopsis* calli. In order to study the effects of the overexpression of ZmIPT2 at the whole plant level, *Arabidopsis* plants were transformed with an *Agrobacterium tumefaciens* strain containing a plasmid comprising the construct 35S-AdhI-ZmIPT2-PinII with the bar herbicide resistance gene as a marker. (Thompson, et al., (1987) *EMBO J.* 6(9):2519-2523; White, et al., (1990) *Nucleic Acids Res.* 18(4):1062). The simplified *Abrabidopsis* transformation protocol (Clough and Bent, (1998) *Plant J.* 16:735-743) was used. Seeds were sown in flats containing soil and incubated for 2 days at 4° C. to optimize germination. After 10 days in the greenhouse, transformants were selected by spraying the seedlings daily for 5 days with a 1/1000 dilution of Finale™ herbicide.

After selection, several plants resistant to the herbicide treatment were identified. Some plants appeared small and dark green compared to others. Leaf greenness is linked to cytokinin levels, suggesting that the dark green transformed plants have elevated levels of cytokinin. Some transgenic plants appeared more affected than others, possibly linked to the level of expression of the transgene which is known to be variable depending on position effects related to insertion in the genome.

At an early stage of development, some transgenic plants showed signs of anthocyanin accumulation in leaves compared to non transgenic plants. Some transgenics had highly serrated leaves compared to wild-type *Arabidopsis*. This phenotype has previously been reported in *Arabidopsis* plants over-expressing the *Agrobacterium* ipt gene (van der Graaff, et al., (2001) *Plant Growth Regul.* 34(3):305-315). High levels of cytokinin are often detrimental to plant growth (van der Graaff, et al., 2001) and some transgenic plants appeared to struggle in their development compared to control plants. Some transgenics appeared to have a decreased apical dominance in inflorescence stems compared to controls, which was previously reported in *Arabidopsis* and tobacco plants with high levels of cytokinins (van der Graaff, et al., 2001; Crozier, et al., (2000) Biosynthesis of hormones and ellicitor molecules. In Biochemistry and molecular biology of plants, Buchanan, et al., eds (Rockville, Md.: American Society of Plant Biologists), pp. 850-929)

Some transgenics appeared to have a "bushy" phenotype, most likely due to a larger number of leaves resulting from decreased apical dominance. Some plants also had a poor seed set due to the absence of siliques or smaller siliques with few seeds. They also displayed anthocyanin accumulation in leaves and along inflorescence stems. Plants often displayed serrated cauline leaves. The most extreme phenotype was a transgenic plant with a rosette of approximately 5 mm in diameter with very small curly leaves showing signs of anthocyanin accumulation. The plant was able to flower but never yielded seeds. It also displayed an unusual abundance of large trichomes. Curly leaf phenotype was previously described in tobacco with higher cytokinin levels (Crozier, et al., 2000).

Thus, over-expression of the protein in *Arabidopsis* further confirmed the protein's function by creating a range of phenotypes in agreement with previous attempts to over-express the IPT gene in *Arabidopsis* and tobacco (Van der Graaff, et al., 2001; Crozier, et al., 2000). The phenotypes observed in several independent transgenic plants are consistent with a phenotype of cytokinin accumulation, confirming that ZmIPT2 is a cytokinin biosynthetic enzyme.

Example 21

Determining Gene Function Through Mu Tagging

Gene function can be further confirmed and described by the study of mutants in which transcription and/or translation of the sequence of interest is disrupted. In certain embodiments this is accomplished through use of methods disclosed in U.S. Pat. No. 5,962,764. The Trait Utility System for Corn (TUSC) is a proprietary resource for selecting gene-specific transposon insertions from a saturated collection of maize mutants created using the Mutator transposable element system. For example, effect of the ZmIPT sequences of the invention on traits such as plant sink strength may be investigated. The following methods were applied to identify and characterize a TUSC mutant for ZmIPT2.

A 1495 bp genomic sequence was supplied for TUSC screening to identify germinal Mutator insertions in the maize IPT2 gene (ZmIPT2). This working annotation of the gene contained a 966 bp open reading frame (ORF; nt83-1048) that is uninterrupted by introns.

Primary screening against TUSC DNA Pools was initiated with two ZmIPT2-specific primers (PHN79087 and PHN79088), each in combination with the Mutator terminal inverted repeat (TIR) primer as described in U.S. Pat. No. 5,962,764. Primer sequences are listed below and provided as SEQ ID Nos: 82-84, respectively.

```
PHN79087
zmIPT2-F 5'  >  TGTTGTGTGCACAGAATCGAGCGG  <  3'

PHN79088
zmIPT2-R 5'  >  CGTCCGCTAGCTACTTATGCATCAG  <  3'

PHN9242
MuTIR    5'  >  AGAGAAGCCAACGCCAWCGCCTCYATTTCGTC  <  3'
```

Primers were validated prior to use by performing gene-specific amplification of ZmIPT2 using B73 genomic DNA and the PHN79087+79088 primer combination. The control amplification product was excised from an agarose gel and used as a $^{32}$P-labeled hybridization probe for the TUSC screening.

| Primer Pair | expected (re. reference seq) (bp) | observed B73 gDNA (bp) |
|---|---|---|
| 79087 + 79088 | 1033 | ~1050 |

Following successive rounds of screening the TUSC DNA template Pools and Individual samples by PCR and ZmIPT2 hybridization, prospective zmIPT2::Mu alleles were tested for their heritability through the germline. This was achieved by repeating the ZmIPT2::Mu PCR assays against DNA template prepared from 5 kernels of selfed (F2) seed from selected Individual TUSC plants. One TUSC family, PV03_13 H-07 (from Pool 26), showed strong positive results in the F2 template assay for both 79087+9242 and 79088+9242 primer combinations. These PCR products were cloned into Topo-TA vector (Invitrogen) for DNA sequence confirmation of the Mu insertion allele of zmIPT2 harbored by family PV03 13 H-07. Each PCR fragment was expected to be homologous to the ZmIPT2 locus, and also share ~71 bp of Mutator TIR homology. An expected 9 bp host site duplication, which is created upon insertion of Mu elements into maize genomic DNA, was also an expected outcome of the PV03 13 H-07 ZmIPT2::Mu allele.

As shown in FIG. 16, DNA sequence characterization of each TUSC PCR product exhibits these expected features. The 79087+9242 PCR product contains 600 bp of direct homology to ZmIPT2 from the left flank of the PV03 13 H-07 Mu insertion site. This product contains the PHN79087 PCR primer site. The 79088+9242 PCR product contains 442 bp of DNA sequence identity with ZmIPT2, representing the right flank of the Mu insertion site, and contains the PHN79088 primer site. When trimmed of Mutator TIR sequences and aligned to the zmIPT2 reference sequence, these PCR fragments overlap by 9 bp (nt 624-632 of the 1495 bp ZmIPT2 reference sequence), representing the expected 9 bp host site duplication created upon insertion of Mutator into ZmIPT2.

Thus, TUSC family PV03 13 H-07 contains a heritable Mutator insertion into the coding sequence (ORF) of the ZmIPT2 gene. This allele is expected to produce a null mutation or "knockout" of the ZmIPT2 locus. F2 progeny seed from PV03 13 H-07, which genetically segregates for the ZmIPT2::Mu mutation, known as zmIPT2-H07, was withdrawn from the TUSC seed bank and propagated for phenotypic and biomolecular analyses.

FIG. 16 graphically summarizes this TUSC result, and the corresponding sequence is provided as SEQ ID NO: 85.

As added characterization, BLAST searches of the MuTIR portions of each zmIPT2::Mu PCR product were conducted to ascribe an identity for the Mu element residing at the ZmIPT2 locus. TUSC PCR products amplified with the Mutator PHN9242 primer contain 39 bp of flanking TIR sequence that are specific to the resident element being amplified. BLAST results are consistent with the zmIPT2::Mu element being either a Mu4 or a Mu3 element.

>IPT2_TIR_L
(SEQ ID NO:86)
GAGATAATTGCCATTATAGAAGAAGAGAGAAGGGGATTCGACGAAATAGA
GGCGATGGCGTTGGCTTCTCT

>IPT2_TIR_R
(SEQ ID NO:87)
AAGCCAACGCCAACGCCTCTATTTCGTCGAATCCCCTTCTCTCTTCTTCT
ATAATGGCAATTATCTC

In certain embodiments the nucleic acid constructs of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression affecting cytokinin activity. For example, up-regulation of cytokinin synthesis may be combined with down-regulation of cytokinin degradation. Other combinations may be designed to produce plants with a variety of desired traits, such as those previously described.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression cassette comprising a polynucleotide comprising a nucleotide sequence of SEQ ID NO: 1 or 3, wherein said polynucleotide encodes a functional isopentenyl transferase, and wherein said polynucleotide is operably linked to a heterologous promoter.

2. An expression cassette comprising a polynucleotide comprising a nucleotide sequence operably linked to a heterologous promoter, wherein the nucleotide sequence is selected from the group consisting of:
   (a) a nucleotide sequence encoding an amino acid sequence comprising SEQ ID NO: 2; and
   (b) a nucleotide sequence comprising at least 92% sequence identity to the full length of SEQ ID NO: 1 or 3, wherein said polynucleotide encodes a functional isopentenyl transferase polypeptide comprising the consensus sequence of SEQ ID NO: 32.

3. A transgenic plant comprising a heterologous polynucleotide operably linked to a promoter that drives expression in the plant, wherein said polynucleotide comprises a nucleotide sequence selected from the group consisting of:
   (a) a nucleotide sequence encoding an amino acid sequence comprising SEQ ID NO: 2; and
   (b) a nucleotide sequence comprising at least 92% sequence identity to the full length of SEQ ID NO: 1 or 3, wherein said polynucleotide encodes a functional isopentenyl transferase polypeptide comprising the consensus sequence of SEQ ID NO: 32.

4. The plant of claim 3, wherein said polynucleotide is operably linked to a tissue-preferred promoter, a constitutive promoter, or an inducible promoter.

5. The plant of claim 4, wherein said promoter is a root-preferred promoter, a leaf-preferred promoter, a shoot-preferred promoter, or an inflorescence-preferred promoter.

6. The plant of claim 3, wherein said promoter is stress-insensitive or stress-induced and is preferentially expressed in a tissue of the developing seed or related maternal tissue at or about the time of anthesis.

7. A seed of the plant of claim 3, wherein said seed comprises the heterologous polynucleotide.

8. The plant of claim 3, wherein said plant is maize, wheat, rice, barley, sorghum, or rye.

9. A method of modulating plant phenotype, comprising transforming said plant with the expression cassette of claim 2.

10. An expression cassette comprising a polynucleotide comprising a nucleotide sequence comprising at least 95% sequence identity to the full length of SEQ ID NO: 1 or 3, wherein said polynucleotide encodes a functional isopentenyl transferase comprising the consensus sequence of SEQ ID NO: 32, and wherein said polynucleotide is operably linked to a heterologous promoter.

11. An expression cassette comprising a polynucleotide comprising a nucleotide sequence comprising at least 98% sequence identity to the full length of SEQ ID NO: 1 or 3, wherein said polynucleotide encodes a functional isopentenyl transferase comprising the consensus sequence of SEQ ID NO: 32, and wherein said polynucleotide is operably linked to a heterologous promoter.

12. An expression cassette comprising a polynucleotide comprising a nucleotide sequence encoding the amino acid sequence of SEQ ID NO: 2, wherein said polynucleotide encodes a functional isopentenyl transferase comprising the consensus sequence of SEQ ID NO: 32, and wherein said polynucleotide is operably linked to a heterologous promoter.

* * * * *

SEQUENCE LISTING

```
<160> NUMBER OF SEQ ID NOS: 87

<210> SEQ ID NO 1
<211> LENGTH: 1495
<212> TYPE: DNA
<213> ORGANISM: Zea mays
<220> FEATURE:
<221> NAME/KEY: CDS
<222> LOCATION: (83)...(1051)
<220> FEATURE:
<221> NAME/KEY: misc_feature
<222> LOCATION: (0)...(0)
<223> OTHER INFORMATION: ZmIPT2 full length sequence

<400> SEQUENCE: 1
aaaaggcacg gactgcttct ttttctattt tttgttgtgt gcacagaatc gagcggctac    60
```

```
aataatcaag atcatcaaga ca atg gag cac ggt gcc gtc gcc ggg aag ccc    112
                        Met Glu His Gly Ala Val Ala Gly Lys Pro
                         1               5                  10 aag gtg gtg ttc gtc ctc ggc gcc aca gcg aca ggg aag tcg aag ctc    160
Lys Val Val Phe Val Leu Gly Ala Thr Ala Thr Gly Lys Ser Lys Leu
            15                  20                  25 gcc atc gcc ctc gcc gag cgc ttc aac ggt gag gtt atc aac gct gac    208
Ala Ile Ala Leu Ala Glu Arg Phe Asn Gly Glu Val Ile Asn Ala Asp
        30                  35                  40 aaa atc cag gtc cac gat ggc gtg ccc atc atc acg aac aag gtc aca    256
Lys Ile Gln Val His Asp Gly Val Pro Ile Ile Thr Asn Lys Val Thr
    45                  50                  55 gag gaa gag cag ggc ggg gtg ccc cac cac ctg ctc agc gtc cgc cac    304
Glu Glu Glu Gln Gly Gly Val Pro His His Leu Leu Ser Val Arg His
60                  65                  70 ccg gac gcc gac ttc act gcg gag gag ttc cga cgt gag gcg gcc agc    352
Pro Asp Ala Asp Phe Thr Ala Glu Glu Phe Arg Arg Glu Ala Ala Ser
75                  80                  85                  90 gcc gtg gcc cgc gtg ctc tcg gcg ggc cgc ctc ccc gtc gtg gca ggc    400
Ala Val Ala Arg Val Leu Ser Ala Gly Arg Leu Pro Val Val Ala Gly
                95                  100                 105 ggg tcc aac acc tac atc gag gca ctg gtg gaa ggc gac ggc gcc gcc    448
Gly Ser Asn Thr Tyr Ile Glu Ala Leu Val Glu Gly Asp Gly Ala Ala
            110                 115                 120 ttc cgc gcg gcg cac gac ctc ctc ttc gtc tgg gtg gac gcg gag cag    496
Phe Arg Ala Ala His Asp Leu Leu Phe Val Trp Val Asp Ala Glu Gln
        125                 130                 135 gag ctg ctg gag tgg tac gcc gcg ctg cgc gtg gac gag atg gtg gcc    544
Glu Leu Leu Glu Trp Tyr Ala Ala Leu Arg Val Asp Glu Met Val Ala
    140                 145                 150 cgc ggg ctg gtg agc gag gct cgc gcg gcg ttc ggc ggc gcc ggg gtt    592
Arg Gly Leu Val Ser Glu Ala Arg Ala Ala Phe Gly Gly Ala Gly Val
155                 160                 165                 170 gac tac aac cat ggc gtg cgc cgc gcc atc ggc ctg ccg gag atg cac    640
Asp Tyr Asn His Gly Val Arg Arg Ala Ile Gly Leu Pro Glu Met His
                175                 180                 185 gcc tac ctg gtg gcg gag cgc gag ggc gtc gct ggg gag gcc gag ctc    688
Ala Tyr Leu Val Ala Glu Arg Glu Gly Val Ala Gly Glu Ala Glu Leu
            190                 195                 200 gcg gcc atg ctg gaa cgc gcg gtg cgc gag atc aag gac aac acc ttc    736
Ala Ala Met Leu Glu Arg Ala Val Arg Glu Ile Lys Asp Asn Thr Phe
        205                 210                 215 cgc ctc gcg cgc acg cag gcg gag aag atc cgg cgc ctc agc acg ctc    784
Arg Leu Ala Arg Thr Gln Ala Glu Lys Ile Arg Arg Leu Ser Thr Leu
    220                 225                 230 gac ggc tgg gac gtc cgc cgc atc gac gtg acc ccc gtg ttc gcg cgc    832
Asp Gly Trp Asp Val Arg Arg Ile Asp Val Thr Pro Val Phe Ala Arg
235                 240                 245                 250 aag gcc gat ggc act gag tgc cac gag ctg act tgg aag aag cag gtg    880
Lys Ala Asp Gly Thr Glu Cys His Glu Leu Thr Trp Lys Lys Gln Val
                255                 260                 265 tgg gag ccg tgc gag gag atg gtg agg gct ttc ctc gag ccg tcc ctg    928
Trp Glu Pro Cys Glu Glu Met Val Arg Ala Phe Leu Glu Pro Ser Leu
            270                 275                 280 act gcc gtt cca ggt gtt gca gta act gaa gaa ggg aac gcc ggc gtc    976
Thr Ala Val Pro Gly Val Ala Val Thr Glu Glu Gly Asn Ala Gly Val
        285                 290                 295 gtc gct act gct gca ccc gct ggt gat gtc gtc gtc cca act ggc gat   1024
Val Ala Thr Ala Ala Pro Ala Gly Asp Val Val Val Pro Thr Gly Asp
```

```
              300                 305                 310
gtc gtc acc gcc gtg gct gat gca taa gtagctagcg gacgtagcgc         1071
Val Val Thr Ala Val Ala Asp Ala *
315                 320 atgcatgcaa tgcatgcagg ctggctggct ggcttaatta gtgcctccga cttgctttaa   1131
actcatgtag ctgcgtccat gggagagggt gagatacaag tttatgcgac ttatatttct   1191
ttctaaattt aaatggatct cggatccgta gtatctggtt taatataatt ataaatattc   1251
cttcgaatta ttatatatat atgctcacac tcagttaggg atatatactc cctccattca   1311
ctctatgtat ttggattcat atgcaaaagt atttttaaaat tatactacct ccattctcga   1371
atatttgtta cccgcttgtt tattttctaa aacatgataa ataaaaaaac ggagagaata   1431 gtatttatt atttgttgat gatatatttt gtaagatatg aacggtgaaa gttttaccat    1491
aaag                                                                1495

<210> SEQ ID NO 2
<211> LENGTH: 322
<212> TYPE: PRT
<213> ORGANISM: Zea mays

<400> SEQUENCE: 2

Met Glu His Gly Ala Val Ala Gly Lys Pro Lys Val Val Phe Val Leu
  1               5                  10                  15

Gly Ala Thr Ala Thr Gly Lys Ser Lys Leu Ala Ile Ala Leu Ala Glu
             20                  25                  30

Arg Phe Asn Gly Glu Val Ile Asn Ala Asp Lys Ile Gln Val His Asp
         35                  40                  45

Gly Val Pro Ile Ile Thr Asn Lys Val Thr Glu Glu Gln Gly Gly
     50                  55                  60

Val Pro His His Leu Leu Ser Val Arg His Pro Asp Ala Asp Phe Thr
 65                  70                  75                  80

Ala Glu Glu Phe Arg Arg Glu Ala Ala Ser Ala Val Ala Arg Val Leu
                 85                  90                  95

Ser Ala Gly Arg Leu Pro Val Val Ala Gly Gly Ser Asn Thr Tyr Ile
            100                 105                 110

Glu Ala Leu Val Glu Gly Asp Gly Ala Ala Phe Arg Ala Ala His Asp
        115                 120                 125

Leu Leu Phe Val Trp Val Asp Ala Glu Gln Glu Leu Leu Glu Trp Tyr
    130                 135                 140

Ala Ala Leu Arg Val Asp Glu Met Val Ala Arg Gly Leu Val Ser Glu
145                 150                 155                 160

Ala Arg Ala Ala Phe Gly Gly Ala Gly Val Asp Tyr Asn His Gly Val
                165                 170                 175

Arg Arg Ala Ile Gly Leu Pro Glu Met His Ala Tyr Leu Val Ala Glu
            180                 185                 190

Arg Glu Gly Val Ala Gly Glu Ala Glu Leu Ala Ala Met Leu Glu Arg
        195                 200                 205

Ala Val Arg Glu Ile Lys Asp Asn Thr Phe Arg Leu Ala Arg Thr Gln
    210                 215                 220

Ala Glu Lys Ile Arg Arg Leu Ser Thr Leu Asp Gly Trp Asp Val Arg
225                 230                 235                 240

Arg Ile Asp Val Thr Pro Val Phe Ala Arg Lys Ala Asp Gly Thr Glu
                245                 250                 255

Cys His Glu Leu Thr Trp Lys Lys Gln Val Trp Glu Pro Cys Glu Glu
```

```
                  260               265               270
Met Val Arg Ala Phe Leu Glu Pro Ser Leu Thr Ala Val Pro Gly Val
                275               280               285

Ala Val Thr Glu Glu Gly Asn Ala Gly Val Val Ala Thr Ala Ala Pro
            290               295               300

Ala Gly Asp Val Val Val Pro Thr Gly Asp Val Val Thr Ala Val Ala
305               310               315               320

Asp Ala

<210> SEQ ID NO 3
<211> LENGTH: 969
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT2 coding sequence

<400> SEQUENCE: 3
atggagcacg gtgccgtcgc cgggaagccc aaggtggtgt tcgtgctcgg cgccacagcg      60
acagggaagt cgaagctcgc catcgccctc gccgagcgct tcaacggtga ggttatcaac     120
gctgacaaaa tccaggtcca cgatggcgtg cccatcatca cgaacaaggt cacagaggaa     180
gagcagggcg gggtgcccca ccacctgctc agcgtccgcc accggacgc cgacttcact      240 gcggaggagt tccgacgtga ggcggccagc gccgtggccc gcgtgctctc ggcgggccgc     300
ctccccgtcg tggcaggcgg gtccaacacc tacatcgagg cactggtgga aggcgacggc     360
gccgccttcc gcgcggcgca cgacctcctc ttcgtctggg tggacgcgga gcaggagctg     420
ctggagtggt acgccgcgct gcgcgtggac gagatggtgg cccgcggggct ggtgagcgag    480 gctcgcgcgg cgttcggcgg cgccggggtt gactacaacc atggcgtgcg ccgcgccatc     540
ggcctgccgg agatgcacgc ctacctggtg gcggagcgcg agggcgtcgc tggggaggcc     600
gagctcgcgg ccatgctgga acgcgcggtg cgcgagatca aggacaacac cttccgcctc     660
gcgcgcacgc aggcggagaa gatccggcgc ctcagcacgc tcgacggctg ggacgtccgc     720
cgcatcgacg tgaccccgt gttcgcgcgc aaggccgatg cactgagtg ccacgagctg       780 acttggaaga gcaggtgtg ggagccgtgc gaggagatgg tgagggcttt cctcgagccg      840
tccctgactg ccgttccagg tgttgcagta actgaagaag ggaacgccgg cgtcgtcgct     900
actgctgcac ccgctggtga tgtcgtcgtc ccaactggcg atgtcgtcac cgccgtggct     960
gatgcataa                                                            969

<210> SEQ ID NO 4
<211> LENGTH: 2901
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT1 partial sequence

<400> SEQUENCE: 4
gccgactatt tgttagtcag ctaactatta gctctagtaa attcaaatgg agtctaagct       60
cttagttgtg ctatggttgt atttatcaa taattataac taaatttggc aagtgtttat      120
taattgagcg tctagattcc atgtgattca tgtgataaag catgccaatt aggccccgtt      180
tgactcctct tacaaaagtt tagcactaca ttttttggt aaagtttagc tactaaagaa       240
```

```
acaacagaat tcctataagt ggtgtaccaa aatttagcat tcattagcat taccaaagat    300
gctaaactat attaaaaata gtcccctaga accatttctc actcccccct cccaccaaat    360
tcttctctct ctctctcctc ccacaactga ccgctagctt ctgctgtcac gcaggtgacg    420
ctagcttcca cattaattag ggataatatg ttaaacactt gcatcaaaca tgtctcaagt    480
tctaaagttt aaccaaagtt taagcccatt ttagaaacca cagttttaa aatactataa     540 tatactttag tcattacaat accacagttt gaaataatac agtttttact ttagtaatta    600
caataccaca gtttgaaata atacagttttt acaaactgtg gtcaatacag ttttgcaaac   660
taaggtccag acctaagttt agaatagctt aaaataacta cagtatttgc aatacttcgg    720
ttttgaaaat agagatttta gcaatcttaa acacctcctt agcatatgct aaactttagc    780
agtatagaaa gatggaccat tgttcaagta tctatccact tccacactac gtttctgtgg    840
cttctagacc cgtcgtacgt gtggtacaat acttttgata agcagttctt tggtgcctgc    900
ttcttccgct gctaaaaggc atggaggtag tccccccgtc gacgtgccag gaattcggga    960
ttgggaaagc atgtcgctgt caggctggca cgcttttttg ggtgggacga gacgaccatg   1020
tccacgtcaa cgtccccgtc ccacttctcg ccggttctgc tgtgaaaaag ttaccatcag   1080
ctgcggtctt ggggcagcag cgatggccat ggcctcaggc tcttctgctt caggcgctgc   1140
actcgcttcc ggtggcctcg cccttgcctg tgctgctccc actcgtgcgc acctcgcagc   1200
acccggttgc cgcaggcctg tacatccgca tgcatgcttt tcttatgtct gcttttcctt   1260
cctatgcaga cagtacagct ctcagaaaga aggaaaaaaa actagactca cctcgcacac   1320
atattgcgtc cacagctctc ttgaagaggg gtcacttgcg cttgtgcttg gcaaaacagt   1380
ggaattgtcc gacaaaaacc ttcttacgac atccacacat ggtttgacaa cttttcttttg  1440 ccatgagtcg tcagtggcac ctatcaaaat atgagaggga gattatgagt tgctacagag   1500
aaggcatacg catctgacag ggtaccaatg gacttacaga agaatgcttc ggttgcgtca    1560
acacgatgca agttccaccc aaaatcttta ctcagccgat gcaatctccg tctcttttat   1620
ttaatggaga aaaaaaaga aacgctaaga agtctacatt gagccaagta tccgtgtgtt    1680
cagtcgcaca gtattctaaa acaacacaac aacataaaaa aatacacagg atactaagtg   1740
cttacttgac gtcgaactag tctacgagtg tttgccttca gctgggaaac agcttcgtcc   1800
aacaagctct taagctgatc gtcatgcata cctaacaggc ttgcacagga ccctcacca    1860 gattcttttc tgggtaaata tgctctgaaa aactcgtcaa actcacgaac cccaatagcc   1920
tgccgcagcc cctgggtata gacagcatcc gcatcatata tgctgcatac ttcgtccagc   1980
aggccaccat ccatcatgca atcgacccct ttgttgacat aactgtccag gacttgaaga   2040
tcagcatcta cccacaggaa acagcagtcg agtctggagt tactaggccg accccatttc   2100
tgttctgaca tgatgagcag gaattcccag caagtttata ctcaattagg gaaacaaaac   2160 caaaaaaga agagccttgt gaggcaattg tcggctcatg ttcatgacaa agggaggata    2220
ttatacaagc agagcagaca agtgcagcga aaaattcctc accttagcgg cctctccttg   2280
gaacagatcg ctgggtaggg caccgtggt tgcatacaac tcgaggtagc gtttgatctt    2340
tgtgatacac caacccatgc agaacgaaaa atacacaagc aatcaacggc agtaggaaaa   2400
tgagcacctg tacaagaagg aattctaaca tggtagagct caagagctgc ataaagtcag   2460
gaaaaacttg gcaacacccc ttactttct atggtcgttt ggatggatcc tctgcgcagc    2520
cacaggatcg atctccttca agcgttcaaa cccattgcct tcatcttcat cagtaagacc   2580
tgacgattgg catacatgtc aaccgctgat tgttcatact aagaacaagg aacatttagc   2640
```

```
atgactcatt attcgcctat accatcatct atgtgatctc tcagagtaca gccctgcatt      2700
tcttctgcca tatcatccaa gaggaatggg ctaacgagag cctggagtat tttgtgggca      2760
aaaacacacg gtggttcaga cactgcggtc acccagaaaa ccatacagaa atcaggacac      2820
ttcaaatttg aacctggatg tagaagtttg tgccgccgac aaccacaggg aggccaccgc      2880
ggtccactat ttcctgtata a                                                2901

<210> SEQ ID NO 5
<211> LENGTH: 2654
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT4 full length
<220> FEATURE:
<221> NAME/KEY: CDS
<222> LOCATION: (904)...(1998)

<400> SEQUENCE: 5
ttttggggga tcccaaagaa actagtatgt ggattgctcg tcgccgcgct gcacacatgc       60
ttcgtgcgct gcaaaatctg tccacgcgcg cgggcgcaca cacattattt tttcgttcat      120
ttgtatctgt gaaagatacg tacaaaatct gcgtgtatct tccatgattt gacaagaatt      180
tcagacacca aggcaaattt tgttggtaca tacagctcag cagcagtcct ttctgttgac      240
ctgctgcccc cttttgcttc cgttctcgat ccaaatctat ggttgaatct ttcttctgat      300
caccaggatt gttgttgttt agactttaga tcatcctgat cctgcgtgtc cggatcaaat      360
ctgcaaatcc aacgcaaaaa aaatggttca cgtgctaggt acagtttctc aaacatcaca      420
tatttggtcg tttatggtct aatgccaatt tcaaatggg agatttcgtt ttcctcaaat      480
cgtacaagaa tgaagctgcc atatagtacg aaattcctct gaaattccag agcttcgaat      540
tacacaatcc aattaattgg ctacatgaag gtagcgccgt agcggccgac gtaccattcc      600
gacgacccca tcaatataat gggcatgggg gggcatctga atctttatct aaaatacatt      660
tgttttcgtt tcaatctaat ctaaccccaa attaaaggaa cgcatttgca cattttgta       720 ttgcaacgag gaggatccat ttgcccactt gttttcgcca gcacaagata aatagcagcc      780
acacccagca catcgacctg cagccaactc acgaactaac taccagaaga tctcaaaggc      840
ttcgattctt gaccccaagc aagtggttaa gcataagcaa cttaaacgac agcgacagaa      900 acc atg tca ctc tac ttg gcg ccc acg gcc gcc gct gcc acc acc acc          948
    Met Ser Leu Tyr Leu Ala Pro Thr Ala Ala Ala Ala Thr Thr Thr
     1               5                  10                  15 acc acc acc ctc cca agg cag ctg cta cca gcg ccg tcc atc gac cta          996
Thr Thr Thr Leu Pro Arg Gln Leu Leu Pro Ala Pro Ser Ile Asp Leu
             20                  25                  30 agg cgg ctg gaa cga cgt ggc atg gcg ctg ccc ctg cca ccg gcg ccg         1044
Arg Arg Leu Glu Arg Arg Gly Met Ala Leu Pro Leu Pro Pro Ala Pro
 35                  40                  45 gcg ccg ccg cca ccg ctg gtc agt gcc aac aac agg cat gcc gga gcg         1092
Ala Pro Pro Pro Pro Leu Val Ser Ala Asn Asn Arg His Ala Gly Ala
                 50                  55                  60 aag cac aag gcc gtg gtg gtg atg ggc gcc acg ggg acc ggc aag tcg         1140
Lys His Lys Ala Val Val Val Met Gly Ala Thr Gly Thr Gly Lys Ser
             65                  70                  75 cgg ctg gcg gtg gac ctg gcg ctc cgg ttc ggc ggc gag gtc atc aac         1188
Arg Leu Ala Val Asp Leu Ala Leu Arg Phe Gly Gly Glu Val Ile Asn
 80                  85                  90                  95
```

```
tcg gac aag atc cag ctg cac gcc ggc ctg gac gtg acc acg aac aag    1236
Ser Asp Lys Ile Gln Leu His Ala Gly Leu Asp Val Thr Thr Asn Lys
            100                 105                 110 gtg acc gag cag gag cgc gcc ggc gtg ccg cac cac ctg ctc ggg gtg    1284
Val Thr Glu Gln Glu Arg Ala Gly Val Pro His His Leu Leu Gly Val
        115                 120                 125 gcg cgg ccc gac gag gag ttc acg gcc gcg gac ttc cgg cgc gag gcg    1332
Ala Arg Pro Asp Glu Glu Phe Thr Ala Ala Asp Phe Arg Arg Glu Ala
    130                 135                 140 acc cgc gcc gcg cgc gcc atc acc gcg cgc ggc cgc ctg ccc atc gtc    1380
Thr Arg Ala Ala Arg Ala Ile Thr Ala Arg Gly Arg Leu Pro Ile Val
145                 150                 155 gcg gga ggg tcc aac tcg tac gtg gag gag ctg gtg gac ggc gac cgc    1428
Ala Gly Gly Ser Asn Ser Tyr Val Glu Glu Leu Val Asp Gly Asp Arg
160                 165                 170                 175 gcc gcg ttc cgc gac cgc tac gac tgc tgc ttc ctc tgg gtg gac gtg    1476
Ala Ala Phe Arg Asp Arg Tyr Asp Cys Cys Phe Leu Trp Val Asp Val
                180                 185                 190 cag cgc gcc gtg ctg cac ggc tgc gtc gcg cgg cgc gtc gac gag atg    1524
Gln Arg Ala Val Leu His Gly Cys Val Ala Arg Arg Val Asp Glu Met
            195                 200                 205 cgc gcc cgc ggc ctg gtg gac gag gtc gcg gcg gcc ttc gac ccg cgc    1572
Arg Ala Arg Gly Leu Val Asp Glu Val Ala Ala Ala Phe Asp Pro Arg
        210                 215                 220 cgc aac gac tac tcg cgc ggc ctc tgg cgc gcc att ggc gcg ccc gag    1620
Arg Asn Asp Tyr Ser Arg Gly Leu Trp Arg Ala Ile Gly Ala Pro Glu
    225                 230                 235 ctc gac gcg tac ctg cgg tgg ccg gga ccg ggt gta gac ggc gac gcg    1668
Leu Asp Ala Tyr Leu Arg Trp Pro Gly Pro Gly Val Asp Gly Asp Ala
240                 245                 250                 255 gaa agc gag ggc gag cgc gac cgg ctg ctg gcc gcc gcc atc gag gac    1716
Glu Ser Glu Gly Glu Arg Asp Arg Leu Leu Ala Ala Ala Ile Glu Asp
                260                 265                 270 atc aag tcc aac acc cgc cgc ctg tcg tgc cgg cag cgc gcc aag atc    1764
Ile Lys Ser Asn Thr Arg Arg Leu Ser Cys Arg Gln Arg Ala Lys Ile
            275                 280                 285 cag cgc ctg gcc aag atg tgg ggc gtc cgg cgc gtc gac gcc acc gag    1812
Gln Arg Leu Ala Lys Met Trp Gly Val Arg Arg Val Asp Ala Thr Glu
        290                 295                 300 gtc ttc cgg agg cgc ggc gac gag gcc gac gag gcc tgg cag cgg ctc    1860
Val Phe Arg Arg Arg Gly Asp Glu Ala Asp Glu Ala Trp Gln Arg Leu
    305                 310                 315 gtc gcc gcg ccg tgc atc gac gcc gtg cgc tcc ttc cta cga acc gac    1908
Val Ala Ala Pro Cys Ile Asp Ala Val Arg Ser Phe Leu Arg Thr Asp
320                 325                 330                 335 gac gcc gcg gcg acc gtc gcc agt gac ctg gcg gtg gac gga gtc gtg    1956
Asp Ala Ala Ala Thr Val Ala Ser Asp Leu Ala Val Asp Gly Val Val
                340                 345                 350 ccc gtg ttc gct ccc gcg ccg gct gcg gcc gta gca gga taa             1998
Pro Val Phe Ala Pro Ala Pro Ala Ala Ala Val Ala Gly  *
            355                 360 cggacgacga agctcctcca tgagcgcgtt gacagctgca ctgcattcac gaatagccat   2058
tatgtataag gacaccatta cttggtgcga tggctgcgat cgtcgtcaag aaggaaaaag   2118
ggagtggtcg agaagcgagg ggaatgacga gcatgattat agtagtatct acgtcggaac   2178
ttgcatggga ctcagtcgca caaagagatt ggcgtgattg cttcgagaat cgtgcgtttg   2238
aaatcctagc taggagagga ggagagaagc aaacggagaa agtggattta ctatcatata   2298
```

```
tatggccgca tatatagcac ttgcatacag ataaatgcgt tacatgtatg ttcgagcgag   2358
gagcatgcat tatttgcacg agttggcacc tgctgtgttt gacttatcac ctgtcctttt   2418
cacccggttt ctgttttatt tgttatatga aagtgatgct agcttattcc tgttttcctt   2478
ttcatttggt tgctacaacg tgcatacatg gttgtgttgt gcgcgcaatc gagtttgtac   2538
aatcgaggtt gtgcatattt acaaggaaat attagttgca aactagcaat attaatgaca   2598 cattttaat atatttatca tatacttcct ccttaaaata taaggcaatc ctttaa        2654
```

<210> SEQ ID NO 6
<211> LENGTH: 364
<212> TYPE: PRT
<213> ORGANISM: Zea mays

<400> SEQUENCE: 6

```
Met Ser Leu Tyr Leu Ala Pro Thr Ala Ala Ala Thr Thr Thr Thr
 1               5                  10                  15

Thr Thr Leu Pro Arg Gln Leu Leu Pro Ala Pro Ser Ile Asp Leu Arg
                20                  25                  30

Arg Leu Glu Arg Arg Gly Met Ala Leu Pro Leu Pro Pro Ala Pro Ala
            35                  40                  45

Pro Pro Pro Leu Val Ser Ala Asn Asn Arg His Ala Gly Ala Lys
        50                  55                  60

His Lys Ala Val Val Met Gly Ala Thr Gly Thr Gly Lys Ser Arg
 65                  70                  75                  80

Leu Ala Val Asp Leu Ala Leu Arg Phe Gly Gly Glu Val Ile Asn Ser
                85                  90                  95

Asp Lys Ile Gln Leu His Ala Gly Leu Asp Val Thr Thr Asn Lys Val
           100                 105                 110

Thr Glu Gln Glu Arg Ala Gly Val Pro His His Leu Leu Gly Val Ala
       115                 120                 125

Arg Pro Asp Glu Glu Phe Thr Ala Ala Asp Phe Arg Arg Glu Ala Thr
   130                 135                 140

Arg Ala Ala Arg Ala Ile Thr Ala Arg Gly Arg Leu Pro Ile Val Ala
145                 150                 155                 160

Gly Gly Ser Asn Ser Tyr Val Glu Glu Leu Val Asp Gly Asp Arg Ala
                165                 170                 175

Ala Phe Arg Asp Arg Tyr Asp Cys Cys Phe Leu Trp Val Asp Val Gln
            180                 185                 190

Arg Ala Val Leu His Gly Cys Val Ala Arg Arg Val Asp Glu Met Arg
        195                 200                 205

Ala Arg Gly Leu Val Asp Glu Val Ala Ala Ala Phe Asp Pro Arg Arg
    210                 215                 220

Asn Asp Tyr Ser Arg Gly Leu Trp Arg Ala Ile Gly Ala Pro Glu Leu
225                 230                 235                 240

Asp Ala Tyr Leu Arg Trp Pro Gly Pro Gly Val Asp Gly Asp Ala Glu
                245                 250                 255

Ser Glu Gly Glu Arg Asp Arg Leu Leu Ala Ala Ala Ile Glu Asp Ile
            260                 265                 270

Lys Ser Asn Thr Arg Arg Leu Ser Cys Arg Gln Arg Ala Lys Ile Gln
        275                 280                 285

Arg Leu Ala Lys Met Trp Gly Val Arg Val Asp Ala Thr Glu Val
    290                 295                 300

Phe Arg Arg Arg Gly Asp Glu Ala Asp Glu Ala Trp Gln Arg Leu Val
305                 310                 315                 320
```

```
Ala Ala Pro Cys Ile Asp Ala Val Arg Ser Phe Leu Arg Thr Asp Asp
            325                 330                 335

Ala Ala Ala Thr Val Ala Ser Asp Leu Ala Val Asp Gly Val Val Pro
        340                 345                 350

Val Phe Ala Pro Ala Pro Ala Ala Val Ala Gly
        355                 360

<210> SEQ ID NO 7
<211> LENGTH: 1095
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT4 coding sequence

<400> SEQUENCE: 7
atgtcactct acttggcgcc cacggccgcc gctgccacca ccaccaccac caccctccca      60
aggcagctgc taccagcgcc gtccatcgac ctaaggcggc tggaacgacg tggcatggcg     120
ctgcccctgc caccggcgcc ggcgccgccg ccaccgctgg tcagtgccaa caacaggcat     180
gccggagcga agcacaaggc cgtggtggtg atgggcgcca cggggaccgg caagtcgcgg     240
ctggcggtgg acctggcgct ccggttcggc ggcgaggtca tcaactcgga caagatccag     300
ctgcacgccg gcctggacgt gaccacgaac aaggtgaccg agcaggagcg cgccggcgtg     360
ccgcaccacc tgctcggggt ggcgcggccc gacgaggagt tcacggccgc ggacttccgg     420
cgcgaggcga cccgcgccgc gcgcgccatc accgcgcgcg ccgcctgcc catcgtcgcg      480 ggagggtcca actcgtacgt ggaggagctg gtggacggcg accgcgccgc gttccgcgac     540
cgctacgact gctgcttcct ctgggtggac gtgcagcgcg ccgtgctgca cggctgcgtg     600
gcgcggcgcg tcgacgagat gcgcgcccgc ggcctggtgg acgaggtcgc ggcggccttc     660
gacccgcgcc gcaacgacta ctcgcgcggc ctctggcgcg ccattggcgc gcccgagctc     720
gacgcgtacc tgcggtggcc gggaccgggt gtagacggcg acgcggaaag cgagggcgag     780
cgcgaccggc tgctggccgc cgccatcgag gacatcaagt ccaacacccg ccgcctgtcg     840
tgccggcagc gcgccaagat ccagcgcctg gccaagatgt ggggcgtccg gcgcgtcgac     900
gccaccgagg tcttccggag gcggcggac gaggccgacg aggcctggca gcggtcgtc     960 gccgcgccgt gcatcgacgc cgtgcgctcc ttcctacgaa ccgacgacgc cgcggcgacc    1020
gtcgccagtg acctggcggt ggacggagtc gtgcccgtgt tcgctcccgc gccggctgcg    1080
gccgtagcag gataa                                                    1095

<210> SEQ ID NO 8
<211> LENGTH: 4595
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT5 full length sequence
<220> FEATURE:
<221> NAME/KEY: CDS
<222> LOCATION: (1952)...(2965)

<400> SEQUENCE: 8
ggaggccggc gccgtggagg cgcgagggtg gtggcccgcc gggttctcgc cggcttacat      60
ggtgtccaag gcggcgctga acgcctactc gcgcgtcctg gcgcggaggc accccgcgct     120
```

-continued

```
gcgcgtcaac tgcgtgcacc cgggcttcgt caggaccgac atgaccgtca acttcggcat      180
gctcacgccc gaggaaggcg gcagcagggt ggtggccgtc gctctgctcc ccgacggcgg      240
gcccaccggc gcctacttcc aggagcgcca gcaggcgccg ttcgtgtgac gcgctctgcc      300
tctgctctgc ttccttcacc acccgatgct tgatagctat gtatctcttg aagttttcgc      360
ttgataatag ttgatacaca ttcaatcccc gcgcgtaatc tctccgttgc aaaaataatg      420
gaatcctaag ttttggacaa gtaaaaattt ctcaacttt tgatcaaccta tcgacgagat      480 gaatcatggg ataaatacat atgttttgcg aagatggaga cacaaaattt ctccatggga      540
atccatcctc gacggagaat cgacggggtg gatgctgccg agccgtgcat tttcgcactc      600
gtagatgacg cgtctacgca gtacgcaggt gcttcgaact gctgcacgcg cttttgcacag     660 gaacttgcat ttgctgaacc catttcccgt gctcctgttt gtccgctgtt tccatcgtcc      720
gactccgacc ggcggcactc ctctggtctg cctctcgtag caggctagcg gcggctagta     780
ggccccgtgg taccgggccg gaccgattgg attggacgga ggcgggcgcg cacgcaccac      840 acgccccgg tgtccgggcg tccgtacgcc gtactccctc cccgctgccc gcgtcacgcg      900
tccctccaac caggcgacga aacgactcca ccctccactc actcggccgc cgcacgcagc      960
cctaggccgt agcccaatat gagtgcgcgc gcggcggct aggcctcccg agtcccgccg     1020
cctccccaac cccgcccagg cgcaggcggg gcggcggcca ccaccagcac ggcacgcacc    1080
acaccaccag tctctgtccg cgatccgatc agtagcgtag cgctagcggc agtcgctctc    1140
gagcgcgggg cgctgttgct gccctgtggt ctgtggacgt ccggcggtcc ggaggccgtg    1200
cagtgcacga tcgtcctgta cgttggaatt ggatcgcctt tgctgctgct gctgcgcgag    1260
tgggtggctc aattcttcga tgcgtttccg acggcccttt tgccctttat tttccctcct    1320
ccttggcagc ttgcggcgga cgacatggtg gtgtcctgtc ctctcgtcgt cctcaccaca    1380
gagaaggcca ccgcagctaa gctagtgcaa accatgcggg gctaagctag taacattatt    1440
ctccgtgcat gcactgtgtc actgcatgat gatcgtcgtt ttcgaaagaa gctagatgac    1500
gaccaagacc agcaggtagt ccgcgcggaa gaaagcgacg agacactcta gtcaactctc    1560
tcttgggcct tggcttgccg tggatataca tggatcggag gtcaactctc ccatggtggc    1620
ttgccgcttg cctgctctgc tcaatctgt tgccttgttc gtcgtcgtcg tcgtgtcgtg    1680
cgacggcaaa agagaaagcc actcgctgcc ggtacttgca tcgccagtcg ccactcgcca   1740
ccttatctaa accgaatcat gcagtgcggt caaccgcggt cgctgtagcg cgcggccctg    1800
catttggaga cgccccgcc ctataaatac ccatgctttg ctctgcttct gctcccacac    1860
cacgcagacg cagccaagca agcagccaag gaaggaagct agctagctag ctgatcacaa    1920
agcagggccg attcccgatc cggcagcatc c atg gcg gcc ccc gcg atg gca      1972
                                    Met Ala Ala Pro Ala Met Ala
                                    1               5 gcg ccg ccg cca ccg ccg gcc tgc ttc ccc atg ccc acc agg ctg acg      2020
Ala Pro Pro Pro Pro Ala Cys Phe Pro Met Pro Thr Arg Leu Thr
    10              15                  20 atg ccg ccg acg tcg atc acg ctc ccg gac ccg ccg ctg tct gtc          2068
Met Pro Pro Thr Ser Ile Thr Leu Pro Asp Pro Pro Leu Ser Val
 25                  30                  35 ggc ggc gcc tgc agg cgc gtg gcg gcc aag cac aag gcc gtg gtg gtg      2116
Gly Gly Ala Cys Arg Arg Val Ala Ala Lys His Lys Ala Val Val Val
 40              45                  50                  55 ctg ggc gcc acg ggc acc ggc aag tcc cgc ctg gcg atc gac ctc gcg      2164
Leu Gly Ala Thr Gly Thr Gly Lys Ser Arg Leu Ala Ile Asp Leu Ala
             60                  65                  70
```

```
ctg cgc ttc ggc ggc gag gtc atc aac tcg gac aag atc cag gcg cac      2212
Leu Arg Phe Gly Gly Glu Val Ile Asn Ser Asp Lys Ile Gln Ala His
             75                  80                  85 gcc ggc ctg gac gtg gcc acc aac aag gtg ggc ctc gcc gag cgc ggg      2260
Ala Gly Leu Asp Val Ala Thr Asn Lys Val Gly Leu Ala Glu Arg Gly
         90                  95                 100 cgg gtg ccg cac cac ctg ctg ggc gtg gtg cac ccg gac gcc gag ttc      2308
Arg Val Pro His His Leu Leu Gly Val Val His Pro Asp Ala Glu Phe
    105                 110                 115 acg gcg gcc gac ttc cgc cgc gag gcc tcg cgc gcg gac cgc gcc          2356
Thr Ala Ala Asp Phe Arg Arg Glu Ala Ser Arg Ala Asp Arg Ala
120                 125                 130                 135 gcg gcg cgg ggc cgg gtg ccc gtc atc gcc ggc ggc tcc aac tcg tac      2404
Ala Ala Arg Gly Arg Val Pro Val Ile Ala Gly Gly Ser Asn Ser Tyr
                140                 145                 150 gtg gag gag ctc gtc gag ggg gac cgg cgc gcg ttc cgg gac cgg tac      2452
Val Glu Glu Leu Val Glu Gly Asp Arg Arg Ala Phe Arg Asp Arg Tyr
            155                 160                 165 gag tgc tgc ttc ctc tgg gtg gac gcg cag ctc ccc gtg ctg cac ggc      2500
Glu Cys Cys Phe Leu Trp Val Asp Ala Gln Leu Pro Val Leu His Gly
        170                 175                 180 ttc gtc gcc cgc cgc gtc gac gac atg tgc cgg cgc ggc ctc gtc gac      2548
Phe Val Ala Arg Arg Val Asp Asp Met Cys Arg Arg Gly Leu Val Asp
    185                 190                 195 gag gtg gcg gcc gcg ttc gac ccc cgc cgc acc gac tac tcc agg ggc      2596
Glu Val Ala Ala Ala Phe Asp Pro Arg Arg Thr Asp Tyr Ser Arg Gly
200                 205                 210                 215 atc tgg cgc gcc atc ggc gtg ccg gag ctc gac gcc tac ctc cgg gcg      2644
Ile Trp Arg Ala Ile Gly Val Pro Glu Leu Asp Ala Tyr Leu Arg Ala
                220                 225                 230 cgc ggc cgc ggc cac ggc cac cac cac gac cag atg ctc gcc gcg gcc      2692
Arg Gly Arg Gly His Gly His His His Asp Gln Met Leu Ala Ala Ala
            235                 240                 245 ctc cac gag atc aag gcc aac acg tcc cgc ctc gcc gtg cgc cag cgc      2740
Leu His Glu Ile Lys Ala Asn Thr Ser Arg Leu Ala Val Arg Gln Arg
        250                 255                 260 ggc aag atc cag cgg ctc gag cgc atg tgg cgc gtc cgc cgc gtc gac      2788
Gly Lys Ile Gln Arg Leu Glu Arg Met Trp Arg Val Arg Arg Val Asp
    265                 270                 275 gcc acg gag gtg ttc ctg aag cgc ggc ctc gcc gcc gac gag gcc tgg      2836
Ala Thr Glu Val Phe Leu Lys Arg Gly Leu Ala Ala Asp Glu Ala Trp
280                 285                 290                 295 cag cgg ctg gtc gcc gcg ccc tgc att gac gcc gtc agg tcc ttc ctg      2884
Gln Arg Leu Val Ala Ala Pro Cys Ile Asp Ala Val Arg Ser Phe Leu
                300                 305                 310 ctg gag gac caa caa gag tac agc agc atg ggc acc gcc ggc gcc atg      2932
Leu Glu Asp Gln Gln Glu Tyr Ser Ser Met Gly Thr Ala Gly Ala Met
            315                 320                 325 ttg cct gcc gcc gtc gca gcc gcg gct gtc taa cacaacacaa gtacacaata    2985
Leu Pro Ala Ala Val Ala Ala Ala Ala Val *
        330                 335 acacaacaca cacggaaccg gaacgctgcc cagagtcctc cacacgtggc cacgcgcgcc    3045
agcctccatt ggcgatcggc gcaatgctct gctgcggtca accgcgcggt gacccggcag    3105
agtagcgcag atcatatagt tgatcctggt caggggaaac tgggaaaagt aatgattttg    3165
tccccatttt ctctgtaata ttttttttg gcacgagata tgatgcgatc gagcgcggga    3225
gcgagttttg agtatggaat aaggccctgt tccaagaatg cgaagtagac gccggcactg    3285
```

```
ttggttttgg ggggtggtga tgtatttctt attatgagat tagatgtgaa tagtgtctag    3345
tcagtatcgt aatctgaacg tttcatgctc accattgaga tgtgttatca agaatctagc    3405
tggttgcgca cttgcaatag tctagaactc tctctacact cgtttcgatc gcttctgttc    3465
tttttcaata tgtcctttgc attgtgtgat atgaaattgc agcagatatt ggccaaacac    3525
aacaaattgc catgtctctc gtaaatgagc catatttatc cggccggatc atctgcagtt    3585
tcgtccgtgg atgttgctgt agataggccg ctgttgtgtg ggatggtcgt ggtctgctct    3645
atatatcagc ggttagacgt aactggactg ggagttggct gttggcatat gacctgcttc    3705
tgttgtccct ttccatgccc tcgttttcca gctctagcac ttgatgcgag aaacattctc    3765
atgcataatt gagatcagtt agcagatgac ttggaatgcc aattaaggtc aaaccatcgc    3825
accgtcagtg cctgtttgtt gtatttgtat ccgtcctgga gatcaaggtc aactcccagc    3885
gtgctaataa tcggccaaag cctaagcatg gtttcaattc ccagcgtgtg ttatcttctt    3945
gaaactaaca ccgtcaaact ctagaacgta ctagatagtg tgtggccctc aaggtcaacc    4005
aagccacacc ttactagaat cttgtgacgg cagcgagaac gaaccaattg tgcaagtgcc    4065
tttttttctt cttcttcgat ctgtttcgtt tctttgaata gattcttcag gcaacaccac    4125
cagccatgac caaccgcttc gatgccactg atgaatgata atagtcacag atacatagta    4185
cttcacttgc acaacatgat gtgttctaga ggttaaggat ggtgctaaga aagtcaaagc    4245
ttttctatga ggaagaaaaa aaagaagtca aactgcagca tgctctgctc gttttttttaa    4305 attttttttaa tccttttaaa taattttaag atttattttc atcaaaaatt tatttctaaa    4365
catatggtct tttacacttt gcctactagg tgtagtatga ttatttcccc tttctcttac    4425
gtcgtgaaga tgattccgct gcgtcttttg taccatcact ttcgaacttg agggttgttt    4485
cattgtcgta gcacatacac aaggtaccaa gacgtactcg aggaaggatt gatagggaag    4545
taaggaatga gtcataacac cgtacaatat taaggtcatg acatcaagaa              4595
```

<210> SEQ ID NO 9
<211> LENGTH: 337
<212> TYPE: PRT
<213> ORGANISM: Zea mays

<400> SEQUENCE: 9

```
Met Ala Pro Ala Met Ala Ala Pro Pro Pro Pro Ala Cys Phe
  1               5                  10                  15

Pro Met Pro Thr Arg Leu Thr Met Pro Pro Thr Ser Ile Thr Leu Pro
             20                  25                  30

Asp Pro Pro Leu Ser Val Gly Gly Ala Cys Arg Val Ala Ala
         35                  40                  45

Lys His Lys Ala Val Val Val Leu Gly Ala Thr Gly Thr Gly Lys Ser
     50                  55                  60

Arg Leu Ala Ile Asp Leu Ala Leu Arg Phe Gly Gly Glu Val Ile Asn
 65                  70                  75                  80

Ser Asp Lys Ile Gln Ala His Ala Gly Leu Asp Val Ala Thr Asn Lys
                 85                  90                  95

Val Gly Leu Ala Glu Arg Gly Arg Val Pro His His Leu Leu Gly Val
            100                 105                 110

Val His Pro Asp Ala Glu Phe Thr Ala Ala Asp Phe Arg Arg Glu Ala
        115                 120                 125

Ser Arg Ala Ala Asp Arg Ala Ala Arg Gly Arg Val Pro Val Ile
    130                 135                 140
```

```
Ala Gly Gly Ser Asn Ser Tyr Val Glu Glu Leu Val Glu Gly Asp Arg
145                 150                 155                 160

Arg Ala Phe Arg Asp Arg Tyr Glu Cys Cys Phe Leu Trp Val Asp Ala
                165                 170                 175

Gln Leu Pro Val Leu His Gly Phe Val Ala Arg Arg Val Asp Asp Met
            180                 185                 190

Cys Arg Arg Gly Leu Val Asp Glu Val Ala Ala Ala Phe Asp Pro Arg
        195                 200                 205

Arg Thr Asp Tyr Ser Arg Gly Ile Trp Arg Ala Ile Gly Val Pro Glu
    210                 215                 220

Leu Asp Ala Tyr Leu Arg Ala Arg Gly Arg Gly His Gly His His His
225                 230                 235                 240

Asp Gln Met Leu Ala Ala Ala Leu His Glu Ile Lys Ala Asn Thr Ser
                245                 250                 255

Arg Leu Ala Val Arg Gln Arg Gly Lys Ile Gln Arg Leu Glu Arg Met
                260                 265                 270

Trp Arg Val Arg Arg Val Asp Ala Thr Glu Val Phe Leu Lys Arg Gly
            275                 280                 285

Leu Ala Ala Asp Glu Ala Trp Gln Arg Leu Val Ala Ala Pro Cys Ile
290                 295                 300

Asp Ala Val Arg Ser Phe Leu Leu Glu Asp Gln Gln Glu Tyr Ser Ser
305                 310                 315                 320

Met Gly Thr Ala Gly Ala Met Leu Pro Ala Ala Val Ala Ala Ala Ala
                325                 330                 335

Val

<210> SEQ ID NO 10
<211> LENGTH: 1014
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT5 coding sequence

<400> SEQUENCE: 10
atggcggccc cgcgatggc agcgccgccg ccaccgccgg cctgcttccc catgcccacc      60
aggctgacga tgccgccgac gtcgatcacg ctcccggacc cgccgccgct gtctgtcggc    120
ggcgcctgca ggcgcgtggc ggccaagcac aaggccgtgg tggtgctggg cgccacgggc    180
accggcaagt cccgcctggc gatcgacctc gcgctcgcgct tcggcggcga ggtcatcaac    240
tcggacaaga tccaggcgca cgccggcctg acgtggcca ccaacaaggt gggcctcgcc     300
gagcgcgggc gggtgccgca ccacctgctg gcgtggtgc acccggacgc cgagttcacg    360
gcggccgact tccgccgcga ggcctcgcgc gccgcgacc gcgccgcggc gcggggccgg    420
gtgcccgtca tcgccggcgg ctccaactcg tacgtggagg agctcgtcga ggggaccgg   480 cgcgcgttcc gggaccggta cgagtgctgc ttcctctggg tggacgcgca gctccccgtg    540
ctgcacggct tcgtcgcccg ccgcgtcgac gacatgtgcc ggcgcggcct cgtcgacgag    600
gtggcggccg cgttcgaccc ccgccgcacc gactactcca gggcatctg gcgcgccatc    660 ggcgtgccgg agctcgacgc ctacctccgg gcgcgcggcc gcggccacgg ccaccaccac    720
gaccagatgc tcgccgcggc cctccacgag atcaaggcca acacgtcccg cctcgccgtg    780
cgccagcgcg gcaagatcca gcggctcgag cgcatgtggc gcgtccgccg cgtcgacgcc    840
acggaggtgt tcctgaagcg cggcctcgcc gccgacgagg cctggcagcg gctggtcgcc    900
```

-continued

```
gcgccctgca ttgacgccgt caggtccttc ctgctggagg accaacaaga gtacagcagc      960
atgggcaccg ccggcgccat gttgcctgcc gccgtcgcag ccgcggctgt ctaa           1014
```

```
<210> SEQ ID NO 11
<211> LENGTH: 1955
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT6 full length sequence
<220> FEATURE:
<221> NAME/KEY: CDS
<222> LOCATION: (659)...(1675)

<400> SEQUENCE: 11
```

```
ataacatt tagtaatttg tttttctttt atttatatgg accagcagct agtgtatgtg       60 agggctgta aaaatggttc tttacatcct acatgtaaag aattttttcc cctcccatat     120
gcatacaagc tctttgaatg aaagaactgc agtggtgtgg gtctcaggca aacaatccac    180
gtcggaggag gagtgttacg gcgttgcatt tcaccacggt ttactggtga gtgattttt    240 ttttctttaa ggcctccttt agaacacatg gattttatag aaatgatata tgaatttac    300 agaaaatagt tcaaaaccat agaaaaaatg caggattcac gaaataatcg tttgttccaa   360
aggatgcgtt agacttcggc aaatcccatt cgccgcatcc aatccatcca ctacggagtg   420
ttcagccaaa gctttaaact agtcgtcatt cgtcaagaac acaaccacca gcggacaacc   480
cgaccagtga aaccctctgt cccgcccat aaataccca gctttcttct gctcctacac    540
cacgcaccca agcaagccaa gcgacgacca gcagcaagca gccaaggaag ctagctagct   600
agctgaccga ccagctgtga tcgcaagcag ggccgacccc gaccggcagc gtatatac     658
```

```
atg aca ctg tcc atg acg gcc ccc gcg atg gca gca gcg cca ccg gcc      706
Met Thr Leu Ser Met Thr Ala Pro Ala Met Ala Ala Ala Pro Pro Ala
  1               5                  10                  15 tgc tcc ccc atg gcg gcc agg ctg acg atg ccg ccg ctg ccg gac gcc      754
Cys Ser Pro Met Ala Ala Arg Leu Thr Met Pro Pro Leu Pro Asp Ala
             20                  25                  30 gcg gcg ccg ctg tcg gtc gtg ggc tgc agg cgc atg gcg gcc aag cac      802
Ala Ala Pro Leu Ser Val Val Gly Cys Arg Arg Met Ala Ala Lys His
         35                  40                  45 aag gcc gtc gtg gtg ctg ggc gcc acg ggc acc ggc aag tcc cgc ctg      850
Lys Ala Val Val Val Leu Gly Ala Thr Gly Thr Gly Lys Ser Arg Leu
     50                  55                  60 gcg atc gac ctc gct ctg cgc ttc ggc ggc gag gtc atc aac tcc gac      898
Ala Ile Asp Leu Ala Leu Arg Phe Gly Gly Glu Val Ile Asn Ser Asp
 65                  70                  75                  80 aag atc cag gcg tac gcc ggc ctg gac gtg gcc acc aac aag gtg ggg      946
Lys Ile Gln Ala Tyr Ala Gly Leu Asp Val Ala Thr Asn Lys Val Gly
                 85                  90                  95 ccc gcc gag cgc gcg gcg gtg ccg cac cac ctg ctg ggc gtc gtg cac      994
Pro Ala Glu Arg Ala Ala Val Pro His His Leu Leu Gly Val Val His
            100                 105                 110 ccg gac gcc gag ttc acg gcg gcg gac ttc cgg cgc gag gcc gcg ggc     1042
Pro Asp Ala Glu Phe Thr Ala Ala Asp Phe Arg Arg Glu Ala Ala Gly
        115                 120                 125 gcc gcg gcc cgc gtc gcg tcg cgg ggc cgc gtg ccc atc atc gcg ggc     1090
Ala Ala Ala Arg Val Ala Ser Arg Gly Arg Val Pro Ile Ile Ala Gly
    130                 135                 140 ggc tcc aac tcg tac gtg gag gag ctc gtc gag ggg gac cgc cgc gcg     1138
Gly Ser Asn Ser Tyr Val Glu Glu Leu Val Glu Gly Asp Arg Arg Ala
```

```
Gly Ser Asn Ser Tyr Val Glu Glu Leu Val Glu Gly Asp Arg Arg Ala
145                 150                 155                 160 ttc cgg gag agg tac gac tgc tgc ttc ctg tgg gtg gac gcg cgg ctc    1186
Phe Arg Glu Arg Tyr Asp Cys Cys Phe Leu Trp Val Asp Ala Arg Leu
                165                 170                 175 ccc gtg ctg cac ggc ttc gtg gcc cgc cgc gtg gac gag atg tgc cgg    1234
Pro Val Leu His Gly Phe Val Ala Arg Arg Val Asp Glu Met Cys Arg
            180                 185                 190 cgc ggg ctc gtg gac gag gtg gcg gcc gcg ttc gac ccg cgc cgc acc    1282
Arg Gly Leu Val Asp Glu Val Ala Ala Ala Phe Asp Pro Arg Arg Thr
        195                 200                 205 gac tac tcg agg ggc atc tgg cgc gcc atc ggc gtg ccg gag atg gac    1330
Asp Tyr Ser Arg Gly Ile Trp Arg Ala Ile Gly Val Pro Glu Met Asp
    210                 215                 220 gcc tac ctc cgc gcg ggc ggc cac ggc gac ggc gac ggc gac gag cag    1378
Ala Tyr Leu Arg Ala Gly Gly His Gly Asp Gly Asp Gly Asp Glu Gln
225                 230                 235                 240 gag cag cgc gcg cgc atg ctc gcc gcg gcg ctc gac gag atc aag gtc    1426
Glu Gln Arg Ala Arg Met Leu Ala Ala Ala Leu Asp Glu Ile Lys Val
                245                 250                 255 aac acg tcc cgg ctc gcc ctg cgt cag cgc ggc aag atc cag cgg ctg    1474
Asn Thr Ser Arg Leu Ala Leu Arg Gln Arg Gly Lys Ile Gln Arg Leu
            260                 265                 270 gca cgc atg tgg cgc gtc cgc cgc gtc gac gcc acg gag gtg ttc ctg    1522
Ala Arg Met Trp Arg Val Arg Arg Val Asp Ala Thr Glu Val Phe Leu
        275                 280                 285 aag cgc ggc cac gcc gcc gac gag gcc tgg cag cgg ctg gtc gcc gcg    1570
Lys Arg Gly His Ala Ala Asp Glu Ala Trp Gln Arg Leu Val Ala Ala
    290                 295                 300 ccg tgc att gac gcc gtc agg tcc ttc ctg ctg gag gag caa gag tac    1618
Pro Cys Ile Asp Ala Val Arg Ser Phe Leu Leu Glu Glu Gln Glu Tyr
305                 310                 315                 320 agc agc agc atg gtc acc gcc tcc atg ttt gcc tcc acg gcg gcc gcg    1666
Ser Ser Ser Met Val Thr Ala Ser Met Phe Ala Ser Thr Ala Ala Ala
                325                 330                 335 gct gtc tag cctccccca gtggctcacc agctcagcga atggaagaat              1715
Ala Val * gaatggccag cttggctgtg ctgcatgctc tgctgcggtc aaccgcgcgc tgaccggcag   1775
agtggcgctg atgatatagt tgaccctgtc acaagagcag ggaaagtaat tattttgtcc   1835 ccatttctc tgtattttg tacgagatga tgcgatcgag cgcgagagcg agttttgagt    1895
accctgtccc aagagcactg ttgatttggg gtgagactgt gttcagcggt taccccctaaa   1955

<210> SEQ ID NO 12
<211> LENGTH: 338
<212> TYPE: PRT
<213> ORGANISM: Zea mays

<400> SEQUENCE: 12

Met Thr Leu Ser Met Thr Ala Pro Ala Met Ala Ala Pro Pro Ala
 1               5                  10                  15

Cys Ser Pro Met Ala Ala Arg Leu Thr Met Pro Pro Leu Pro Asp Ala
                20                  25                  30

Ala Ala Pro Leu Ser Val Val Gly Cys Arg Arg Met Ala Ala Lys His
            35                  40                  45

Lys Ala Val Val Val Leu Gly Ala Thr Gly Thr Gly Lys Ser Arg Leu
        50                  55                  60

Ala Ile Asp Leu Ala Leu Arg Phe Gly Gly Glu Val Ile Asn Ser Asp
```

Lys Ile Gln Ala Tyr Ala Gly Leu Asp Val Ala Thr Asn Lys Val Gly
65                  70                  75                  80

Pro Ala Glu Arg Ala Ala Val Pro His His Leu Leu Gly Val Val His
            85                  90                  95

Pro Asp Ala Glu Phe Thr Ala Ala Asp Phe Arg Arg Glu Ala Ala Gly
        100                 105                 110

Ala Ala Ala Arg Val Ala Ser Arg Gly Arg Val Pro Ile Ile Ala Gly
    115                 120                 125

Gly Ser Asn Ser Tyr Val Glu Glu Leu Val Glu Gly Asp Arg Arg Ala
145                 150                 155                 160

Phe Arg Glu Arg Tyr Asp Cys Cys Phe Leu Trp Val Asp Ala Arg Leu
                165                 170                 175

Pro Val Leu His Gly Phe Val Ala Arg Val Asp Glu Met Cys Arg
            180                 185                 190

Arg Gly Leu Val Asp Glu Val Ala Ala Ala Phe Asp Pro Arg Arg Thr
        195                 200                 205

Asp Tyr Ser Arg Gly Ile Trp Arg Ala Ile Gly Val Pro Glu Met Asp
    210                 215                 220

Ala Tyr Leu Arg Ala Gly Gly His Gly Asp Gly Asp Gly Asp Glu Gln
225                 230                 235                 240

Glu Gln Arg Ala Arg Met Leu Ala Ala Leu Asp Glu Ile Lys Val
                245                 250                 255

Asn Thr Ser Arg Leu Ala Leu Arg Gln Arg Gly Lys Ile Gln Arg Leu
            260                 265                 270

Ala Arg Met Trp Arg Val Arg Arg Val Asp Ala Thr Glu Val Phe Leu
        275                 280                 285

Lys Arg Gly His Ala Ala Asp Glu Ala Trp Gln Arg Leu Val Ala Ala
    290                 295                 300

Pro Cys Ile Asp Ala Val Arg Ser Phe Leu Leu Glu Glu Gln Glu Tyr
305                 310                 315                 320

Ser Ser Ser Met Val Thr Ala Ser Met Phe Ala Ser Thr Ala Ala Ala
                325                 330                 335

Ala Val

<210> SEQ ID NO 13
<211> LENGTH: 1017
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT6 coding sequence

<400> SEQUENCE: 13
atgacactgt ccatgacggc ccccgcgatg gcagcagcgc caccggcctg ctcccccatg      60
gcggccaggc tgacgatgcc gccgctgccg gacgccgcgg cgccgctgtc ggtcgtgggc     120
tgcaggcgca tggcggccaa gcacaaggcc gtcgtggtgc tgggcgccac gggcaccggc     180
aagtcccgcc tggcgatcga cctcgctctg cgcttcggcg cgaggtcat caactccgac     240 aagatccagg cgtacgccgg cctggacgtg gccaccaaca aggtgggggcc cgccgagcgc     300 gcggcggtgc cgcaccacct gctgggcgtc gtgcacccgg acgccgagtt cacggcggcg     360
gacttccggc gcgaggccgc gggcgccgcg gcccgcgtcg cgtcgcgggg ccgcgtgccc     420
atcatcgcgg gcggctccaa ctcgtacgtg gaggagctcg tcgagggga ccgccgcgcg     480

-continued

```
ttccgggaga ggtacgactg ctgcttcctg tgggtggacg cgcggctccc cgtgctgcac      540
ggcttcgtgg cccgccgcgt ggacgagatg tgccggcgcg ggctcgtgga cgaggtggcg      600
gccgcgttcg acccgcgccg caccgactac tcgaggggca tctggcgcgc catcggcgtg      660
ccggagatgg acgcctacct ccgcgcgggc ggccacggcg acggcgacgg cgacgagcag      720
gagcagcgcg cgcgcatgct cgccgcggcg ctcgacgaga tcaaggtcaa cacgtcccgg      780
ctcgccctgc gtcagcgcgg caagatccag cggctggcac gcatgtggcg cgtccgccgc      840
gtcgacgcca cggaggtgtt cctgaagcgc ggccacgccg ccgacgaggc ctggcagcgg      900
ctggtcgccg cgccgtgcat tgacgccgtc aggtccttcc tgctggagga gcaagagtac      960
agcagcagca tggtcaccgc ctccatgttt gcctccacgg cggccgcggc tgtctag      1017
```

<210> SEQ ID NO 14
<211> LENGTH: 1652
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT7 full length sequence
<220> FEATURE:
<221> NAME/KEY: CDS
<222> LOCATION: (298)...(1356)

<400> SEQUENCE: 14

```
tcaaagactg aaaagtaatt taattgaccc ccggtcaggt caggtcaggt caggtcatgt       60
caggcacaag gcgtgtgtta gggtttcctt gtcgcgtact aacgaagaca tacatacgaa      120
ctgacgggaa acaccagtc aagtctgtgg ctgacttcgt gccgtgcgct cttgaacccg      180
agcactataa aaacggagac ctatgcacgc ttttcattca cccatataca cagccgctac      240
actactacaa gctagcttgt acgtggtaac actgtgaaag acagtcgtac actcacg atg    300
                                                                  Met
                                                                    1
```

```
gcg gga gtt aac ggt gcc acg gcg agc gga ggc gac aac aag gcc aag      348
Ala Gly Val Asn Gly Ala Thr Ala Ser Gly Gly Asp Asn Lys Ala Lys
          5                  10                  15 gtg gtg ctg gtg atg ggc gcc acg gcc acc ggc aag tcc aag ctg gcc      396
Val Val Leu Val Met Gly Ala Thr Ala Thr Gly Lys Ser Lys Leu Ala
     20                  25                  30 atc gac ctc gcg ctg cgc ttc ggc gga gag gtc gtc aac tcc gac aag      444
Ile Asp Leu Ala Leu Arg Phe Gly Gly Glu Val Val Asn Ser Asp Lys
 35                  40                  45 atc cag gtg cac gac ggc ctc gac gtg gtc acc aac aag gtc acc gcc      492
Ile Gln Val His Asp Gly Leu Asp Val Val Thr Asn Lys Val Thr Ala
 50                  55                  60                  65 gcg gag cgc cag ggc gtg cca cac cac ctt atc gac ggg gtg gcg ccc      540
Ala Glu Arg Gln Gly Val Pro His His Leu Ile Asp Gly Val Ala Pro
                 70                  75                  80 gac gcc gac tac acc acc gcc gac ttc tgc agg gac gcc gtg cgc gct      588
Asp Ala Asp Tyr Thr Thr Ala Asp Phe Cys Arg Asp Ala Val Arg Ala
             85                  90                  95 gtg gag tcc att ctc gag agg ggc cgc gtc ccg atc atc gcc ggg ggc      636
Val Glu Ser Ile Leu Glu Arg Gly Arg Val Pro Ile Ile Ala Gly Gly
        100                 105                 110 tcc aac aga tac ctg gag gcg ctg ctg gac ggg gaa cct cct gca ggc      684
Ser Asn Arg Tyr Leu Glu Ala Leu Leu Asp Gly Glu Pro Pro Ala Gly
    115                 120                 125 ttc cgc ggc cgc tac gaa tgc tgc ttc ctc tgg gtc gac agc gac ctg      732
```

```
                Phe Arg Gly Arg Tyr Glu Cys Cys Phe Leu Trp Val Asp Ser Asp Leu
                130                 135                 140                 145 gcg gtg ytg gac cgc tac ata ggg agc cgc gtg gac tgc atg ctg gag              780
Ala Val Xaa Asp Arg Tyr Ile Gly Ser Arg Val Asp Cys Met Leu Glu
            150                 155                 160 cag ggg ctc gtc cgc gag gtg cgg gcc ttc ttt cgg cac gac gac gcc              828
Gln Gly Leu Val Arg Glu Val Arg Ala Phe Phe Arg His Asp Asp Ala
        165                 170                 175 gac tac tcc agg ggt atc cgg agg gcc atc ggc gtg ccg gag atg gac              876
Asp Tyr Ser Arg Gly Ile Arg Arg Ala Ile Gly Val Pro Glu Met Asp
    180                 185                 190 atg tac ttc cgg atg gag gcc gca ggg gct ctc gac ggc gac gat gat              924
Met Tyr Phe Arg Met Glu Ala Ala Gly Ala Leu Asp Gly Asp Asp Asp
195                 200                 205 gat cag ctg cga gtg cgg ctc ctc gcc gcg gcc gtt aac gag atc aag              972
Asp Gln Leu Arg Val Arg Leu Leu Ala Ala Ala Val Asn Glu Ile Lys
210                 215                 220                 225 gcc aac acg tgc ggc ctg gcg cgc cgc cag ctg cag aag atc cac cgg             1020
Ala Asn Thr Cys Gly Leu Ala Arg Arg Gln Leu Gln Lys Ile His Arg
                230                 235                 240 ctc cac ggt ctc caa ggc tgg agc gac atc cac cgc ctc gac gtc acg             1068
Leu His Gly Leu Gln Gly Trp Ser Asp Ile His Arg Leu Asp Val Thr
            245                 250                 255 gag gtg ctt cag ctc aag gtc ggg aac gcc ggg aac cca aag gca cag             1116
Glu Val Leu Gln Leu Lys Val Gly Asn Ala Gly Asn Pro Lys Ala Gln
        260                 265                 270 cgc gac gcg tgg gag acg gac gtc gtc agc cct gcg gcg agg atc gtg             1164
Arg Asp Ala Trp Glu Thr Asp Val Val Ser Pro Ala Ala Arg Ile Val
    275                 280                 285 gga atg ttt ctg gct gtt gag gga gct agg gac aag gac aag gac cgt             1212
Gly Met Phe Leu Ala Val Glu Gly Ala Arg Asp Lys Asp Lys Asp Arg
290                 295                 300                 305 ttc ttg ttg acg acg ccc aaa gaa gtg gcc gtg cca ggc att tgc acg             1260
Phe Leu Leu Thr Thr Pro Lys Glu Val Ala Val Pro Gly Ile Cys Thr
                310                 315                 320 gcc acg gca gat tgg ttc ggc cag cag ctg gac atg acg gtc atg tct             1308
Ala Thr Ala Asp Trp Phe Gly Gln Gln Leu Asp Met Thr Val Met Ser
            325                 330                 335 cca agc aaa ggg ttt gct gga ttg ggc tcg gcg gcc gcc gcg gtt taa             1356
Pro Ser Lys Gly Phe Ala Gly Leu Gly Ser Ala Ala Ala Ala Val *
        340                 345                 350 gctgtgatga cgatgaactc atctgctgat gatcaatcac tgaacggact ccaaatgcat           1416
gtacattcat ttatttcatg tagggaataa gttgttgtaa tgtattgctc ccccactaat           1476
aattaattta aggccaggta taggagaaat tgtaggggag gctgaacgac atagctcata           1536
ctttggaacg ttgtaatcta gccgatcaat ttcacgaaac catatttttt gaaacataat           1596
ctctattcag cattatgcca cgccatttac acaagacctt gtatatatat aaaaag              1652

<210> SEQ ID NO 15
<211> LENGTH: 352
<212> TYPE: PRT
<213> ORGANISM: Zea mays
<220> FEATURE:
<221> NAME/KEY: VARIANT
<222> LOCATION: 148
<223> OTHER INFORMATION: Xaa = Any Amino Acid

<400> SEQUENCE: 15

Met Ala Gly Val Asn Gly Ala Thr Ala Ser Gly Gly Asp Asn Lys Ala
1               5                   10                  15
```

```
Lys Val Val Leu Val Met Gly Ala Thr Ala Thr Gly Lys Ser Lys Leu
             20                  25                  30

Ala Ile Asp Leu Ala Leu Arg Phe Gly Gly Glu Val Asn Ser Asp
         35                  40                  45

Lys Ile Gln Val His Asp Gly Leu Asp Val Val Thr Asn Lys Val Thr
 50                  55                  60

Ala Ala Glu Arg Gln Gly Val Pro His His Leu Ile Asp Gly Val Ala
 65                  70                  75                  80

Pro Asp Ala Asp Tyr Thr Thr Ala Asp Phe Cys Arg Asp Ala Val Arg
                 85                  90                  95

Ala Val Glu Ser Ile Leu Glu Arg Gly Arg Val Pro Ile Ile Ala Gly
             100                 105                 110

Gly Ser Asn Arg Tyr Leu Glu Ala Leu Leu Asp Gly Glu Pro Pro Ala
         115                 120                 125

Gly Phe Arg Gly Arg Tyr Glu Cys Cys Phe Leu Trp Val Asp Ser Asp
130                 135                 140

Leu Ala Val Xaa Asp Arg Tyr Ile Gly Ser Arg Val Asp Cys Met Leu
145                 150                 155                 160

Glu Gln Gly Leu Val Arg Glu Val Arg Ala Phe Phe Arg His Asp Asp
                165                 170                 175

Ala Asp Tyr Ser Arg Gly Ile Arg Arg Ala Ile Gly Val Pro Glu Met
            180                 185                 190

Asp Met Tyr Phe Arg Met Glu Ala Ala Gly Ala Leu Asp Gly Asp Asp
        195                 200                 205

Asp Asp Gln Leu Arg Val Arg Leu Leu Ala Ala Val Asn Glu Ile
210                 215                 220

Lys Ala Asn Thr Cys Gly Leu Ala Arg Arg Gln Leu Gln Lys Ile His
225                 230                 235                 240

Arg Leu His Gly Leu Gln Gly Trp Ser Asp Ile His Arg Leu Asp Val
                245                 250                 255

Thr Glu Val Leu Gln Leu Lys Val Gly Asn Ala Gly Asn Pro Lys Ala
            260                 265                 270

Gln Arg Asp Ala Trp Glu Thr Asp Val Val Ser Pro Ala Ala Arg Ile
        275                 280                 285

Val Gly Met Phe Leu Ala Val Glu Gly Ala Arg Asp Lys Asp Lys Asp
290                 295                 300

Arg Phe Leu Leu Thr Thr Pro Lys Glu Val Ala Val Pro Gly Ile Cys
305                 310                 315                 320

Thr Ala Thr Ala Asp Trp Phe Gly Gln Gln Leu Asp Met Thr Val Met
                325                 330                 335

Ser Pro Ser Lys Gly Phe Ala Gly Leu Gly Ser Ala Ala Ala Ala Val
            340                 345                 350

<210> SEQ ID NO 16
<211> LENGTH: 1059
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT7 coding sequence

<400> SEQUENCE: 16
atggcgggag ttaacggtgc cacggcgagc ggaggcgaca caaggccaa ggtggtgctg      60 gtgatgggcg ccacggccac cggcaagtcc aagctggcca tcgacctcgc gctgcgcttc     120
```

```
ggcggagagg tcgtcaactc cgacaagatc caggtgcacg acggcctcga cgtggtcacc      180
aacaaggtca ccgccgcgga gcgccagggc gtgccacacc accttatcga cggggtggcg      240
cccgacgccg actacaccac cgccgacttc tgcaggggacg ccgtgcgcgc tgtggagtcc     300
attctcgaga ggggccgcgt cccgatcatc gccgggggct ccaacagata cctggaggcg      360
ctgctggacg gggaacctcc tgcaggcttc cgcggccgct acgaatgctg cttcctctgg      420
gtcgacagcg acctggcggt gytgaccgc tacatagggga ccgcgtgga ctgcatgctg       480 gagcaggggc tcgtccgcga ggtgcgggcc ttctttcggc acgacgacgc cgactactcc      540
aggggtatcc ggagggccat cggcgtgccg gagatgacga tgtacttccg gatgggaggcc    600 gcagggggctc tcgacggcga cgatgatgat cagctgcgag tgcggctcct cgccgcggcc     660
gttaacgaga tcaaggccaa cacgtgcggc ctggcgcgcc gccagctgca gaagatccac     720
cggctccacg gtctccaagg ctggagcgac atccaccgcc tcgacgtcac ggaggtgctt      780
cagctcaagg tcgggaacgc cgggaaccca aaggcacagc gcgacgcgtg ggagacggac      840
gtcgtcagcc ctgcggcgag gatcgtggga atgtttctgg ctgttgaggg agctagggac      900
aaggacaagg accgtttctt gttgacgacg cccaaagaag tggccgtgcc aggcatttgc      960
acggccacgg cagattggtt cggccagcag ctggacatga cggtcatgtc tccaagcaaa     1020
gggtttgctg gattgggctc ggcggccgcc gcggtttaa                            1059
```

<210> SEQ ID NO 17
<211> LENGTH: 3419
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT8 full length sequence
<220> FEATURE:
<221> NAME/KEY: CDS
<222> LOCATION: (1897)...(3063)

<400> SEQUENCE: 17

```
gtcttagtgc atcgattcta agagtgaagc aggtagaata ctcacctatt ctctgtaaga       60
tatatgagtg agtttaaata cctctctaca gaccaaattc tagagttttt ttttttccaaa    120 ccgatactga tcggtctcca gtggttggat aaataccgac cttattattc ggtcagcagg     180
cgaagcgacc gcagtgttag cgatcgacga taaaaccatg gtggtcagca ctgatcgcag     240
gcgaggccac gtcgtcgttc cgtaacgctc gtgctgaaac cagcccgagt aaactgtgag    300
ccgcttcttt ttcgagtacg atccgggacc agacgttaca gaaaaaaaaa aggatgagca    360
tgaagctgct gccgaggctg agcatcaagg ctgccttttcc gttcattggc tgggtgcggt     420
tatgggtgca gtactgcagt gctgcgcagt cgagtcgtgc tcgtctccat cctactcacc    480
atgtgcagcc gactttcata tagaaccgga ggctgacaga cagacagaca cagagccg       540 ctacgctact ggatcaccgc cggccagggg aacgagaggc atggccgcat catcaccagc     600
catgggttag tagtcaccca aattcttcct cgcatcgcac gcgccgcgcg gtcaagccac     660
gacacgagac ggaggattac gaaaaggaac ggaacggaac cgcccgtcgc gtcgcacgcc    720
gggaccggga tgggcgcgga cgcgagcccg gaggcaggcc gaaaggtcgc cggccggctg    780
gccggacgga cggaagggga ggcgggagga aacgaagcct gtcgtgtcgt gtcgtgtcgt     840
gcgaggcagc cagcgccgca ggtcgcagtc tctggagtct ggaccggcc gaaaaggcgt       900 gccgggacca ggaccagaac ccggacccgg atccaacaga agatgtacta ttggcaggag    960
```

```
cagtcggaag cggacgcgcg cgcacccgac acgatggggg cgccagtgcc accaactcag    1020
cagccagtgg ccggccgggc ccaaagcggc tggagcttgc cgtgccggct gcctgccgaa    1080
tccaagcgaa gcgcaccggc gcggctaccc gcacccgctc gcggctgccc tgccctccca    1140
ctagtcccgg ctctgctgct cgcctcggaa tgttctcgcc gcctgcgggg acgacacgcg    1200
acgcttatta taaccacgcc tctgtccggc ggtcgccctg ccaccgcccg gcacccggca    1260
cccgccacct ggttttgttg gcgtccctcg cgctgccact gcgagctggg tggggatcgg    1320
ggccccggtc catccggaca ggaagccccg catggccgcg accgccatca tgggccgacg    1380
tacagcgtcc gcttttgttt aaggtccccc gcgcatcgca tcgatcgtgt cgtgtcgtgg    1440
caattgcttt cggagtgtcg agcgccactc ctgcaaagcc tgtgctgtgc tgctgccttg    1500
tattgtatat atacacacgc acacacaacg agtcgagccg agcaatactg gcacggcgcg    1560 ttgcccccctg ccagacagca cggccaacgc caccccacca gtccaacagc aggcggtggc    1620
cgaggaggag ggaatagccg aatagggatt tttgaggttt tcggcggcag aaatacgagc    1680
gaaaactcaa acaggcgcg cgactgaaga gagagcgcta gctggaagag acgggcgagc    1740
cgatctggcg tggcagccgt tccctgcccc gtccccgcat aaatcccaac aaggacgctg    1800
gcgctgcgtg tatctccctc gcaagagaca aaaaaaaata tcacacacac ggcgcggcgg    1860
tcatagtgcg gctgattcgg atcgggcact agctac atg acc acc ctc ctc gcc    1914
                                        Met Thr Thr Leu Leu Ala
                                          1               5 aat agg atc act acg ctc gtg cgc gcc cct cct cct ccc atg gcc gcc    1962
Asn Arg Ile Thr Thr Leu Val Arg Ala Pro Pro Pro Pro Met Ala Ala
            10                  15                  20 gcc gcc gtc gcg gga gcg cgg agg cca ttg cac cgg acc ttg gcg cac    2010
Ala Ala Val Ala Gly Ala Arg Arg Pro Leu His Arg Thr Leu Ala His
        25                  30                  35 ccg cca ccg ccc gag gag gac gag cat cag cag cag cgc gcg tgc cgc    2058
Pro Pro Pro Pro Glu Glu Asp Glu His Gln Gln Gln Arg Ala Cys Arg
    40                  45                  50 agc agg gga tcc tcg tcc tcc tgc tcg gct tcc tcg tca tcg acg ccc    2106
Ser Arg Gly Ser Ser Ser Ser Cys Ser Ala Ser Ser Ser Ser Thr Pro
55                  60                  65                  70 gcc cgg ccc cgg ggc acg ggg atg gtg gtg atc gtc ggc gcc acg ggc    2154
Ala Arg Pro Arg Gly Thr Gly Met Val Val Ile Val Gly Ala Thr Gly
                75                  80                  85 acc ggg aag acc aag ctg tcc atc gac gcc gcg gag gcg gtc ggc ggg    2202
Thr Gly Lys Thr Lys Leu Ser Ile Asp Ala Ala Glu Ala Val Gly Gly
            90                  95                  100 gag gtg gtg aac gcg gat aag atc cag ctc tac gcc ggg ctg gac gtg    2250
Glu Val Val Asn Ala Asp Lys Ile Gln Leu Tyr Ala Gly Leu Asp Val
        105                 110                 115 acc acg aac aag gtg gcc ccc gcg gac cgc cgc ggc gtg ccg cac cac    2298
Thr Thr Asn Lys Val Ala Pro Ala Asp Arg Arg Gly Val Pro His His
    120                 125                 130 ctc ctc ggc gcc atc cgc ccc gag gcc ggc gag ctc ccg ccc tcc acg    2346
Leu Leu Gly Ala Ile Arg Pro Glu Ala Gly Glu Leu Pro Pro Ser Thr
135                 140                 145                 150 ttc cgc tcc ctc gcc gcc gcc acg gcc gcc tcg atc gcc gcg cgc ggc    2394
Phe Arg Ser Leu Ala Ala Ala Thr Ala Ala Ser Ile Ala Ala Arg Gly
                155                 160                 165 cgc ctg ccg gtc gtc gcg ggc ggc tcc aac tcc ctc atc cac gcg ctc    2442
Arg Leu Pro Val Val Ala Gly Gly Ser Asn Ser Leu Ile His Ala Leu
            170                 175                 180
```

```
ctc gcc gac cgc ctc gac gcc ggc gcc gcc gac ccc ttc tcc gct cca      2490
Leu Ala Asp Arg Leu Asp Ala Gly Ala Ala Asp Pro Phe Ser Ala Pro
        185                 190                 195 ccg cag ccg gcg ccg ccg cgg tgg ggc cgc cgg ccc gcg ctc cga tcc      2538
Pro Gln Pro Ala Pro Pro Arg Trp Gly Arg Arg Pro Ala Leu Arg Ser
200                 205                 210 ccg tgc tgt ctc ctc tgg gtc cac gtc gac gcc gcg ctc ctc gcg gag      2586
Pro Cys Cys Leu Leu Trp Val His Val Asp Ala Ala Leu Leu Ala Glu
215                 220                 225                 230 tac ctg gac cgg cgc gtg gac gac atg gtg cgc ggc ggc atg gtg gag      2634
Tyr Leu Asp Arg Arg Val Asp Asp Met Val Arg Gly Gly Met Val Glu
            235                 240                 245 gag ctg cgg gag tac ttc gcc gcg acc acc gcc gcc gag cgc gcc gcg      2682
Glu Leu Arg Glu Tyr Phe Ala Ala Thr Thr Ala Ala Glu Arg Ala Ala
        250                 255                 260 cac gcc gcg ggg ctg ggc agg gcc atc ggc gtg ccc gag ctg ggc gcc      2730
His Ala Ala Gly Leu Gly Arg Ala Ile Gly Val Pro Glu Leu Gly Ala
        265                 270                 275 tgc ttc gcg ggg cgc gcc agc ttc cgc gcc gcg atc gac gac atc aag      2778
Cys Phe Ala Gly Arg Ala Ser Phe Arg Ala Ala Ile Asp Asp Ile Lys
280                 285                 290 gcc aac acg cgg gac ctg gcc gcc gcg cag gtg cgc aag atc cga cgc      2826
Ala Asn Thr Arg Asp Leu Ala Ala Ala Gln Val Arg Lys Ile Arg Arg
295                 300                 305                 310 atg gcc gat gcc tgg ggc tgg ccc atc cag cgg ctc gac gcg tcg gcc      2874
Met Ala Asp Ala Trp Gly Trp Pro Ile Gln Arg Leu Asp Ala Ser Ala
            315                 320                 325 aca gtc cgc gcg cgc ctc cgc ggc gcg ggg ccc gac gcg gag tcg gcg      2922
Thr Val Arg Ala Arg Leu Arg Gly Ala Gly Pro Asp Ala Glu Ser Ala
        330                 335                 340 tgc tgg gag cgc gac gtg cgc gcg ccc ggg ctc gcc gcc atc cgg agc      2970
Cys Trp Glu Arg Asp Val Arg Ala Pro Gly Leu Ala Ala Ile Arg Ser
        345                 350                 355 ttc ctt cta gag ctg gac ggc ggc agc gtc gtc gac ggc gct gtg gtg      3018
Phe Leu Leu Glu Leu Asp Gly Gly Ser Val Val Asp Gly Ala Val Val
360                 365                 370 gag gag gtg gag ccg cgg gtg cga tgc tgc gac gtg gtg ggg tga          3063
Glu Glu Val Glu Pro Arg Val Arg Cys Cys Asp Val Val Gly *
375                 380                 385 gcgagctcgg tcctcagctg ctgtcacttt ccgggcggag ttattcgcga tatacgccgc    3123
gaaaaggctg cggggggctt ttggactcga gggtttaggc cgccgatttt gcagggtccc    3183
ggcggccgct gaccggtggg gtccggcgaa gggcacagcg agtgagtgag tgacacaggg    3243
acatgagaat gagagaagga gacagaggga gaaaagaaaa tgcttcatgt ttagtgttta    3303
ctacaaatca ttactattag ttaccattag tgtaggcaga gataagcatt gatgaaggga    3363
gagggaggag actgtgaatt cgagggtat ctttcttct ttttgctttt ggttcg         3419

<210> SEQ ID NO 18
<211> LENGTH: 388
<212> TYPE: PRT
<213> ORGANISM: Zea mays

<400> SEQUENCE: 18

Met Thr Thr Leu Leu Ala Asn Arg Ile Thr Thr Leu Val Arg Ala Pro
1               5                   10                  15

Pro Pro Pro Met Ala Ala Ala Val Ala Gly Ala Arg Arg Pro Leu
            20                  25                  30

His Arg Thr Leu Ala His Pro Pro Pro Pro Glu Glu Asp Glu His Gln
```

-continued

```
                      35                  40                  45
Gln Gln Arg Ala Cys Arg Ser Arg Gly Ser Ser Ser Cys Ser Ala
 50                  55                  60

Ser Ser Ser Ser Thr Pro Ala Arg Pro Arg Gly Thr Gly Met Val Val
 65                  70                  75                  80

Ile Val Gly Ala Thr Gly Thr Gly Lys Thr Lys Leu Ser Ile Asp Ala
                     85                  90                  95

Ala Glu Ala Val Gly Gly Glu Val Val Asn Ala Asp Lys Ile Gln Leu
                100                 105                 110

Tyr Ala Gly Leu Asp Val Thr Thr Asn Lys Val Ala Pro Ala Asp Arg
                115                 120                 125

Arg Gly Val Pro His His Leu Leu Gly Ala Ile Arg Pro Glu Ala Gly
            130                 135                 140

Glu Leu Pro Pro Ser Thr Phe Arg Ser Leu Ala Ala Thr Ala Ala
145                 150                 155                 160

Ser Ile Ala Ala Arg Gly Arg Leu Pro Val Val Ala Gly Ser Asn
                165                 170                 175

Ser Leu Ile His Ala Leu Leu Ala Asp Arg Leu Asp Ala Gly Ala Ala
                180                 185                 190

Asp Pro Phe Ser Ala Pro Pro Gln Pro Ala Pro Arg Trp Gly Arg
            195                 200                 205

Arg Pro Ala Leu Arg Ser Pro Cys Cys Leu Leu Trp Val His Val Asp
210                 215                 220

Ala Ala Leu Leu Ala Glu Tyr Leu Asp Arg Arg Val Asp Asp Met Val
225                 230                 235                 240

Arg Gly Gly Met Val Glu Glu Leu Arg Glu Tyr Phe Ala Ala Thr Thr
                245                 250                 255

Ala Ala Glu Arg Ala Ala His Ala Gly Leu Gly Arg Ala Ile Gly
                260                 265                 270

Val Pro Glu Leu Gly Ala Cys Phe Ala Gly Arg Ala Ser Phe Arg Ala
            275                 280                 285

Ala Ile Asp Asp Ile Lys Ala Asn Thr Arg Asp Leu Ala Ala Ala Gln
290                 295                 300

Val Arg Lys Ile Arg Arg Met Ala Asp Ala Trp Gly Trp Pro Ile Gln
305                 310                 315                 320

Arg Leu Asp Ala Ser Ala Thr Val Arg Ala Arg Leu Arg Gly Ala Gly
                325                 330                 335

Pro Asp Ala Glu Ser Ala Cys Trp Glu Arg Asp Val Arg Ala Pro Gly
            340                 345                 350

Leu Ala Ala Ile Arg Ser Phe Leu Leu Glu Leu Asp Gly Gly Ser Val
                355                 360                 365

Val Asp Gly Ala Val Val Glu Glu Val Glu Pro Arg Val Arg Cys Cys
            370                 375                 380

Asp Val Val Gly
385

<210> SEQ ID NO 19
<211> LENGTH: 1167
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT8 coding sequence

<400> SEQUENCE: 19
```

```
atgaccaccc tcctcgccaa taggatcact acgctcgtgc gcgcccctcc tcctcccatg      60
gccgccgccg ccgtcgcggg agcgcggagg ccattgcacc ggaccttggc gcacccgcca     120
ccgcccgagg aggacgagca tcagcagcag cgcgcgtgcc gcagcagggg atcctcgtcc     180
tcctgctcgg cttcctcgtc atcgacgccc gcccggcccc ggggcacggg gatggtggtg     240
atcgtcggcg ccacgggcac cgggaagacc aagctgtcca tcgacgccgc ggaggcggtc     300
ggcggggagg tggtgaacgc ggataagatc cagctctacg ccgggctgga cgtgaccacg     360
aacaaggtgg cccccgcgga ccgccgcggc gtgccgcacc acctcctcgg cgccatccgc     420
cccgaggccg cgagctccc gccctccacg ttccgctccc tcgccgccgc cacggccgcc     480
tcgatcgccg cgcgcggccg cctgccggtc gtcgcgggcg gctccaactc cctcatccac     540
gcgctcctcg ccgaccgcct cgacgccggc gccgccgacc ccttctccgc tccaccgcag     600
ccggcgccgc cgcggtgggg ccgccggccc gcgctccgat ccccgtgctg tctcctctgg     660
gtccacgtcg acgccgcgct cctcgcggag tacctggacc ggcgcgtgga cgacatggtg     720
cgcggcggca tggtggagga gctgcgggag tacttcgccg cgaccaccgc cgccgagcgc     780
gccgcgcacg ccgcggggct gggcagggcc atcggcgtgc ccgagctggg cgcctgcttc     840
gcggggcgcg ccagcttccg cgccgcgatc gacgacatca aggccaacac gcgggacctg     900
gcggccgcgc aggtgcgcaa gatccgacgc atggccgatg cctggggctg gcccatccag     960
cggctcgacg cgtcggccac agtccgcgcg cgcctccgcg gcgcggggcc cgacgcggag    1020
tcggcgtgct gggagcgcga cgtgcgcgcg cccgggctcg ccgccatccg gagcttcctt    1080
ctagagctgg acggcggcag cgtcgtcgac ggcgctgtgg tggaggaggt ggagccgcgg    1140
gtgcgatgct gcgacgtggt ggggtga                                        1167
```

<210> SEQ ID NO 20
<211> LENGTH: 1535
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT9 full length sequence

<400> SEQUENCE: 20

```
gcttgcttgt aaccgatggc actacttgca gagttcatac gtggctgcaa cccgatatca      60
agcagccatg aggcttccga agtaagccg cctgtgtcaa ccagcatttc ttcacacctc     120
agatcaattg accggtacag ttcaatgcgt ggacttgcga ggaaaatgca gaagaagtca     180
tactccatct ccctggcctc gtagtttcca gcggatgagg gagcctcagt taggtcagtg     240
tcatgctgtt cacagaatgc atcgtacggt aaggcgaagg cagaaggagg ggagcctgat     300
gacctgataa tctcgaggct gcggctcaat ctgttccagt tattgacaga caagtcccgg     360
gctctggggt caccagcctg caccaccagc tctaccgctt cctcccactg gccgttctcc     420
cgaaaatcag cgagctcaga ccacacggcc aaagtggact ccatggatga ctgtggaacg     480
ttcggcttgc catagatgta ccatctcagg tacagcccag tcctcctgc gataacgggc     540 acgcagcctc tgtcaagaac atcctgcgtc gcctccggg catcgcggaa aaaggctcca     600
gccgagtaat cgtcggacgt gtccagtatg tcgatcaagt gatgcggcac taggctcatc     660 tccgccgcg acggtttggc agaaccaacg tcaaggccac ggtagacttg cacggagtcc     720
gcactgatga tctcccctcc gagcctcctg gccacctcca gcgccagcct gctctttcca     780
```

| | |
|---|---|
| gcaccagtag gaccagagat gacgatgacc gtgtccttct tcttatgatg agttggtggt | 840 |
| ggcagagacg aggcggccat cgtggcggcc ttggttgagg cacagaaaga tggtagaagc | 900 |
| ctgtgctgtg actgcaagca caggataggc cagctcctcc agatggcacg ccgcatcgcc | 960 |
| cccagctgct gtggcctcat ctcgccggac atgataaagg aagagtatct gccaaagacg | 1020 |
| cagacagaaa ttcagggtag gctacgtgat ttgctgagat gaaaatgctg cttgacagcg | 1080 |
| tttgaagtcc tgcaggcatt tcatcataca cctaggtagg actcagtcga gagccattgc | 1140 |
| tcctggcttg gctcggagtc atagagtggt agccttattt agccatcgtt agcaacaagg | 1200 |
| aagtggtgag tgtgaatgtg caggaagaag tacccatgga gaactgtatg tgaattcaaa | 1260 |
| cggaggatgc gtacttgtgg ctgtggctgc ggcggcgagc tccgacaagg ttgctctcgc | 1320 |
| aagctacaag gaggggagga gtgggggaac ggaagccatt ccgcttacct tgagccagca | 1380 |
| acttccggcc tctcctccgt cccaccgccg gcgtggcgtg gtgcgcctca gcgcctggcc | 1440 |
| gccgcgcttc cgaggacggc cagggagcag ccgtcggcgc ctcgggcgtt aggctatccg | 1500 |
| cactcatata actctaaatt tctactctaa aagaa | 1535 |

<210> SEQ ID NO 21
<211> LENGTH: 3000
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT1 genomic sequence

<400> SEQUENCE: 21

| | |
|---|---|
| tttctgcaaa agtatctaag ttgattcttg ttaaagcctc tccttgattc ccaaatccag | 60 |
| catacccttg agagtctttt ctttagtcgg gtaagtcttg ctgagtaatt ccatactcag | 120 |
| ggttttattc cctgttgttt ttcaggtcat agttttgtgc tgttgatgat ggtgttaagt | 180 |
| gccggtgggc tcggccttct tataagtcta agtaacccct ctaaacttct taatgaggat | 240 |
| ggtcccttga gctagcatat atttcaaact tatactttg caatcactcc gataaaataa | 300 |
| tataaaattt ttgtaacttg taaaatttgg taacaaggtt ttcgctgcaa aaatattggt | 360 |
| gtgtgtgatt tgtgttactt aatcccgagg ttctggttgt aagtggttta tccggtgtcc | 420 |
| ttggggcaat cggacggatc ctgttaagtt atctggtgca catgcatagc agtctgaggt | 480 |
| ctttgagaca aggacaggtg catgtgggcc caataacttg ggaggttctg ccacaattat | 540 |
| tagcaagata tcggagatat ttatgtgcta tatttttact atagaggagt gagacgaaga | 600 |
| gtgttatgta agttacagag tagaaacaaa ttctactact gtataaaatc atttcacatc | 660 |
| ccccatccca tgaatttgag ataggcttat atctaaactt tggaaagtgg tggaatgtca | 720 |
| aattccaaac taaataagtt actttagtga gtgaattcca attcctttaa aatgaaggga | 780 |
| tccaaacgcc ccgtaaggaa aatagaaatc ccttaggctt tgtttgggta aagagagatt | 840 |
| gaagtggatt aaggtgtatt gaaggagatt aaaataaaaa ttagttcata ttacacttca | 900 |
| atacacctca taccacctca atccactcca atctgagatt acccaaacaa gtccttagta | 960 |
| aaattgtgtt cccaaactat gctctaattt tactagcatt ttttatccac taactattag | 1020 |
| ctccaaacac cccctaattt tagtagcaag agcaaggaaa accccccagc catcttcatc | 1080 |
| tgcctgctgg tgccggactg acggttagag atggcccacc cctcctccgc cgccgccgta | 1140 |
| tcctccacgg cgcccgctgc aaaccctagt tatggcgccc gcgaggaagg aggcgcccgc | 1200 |
| tctccgccgt ctccgtctcc gtctccgtct cagaggggc gggccaaggt ggtgatcgtt | 1260 |

```
atgggcgcca cgggcgccgg caagtcgcgg ctggccgtcg acctcgcggc ccacttcgcc    1320
ggcgtcgagg tggtcagcgc cgactccatg cagctctacc gcggcctcga cgtcctcacc    1380
aacaaggctc ccctccacga gcagaacggt ctgtttctga ctcctcaccg cctcccccct    1440
aatttcagtt tcctgtcaga ttaaatgctc gagcctgttc catgcgtgtt tgcaggtgtt    1500
cctcatcatc tacttagcgt gattgatccc tctgtcgagt tcacttgccg tgatttccgc    1560
gaccgtgccc tgccggtaag ccagtgctgc tgccagccac tgcctctaca agttccagca    1620
cttgctttag ttggtcacat gatagctaag gccttcccct ctgctcacag attatacagg    1680
aaatagtgga ccgcggtggc ctccctgtgg ttgtcggcgg cacaaacttc tacatccagg    1740
ttcaaatttg aagtgtccta atttctgtat ggttttctgg gtgaccgcag tgtctgaacc    1800
accgtcgtgt ttttgcccac aaaatactcc aggctctcgt tagcccattc ctcttggatg    1860
atatggcaga agaaatgcag ggctgtactc tgagagatca catagatgat ggtataggcg    1920
agtaatgagt catgctaaat gttccttgtt cttagtatga acaatcagcg gttgacatgt    1980
atgccaatcg tcaggcctta ccgatgaaga tgaaggcaat gggtttgaac gcttgaagga    2040
gatcgatcct gtggctgcgc agaggatcca tccaaacgac catagaaaag taagggtgtt    2100
gcccaagttt ttcctgactt tatgcagctc ttgagctcta ccatgttaga attacttctt    2160
gtacaggtgc tcattttcct actgccgttg attgcttgtg tatttttcgt tctgcatggg    2220
ttggtgtatc acaaagatca aacgctacct cgagttgtat gcaaccacgg gtgccctacc    2280
cagcgatctg ttccaaggag aggccgctaa ggtgaggaat ttttcgctgc acttgtctgc    2340
tctgcttgta taatatcctc cctttgtcat gaacatgagc cgacaattgc ctcacaaggc    2400
tcttcttttt ttggttttgt ttccctaatt gagtataaac ttgctgggaa ttcctgctca    2460
tcatgtcaga acagaaatgg ggtcggccta gtaactccag actcgactgc tgtttcctgt    2520
gggtagatgc tgatcttcaa gtcctggaca gttatgtcaa caaaagggtc gattgcatga    2580
tggatggtgg cctgctggac gaagtatgca gcatatatga tgcggatgct gtctataccc    2640
aggggctgcg gcaggctatt ggggttcgtg agtttgacga ttttttcaga gcatatttac    2700
ccagaaaaga atctggtgag ggttcctgtg caagcctgtt aggtatgcat gacgatcagc    2760
ttaagagctt gttggacgaa gctgtttccc agctgaaggc aaacactcgt agactagttc    2820
gacgtcaagt aagcacttag tatcctgtgt atttttttat gttgttgtgt tgttttagaa    2880
tactgtgcga ctgaacacac ggatacttgg ctcaatgtag acttcttagc gtttcttttt    2940
ttttctccat taaataaaag agacggagat tgcatcggct gagtaaagat tttgggtgga    3000
```

<210> SEQ ID NO 22
<211> LENGTH: 1209
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT1 full length (derived from ZmIPT1 genomic clone)
<220> FEATURE:
<221> NAME/KEY: CDS
<222> LOCATION: (1)...(1062)

<400> SEQUENCE: 22

```
atg gcc cac ccc tcc tcc gcc gcc gcc gta tcc tcc acg gcg ccc gct       48
Met Ala His Pro Ser Ser Ala Ala Ala Val Ser Ser Thr Ala Pro Ala
1               5                   10                  15
```

-continued

| | |
|---|---|
| gca aac cct agt tat ggc gcc cgc gag gaa gga ggc gcc cgc tct ccg<br>Ala Asn Pro Ser Tyr Gly Ala Arg Glu Glu Gly Gly Ala Arg Ser Pro<br>    20       25       30 | 96 |
| ccg tct ccg tct ccg tct ccg tct cag agg ggg cgg gcc aag gtg gtg<br>Pro Ser Pro Ser Pro Ser Pro Ser Gln Arg Gly Arg Ala Lys Val Val<br>    35       40       45 | 144 |
| atc gtt atg ggc gcc acg ggc gcc ggc aag tcg cgg ctg gcc gtc gac<br>Ile Val Met Gly Ala Thr Gly Ala Gly Lys Ser Arg Leu Ala Val Asp<br>50        55       60 | 192 |
| ctc gcg gcc cac ttc gcc ggc gtc gag gtg gtc agc gcc gac tcc atg<br>Leu Ala Ala His Phe Ala Gly Val Glu Val Val Ser Ala Asp Ser Met<br>65        70       75       80 | 240 |
| cag ctc tac cgc ggc ctc gac gtc ctc acc aac aag gct ccc ctc cac<br>Gln Leu Tyr Arg Gly Leu Asp Val Leu Thr Asn Lys Ala Pro Leu His<br>        85       90       95 | 288 |
| gag cag aac ggt gtt cct cat cat cta ctt agc gtg att gat ccc tct<br>Glu Gln Asn Gly Val Pro His His Leu Leu Ser Val Ile Asp Pro Ser<br>    100       105       110 | 336 |
| gtc gag ttc act tgc cgt gat ttc cgc gac cgt gcc ctg ccg att ata<br>Val Glu Phe Thr Cys Arg Asp Phe Arg Asp Arg Ala Leu Pro Ile Ile<br>        115       120       125 | 384 |
| cag gaa ata gtg gac cgc ggt ggc ctc cct gtg gtt gtc ggc ggc aca<br>Gln Glu Ile Val Asp Arg Gly Gly Leu Pro Val Val Val Gly Gly Thr<br>130        135       140 | 432 |
| aac ttc tac atc cag gct ctc gtt agc cca ttc ctc ttg gat gat atg<br>Asn Phe Tyr Ile Gln Ala Leu Val Ser Pro Phe Leu Leu Asp Asp Met<br>145        150       155       160 | 480 |
| gca gaa gaa atg cag ggc tgt act ctg aga gat cac ata gat gat ggc<br>Ala Glu Glu Met Gln Gly Cys Thr Leu Arg Asp His Ile Asp Asp Gly<br>        165       170       175 | 528 |
| ctt acc gat gaa gat gaa ggc aat ggg ttt gaa cgc ttg aag gag atc<br>Leu Thr Asp Glu Asp Glu Gly Asn Gly Phe Glu Arg Leu Lys Glu Ile<br>    180       185       190 | 576 |
| gat cct gtg gct gcg cag agg atc cat cca aac gac cat aga aaa atc<br>Asp Pro Val Ala Ala Gln Arg Ile His Pro Asn Asp His Arg Lys Ile<br>        195       200       205 | 624 |
| aaa cgc tac ctc gag ttg tat gca acc acg ggt gcc cta ccc agc gat<br>Lys Arg Tyr Leu Glu Leu Tyr Ala Thr Thr Gly Ala Leu Pro Ser Asp<br>210        215       220 | 672 |
| ctg ttc caa gga gag gcc gct aag aaa tgg ggt cgg cct agt aac tcc<br>Leu Phe Gln Gly Glu Ala Ala Lys Lys Trp Gly Arg Pro Ser Asn Ser<br>225        230       235       240 | 720 |
| aga ctc gac tgc tgt ttc ctg tgg gta gat gct gat ctt caa gtc ctg<br>Arg Leu Asp Cys Cys Phe Leu Trp Val Asp Ala Asp Leu Gln Val Leu<br>        245       250       255 | 768 |
| gac agt tat gtc aac aaa agg gtc gat tgc atg atg gat ggt ggc ctg<br>Asp Ser Tyr Val Asn Lys Arg Val Asp Cys Met Met Asp Gly Gly Leu<br>    260       265       270 | 816 |
| ctg gac gaa gta tgc agc ata tat gat gcg gat gct gtc tat acc cag<br>Leu Asp Glu Val Cys Ser Ile Tyr Asp Ala Asp Ala Val Tyr Thr Gln<br>275        280       285 | 864 |
| ggg ctg cgg cag gct att ggg gtt cgt gag ttt gac gag ttt ttc aga<br>Gly Leu Arg Gln Ala Ile Gly Val Arg Glu Phe Asp Glu Phe Phe Arg<br>    290       295       300 | 912 |
| gca tat tta ccc aga aaa gaa tct ggt gag ggt tcc tgt gca agc ctg<br>Ala Tyr Leu Pro Arg Lys Glu Ser Gly Glu Gly Ser Cys Ala Ser Leu<br>305        310       315       320 | 960 |
| tta ggt atg cat gac gat cag ctt aag agc ttg ttg gac gaa gct gtt<br>Leu Gly Met His Asp Asp Gln Leu Lys Ser Leu Leu Asp Glu Ala Val<br>        325       330       335 | 1008 |

```
tcc cag ctg aag gca aac act cgt aga cta gtt cga cgt caa gta agc    1056
Ser Gln Leu Lys Ala Asn Thr Arg Arg Leu Val Arg Arg Gln Val Ser
            340                 345                 350 act tag tatcctgtgt attttttat gttgttgtgt tgttttagaa tactgtgcga       1112
Thr * ctgaacacac ggatacttgg ctcaatgtag acttcttagc gtttcttttt ttttctccat   1172
taaataaaag agacggagat tgcatcggct gagtaaa                            1209
```

<210> SEQ ID NO 23
<211> LENGTH: 353
<212> TYPE: PRT
<213> ORGANISM: Zea mays

<400> SEQUENCE: 23

```
Met Ala His Pro Ser Ser Ala Ala Val Ser Ser Thr Ala Pro Ala
 1               5                  10                  15

Ala Asn Pro Ser Tyr Gly Ala Arg Glu Glu Gly Gly Ala Arg Ser Pro
                20                  25                  30

Pro Ser Pro Ser Pro Ser Pro Ser Gln Arg Gly Arg Ala Lys Val Val
            35                  40                  45

Ile Val Met Gly Ala Thr Gly Ala Gly Lys Ser Arg Leu Ala Val Asp
50                  55                  60

Leu Ala Ala His Phe Ala Gly Val Glu Val Ser Ala Asp Ser Met
65                  70                  75                  80

Gln Leu Tyr Arg Gly Leu Asp Val Leu Thr Asn Lys Ala Pro Leu His
                85                  90                  95

Glu Gln Asn Gly Val Pro His His Leu Leu Ser Val Ile Asp Pro Ser
            100                 105                 110

Val Glu Phe Thr Cys Arg Asp Phe Arg Asp Arg Ala Leu Pro Ile Ile
        115                 120                 125

Gln Glu Ile Val Asp Arg Gly Gly Leu Pro Val Val Gly Gly Thr
130                 135                 140

Asn Phe Tyr Ile Gln Ala Leu Val Ser Pro Phe Leu Leu Asp Asp Met
145                 150                 155                 160

Ala Glu Glu Met Gln Gly Cys Thr Leu Arg Asp His Ile Asp Asp Gly
                165                 170                 175

Leu Thr Asp Glu Asp Glu Gly Asn Gly Phe Glu Arg Leu Lys Glu Ile
            180                 185                 190

Asp Pro Val Ala Ala Gln Arg Ile His Pro Asn Asp His Arg Lys Ile
        195                 200                 205

Lys Arg Tyr Leu Glu Leu Tyr Ala Thr Thr Gly Ala Leu Pro Ser Asp
210                 215                 220

Leu Phe Gln Gly Glu Ala Ala Lys Lys Trp Gly Arg Pro Ser Asn Ser
225                 230                 235                 240

Arg Leu Asp Cys Cys Phe Leu Trp Val Asp Ala Asp Leu Gln Val Leu
                245                 250                 255

Asp Ser Tyr Val Asn Lys Arg Val Asp Cys Met Met Asp Gly Gly Leu
            260                 265                 270

Leu Asp Glu Val Cys Ser Ile Tyr Asp Ala Asp Ala Val Tyr Thr Gln
        275                 280                 285

Gly Leu Arg Gln Ala Ile Gly Val Arg Glu Phe Asp Glu Phe Phe Arg
    290                 295                 300

Ala Tyr Leu Pro Arg Lys Glu Ser Gly Glu Gly Ser Cys Ala Ser Leu
305                 310                 315                 320
```

```
Leu Gly Met His Asp Asp Gln Leu Lys Ser Leu Leu Asp Glu Ala Val
            325                 330                 335

Ser Gln Leu Lys Ala Asn Thr Arg Arg Leu Val Arg Arg Gln Val Ser
            340                 345                 350

Thr

<210> SEQ ID NO 24
<211> LENGTH: 1062
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT1 coding sequence

<400> SEQUENCE: 24
atggcccacc cctcctccgc cgccgccgta tcctccacgg cgcccgctgc aaaccctagt      60 tatgcgccc  gcgaggaagg aggcgcccgc tctccgccgt ctccgtctcc gtctccgtct     120 cagaggggggc gggccaaggt ggtgatcgtt atgggcgcca cgggcgccgg caagtcgcgg    180
ctggccgtcg acctcgcggc ccacttcgcc ggcgtcgagg tggtcagcgc cgactccatg    240
cagctctacc gcggcctcga cgtcctcacc aacaaggctc ccctccacga gcagaacggt    300
gttcctcatc atctacttag cgtgattgat ccctctgtcg agttcacttg ccgtgatttc    360
cgcgaccgtg ccctgccgat tatacaggaa atagtggacc gcggtggcct ccctgtggtt    420
gtcggcggca caaacttcta catccaggct ctcgttagcc cattcctctt ggatgatatg    480
gcagaagaaa tgcagggctg tactctgaga gatcacatag atgatggcct taccgatgaa    540
gatgaaggca atgggtttga acgcttgaag gagatcgatc ctgtggctgc gcagaggatc    600
catccaaacg accatagaaa aatcaaacgc tacctcgagt tgtatgcaac cacgggtgcc    660
ctacccagcg atctgttcca aggagaggcc gctaagaaat ggggtcggcc tagtaactcc    720
agactcgact gctgtttcct gtgggtagat gctgatcttc aagtcctgga cagttatgtc    780
aacaaagggt cgattgcat  gatggatggt ggcctgctgg acgaagtatg cagcatatat    840
gatgcggatg ctgtctatac ccaggggctg cggcaggcta ttggggttcg tgagtttgac    900
gagtttttca gagcatattt acccagaaaa gaatctggtg agggttcctg tgcaagcctg    960
ttaggtatgc atgacgatca gcttaagagc ttgttggacg aagctgtttc ccagctgaag   1020
gcaaacactc gtagactagt tcgacgtcaa gtaagcactt ag                      1062

<210> SEQ ID NO 25
<211> LENGTH: 1082
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmIPT1 promoter

<400> SEQUENCE: 25
tttctgcaaa agtatctaag ttgattcttg ttaaagcctc tccttgattc ccaaatccag     60
catacccttg agagtctttt ctttagtcgg gtaagtcttg ctgagtaatt ccatactcag    120
ggttttattc cctgttgttt ttcaggtcat agttttgtgc tgttgatgat ggtgttaagt    180
gccggtgggc tcggccttct tataagtcta agtaacccct ctaaacttct taatgaggat    240
ggtcccttga gctagcatat atttcaaact tatactttg caatcactcc gataaaataa    300
```

-continued

```
tataaaattt ttgtaacttg taaaatttgg taacaaggtt ttcgctgcaa aaatattggt      360
gtgtgtgatt tgtgttactt aatcccgagg ttctggttgt aagtggttta tccggtgtcc      420
ttggggcaat cggacggatc ctgttaagtt atctggtgca catgcatagc agtctgaggt      480
ctttgagaca aggacaggtg catgtgggcc caataacttg ggaggttctg ccacaattat      540
tagcaagata tcggagatat ttatgtgcta tattttact atagaggagt gagacgaaga       600
gtgttatgta agttacagag tagaaacaaa ttctactact gtataaaatc atttcacatc      660
ccccatccca tgaatttgag ataggcttat atctaaactt tggaaagtgg tggaatgtca      720
aattccaaac taaataagtt acttagtga gtgaattcca attcctttaa atgaaggga        780 tccaaacgcc ccgtaaggaa aatagaaatc ccttaggctt tgtttgggta aagagagatt      840
gaagtggatt aaggtgtatt gaaggagatt aaaataaaaa ttagttcata ttacacttca      900
atacacctca taccacctca atccactcca atctgagatt acccaaacaa gtccttagta      960
aaattgtgtt cccaaactat gctctaattt tactagcatt ttttatccac taactattag     1020
ctccaaacac cccctaattt tagtagcaag agcaaggaaa accccccagc catcttcatc     1080
tg                                                                    1082
```

<210> SEQ ID NO 26
<211> LENGTH: 1299
<212> TYPE: DNA
<213> ORGANISM: Zea mays
<220> FEATURE:
<221> NAME/KEY: misc_feature
<222> LOCATION: (0)...(0)
<223> OTHER INFORMATION: variant of ZmIPT1, full length, derived from B73 EST
<220> FEATURE:
<221> NAME/KEY: CDS
<222> LOCATION: (31)...(1086)

<400> SEQUENCE: 26

```
ccacgcgtcc ggccggactg acggttagag atg gcc cac ccc tcc gcc gcc gcc       54
                                 Met Ala His Pro Ser Ala Ala Ala
                                  1               5 gcc gcc gta tcc tcc acg gcg ccc gct gca aac cct agt tct ggc gcc       102
Ala Ala Val Ser Ser Thr Ala Pro Ala Ala Asn Pro Ser Ser Gly Ala
        10                  15                  20 cgc gag gaa gga ggc gcc cgc tct ccg ccg tcg ccg tct ccg tct cag       150
Arg Glu Glu Gly Gly Ala Arg Ser Pro Pro Ser Pro Ser Pro Ser Gln
 25                  30                  35                  40 agg ggg cgg gcc aag gtg gtg atc gtt atg ggc gcc acg ggc gcc ggc       198
Arg Gly Arg Ala Lys Val Val Ile Val Met Gly Ala Thr Gly Ala Gly
                45                  50                  55 aag tcg cgg ctg gcc gtc gac ctc gcg gcc cac ttc gcc ggc gtc gaa       246
Lys Ser Arg Leu Ala Val Asp Leu Ala Ala His Phe Ala Gly Val Glu
             60                  65                  70 gtg gtc agc gcc gac tcc atg cag ctc tac cgc ggc ctc gac gtc ctc       294
Val Val Ser Ala Asp Ser Met Gln Leu Tyr Arg Gly Leu Asp Val Leu
         75                  80                  85 acc aac aag gct ccc ctc cac gag cag aac ggt gtt cct cat cat cta       342
Thr Asn Lys Ala Pro Leu His Glu Gln Asn Gly Val Pro His His Leu
     90                  95                 100 ctt agc gtg att gat ccc tct gtc gag ttc act tgc cgt gat ttc cgc       390
Leu Ser Val Ile Asp Pro Ser Val Glu Phe Thr Cys Arg Asp Phe Arg
105                 110                 115                 120 gac cgt gcc gtg ccg att ata cag gaa ata gtg gac cgc ggt ggc ctc       438
Asp Arg Ala Val Pro Ile Ile Gln Glu Ile Val Asp Arg Gly Gly Leu
                125                 130                 135
```

```
cct gtg gtt gtc ggc ggc aca aac ttc tac atc cag gct ctc gtt agc     486
Pro Val Val Gly Gly Thr Asn Phe Tyr Ile Gln Ala Leu Val Ser
            140                 145                 150 cca ttc ctc ttg gat gat atg gca gaa gaa atg cag ggc tgt act ctg     534
Pro Phe Leu Leu Asp Asp Met Ala Glu Glu Met Gln Gly Cys Thr Leu
        155                 160                 165 aga gat cac ata gat gat ggt ctt act gat gaa gat gaa ggc aat ggg     582
Arg Asp His Ile Asp Asp Gly Leu Thr Asp Glu Asp Glu Gly Asn Gly
    170                 175                 180 ttt gaa cgc ttg aag gag atc gat cct gtg gct gcg cag agg atc cat     630
Phe Glu Arg Leu Lys Glu Ile Asp Pro Val Ala Ala Gln Arg Ile His
185                 190                 195                 200 cca aac gac cat aga aaa atc aaa cgc tac ctc gag ttg tat gca acc     678
Pro Asn Asp His Arg Lys Ile Lys Arg Tyr Leu Glu Leu Tyr Ala Thr
                205                 210                 215 acg ggt gcc cta ccc agc gat ctg ttc caa gga gag gcc gct aag aaa     726
Thr Gly Ala Leu Pro Ser Asp Leu Phe Gln Gly Glu Ala Ala Lys Lys
            220                 225                 230 tgg ggt cgg cct agt aac tcc aga ctc gac tgc tgt ttc ctg tgg gta     774
Trp Gly Arg Pro Ser Asn Ser Arg Leu Asp Cys Cys Phe Leu Trp Val
        235                 240                 245 gat gct gat ctt caa gtc ctg gac agt tat gtc aac aaa agg gtc gat     822
Asp Ala Asp Leu Gln Val Leu Asp Ser Tyr Val Asn Lys Arg Val Asp
    250                 255                 260 tgc atg atg gat ggt ggc ctg ctg gac gaa gta tgc agc ata tat gat     870
Cys Met Met Asp Gly Gly Leu Leu Asp Glu Val Cys Ser Ile Tyr Asp
265                 270                 275                 280 gcg gat gct gtc tat acc cag ggg ctg cgg cag gct att ggg gtt cgt     918
Ala Asp Ala Val Tyr Thr Gln Gly Leu Arg Gln Ala Ile Gly Val Arg
                285                 290                 295 gag ttt gac gag ttt ttc aga gca tat tta ccc aga aaa gaa tct ggt     966
Glu Phe Asp Glu Phe Phe Arg Ala Tyr Leu Pro Arg Lys Glu Ser Gly
            300                 305                 310 gag ggt tcc tgt gca agc ctg tta ggt atg cat gac gat cag ctt aag    1014
Glu Gly Ser Cys Ala Ser Leu Leu Gly Met His Asp Asp Gln Leu Lys
        315                 320                 325 agc ttg ttg gac gaa gct gtt tcc cag ctg aag gca aac act cgt aga    1062
Ser Leu Leu Asp Glu Ala Val Ser Gln Leu Lys Ala Asn Thr Arg Arg
    330                 335                 340 cta gtt cga cgt caa gta agc act tagtatcctg tgtattttt tatgttgttg    1116
Leu Val Arg Arg Gln Val Ser Thr
345                 350 tgttgtttta gaatactgtg cgactgaaca cacggatact tggctcaatg tagacttctt  1176
agcgtttctt ttttttctc cattaaataa aagagacgga gattgcatcg gctgagtaaa   1236
aaaaaaaaaa aaaaaaaaaa aaaaaaaaaa aaaaaaaaaa aaaaaaaaaa aaaaaaaaaa  1296
aaa                                                                1299

<210> SEQ ID NO 27
<211> LENGTH: 352
<212> TYPE: PRT
<213> ORGANISM: Zea mays

<400> SEQUENCE: 27

Met Ala His Pro Ser Ala Ala Ala Ala Val Ser Ser Thr Ala Pro
 1               5                  10                  15

Ala Ala Asn Pro Ser Ser Gly Ala Arg Glu Glu Gly Gly Ala Arg Ser
                20                  25                  30
```

```
Pro Pro Ser Pro Ser Pro Ser Gln Arg Gly Arg Ala Lys Val Val Ile
        35                  40                  45

Val Met Gly Ala Thr Gly Ala Gly Lys Ser Arg Leu Ala Val Asp Leu
 50                  55                  60

Ala Ala His Phe Ala Gly Val Glu Val Val Ser Ala Asp Ser Met Gln
 65                  70                  75                  80

Leu Tyr Arg Gly Leu Asp Val Leu Thr Asn Lys Ala Pro Leu His Glu
                 85                  90                  95

Gln Asn Gly Val Pro His His Leu Leu Ser Val Ile Asp Pro Ser Val
            100                 105                 110

Glu Phe Thr Cys Arg Asp Phe Arg Asp Arg Ala Val Pro Ile Ile Gln
        115                 120                 125

Glu Ile Val Asp Arg Gly Gly Leu Pro Val Val Val Gly Gly Thr Asn
130                 135                 140

Phe Tyr Ile Gln Ala Leu Val Ser Pro Phe Leu Leu Asp Asp Met Ala
145                 150                 155                 160

Glu Glu Met Gln Gly Cys Thr Leu Arg Asp His Ile Asp Gly Leu
                165                 170                 175

Thr Asp Glu Asp Glu Gly Asn Gly Phe Glu Arg Leu Lys Glu Ile Asp
            180                 185                 190

Pro Val Ala Ala Gln Arg Ile His Pro Asn Asp His Arg Lys Ile Lys
        195                 200                 205

Arg Tyr Leu Glu Leu Tyr Ala Thr Thr Gly Ala Leu Pro Ser Asp Leu
210                 215                 220

Phe Gln Gly Glu Ala Ala Lys Lys Trp Gly Arg Pro Ser Asn Ser Arg
225                 230                 235                 240

Leu Asp Cys Cys Phe Leu Trp Val Asp Ala Asp Leu Gln Val Leu Asp
                245                 250                 255

Ser Tyr Val Asn Lys Arg Val Asp Cys Met Met Asp Gly Gly Leu Leu
            260                 265                 270

Asp Glu Val Cys Ser Ile Tyr Asp Ala Asp Ala Val Tyr Thr Gln Gly
        275                 280                 285

Leu Arg Gln Ala Ile Gly Val Arg Glu Phe Asp Glu Phe Phe Arg Ala
290                 295                 300

Tyr Leu Pro Arg Lys Glu Ser Gly Glu Gly Ser Cys Ala Ser Leu Leu
305                 310                 315                 320

Gly Met His Asp Asp Gln Leu Lys Ser Leu Leu Asp Glu Ala Val Ser
                325                 330                 335

Gln Leu Lys Ala Asn Thr Arg Arg Leu Val Arg Arg Gln Val Ser Thr
            340                 345                 350

<210> SEQ ID NO 28
<211> LENGTH: 1056
<212> TYPE: DNA
<213> ORGANISM: Zea mays
<220> FEATURE:
<221> NAME/KEY: misc_feature
<222> LOCATION: (0)...(0)
<223> OTHER INFORMATION: Variant ZmIPT1, cds, derived from B73 EST

<400> SEQUENCE: 28
atggcccacc cctccgccgc cgccgccgcc gtatcctcca cggcgccgc tgcaaaccct      60 agttctggcg cccgcgagga aggaggcgcc cgctctccgc cgtcgccgtc tccgtctcag    120
agggggcggg ccaaggtggt gatcgttatg ggcgccacgg gcgccggcaa gtcgcggctg    180
gccgtcgacc tcgcggccca cttcgccggc gtcgaagtgg tcagcgccga ctccatgcag    240
```

-continued

```
ctctaccgcg gcctcgacgt cctcaccaac aaggctcccc tccacgagca gaacggtgtt    300
cctcatcatc tacttagcgt gattgatccc tctgtcgagt tcacttgccg tgatttccgc    360
gaccgtgccg tgccgattat acaggaaata gtggaccgcg gtggcctccc tgtggttgtc    420
ggcggcacaa acttctacat ccaggctctc gttagcccat tcctcttgga tgatatggca    480
gaagaaatgc agggctgtac tctgagagat cacatagatg atggtcttac tgatgaagat    540
gaaggcaatg ggtttgaacg cttgaaggag atcgatcctg tggctgcgca gaggatccat    600
ccaaacgacc atagaaaaat caaacgctac ctcgagttgt atgcaaccac gggtgccta    660
cccagcgatc tgttccaagg agaggccgct aagaaatggg gtcggcctag taactccaga    720
ctcgactgct gtttcctgtg ggtagatgct gatcttcaag tcctggacag ttatgtcaac    780
aaaagggtcg attgcatgat ggatggtggc ctgctggacg aagtatgcag catatatgat    840
gcggatgctg tctataccca ggggctgcgg caggctattg gggttcgtga gtttgacgag    900
ttttcagag catatttacc cagaaaagaa tctggtgagg gttcctgtgc aagcctgtta     960
ggtatgcatg acgatcagct taagagcttg ttggacgaag ctgtttccca gctgaaggca   1020
aacactcgta gactagttcg acgtcaagta agcact                             1056
```

<210> SEQ ID NO 29
<211> LENGTH: 357
<212> TYPE: PRT
<213> ORGANISM: Arabidopsis thaliana

<400> SEQUENCE: 29

```
Met Thr Glu Leu Asn Phe His Leu Leu Pro Ile Ile Ser Asp Arg Phe
  1               5                  10                  15

Thr Thr Thr Thr Thr Thr Ser Pro Ser Phe Ser Ser His Ser Ser Ser
                 20                  25                  30

Ser Ser Ser Leu Leu Ser Phe Thr Lys Arg Arg Arg Lys His Gln Pro
             35                  40                  45

Leu Val Ser Ser Ile Arg Met Glu Gln Ser Arg Ser Arg Asn Arg Lys
         50                  55                  60

Asp Lys Val Val Ile Leu Gly Ala Thr Gly Ala Gly Lys Ser Arg
 65                  70                  75                  80

Leu Ser Val Asp Leu Ala Thr Arg Phe Pro Ser Glu Ile Ile Asn Ser
                 85                  90                  95

Asp Lys Ile Gln Val Tyr Glu Gly Leu Glu Ile Thr Thr Asn Gln Ile
            100                 105                 110

Thr Leu Gln Asp Arg Arg Gly Val Pro His His Leu Leu Gly Val Ile
        115                 120                 125

Asn Pro Glu His Gly Glu Leu Thr Ala Gly Phe Arg Ser Ala Ala
    130                 135                 140

Ser Asn Val Val Lys Glu Ile Thr Ser Arg Gln Lys Val Pro Ile Ile
145                 150                 155                 160

Ala Gly Gly Ser Asn Ser Phe Val His Ala Leu Leu Ala Gln Arg Phe
                165                 170                 175

Asp Pro Lys Phe Asp Pro Phe Ser Ser Gly Ser Cys Leu Ile Ser Ser
            180                 185                 190

Asp Leu Arg Tyr Glu Cys Cys Phe Ile Trp Val Asp Val Ser Glu Thr
        195                 200                 205

Val Leu Tyr Glu Tyr Leu Leu Arg Arg Val Asp Glu Met Met Asp Ser
    210                 215                 220
```

Gly Met Phe Glu Glu Leu Ser Arg Phe Tyr Asp Pro Val Lys Ser Gly
225                 230                 235                 240

Leu Glu Thr Arg Phe Gly Ile Arg Lys Ala Ile Gly Val Pro Glu Phe
            245                 250                 255

Asp Gly Tyr Phe Lys Glu Tyr Pro Pro Glu Lys Lys Met Ile Lys Trp
            260                 265                 270

Asp Ala Leu Arg Lys Ala Ala Tyr Asp Lys Ala Val Asp Asp Ile Lys
            275                 280                 285

Arg Asn Thr Trp Thr Leu Ala Lys Arg Gln Val Lys Lys Ile Glu Met
290                 295                 300

Leu Lys Asp Ala Gly Trp Glu Ile Glu Arg Val Asp Ala Thr Ala Ser
305                 310                 315                 320

Phe Lys Ala Val Met Met Lys Ser Ser Glu Lys Lys Trp Arg Glu
                325                 330                 335

Asn Trp Glu Glu Gln Val Leu Glu Pro Ser Val Lys Ile Val Lys Arg
            340                 345                 350

His Leu Val Gln Asn
            355

<210> SEQ ID NO 30
<211> LENGTH: 318
<212> TYPE: PRT
<213> ORGANISM: Arabidopsis thaliana

<400> SEQUENCE: 30

Met Lys Cys Asn Asp Lys Met Val Val Ile Met Gly Ala Thr Gly Ser
1               5                   10                  15

Gly Lys Ser Ser Leu Ser Val Asp Leu Ala Leu His Phe Lys Ala Glu
            20                  25                  30

Ile Ile Asn Ser Asp Lys Met Gln Phe Tyr Asp Gly Leu Lys Ile Thr
        35                  40                  45

Thr Asn Gln Ser Thr Ile Glu Asp Arg Arg Gly Val Pro His His Leu
    50                  55                  60

Leu Gly Glu Leu Asn Pro Glu Ala Gly Glu Val Thr Ala Ala Glu Phe
65                  70                  75                  80

Arg Val Met Ala Ala Glu Ala Ile Ser Glu Ile Thr Gln Arg Lys Lys
                85                  90                  95

Leu Pro Ile Leu Ala Gly Gly Ser Asn Ser Tyr Ile His Ala Leu Leu
            100                 105                 110

Ala Lys Ser Tyr Asp Pro Glu Asn Tyr Pro Phe Ser Asp His Lys Gly
        115                 120                 125

Ser Ile Cys Ser Glu Leu Lys Tyr Asp Cys Cys Phe Ile Trp Ile Asp
    130                 135                 140

Val Asp Gln Ser Val Leu Phe Glu Tyr Leu Ser Leu Arg Leu Asp Leu
145                 150                 155                 160

Met Met Lys Ser Gly Met Phe Glu Glu Ile Ala Glu Phe His Arg Ser
                165                 170                 175

Lys Lys Ala Pro Lys Glu Pro Leu Gly Ile Trp Lys Ala Ile Gly Val
            180                 185                 190

Gln Glu Phe Asp Asp Tyr Leu Lys Met Tyr Lys Trp Asp Asn Asp Met
        195                 200                 205

Asp Lys Trp Asp Pro Met Arg Lys Glu Ala Tyr Glu Lys Ala Val Arg
    210                 215                 220

Ala Ile Lys Glu Asn Thr Phe Gln Leu Thr Lys Asp Gln Ile Thr Lys
225                 230                 235                 240

```
Ile Asn Lys Leu Arg Asn Ala Gly Trp Asp Ile Lys Lys Val Asp Ala
            245                 250                 255

Thr Ala Ser Phe Arg Glu Ala Ile Arg Ala Ala Lys Glu Gly Glu Gly
            260                 265                 270

Val Ala Glu Met Gln Arg Lys Ile Trp Asn Lys Glu Val Leu Glu Pro
            275                 280                 285

Cys Val Lys Ile Val Arg Ser His Leu Asp Gln Pro Ile Asn Tyr Tyr
            290                 295                 300

Tyr Tyr Tyr Phe Tyr Leu Leu Lys Arg Phe Leu Ser Leu Asn
305                 310                 315

<210> SEQ ID NO 31
<211> LENGTH: 350
<212> TYPE: PRT
<213> ORGANISM: Petunia x hybrida

<400> SEQUENCE: 31

Met Leu Ile Val Val His Ile Ile Ser Ile Thr Arg Ile Ile Phe Ile
1               5                   10                  15

Thr Leu Thr His Asn His Leu His Phe Leu Met Phe Arg Ser Leu Ser
            20                  25                  30

Tyr Asn His Lys His Leu Lys Phe Leu Thr Asn Pro Thr Thr Arg Val
            35                  40                  45

Leu Arg Arg Asn Met Ser Ser Ser Thr Val Val Thr Ile Pro Gly Pro
50                  55                  60

Thr Gln Lys Asn Lys Asn Lys Ile Ile Val Ile Met Gly Ala Thr Gly
65                  70                  75                  80

Ser Gly Lys Ser Lys Leu Ser Ile Asp Leu Val Thr Arg His Tyr Pro
            85                  90                  95

Phe Ser Glu Ile Ile Asn Ser Asp Lys Ile Gln Ile Thr Lys Gly Leu
            100                 105                 110

Asn Ile Thr Thr Asn Lys Ile Thr Val Pro Asp Arg Arg Gly Val Val
            115                 120                 125

His His Leu Leu Gly Glu Ile Asp Pro Asp Phe Asn Phe Ser Pro Ser
130                 135                 140

His Phe Arg Ser Ile Ala Gly Gln Arg Ile Asn Ser Ile Ile Asn Arg
145                 150                 155                 160

His Lys Leu Pro Phe Leu Val Gly Gly Ser Asn Ser Tyr Ile Tyr Ala
            165                 170                 175

Leu Leu Thr Asn Arg Phe Asp Pro Asp Phe Asn Pro Asp Ser Asn Pro
            180                 185                 190

Val His Phe Ile Ser Asn Glu Leu Arg Tyr Asn Cys Cys Phe Ile Trp
            195                 200                 205

Val Asp Val Leu Asn Pro Val Leu Asn Glu Tyr Leu Asp Lys Arg Val
            210                 215                 220

Asp Glu Met Met Asn Ser Gly Met Tyr Glu Glu Leu Glu Gln Phe Phe
225                 230                 235                 240

Lys Glu Asn Arg Phe Ser Asp Pro Gly Leu Glu Pro Gly Arg Ala Thr
            245                 250                 255

Gly Leu Arg Lys Ala Ile Gly Val Pro Glu Met Glu Tyr Phe Lys
            260                 265                 270

Lys Ser Cys Thr Tyr Glu Glu Ala Val Arg Glu Ile Lys Glu Asn Thr
            275                 280                 285

Trp Arg Leu Ala Lys Lys Gln Met Trp Lys Ile Gln Arg Leu Arg Glu
```

```
                    290                 295                 300

Ala Gly Trp Asp Leu Gln Arg Val Asp Ala Thr Glu Ala Phe Val Glu
305                 310                 315                 320

Ala Met Ser Asn Lys Lys Glu Lys Gly Ile Ile Trp Glu Lys Gln Val
                    325                 330                 335

Val Glu Pro Ser Val Lys Ile Val Asn Arg Phe Leu Leu Asp
                340                 345                 350

<210> SEQ ID NO 32
<211> LENGTH: 92
<212> TYPE: PRT
<213> ORGANISM: Artificial Sequence
<220> FEATURE:
<223> OTHER INFORMATION: cytokinin biosynthetic enzyme consensus
      sequence
<220> FEATURE:
<221> NAME/KEY: VARIANT
<222> LOCATION: (8)...(8)
<223> OTHER INFORMATION: The amino acid at position 8 can also be T.
<220> FEATURE:
<221> NAME/KEY: VARIANT
<222> LOCATION: (14)...(14)
<223> OTHER INFORMATION: The amino acid at position 14 can also be L or
      I.
<220> FEATURE:
<221> NAME/KEY: VARIANT
<222> LOCATION: (22)...(23)
<223> OTHER INFORMATION: The amino acid at position 22 or 23 can also be
      L or I.
<220> FEATURE:
<221> NAME/KEY: VARIANT
<222> LOCATION: (87)...(88)
<223> OTHER INFORMATION: The amino acid at position 87 or 88 can also be
      L or I.
<220> FEATURE:
<221> NAME/KEY: VARIANT
<222> LOCATION: (92)...(92)
<223> OTHER INFORMATION: The amino acid at position 92 can also be T.
<220> FEATURE:
<221> NAME/KEY: VARIANT
<222> LOCATION: (2)...(89)
<223> OTHER INFORMATION: Xaa = any amino acid

<400> SEQUENCE: 32

Gly Xaa Thr Xaa Xaa Gly Lys Ser Xaa Xaa Xaa Xaa Val Xaa Xaa
1               5                   10                  15

Xaa Xaa Xaa Xaa Xaa Val Val Xaa Xaa Asp Xaa Xaa Gln Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Val Val Xaa Gly Gly Ser
            85                  90

<210> SEQ ID NO 33
<211> LENGTH: 23
<212> TYPE: PRT
<213> ORGANISM: Artificial Sequence
<220> FEATURE:
<223> OTHER INFORMATION: consensus zinc finger motif found in tRNA IPTs
<220> FEATURE:
<221> NAME/KEY: VARIANT
<222> LOCATION: 2, 3, 5, 6, 7, 8, 9, 10, 11, 12, 13, 14, 15, 16, 18, 19,
      20, 21, 22
<223> OTHER INFORMATION: Xaa = Any Amino Acid
```

```
<400> SEQUENCE: 33

Cys Xaa Xaa Cys Xaa Xaa Xaa Xaa Xaa Xaa Xaa Xaa Xaa Xaa Xaa
1               5                   10                  15

His Xaa Xaa Xaa Xaa Xaa His
            20

<210> SEQ ID NO 34
<211> LENGTH: 336
<212> TYPE: PRT
<213> ORGANISM: Arabidopsis thaliana

<400> SEQUENCE: 34

Met Ile Met Lys Ile Ser Met Ala Met Cys Lys Gln Pro Leu Pro Pro
1               5                   10                  15

Ser Pro Thr Leu Asp Phe Pro Pro Ala Arg Phe Gly Pro Asn Met Leu
            20                  25                  30

Thr Leu Asn Pro Tyr Gly Pro Lys Asp Lys Val Val Ile Met Gly
        35                  40                  45

Ala Thr Gly Thr Gly Lys Ser Arg Leu Ser Val Asp Ile Ala Thr Arg
50                  55                  60

Phe Arg Ala Glu Ile Ile Asn Ser Asp Lys Ile Gln Val His Gln Gly
65                  70                  75                  80

Leu Asp Ile Val Thr Asn Lys Ile Thr Ser Glu Glu Ser Cys Gly Val
                85                  90                  95

Pro His His Leu Leu Gly Val Leu Pro Pro Glu Ala Asp Leu Thr Ala
            100                 105                 110

Ala Asn Tyr Cys His Met Ala Asn Leu Ser Ile Glu Ser Val Leu Asn
        115                 120                 125

Arg Gly Lys Leu Pro Ile Ile Val Gly Gly Ser Asn Ser Tyr Val Glu
    130                 135                 140

Ala Leu Val Asp Asp Lys Glu Asn Lys Phe Arg Ser Arg Tyr Asp Cys
145                 150                 155                 160

Cys Phe Leu Trp Val Asp Val Ala Leu Pro Val Leu His Gly Phe Val
                165                 170                 175

Ser Glu Arg Val Asp Lys Met Val Glu Ser Gly Met Val Glu Val
            180                 185                 190

Arg Glu Phe Phe Asp Phe Ser Asn Ser Asp Tyr Ser Arg Gly Ile Lys
        195                 200                 205

Lys Ala Ile Gly Phe Pro Glu Phe Asp Arg Phe Phe Arg Asn Glu Gln
    210                 215                 220

Phe Leu Asn Val Glu Asp Arg Glu Glu Leu Leu Ser Lys Val Leu Glu
225                 230                 235                 240

Glu Ile Lys Arg Asn Thr Phe Glu Leu Ala Cys Arg Gln Arg Glu Lys
                245                 250                 255

Ile Glu Arg Leu Arg Lys Val Lys Lys Trp Ser Ile Gln Arg Val Asp
            260                 265                 270

Ala Thr Pro Val Phe Thr Lys Arg Arg Ser Lys Met Asp Ala Asn Val
        275                 280                 285

Ala Trp Glu Arg Leu Val Ala Gly Pro Ser Thr Asp Thr Val Ser Arg
    290                 295                 300

Phe Leu Leu Asp Ile Ala Ser Arg Arg Pro Leu Val Glu Ala Ser Thr
305                 310                 315                 320

Ala Val Ala Ala Ala Met Glu Arg Glu Leu Ser Arg Cys Leu Val Ala
                325                 330                 335
```

<210> SEQ ID NO 35
<211> LENGTH: 330
<212> TYPE: PRT
<213> ORGANISM: Arabidopsis thaliana

<400> SEQUENCE: 35

Met Lys Pro Cys Met Thr Ala Leu Arg Gln Val Ile Gln Pro Leu Ser
1               5                   10                  15

Leu Asn Phe Gln Gly Asn Met Val Asp Val Pro Phe Phe Arg Arg Lys
            20                  25                  30

Asp Lys Val Val Phe Val Met Gly Ala Thr Gly Thr Gly Lys Ser Arg
        35                  40                  45

Leu Ala Ile Asp Leu Ala Thr Arg Phe Pro Ala Glu Ile Val Asn Ser
    50                  55                  60

Asp Lys Ile Gln Val Tyr Lys Gly Leu Asp Ile Val Thr Asn Lys Val
65                  70                  75                  80

Thr Pro Glu Glu Ser Leu Gly Val Pro His His Leu Leu Gly Thr Val
                85                  90                  95

His Asp Thr Tyr Glu Asp Phe Thr Ala Glu Asp Phe Gln Arg Glu Ala
            100                 105                 110

Ile Arg Ala Val Glu Ser Ile Val Gln Arg Asp Arg Val Pro Ile Ile
        115                 120                 125

Ala Gly Gly Ser Asn Ser Tyr Ile Glu Ala Leu Val Asn Asp Cys Val
    130                 135                 140

Asp Phe Arg Leu Arg Tyr Asn Cys Cys Phe Leu Trp Val Asp Val Ser
145                 150                 155                 160

Arg Pro Val Leu His Ser Phe Val Ser Glu Arg Val Asp Lys Met Val
                165                 170                 175

Asp Met Gly Leu Val Asp Glu Val Arg Arg Ile Phe Asp Pro Ser Ser
            180                 185                 190

Ser Asp Tyr Ser Ala Gly Ile Arg Arg Ala Ile Gly Val Pro Glu Leu
        195                 200                 205

Asp Glu Phe Leu Arg Ser Glu Met Arg Asn Tyr Pro Ala Glu Thr Thr
    210                 215                 220

Glu Arg Leu Leu Glu Thr Ala Ile Glu Lys Ile Lys Glu Asn Thr Cys
225                 230                 235                 240

Leu Leu Ala Cys Arg Gln Leu Gln Lys Ile Gln Arg Leu Tyr Lys Gln
                245                 250                 255

Trp Lys Trp Asn Met His Arg Val Asp Ala Thr Glu Val Phe Leu Arg
            260                 265                 270

Arg Gly Glu Glu Ala Asp Glu Ala Trp Asp Asn Ser Val Ala His Pro
        275                 280                 285

Ser Ala Leu Ala Val Glu Lys Phe Leu Ser Tyr Ser Asp Asp His His
    290                 295                 300

Leu Glu Gly Ala Asn Ile Leu Leu Pro Glu Ile Ser Ala Val Pro Pro
305                 310                 315                 320

Leu Pro Ala Ala Val Ala Ala Ile Ser Arg
                325                 330

<210> SEQ ID NO 36
<211> LENGTH: 342
<212> TYPE: PRT
<213> ORGANISM: Arabidopsis thaliana

<400> SEQUENCE: 36

Met Gln Gln Leu Met Thr Leu Leu Ser Pro Pro Leu Ser His Ser Ser
1               5                   10                  15

Leu Leu Pro Thr Val Thr Thr Lys Phe Gly Ser Pro Arg Leu Val Thr
            20                  25                  30

Thr Cys Met Gly His Ala Gly Arg Lys Asn Ile Lys Asp Lys Val Val
            35                  40                  45

Leu Ile Thr Gly Thr Thr Gly Thr Gly Lys Ser Arg Leu Ser Val Asp
50                  55                  60

Leu Ala Thr Arg Phe Phe Pro Ala Glu Ile Ile Asn Ser Asp Lys Met
65                  70                  75                  80

Gln Ile Tyr Lys Gly Phe Glu Ile Val Thr Asn Leu Ile Pro Leu His
            85                  90                  95

Glu Gln Gly Gly Val Pro His His Leu Leu Gly Gln Phe His Pro Gln
            100                 105                 110

Asp Gly Glu Leu Thr Pro Ala Glu Phe Arg Ser Leu Ala Thr Leu Ser
            115                 120                 125

Ile Ser Lys Leu Ile Ser Ser Lys Leu Pro Ile Val Val Gly Gly
130                 135                 140

Ser Asn Ser Phe Asn His Ala Leu Leu Ala Glu Arg Phe Asp Pro Asp
145                 150                 155                 160

Ile Asp Pro Phe Ser Pro Gly Ser Ser Leu Ser Thr Ile Cys Ser Asp
            165                 170                 175

Leu Arg Tyr Lys Cys Cys Ile Leu Trp Val Asp Val Leu Glu Pro Val
            180                 185                 190

Leu Phe Gln His Leu Cys Asn Arg Val Asp Gln Met Ile Glu Ser Gly
            195                 200                 205

Leu Val Glu Gln Leu Ala Glu Leu Tyr Asp Pro Val Val Asp Ser Gly
210                 215                 220

Arg Arg Leu Gly Val Arg Lys Thr Ile Gly Val Glu Phe Asp Arg
225                 230                 235                 240

Tyr Phe Arg Val Tyr Pro Lys Glu Met Asp Lys Gly Ile Trp Asp Leu
            245                 250                 255

Ala Arg Lys Ala Ala Tyr Glu Glu Thr Val Lys Gly Met Lys Glu Arg
            260                 265                 270

Thr Cys Arg Leu Val Lys Lys Gln Lys Glu Lys Ile Met Lys Leu Ile
            275                 280                 285

Arg Gly Gly Trp Glu Ile Lys Arg Leu Asp Ala Thr Ala Ala Ile Met
            290                 295                 300

Ala Glu Leu Asn Gln Ser Thr Ala Lys Gly Glu Gly Lys Asn Gly Arg
305                 310                 315                 320

Glu Ile Trp Glu Lys His Ile Val Asp Glu Ser Val Glu Ile Val Lys
            325                 330                 335

Lys Phe Leu Leu Glu Val
            340

<210> SEQ ID NO 37
<211> LENGTH: 329
<212> TYPE: PRT
<213> ORGANISM: Arabidopsis thaliana

<400> SEQUENCE: 37

Met Lys Phe Ser Ile Ser Ser Leu Lys Gln Val Gln Pro Ile Leu Cys
1               5                   10                  15

Phe Lys Asn Lys Leu Ser Lys Val Asn Val Asn Ser Phe Leu His Pro

```
                20                  25                  30
Lys Glu Lys Val Ile Phe Val Met Gly Ala Thr Gly Ser Gly Lys Ser
            35                  40                  45

Arg Leu Ala Ile Asp Leu Ala Thr Arg Phe Gln Gly Glu Ile Ile Asn
        50                  55                  60

Ser Asp Lys Ile Gln Leu Tyr Lys Gly Leu Asp Val Leu Thr Asn Lys
65                  70                  75                  80

Val Thr Pro Lys Glu Cys Arg Gly Val Pro His His Leu Leu Gly Val
                85                  90                  95

Phe Asp Ser Glu Ala Gly Asn Leu Thr Ala Thr Gln Tyr Ser Arg Leu
            100                 105                 110

Ala Ser Gln Ala Ile Ser Lys Leu Ser Ala Asn Asn Lys Leu Pro Ile
        115                 120                 125

Val Ala Gly Gly Ser Asn Ser Tyr Ile Glu Ala Leu Val Asn His Ser
    130                 135                 140

Ser Gly Phe Leu Leu Asn Asn Tyr Asp Cys Cys Phe Ile Trp Val Asp
145                 150                 155                 160

Val Ser Leu Pro Val Leu Asn Ser Phe Val Ser Lys Arg Val Asp Arg
                165                 170                 175

Met Met Glu Ala Gly Leu Leu Glu Glu Val Arg Glu Val Phe Asn Pro
            180                 185                 190

Lys Ala Asn Tyr Ser Val Gly Ile Arg Arg Ala Ile Gly Val Pro Glu
        195                 200                 205

Leu His Glu Tyr Leu Arg Asn Glu Ser Leu Val Asp Arg Ala Thr Lys
    210                 215                 220

Ser Lys Met Leu Asp Val Ala Val Lys Asn Ile Lys Lys Asn Thr Glu
225                 230                 235                 240

Ile Leu Ala Cys Arg Gln Leu Lys Lys Ile Gln Arg Leu His Lys Lys
                245                 250                 255

Trp Lys Met Ser Met His Arg Val Asp Ala Thr Glu Val Phe Leu Lys
            260                 265                 270

Arg Asn Val Glu Glu Gln Asp Glu Ala Trp Glu Asn Leu Val Ala Arg
        275                 280                 285

Pro Ser Glu Arg Ile Val Asp Lys Phe Tyr Asn Asn Asn Gln Leu
    290                 295                 300

Lys Asn Asp Asp Val Glu His Cys Leu Ala Ala Ser Tyr Gly Gly
305                 310                 315                 320

Ser Gly Ser Arg Ala His Asn Met Ile
            325

<210> SEQ ID NO 38
<211> LENGTH: 330
<212> TYPE: PRT
<213> ORGANISM: Arabidopsis thaliana

<400> SEQUENCE: 38

Met Gln Asn Leu Thr Ser Phe Val Ser Pro Ser Met Ile Pro Ile
1               5                   10                  15

Thr Ser Pro Arg Leu Arg Leu Pro Pro Pro Arg Ser Val Val Pro Met
            20                  25                  30

Thr Thr Val Cys Met Glu Gln Ser Tyr Lys Gln Lys Val Val Val Ile
        35                  40                  45

Met Gly Ala Thr Gly Ser Gly Lys Ser Cys Leu Ser Ile Asp Leu Ala
    50                  55                  60
```

```
Thr Arg Phe Ser Gly Glu Ile Val Asn Ser Asp Lys Ile Gln Phe Tyr
 65                  70                  75                  80

Asp Gly Leu Lys Val Thr Thr Asn Gln Met Ser Ile Leu Glu Arg Cys
                 85                  90                  95

Gly Val Pro His His Leu Leu Gly Glu Leu Pro Pro Asp Asp Ser Glu
            100                 105                 110

Leu Thr Thr Ser Glu Phe Arg Ser Leu Ala Ser Arg Ser Ile Ser Glu
        115                 120                 125

Ile Thr Ala Arg Gly Asn Leu Pro Ile Ile Ala Gly Gly Ser Asn Ser
    130                 135                 140

Phe Ile His Ala Leu Leu Val Asp Arg Phe Asp Pro Lys Thr Tyr Pro
145                 150                 155                 160

Phe Ser Ser Glu Thr Ser Ile Ser Ser Gly Leu Arg Tyr Glu Cys Cys
                165                 170                 175

Phe Leu Trp Val Asp Val Ser Val Ser Val Leu Phe Glu Tyr Leu Ser
            180                 185                 190

Lys Arg Val Asp Gln Met Met Glu Ser Gly Met Phe Glu Leu Ala
                195                 200                 205

Gly Phe Tyr Asp Pro Arg Tyr Ser Gly Ser Ala Ile Arg Ala His Gly
210                 215                 220

Ile His Lys Thr Ile Gly Ile Pro Glu Phe Arg Tyr Phe Ser Leu
225                 230                 235                 240

Tyr Pro Pro Glu Arg Lys Gln Lys Met Ser Glu Trp Asp Gln Ala Arg
                245                 250                 255

Lys Gly Ala Tyr Asp Glu Ala Val Gln Glu Ile Lys Gly Asn Thr Trp
            260                 265                 270

Arg Leu Ala Lys Lys Gln Ile Glu Arg Ile Met Lys Leu Lys Ser Ser
        275                 280                 285

Gly Trp Asp Ile Gln Arg Leu Asp Ala Thr Pro Ser Phe Gly Arg Ser
    290                 295                 300

Ser Arg Glu Ile Trp Asp Asn Thr Val Leu Asp Glu Ser Ile Lys Val
305                 310                 315                 320

Val Lys Arg Phe Leu Val Lys Asp Lys Val
                325                 330

<210> SEQ ID NO 39
<211> LENGTH: 350
<212> TYPE: PRT
<213> ORGANISM: Artificial Sequence
<220> FEATURE:
<223> OTHER INFORMATION: consensus sequence for ZmIPT1

<400> SEQUENCE: 39

Met Ala His Pro Ala Ala Ala Ala Val Ser Ser Thr Ala Pro Ala
  1               5                  10                  15

Ala Asn Pro Ser Gly Ala Arg Glu Glu Gly Gly Ala Arg Ser Pro Pro
                 20                  25                  30

Ser Pro Ser Pro Ser Gln Arg Gly Arg Ala Lys Val Val Ile Val Met
             35                  40                  45

Gly Ala Thr Gly Ala Gly Lys Ser Arg Leu Ala Val Asp Leu Ala Ala
     50                  55                  60

His Phe Ala Gly Val Glu Val Ser Ala Asp Ser Met Gln Leu Tyr
 65                  70                  75                  80

Arg Gly Leu Asp Val Leu Thr Asn Lys Ala Pro Leu His Glu Gln Asn
                 85                  90                  95
```

```
Gly Val Pro His His Leu Leu Ser Val Ile Asp Pro Ser Val Glu Phe
                100                 105                 110

Thr Cys Arg Asp Phe Arg Asp Arg Ala Leu Pro Ile Ile Gln Glu Ile
            115                 120                 125

Val Asp Arg Gly Gly Leu Pro Val Val Gly Gly Thr Asn Phe Tyr
130                 135                 140

Ile Gln Ala Leu Val Ser Pro Phe Leu Leu Asp Asp Met Ala Glu Glu
145                 150                 155                 160

Met Gln Gly Cys Thr Leu Arg Asp His Ile Asp Asp Gly Leu Thr Asp
                165                 170                 175

Glu Asp Glu Gly Asn Gly Phe Glu Arg Leu Lys Glu Ile Asp Pro Val
            180                 185                 190

Ala Ala Gln Arg Ile His Pro Asn Asp His Arg Lys Ile Lys Arg Tyr
        195                 200                 205

Leu Glu Leu Tyr Ala Thr Thr Gly Ala Leu Pro Ser Asp Leu Phe Gln
    210                 215                 220

Gly Glu Ala Ala Lys Lys Trp Gly Arg Pro Ser Asn Ser Arg Leu Asp
225                 230                 235                 240

Cys Cys Phe Leu Trp Val Asp Ala Asp Leu Gln Val Leu Asp Ser Tyr
                245                 250                 255

Val Asn Lys Arg Val Asp Cys Met Met Asp Gly Gly Leu Leu Asp Glu
            260                 265                 270

Val Cys Ser Ile Tyr Asp Ala Asp Ala Val Tyr Thr Gln Gly Leu Arg
        275                 280                 285

Gln Ala Ile Gly Val Arg Glu Phe Asp Glu Phe Phe Arg Ala Tyr Leu
    290                 295                 300

Pro Arg Lys Glu Ser Gly Glu Gly Ser Cys Ala Ser Leu Leu Gly Met
305                 310                 315                 320

His Asp Asp Gln Leu Lys Ser Leu Leu Asp Glu Ala Val Ser Gln Leu
                325                 330                 335

Lys Ala Asn Thr Arg Arg Leu Val Arg Arg Gln Val Ser Thr
            340                 345                 350

<210> SEQ ID NO 40
<211> LENGTH: 4680
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT8 genomic sequence (017718_1)
<220> FEATURE:
<221> NAME/KEY: exon
<222> LOCATION: (225)...(489)
<220> FEATURE:
<221> NAME/KEY: exon
<222> LOCATION: (576)...(655)
<220> FEATURE:
<221> NAME/KEY: exon
<222> LOCATION: (801)...(869)
<220> FEATURE:
<221> NAME/KEY: exon
<222> LOCATION: (966)...(1047)
<220> FEATURE:
<221> NAME/KEY: exon
<222> LOCATION: (1158)...(1252)
<220> FEATURE:
<221> NAME/KEY: exon
<222> LOCATION: (1385)...(1459)
<220> FEATURE:
<221> NAME/KEY: exon
<222> LOCATION: (1641)...(1692)
<220> FEATURE:
```

```
<221> NAME/KEY: exon
<222> LOCATION: (1698)...(1886)
<220> FEATURE:
<221> NAME/KEY: exon
<222> LOCATION: (1923)...(2008)
<220> FEATURE:
<221> NAME/KEY: exon
<222> LOCATION: (2083)...(2158)
<220> FEATURE:
<221> NAME/KEY: exon
<222> LOCATION: (2257)...(2420)
<220> FEATURE:
<221> NAME/KEY: exon
<222> LOCATION: (2563)...(2682)

<400> SEQUENCE: 40
```

| | | | | | |
|---|---|---|---|---|---|
| accatagtga | aagaaaaaat | acgttggagt | acgccgattt | tcttgtaaat | ttgatatttc | 60 |
| actcccctag | tcccctatta | ccaattttt | ttttaaaaa | aagaaaaaac | gcaaccttac | 120 |
| cagcccaaag | gcccaaagcc | cacaacagag | aggagagtgg | gcgacggggg | gctagggcgg | 180 |
| cggcggcgcg | gcgaccagcg | acgggcggcg | cgcacctgac | cggaatggcc | cacctcgcgg | 240 |
| cctctgccgc | cccgcttcca | agcgctgacc | ccgacgccgg | cgaggagtcc | tcccactctc | 300 |
| cgccgccgcc | ggagaagggg | ctgaggaagg | tggtggtggt | gatgggcgcg | actggcgccg | 360 |
| gcaagtcgcg | gctggccgtc | gacctcgcga | gccacttcgc | cggcgtcgag | gtggtcagcg | 420 |
| ccgactccat | gcaagtctac | ggtgggctcg | atgtcctcac | caacaaggtc | cccctccacg | 480 |
| agcagaaagg | tctcctcccg | ggattcccca | gttcttcttt | tgaccaaacc | tgcttcagat | 540 |
| cgagcttaac | agcgctatct | ttgccgtgtt | accaggcgtt | cctcaccatc | tcctgagcgt | 600 |
| gattgatccc | tctgtggagt | tcacttgccg | cgatttccgc | gaccatgctg | tgccggtgag | 660 |
| cctatgatgt | tgctgctacg | acttttagtg | ctcctagtgt | gccatgttta | ctgattagtt | 720 |
| gatgtttctt | agtgctctgc | tcaccaatta | tataaggtat | attggtttac | tgattaattg | 780 |
| ctgtttctga | gtggtcacag | attatagaag | gtatattgga | tcgtggcggc | ctccctgtta | 840 |
| ttgttggtgg | tacaaacttc | tacatccagg | ttgatactta | agcgcatgag | gattcctgta | 900 |
| tattaggcta | ttttcttct | gaattagact | atatctgatt | tttgtccctt | taacacttat | 960 |
| tgtaggctct | tgttagccca | ttcctctttg | atgatatggc | acaggatatt | gagggtctta | 1020 |
| ctttaaatga | ccacctagat | gagataggtg | aatgatgaaa | gcttagcaca | tgtttcttgt | 1080 |
| tgttagcatg | ttttgatcaa | tggttgtgtc | caattagtgt | ttgacttgtt | aaacactgct | 1140 |
| taacacatgc | caagcagggc | ttgataatga | tgatgaagcc | ggtctgtatg | aacatttgaa | 1200 |
| gaagattgat | cctgttgctg | cacaaaggat | acacccgaac | aaccatcgaa | aagtaagggt | 1260 |
| gttgcacagt | tgtgccctta | acctgttagg | tttctttggt | agcaattgga | ttttccttgt | 1320 |
| ggtgttgccc | catttgcctt | atccggttat | cctgttctgc | atgctttttt | gttgtgttga | 1380 |
| ccagataaaa | cgctaccttg | agttgtatga | atccacaggt | gccctaccta | gtgatctttt | 1440 |
| ccaagggcaa | gccacagagg | tgagaaaaaa | atgatttccc | ttttaattaa | tttcttatt | 1500 |
| ctgacttgtt | gctgactcta | tagtccatgt | gaaatgtgca | aggactttat | gcatattatc | 1560 |
| atgcgcacaa | cacattttt | gccgtacgag | ttggacctca | tgcgaactct | aaatgtccta | 1620 |
| atgaggtcat | ttgttgtcag | gacagaagtg | gggtcgacct | agtaactcca | gatttgactg | 1680 |
| ttgtttcttg | tggttagatg | ctgatcttca | tgttctggat | cgttatgtca | atgaaagggt | 1740 |
| cgactgcatg | attgatgatg | gcctgctaga | tgaagtgtgt | aacatatatg | atcgagaggc | 1800 |
| cacttatacc | caagggctgc | ggcaggccat | tggtgttcgt | gaatttgatg | agttttcag | 1860 |

```
attttatttt gcaaggaagg aaaccggtga gataaagatg gattcctgta caactatggc   1920
aggtctccat gatgataacc tgaagggctt attggatgaa gcagtctcac aactaaaagc   1980
aaacactcgc agacttgttc gacgtcaagt aatctcgaca cttttttaag taaataattg   2040
aaaattgcat tttgtgtgtt ttatattctt gcctttcttc agagacgaag gctgcatcgg   2100
ttgaataaat attttgagtg gaacttgcgt catattgatg caacagaagc tttctatggt   2160
aatgatatgt gcatttcatg ttttagttca aagccaaaag atttcatgtc ttacgaaatc   2220
taatgtgttt gcttaacatg tcatgcatat ttctaggtgc cactgctgac tcatggaaca   2280
tgaaagttgt gaaaccttgc gtggatattg ttagagattt cttgtctgat gatacaattt   2340
tggcaagcag agatggttct agtgtaactg gaagccctag gatgtcttca agagagttgt   2400
ggactcaata tgtttgtgag gtaattggga ggcttttctt attcttacca aaagaatgt    2460 tgataactgt atcgtcattt gtgcgttttg ccacattttt tgttagtggg acagcaatca   2520
atctgatgaa actttcttgc ctttcctgct cctattttac aggcctgtga taccgggta    2580 cttcggggaa cgcatgagtg ggagcaacac aagcaaggcc gatgccaccg taaaagagta   2640
caacgtttga aacagaaggc tagtacagtg atatcattat aggcaattag cactgtttgc   2700
actctcggtg ttcatgaacc tttcttcatt ctctgcaact gtccccatgc atcctgtttg   2760
tcaaattggc tgaagactac accattcaga aggtagcaag cagcagatat atttgttaat   2820
agtaccttgc tagattcttg tgccagtccc aaacatccaa tgcagagaat acaaactcta   2880
cagattggtc agcacaagca cgtccgattg agcagcatct acactgatga ccagttggag   2940
tttctccaat ctgctgatca tttctagact agttttccca ttaaggacac cataaattgg   3000
gtaggcggtc cagcttgtta gcaaagtggt gatagtgatt agcaattaag catgacattg   3060
acccatcgaa tatttgcata tcttggtctt ccagattgca tgattttttcc ttcatatgtg   3120 actggaaaca gtggggccat gctaggttac ataaattcct gggcgtgata cactgcgaat   3180
agtagctatc atgtttacta ctgtcgtgtt gagactactg tacagtagct cgtatgtatt   3240
tctcgtatgt ttgtgcataa gtgaggggtc gatgagagtg acttactaga ctttctcat   3300 cctaaattcc taataactag aaaagatgac cgaaattggg aaggcgactt gtgcctcttt   3360
tggaatgatc gaaatataga ggaactttca tgttgacctg attcttacga aaatcatgta   3420
aaactcgtgt tcgttgtcaa aaggcccaac ttcatctcag atgagcataa gtataccata   3480
ttaatgcttc aaaatggtta atgctagctc gttttactg cacaactaat gctcgatgtc    3540
caaatatact tgggttatta ttattttttt gaaggatttt tcatgtgagt ctcgccgagg   3600
tccactaacc ggtacacagg cgccgacctc tggcacatta ttttacacga gaaatttaag   3660
gtaggcatga atcatcagt cgcacggatg caaacgtgac gacatcatca gaaacaatat    3720
actgctgcgc cgatttaaac tacacttaaa ttaaataatt ctattagtgg tacgagagta   3780
gtactactcc tgtatgtaga atagatgtgc acgggcgcac gtgtttcatc cctctaattc   3840
tgaatcccca cgtgacgatc gagcttaaag ccgaacgggc ggggcggggg gataaagcgg   3900
gtcccccagc cgctgtctcc agttcacacc cacaacccga agtcgatcgc tcgtgttcgt   3960
gtccgcctcg acggcgaact cgacgggtcc cgacccgcaa acccaacacc cacacctact   4020
tatacccacc tccactaatc cctcctctca tcgcaccacc acgccactga gctcaagcta   4080
agctaagtgc taacctaggt gttcgaccat ggacaccgag gacacgtcgt cggcttcgtc   4140
ctcgtcggtg tcgccgccgt cgtcgccggg cggcgggcac caccaccggc tgccgccgaa   4200
gcggcgggcg gggcggaaga aattccggga gacgcggcac ccggtgtacc gcggcgtgcg   4260
```

-continued

```
cgcgcgggcg gggggagca ggtgggtgtg cgaggtgcgc gagccgcagg cgcaggcgcg    4320
catctggctc ggcacctacc cgacgccgga gatggcggcg cgcgcgcacg acgtcgcggc    4380
catcgccctc cgcggcgagc gcggcgccga gctcaacttc ccggactccc cctccacgct    4440
cccgcgcgcg cgcacggcgt cgcccgagga catccgcctc gccgccgcgc aggccgccga    4500
gctgtaccgc cgcccgccgc cgccgctggc attgccggag gatccgcagg aaggcacgag    4560
cggcggcggc gccaccgcca cctcggggcg tccggctgcc gtgttcgtgg acgaggacgc    4620
catcttcgac atgccggggc tgatcgacga catggcgagg gggatgatgc tgacgccgcc    4680
```

<210> SEQ ID NO 41
<211> LENGTH: 450
<212> TYPE: PRT
<213> ORGANISM: Oryza sativa
<220> FEATURE:
<221> NAME/KEY: CHAIN
<222> LOCATION: (0)...(0)
<223> OTHER INFORMATION: OsIPT8 amino acid sequence (017718_1)

<400> SEQUENCE: 41

```
Met Ala His Leu Ala Ala Ser Ala Ala Pro Leu Pro Ser Ala Asp Pro
  1               5                  10                  15

Asp Ala Gly Glu Glu Ser Ser His Ser Pro Pro Pro Glu Lys Gly
             20                  25                  30

Leu Arg Lys Val Val Val Met Gly Ala Thr Gly Ala Gly Lys Ser
         35                  40                  45

Arg Leu Ala Val Asp Leu Ala Ser His Phe Ala Gly Val Glu Val Val
     50                  55                  60

Ser Ala Asp Ser Met Gln Val Tyr Gly Gly Leu Asp Val Leu Thr Asn
 65                  70                  75                  80

Lys Val Pro Leu His Glu Gln Lys Gly Val Pro His His Leu Leu Ser
                 85                  90                  95

Val Ile Asp Pro Ser Val Glu Phe Thr Cys Arg Asp Phe Arg Asp His
            100                 105                 110

Ala Val Pro Ile Ile Glu Gly Ile Leu Asp Arg Gly Gly Leu Pro Val
        115                 120                 125

Ile Val Gly Gly Thr Asn Phe Tyr Ile Gln Ala Leu Val Ser Pro Phe
    130                 135                 140

Leu Phe Asp Asp Met Ala Gln Asp Ile Glu Gly Leu Thr Leu Asn Asp
145                 150                 155                 160

His Leu Asp Glu Ile Gly Leu Asp Asn Asp Glu Ala Gly Leu Tyr
                165                 170                 175

Glu His Leu Lys Lys Ile Asp Pro Val Ala Ala Gln Arg Ile His Pro
            180                 185                 190

Asn Asn His Arg Lys Ile Lys Arg Tyr Leu Glu Leu Tyr Glu Ser Thr
        195                 200                 205

Gly Ala Leu Pro Ser Asp Leu Phe Gln Gly Gln Ala Thr Glu Asp Arg
    210                 215                 220

Ser Gly Val Asp Leu Val Thr Pro Asp Leu Thr Val Val Ser Cys Asp
225                 230                 235                 240

Ala Asp Leu His Val Leu Asp Arg Tyr Val Asn Glu Arg Val Asp Cys
                245                 250                 255

Met Ile Asp Asp Gly Leu Leu Asp Glu Val Cys Asn Ile Tyr Asp Arg
            260                 265                 270

Glu Ala Thr Tyr Thr Gln Gly Leu Arg Gln Ala Ile Gly Val Arg Glu
```

```
              275                 280                 285
Phe Asp Glu Phe Phe Arg Phe Tyr Phe Ala Arg Lys Glu Thr Gly Leu
    290                 295                 300

His Asp Asp Asn Leu Lys Gly Leu Leu Asp Glu Ala Val Ser Gln Leu
305                 310                 315                 320

Lys Ala Asn Thr Arg Arg Leu Val Arg Arg Gln Arg Arg Leu His
                325                 330                 335

Arg Leu Asn Lys Tyr Phe Glu Trp Asn Leu Arg His Ile Asp Ala Thr
                340                 345                 350

Glu Ala Phe Tyr Gly Ala Thr Ala Asp Ser Trp Asn Met Lys Val Val
            355                 360                 365

Lys Pro Cys Val Asp Ile Val Arg Asp Phe Leu Ser Asp Asp Thr Ile
        370                 375                 380

Leu Ala Ser Arg Asp Gly Ser Ser Val Thr Gly Ser Pro Arg Met Ser
385                 390                 395                 400

Ser Arg Glu Leu Trp Thr Gln Tyr Val Cys Glu Ala Cys Asp Asn Arg
                405                 410                 415

Val Leu Arg Gly Thr His Glu Trp Glu Gln His Lys Gln Gly Arg Cys
                420                 425                 430

His Arg Lys Arg Val Gln Arg Leu Lys Gln Lys Ala Ser Thr Val Ile
            435                 440                 445

Ser Leu
    450

<210> SEQ ID NO 42
<211> LENGTH: 8463
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT1 genomic sequence (006475_2)
<220> FEATURE:
<221> NAME/KEY: exon
<222> LOCATION: (2001)...(2834)
<220> FEATURE:
<221> NAME/KEY: exon
<222> LOCATION: (3574)...(3597)
<220> FEATURE:
<221> NAME/KEY: exon
<222> LOCATION: (5549)...(6463)

<400> SEQUENCE: 42
tttgttgtga acttgagagg aataagttca tttgtgttcc ctcaacttga cgtcgggttc      60
gaattacgtc cccaaaccac aatacaatat aacacatcct caacttgcaa tacaggctca     120
tattaggtcc caaaacagta ctatacctag ttttggctga tgtagcgcac acgtaactca     180
tttgactagg tcctcatctc acgtggcatt gacatggtgc ttacgtagca attcgacaga     240
taaaataatt aaaactatgg ggctcgcata tcaatagtgg ggccatgcgg ggtccacatg     300
tcaataatag aaatgaaaaa acaaaatggg cccacttgtc atccccgtcc atttctcgcc     360
atccccttcc ctatcttcgg caacaatgag ggaggcggct ggaggaggag ctcaagcggc     420
cgctagcaag tgcggcagct gcggcgggcg cgacaacagt tgatgacgat agggtcatcc     480
gctctcctct cctcccctcc catccctggc caccgccgtc ctcccttacc cccggcgctg     540
actaggtcta ctctgcggcc atggccttct cccgaccat ccacctccac cacccacatt      600
gcctcctcct ctctccaacc ccttgtctat ctcccccctac cacccatggc tctccgcctg    660
atcgagcccc cgccgccatg acccccttcg tcgtccctcc tctactctcg acatcctcct    720
```

```
gagcccttcc cctcctttga cttcggatga ggatgcacgg gcttggagcg ggaggtggag      780
agggcaagga gctcgcttgc tccactctgg ctgcttcacc caccgctcgc tccactctgc      840
ccttctcctc gcaggggaga gaaaggggga acatagcgat gctcacaaaa atgcgtttaa      900
acgcatttaa ttctggttta ggtacttgat gagtgaggat gacatgtggg acccacatgg      960
tcccaccgct ttttaattat tttgtggtgt aactgacaag tgatcccacg gttttattta     1020
ttttctcgga tcaaattgcc acgtaagcac cagagacaat attccacgg acatcttttg      1080 tattggtttt gtaagctaag ggatgtgttg tatctggttt tgcggttaaa gacgaaattc     1140
aaaatgagcg cgactaaata agggacctaa agtgaactat tccaacttgt gatcctgacc     1200
aggaatcacc tggtccatat tgggccgacc cgaaccagat taaagcggat aacttctatg     1260
cttcatcatg tatactagcc acatgtgccc gcgcttcgct gcggatcatg aatttgtaaa     1320
ttaccatagt aaagaaagtt ttttctaata tgtatactga tccattgttt aaatggttgc     1380
catatatttt attacttaat gatacccac gcgttgttgc agaaaattct caaattttag      1440
ttattgggta gaatgtacaa cctaatgcta aaaagttaga gataaacaaa atgatttttt     1500
gaccaataat tgtgtgaata gcgtaagtca aattctaaaa ataatttagg taacacattt     1560
tagcagaaac ttcaaaagat gtacatactt tgaggtcatg agttaacata caatgttgta     1620
ctgtattatt catcaaatat tgtcacaatg tagcttactc gtagatataa gattgtatgt     1680
atctagtgag ggacaattta tattgttcac taacatctaa tattgttctc ggaatggtat     1740
ccagagaaat ttttatgatt tagaataaaa tggaacaatg ttgtataaat ctataaaaat     1800
ataattgcat aattatttat atgcttagat ttggcaccctc taaatgtggc ctaactacca    1860
ttggaccaca gttagtaggg gctcataaag atgcatcccc tataaaagcc aagggacacc     1920
gagagtcctc tacggaagaa ttccacccett cccattagga cagtcaaaca ccttattgct     1980
accccaatct tcctttcagt atggagaact cctcaaagaa aacccaagag ttcttcccta     2040
aaggtgggaa tggaggttat gctgagcagc tggagctctt gctgaagcag cttcgttttc     2100
ctaacaagcc gatccaccat gcggagcaag tgatcaaagg attccggaag gattggacga     2160
tgaagatcta cattcaagcc agggaagaga agtgtcaagg acatgtgttc aagtcccgcc     2220
accttcgagc caacaaagag gcagcactcc aggatgcgtc gcgtgaggca ttcatgcgtc     2280
tatgtaagat ctacagcatc gaggttcaa gtactccgtt cttctacat ccattccgtg       2340 aatgcggtga ccgccgctgc catattcgga aatttagggg ctttgaggag cagtcgccca     2400
tccacttctc catgtggatg tgggctgcag acgaggccta tgaggaggcc ttagaggaat     2460
tagatatgct tcggtcaaag atcgccggct gggaggagcg gtacaaccac cttgctaaag     2520
aacacaccac tcgtggacaa ctattggaag caatcaagct tcgcctccag tggtattttc     2580 gaacccccatc tcaagctcat atccaacgga cttttgccacc accaccacaa agagtgacaa     2640
gaagtgatgg tgaggactat agtcaaatca atgcacatca ggcatgtctg gaaaggtccg     2700
aagttaaact tgatagggca acttcacaag actatctgca aggatacaag cccccatcag     2760
aatccctcga cgctattgtt tggcctcttg ttgaagggaa gcatgacaat acaagcagtg     2820
gtaggaggaa tgaggtaaag gaaactgctc acaataacca agggaccttg ttgggctagt     2880
cctcggaaag agagttggac cagctacata tctagaagac tgctatgtaa gtgataggtg     2940
gctatatctt gtcacgtagg agtagcatgt gggtgggagt tggaccaatt tcacatatag     3000
gagaccgcta tgtaagtgac aggttatggc ctgtcaccta gcagtactat gtgggtggtc     3060
```

```
aagatcacct atcaagtgtg cttgtctatg cctagttgtg gcctaccagt tagagtagta    3120
tgtgagggtg gtagtaagat tgcattccct ttgtccagtt gtgggtggac aagctaggcg    3180
gatagtctag tgtgtttatg tatgcgtggt tgtgatgctt ttgtgcttgg cccgaggaca    3240
ttgagcaata tttgcttaaa aatgcttgtt ttcttctgca atgctacttt gttttcatga    3300
tcatgcaagt tacctaaata catgtgaatt gttctagttg atgggatcta ttgcgataga    3360
atcacatgat ttccaattgt atagtaacgg agctagcaac agtaatataa ccattttgac    3420
caggatggtt caaaagtaaa ccatatagaa aaggagttgt ttattaaata tatgtattgt    3480
atcaactaaa atagtacaca atggccaata atttttgcaat gaatttagtt tataattggc    3540
atggtatggt tattttttt ttgcatttg cagaaggcat gggaaatggc aaaacaagta    3600
aatatataac aaagtaattt ctaacgattg ttagtaaccg gaagatggtt ggtattagat    3660
taccaagttt ggaagtatta ttttaccaga gaacgtataa gtaacatgta tattgttcga    3720
agtgcccaca tttgaattta cgttcgatga agaattgtta tgtaattttt ccttgaaaaa    3780
tgtgcaaaag cacatgttta caaatcatca ccatatctta agatgaaagt aggcataagg    3840
tttaaaaagt caaaggtaat tattaggttt attttttgt tatgcttaca cacgtattga    3900
cgatacaaag gttcgagcca ttaactctga tgcctaaaaa tatctacaaa gaaaaaaaa    3960
tcgatcacaa ttgcttgaat aatagtaaga gtatacctaa ctgaatttag ggcccaccaa    4020
tataattact gtacacatcc aactgcacgt ggattgatat gccaaattac tataatcgga    4080
ggtgcctaga ggaaggattt atcctttggt ctataaacat caagacaata ttggaccggt    4140
cctcgaaaag agagttggac cagctgcaca tctaggagac cgctatgtaa gtgacagggt    4200
catatcacat ctaggagacc tctaagtaag tgacagggtc atatcttgtc acctaggagt    4260
agtatgtggg tgagagttgg accaacttca catataggta accgctatgt aagtgatagg    4320
gtcatagcct gtcacctagt agcactatgt gggtgatcaa aatggcctct ctggtgtgct    4380
tgtctatgcc taattgtaat gcttttgtgc ttggctcgag gccaatgagt aatgtatgct    4440
tgaactgcta tgtaagcgac agggtcatag cctgttagtt agagtagtag gtgagggtgg    4500
taataaaatt gtattccctt tgtctagtta tgggtggaca aggtgggtaa tctagtgtgt    4560
ttgtgtatgc gtggttgtga tgcttttgtg cttggcccga ggataatgag caatatttgc    4620
ttaaagttgc atgttttctt ctccaatgca ggtttgtttt catgagcatg caaattatct    4680
aaatacatgc gaattgttct agttgatggg atctattgcg atagaatcaa atggcctcta    4740
atcgtatagt aacagagcta gcagtaatat aaccatctta accaggatgg ttcaaaagca    4800
agccatatat aaaaggagtt gtttattaaa tatatgtatt gtacaaactg gaatattaca    4860
caagggctaa taattttgca atgaatttat ttgataattg gcattgtatg gctattttgt    4920
tttttgcatt ttgcggaagg catgagaaat gccaaaacaa gtaaatatag agcaaagtat    4980
tttacaacga ttgttagtaa gtattttga ggtagatggt tggtattata ttaccaagtt    5040
tcaaagtatt cttttaccag agaacatata agtaacatat gtatgattcg aagtgcccac    5100
atttgaattt actttcgatg aaggattgat acggattttt tttccttgaa aaatgtgtaa    5160
aagcacatgt ttacaaatca tcaccatatt aagatgaaag taggcatatg gtttaaaaag    5220
ttaaaggagc tcatcaggtt taatttgttt tatgcttaca cacgtattga ggatacaatt    5280
ttaagggttg agccgttagc tcttatgcca aaaatatctc caaagaaaaa aaattgatca    5340
caattgcttg gataattgta tgagtatatc taattgaatt tgggcccat caagatgatt    5400
accatacaca ttcaactgta catggattga tatgccaaat tccggtaagt ggaggtgcca    5460
```

```
agaggaagga ggaaggattt atgctttgat ctagaaacat caaggcggca cactttcccc    5520
tttcctatat actgaggaac tcttccaggt aatacgaacc cttagctact ttcctttcat    5580
gctcaatttt caccttctt gtgattgctt cctcaatatg ctgggaaaca agttagtagt     5640
gattattggt gccacgggaa ctggaaaaac aagactctca attgagatag ccaaggcgat    5700
tggtggggaa gtggtaaatg ctgacaagat gcaaatttac gatggcctgg atattcgac    5760 aaacaaggtt tctttacaag atcgatgcgg catacctcat caccttattg cgtccatccc    5820
tcgcaacgca ggtgattttc ctgtgtcatt ttttcgatct gctgcaaaaa ccacaataaa    5880
ctgcattgcc agacgtggtc acacaccgat tgtggtgggt ggatctaact cacttatcca    5940
tggtctcctt gttgacaatt ttgattcgtc tattgtggat ccttttgggc aattggaggt    6000
tagctatcgg ccgacgcctc gatcgcaatg ttgtttccta tgggttcatg ttaatgaggt    6060
gattcttaat gagtatttga acgtcgtgt tgacaacatg gttgatgctg gttagttga    6120 ggaaattgaa gaatattttg acacattatc agttaatgga catgttccat atgtgggatt    6180
agggaaggcc attggtgttc cagagctaag cgagtatttt actggacggg tgagttgtag    6240
tgatgctctt tctatgatga agaccaatac acagattctt gcacgatctc aagtcacaaa    6300
gattcatcgc atggttgatg tgtggggatg gcatgttcat gcccttgatt gtactgaaac    6360
tattctagca catcttactg gatcaaataa gtatatggag gatttggtgt ggaaacgtga    6420
tgtaagtgac cctggacttg ctgctataca agattttctg tgataatatc agaagatggg    6480
aagctagttt ctcaaacaca tcggctattg attttgtcta caataatggt ttaatcgtct    6540
ggcttgctta gtaattttac agatcatggc atagtaagtt aacttggatc attttgggtg    6600
tgtttggaag gagcaaacat caattggtgt atatgaaatt acttggaggc cttttgtacc    6660
ttaaacactt ggatgccttt tattttacat aatagttata tatagttgtt gttcataatt    6720
ttttgatgtc atcaatattc atacgtgctg atgcgattct tattgattat ctctaataga    6780
tatgatgtgg tgccaacaaa aacaacaaac atggaagtca caaatagcca tataagaaaa    6840
taatagaggg ttcccagttg ttcatgcacc aagcttaata caaataggaa ataaacatga    6900
tagtccaatg acaatggacc aagtttagag tagcaccaca cacaatgctt gttcacttac    6960
tgatacaaca taataataa agagttaagt atgacaacac aaaaaacatc ccctgcaaca    7020
aagagcccac atagagagta tacataaagt ccaaaaacaa tgttttttgt aaatctctgg    7080
ttgggaagta attatttgtc gttacagtcg aaattttcaa acttgaaaac ttaaccatag    7140 gaattttgg agagcccggc ctttgaggat ggacttagaa tttggaggaa attttctaag    7200
aggttgatag aacccaaacc tcaagattca atatttgga tcaagacttt tgggcttggg    7260
atttggtgtt tgaagaaaca gcgggatttg agagtactgg cacataatcc taaatacact    7320
caaagaatca aagattttta acataggtt tcaaataaaa aaatcaacc gaggcaaaac     7380 ccaaggcgtt gcaatcctac cccctattaa tagaatcttg tcctgagatt tcggccaaag    7440
aagggtagca gaatgttatt gtggctcctg ttcagtgata ggctcaatac cagggccatg    7500
ttggatagaa gacattgtgc aaaggaagat gatgatctaa catgtgttgt gtgtaatggt    7560
gagtgtagag aaactcggct tcatctcttc tctgcctacc ctagcattag atgtaggcaa    7620
cacctgggaa ttgaatggaa acataacctg gaatttttcc caacggttgt tctcgcgaga    7680
ttgaggtttg gtcggagagg ttttctagaa atattttta tagcctcatg tatatttgga    7740
aacagagaaa gaggcttatc ttccaaaata tcctgcctat gttccagtct tggaggttgc    7800
```

| | |
|---|---|
| ttttttgtgaa tgaagttctt ctacatatgt gtagaatgaa ggatcctcta aaacaatctg | 7860 |
| tttttgattg gttacaaacc ttataggttt tgagttttcc ctgtaatctg taactcttgt | 7920 |
| aaatatttcc cttgttttaa tgaaccttgt tttaatgaaa atacactgct aggcaaagcc | 7980 |
| ctggcagtat ttgcagttaa aaaaatagg tccttgaaac tatacatggt ctatgtgctg | 8040 |
| accttttcct ttggtggttg cggcattcct atcccatctt ttactgagtg atacatgggc | 8100 |
| cactgtttga cccaaaattt ttgaactcaa gtgtcgactc tgaactgata ctgtctttgt | 8160 |
| tgagaatcta aagttcttct ttggtgtcag tgctggtgtt gttatgtcct gatcgggaaa | 8220 |
| taatggggac ctctatttgg atgtgttgtg gccatatcct gcatccttgc cggttgttat | 8280 |
| gacggtcatt cggggtattc gaggtcattt ctcagcctct atacatgttc accaacatac | 8340 |
| ttttttttac ctcgtgcact tgggtaccca tttcattcag cgcacccta tcttcggggg | 8400 |
| cccgtctctg tctccttgga gtggttttgg tcgtgcacgc aggtgtggcg agtggaggcg | 8460 |
| gtg | 8463 |

<210> SEQ ID NO 43
<211> LENGTH: 590
<212> TYPE: PRT
<213> ORGANISM: Oryza sativa
<220> FEATURE:
<221> NAME/KEY: CHAIN
<222> LOCATION: (0)...(0)
<223> OTHER INFORMATION: OsIPT11 amino acid sequence (006475_2)

<400> SEQUENCE: 43

```
Met Glu Asn Ser Ser Lys Lys Thr Gln Glu Phe Phe Pro Lys Gly Gly
 1               5                  10                  15

Asn Gly Gly Tyr Ala Glu Gln Leu Glu Leu Leu Leu Lys Gln Leu Arg
            20                  25                  30

Phe Pro Asn Lys Pro Ile His His Ala Glu Gln Val Ile Lys Gly Phe
        35                  40                  45

Arg Lys Asp Trp Thr Met Lys Ile Tyr Ile Gln Ala Arg Glu Glu Lys
    50                  55                  60

Cys Gln Gly His Val Phe Lys Ser Arg His Leu Arg Ala Asn Lys Glu
65                  70                  75                  80

Ala Ala Leu Gln Asp Ala Ser Arg Glu Ala Phe Met Arg Leu Cys Lys
                85                  90                  95

Ile Tyr Ser Ile Glu Val Ala Ser Thr Pro Phe Phe Leu His Pro Phe
            100                 105                 110

Arg Glu Cys Gly Asp Arg Arg Cys His Ile Arg Lys Phe Arg Gly Phe
        115                 120                 125

Glu Glu Gln Ser Pro Ile His Phe Ser Met Trp Met Trp Ala Ala Asp
    130                 135                 140

Glu Ala Tyr Glu Glu Ala Leu Glu Glu Leu Asp Met Leu Arg Ser Lys
145                 150                 155                 160

Ile Ala Gly Trp Glu Glu Arg Tyr Asn His Leu Ala Lys Glu His Thr
                165                 170                 175

Thr Arg Gly Gln Leu Leu Glu Ala Ile Lys Leu Arg Leu Gln Trp Tyr
            180                 185                 190

Phe Arg Thr Pro Ser Gln Ala His Ile Gln Arg Thr Leu Pro Pro Pro
        195                 200                 205

Pro Gln Arg Val Thr Arg Ser Asp Gly Glu Asp Tyr Ser Gln Ile Asn
    210                 215                 220

Ala His Gln Ala Cys Leu Glu Arg Ser Glu Val Lys Leu Asp Arg Ala
```

```
            225                 230                 235                 240
        Thr Ser Gln Asp Tyr Leu Gln Gly Tyr Lys Pro Pro Ser Glu Ser Leu
                        245                 250                 255

Asp Ala Ile Val Trp Pro Leu Val Glu Gly Lys His Asp Asn Thr Ser
                        260                 265                 270

Ser Gly Arg Arg Asn Glu Lys Ala Trp Glu Met Ala Lys Gln Val Ile
                        275                 280                 285

Arg Thr Leu Ser Tyr Phe Pro Phe Met Leu Asn Phe His Pro Ser Cys
                        290                 295                 300

Asp Cys Phe Leu Asn Met Leu Gly Asn Lys Leu Val Ile Ile Gly
        305                 310                 315                 320

Ala Thr Gly Thr Gly Lys Thr Arg Leu Ser Ile Glu Ile Ala Lys Ala
                        325                 330                 335

Ile Gly Gly Glu Val Val Asn Ala Asp Lys Met Gln Ile Tyr Asp Gly
                        340                 345                 350

Leu Asp Ile Thr Thr Asn Lys Val Ser Leu Gln Asp Arg Cys Gly Ile
                        355                 360                 365

Pro His His Leu Ile Ala Ser Ile Pro Arg Asn Ala Gly Asp Phe Pro
                        370                 375                 380

Val Ser Phe Phe Arg Ser Ala Ala Lys Thr Thr Ile Asn Cys Ile Ala
        385                 390                 395                 400

Arg Arg Gly His Thr Pro Ile Val Val Gly Gly Ser Asn Ser Leu Ile
                        405                 410                 415

His Gly Leu Leu Val Asp Asn Phe Asp Ser Ser Ile Val Asp Pro Phe
                        420                 425                 430

Gly Gln Leu Glu Val Ser Tyr Arg Pro Thr Pro Arg Ser Gln Cys Cys
                        435                 440                 445

Phe Leu Trp Val His Val Asn Glu Val Ile Leu Asn Glu Tyr Leu Lys
                        450                 455                 460

Arg Arg Val Asp Asn Met Val Asp Ala Gly Leu Val Glu Glu Ile Glu
        465                 470                 475                 480

Glu Tyr Phe Asp Thr Leu Ser Val Asn Gly His Val Pro Tyr Val Gly
                        485                 490                 495

Leu Gly Lys Ala Ile Gly Val Pro Glu Leu Ser Glu Tyr Phe Thr Gly
                        500                 505                 510

Arg Val Ser Cys Ser Asp Ala Leu Ser Met Met Lys Thr Asn Thr Gln
                        515                 520                 525

Ile Leu Ala Arg Ser Gln Val Thr Lys Ile His Arg Met Val Asp Val
                        530                 535                 540

Trp Gly Trp His Val His Ala Leu Asp Cys Thr Glu Thr Ile Leu Ala
        545                 550                 555                 560

His Leu Thr Gly Ser Asn Lys Tyr Met Glu Asp Leu Val Trp Lys Arg
                        565                 570                 575

Asp Val Ser Asp Pro Gly Leu Ala Ala Ile Gln Asp Phe Leu
                        580                 585                 590

<210> SEQ ID NO 44
<211> LENGTH: 4470
<212> TYPE: DNA
<213> ORGANISM: Oryza sativa
<220> FEATURE:
<221> NAME/KEY: CDS
<222> LOCATION: (1484)...(2470)
<220> FEATURE:
<221> NAME/KEY: misc_feature
<222> LOCATION: (0)...(0)
```

```
<223> OTHER INFORMATION: OsIPT2 full length sequence (018830_1)
<220> FEATURE:
<221> NAME/KEY: misc_feature
<222> LOCATION: 2876, 2877, 2878, 2879, 2880, 2881, 2882, 2883, 2884,
      2885, 2886, 2887, 2888, 2889, 2890, 2891, 2892, 2893, 2894, 2895,
      2896, 2897, 2898, 2899, 2900, 2901, 2902, 2903, 2904, 2905,
      2906, 2907, 2908, 2909, 2910, 2911, 2912, 2913, 2914
<223> OTHER INFORMATION: n = A,T,C or G
<220> FEATURE:
<221> NAME/KEY: misc_feature
<222> LOCATION: 2915, 2916, 2917, 2918, 2919, 2920, 2921, 2922, 2923,
      2924, 2925, 2926, 2927, 2928, 2929, 2930, 2931, 2932, 2933, 2934,
      2935, 2936, 2937, 2938, 2939, 2940, 2941, 2942, 2943, 2944,
      2945, 2946, 2947, 2948, 2949, 2950, 2951, 2952, 2953
<223> OTHER INFORMATION: n = A,T,C or G
<220> FEATURE:
<221> NAME/KEY: misc_feature
<222> LOCATION: 2954, 2955, 2956, 2957, 2958, 2959, 2960, 2961, 2962,
      2963, 2964, 2965, 2966, 2967, 2968, 2969, 2970, 2971, 2972, 2973,
      2974, 2975
<223> OTHER INFORMATION: n = A,T,C or G

<400> SEQUENCE: 44
aaaacaatca cacactgtta tgagctctgt tattatgccc gcaataattt ctaatctata      60
ggctacaagt aaaaaaaaag agcagaggta agtactagac tccatgcatt ctgtatattt     120
actttactct ctaagataga gttccactaa attatggatt tcaggatagg gatatcagta     180
ctacatattt tcaggcataa ataaagaata accatgctc acattataca aacttgcgtg      240
atagatgtaa atagatacaa cttaccaatc gttcgtcccg atgcatcaac tttcctagtc     300
cattcaaacc caggctaaaa cattccatgc aaacagaaat aatctatgcg gtacacatgt     360
aagtttaggt attgaaccac atgcttgtgt tatgcactac tatagcaaat taactgaact     420
agagcaaata ggaatacaaa atccctcaga tgcaactgag ttttggcatt gaatcagtac     480
agaagctact gcttgatttt aattctttag tgcttgaacc atcataaaat agccgcaaag     540
attaaaaaaa aaacaacaac acaatatata gagaccatca tagtaatctg atccttccac     600
tttcactttt gtacgaagct gctgcatttc tgctgtctaa tcaacattct ataaacaaca     660
tcataatgtt gtctcattac acaactgtaa cctagagtat cagccagctt gggctaggat     720
atagacctaa atttcatcaa tgagtgccac atcgaatcat tttcacttac gtgcattgtt     780
ttggcccgag tttgcacgag ataagcaagt cgttctatct acttcacgta acatgtgagt     840
ttgtgcaccg cgagtgcaat ttactcaaaa taaattgcat catcatcttt ttgtgatact     900
ccgtggtttc gaaactatta agattcagat agttgtattg catagtttca aatataaaca     960
aatcacattt tttttgtgt gtgtgtgtgt gggggggggg ggggttaaat tatggtgttc    1020
catagtttca cttgacaatt tcactttaaa ttcaaattta aaatttggag cctttaagtt    1080
tgtgaacaaa agtacgagat tggtcctcca caaattgaat catgtgcatg aagttgtcac    1140
aggctcacag cgactgcaca acagcagctg gaataacaca aaaaaggcca tttttatcac    1200
tatgccattc atatgtatta aattatctct actctttctg ttcgagtgat ttgaacattt    1260
tcacatccag gtataatcca tgctaacacc aggacgtgtt ctcatttcag ctataaatag    1320
caaaaaaaat tcaaatatgt ataaacccgt caccgttctc atccaaaatt atctactttc    1380
ccgataattt cattttcatt aactccattc ccgatcagtg agattttgct acgcattgtt    1440
attgatataa aaagatggct ataccttgga tgcgagtgtg gcc atg gag cac tgc       1495
                                              Met Glu His Cys
                                               1 aat ggc atc gcc gcc gtt ggg cgc tgg ttg tcc acc aag ccc aag gtt       1543
Asn Gly Ile Ala Ala Val Gly Arg Trp Leu Ser Thr Lys Pro Lys Val
 5               10                  15                  20
```

```
atc ttc gtg ctc ggc gcc acc gcc acc ggc aag tcc aag ctc gcc atc       1591
Ile Phe Val Leu Gly Ala Thr Ala Thr Gly Lys Ser Lys Leu Ala Ile
            25                      30                      35 cgc ctc gcc gcg cgc ttc gac ggc gag gtc atc aac tcc gac aag atc       1639
Arg Leu Ala Ala Arg Phe Asp Gly Glu Val Ile Asn Ser Asp Lys Ile
        40                      45                      50 cag gcg cac gac ggc ttc ccg gtc atc acc aac aag gtc acc gac gag       1687
Gln Ala His Asp Gly Phe Pro Val Ile Thr Asn Lys Val Thr Asp Glu
    55                      60                      65 gag cgt gcc ggc gtc gcg cac cac ctc ctc ggc ggc gtc agc ccc gac       1735
Glu Arg Ala Gly Val Ala His His Leu Leu Gly Gly Val Ser Pro Asp
70                      75                      80 gcc gac ttc acc gcg gag gac ttc cgc cgc gag gcg gcc gcc gcc gtc       1783
Ala Asp Phe Thr Ala Glu Asp Phe Arg Arg Glu Ala Ala Ala Ala Val
85                      90                      95                  100 gcc cgc gtc cac gcg gcc ggc cgc ctc ccc gtc gtc gcc ggc ggg tcg       1831
Ala Arg Val His Ala Ala Gly Arg Leu Pro Val Val Ala Gly Gly Ser
                105                     110                     115 aac atc tac gtc gag gcg ctc gtg gcc ggc ggc ggc ggc gcg ttc ctc       1879
Asn Ile Tyr Val Glu Ala Leu Val Ala Gly Gly Gly Gly Ala Phe Leu
            120                     125                     130 gcg gcg tac gac tgc ctc ttc ctg tgg acc gac gtc gcg ccg gac ctg       1927
Ala Ala Tyr Asp Cys Leu Phe Leu Trp Thr Asp Val Ala Pro Asp Leu
        135                     140                     145 ctg cgg tgg tac acg gcg gcg cgc gtg gac gac atg gtg cgg cgc ggg       1975
Leu Arg Trp Tyr Thr Ala Ala Arg Val Asp Asp Met Val Arg Arg Gly
    150                     155                     160 ctg gtt ggc gag gcc cgc gcc ggg ttc gac gcc ggg gcg gac tac acc       2023
Leu Val Gly Glu Ala Arg Ala Gly Phe Asp Ala Gly Ala Asp Tyr Thr
165                     170                     175                 180 cgc ggc gtg cgc cgc gcc atc ggg cta ccc gag atg cac ggc tac ctg       2071
Arg Gly Val Arg Arg Ala Ile Gly Leu Pro Glu Met His Gly Tyr Leu
                185                     190                     195 ctg gcg gag cgc gag ggc ggc gcc ggc gcc gag gac gac gac gac ctc       2119
Leu Ala Glu Arg Glu Gly Gly Ala Gly Ala Glu Asp Asp Asp Asp Leu
            200                     205                     210 ctc gcc ggc atg ctc gag gcc gcc gtg cgc gag atc aag gac aac acg       2167
Leu Ala Gly Met Leu Glu Ala Ala Val Arg Glu Ile Lys Asp Asn Thr
        215                     220                     225 ttc cgc ctc acc gtg tcg cag gtg gcc aag atc cgg cgc ctc agc gcg       2215
Phe Arg Leu Thr Val Ser Gln Val Ala Lys Ile Arg Arg Leu Ser Ala
    230                     235                     240 ctg ccc ggg tgg gac gtc cgg cgc gtg gac gcg acg gcg gtg gtg gcg       2263
Leu Pro Gly Trp Asp Val Arg Arg Val Asp Ala Thr Ala Val Val Ala
245                     250                     255                 260 cgc atg gcg gag ggc gcg ccc cac ggc gag acg tgg agg gag gtg gtg       2311
Arg Met Ala Glu Gly Ala Pro His Gly Glu Thr Trp Arg Glu Val Val
                265                     270                     275 tgg gag ccg tgc gag gag atg gtc agc cgc ttc ctc gag acg ccc gcc       2359
Trp Glu Pro Cys Glu Glu Met Val Ser Arg Phe Leu Glu Thr Pro Ala
            280                     285                     290 gcc gcc gcc gcc gtc gtt gcc aac ggc aaa gtc gac gtg aac gtc ggc       2407
Ala Ala Ala Ala Val Val Ala Asn Gly Lys Val Asp Val Asn Val Gly
        295                     300                     305 gac gcg gcc gcc ggc ttg cct gag gct gcc gcc gcc gcc gtc gtt gcg       2455
Asp Ala Ala Ala Gly Leu Pro Glu Ala Ala Ala Ala Ala Val Val Ala
    310                     315                     320 gcg ggt gtg gtc taa ctctaagtag gatacgcggc gacggtgcat gtttgcatgg      2510
Ala Gly Val Val *
```

| | | | | |
|---|---|---|---|---|
| tgggtggcgg | ctcatgttgc | ggttttgggt | tggctttggc gtggctgggc | caggtggctt | 2570 |
| gcaatatttc | attatttatt | tatttatttt | tattttgagc tgcagcgata | tgagattttg | 2630 |
| agtgagaaag | gagagggagg | gagacacaag | tatctttgag cttgtttaag | cttagtgtta | 2690 |
| caagagatta | ttttgttatg | ttttcagaat | atataaaatg ctagcgcctc | tagtataatc | 2750 |
| ggtagtattt | gacaccgcac | aaaatagtag | agaatgctac gcagcgtcaa | atattaccag | 2810 |
| ttgagggaat | acaaattcta | aagtgtttac | ttgtcttttg atttgaagtt | taaaaccatc | 2870 |
| gaaatnnnnn | nnnnnnnnnn | nnnnnnnnnn | nnnnnnnnnn nnnnnnnnnn | nnnnnnnnnn | 2930 |
| nnnnnnnnnn | nnnnnnnnnn | nnnnnnnnnn | nnnnnnnnnn nnnncgtgc | gaggagatgg | 2990 |
| tcagccgctt | cctcgagacg | cccgccgccg | ccgccgccgt cgttgccaac | ggcaaagtcg | 3050 |
| acgtgaacgt | cggcgacgcg | gccgccggcg | tgcctgaggc tgccgccgcc | gccgtcgttg | 3110 |
| cggcgggtgt | ggtctaactc | taagtaggat | acgcggcgac ggtgcatgtt | tgcatggtgg | 3170 |
| gtggcggctc | atgttgcggt | tttggttgg | ctttggcgtg gctgggccag | gtggcttgca | 3230 |
| atatttcatt | atttatttat | ttttattttg | agctgcagtg atatgagatc | ttgagtgaga | 3290 |
| aaggagaggt | agggagacac | aagtatcttt | gagcttgttt aagcttagtg | ttacaagaga | 3350 |
| ttatttgtt | atgttttcag | aatatataaa | atgctagcgc ctctagtata | atcggtagta | 3410 |
| tttgacaccg | cacaaaatag | tagagaatgc | tacgcagcgt caaatattac | cagttgaggg | 3470 |
| aatacaaatt | ctaaagtgtt | tacttgtctt | ttgatttgaa gtttaaaacc | aatcgaaatt | 3530 |
| cttaactgtc | ttttgaaatt | cgaagtgttt | tctcccttat tagggcctgt | tcggaacaaa | 3590 |
| aggataaaaa | acacagaaat | atgatagagc | gtaaattgga aaactcaggg | actgtaaaac | 3650 |
| ttgagctgtt | tggaacagag | gaatgctagg | ggatagatac acaagcacac | aactaatgtg | 3710 |
| aaggaaaatt | tcctttagga | ggaaccttat | ttttctttgt ttccttttaa | agtatatgat | 3770 |
| ttcaaaaaac | aatatttgga | gggagagatg | tccctccaaa taattttaa | gaaaaaaata | 3830 |
| tgagcgtgtt | ggagattaaa | cacggagttc | aaacaaacaa gatttggagg | gagagacgtc | 3890 |
| cctccaaaca | ttttttaaga | aaaaattatg | agcgtgttgg ggattaaaca | cggaacctca | 3950 |
| gggttgaaat | catatatctc | ttgtcactgc | actatcaagt acatctcaaa | gtacagagtt | 4010 |
| tctcaatgct | cttttctttg | atccaaacaa | catcatagga agattttcca | aaggaaacta | 4070 |
| aacctccaca | attcctttaa | aattcctttg | atccaaccat gccttggtta | ctgcatattt | 4130 |
| gttttagtat | aaccttatat | tgcttgaaac | taaacttccc ttcttttcat | actacctgac | 4190 |
| agattgttag | ttctaagagt | atgcttatct | aacatacgga ttataagcca | tagacaattt | 4250 |
| taaaatttcg | atcttaattt | tcgaattaat | ttagttttat ttcttatttt | cagccttagt | 4310 |
| ttttgaaatg | ctaagactag | aagtataaat | ttcttactag ttgctttggt | cacgcgttgt | 4370 |
| tggcttataa | accacagcac | acaagaggaa | attatttatt tgtatttaca | aatctgtacc | 4430 |
| ttcaagtatt | cttagtttac | cgcacggtgg | caaagaaatg | | 4470 |

```
<210> SEQ ID NO 45
<211> LENGTH: 984
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT2 coding sequence (018830_1)
<220> FEATURE:
<221> NAME/KEY: CDS
```

<222> LOCATION: (1)...(984)

<400> SEQUENCE: 45

```
atg gag cac tgc aat ggc atc gcc gcc gtt ggg cgc tgg ttg tcc acc      48
Met Glu His Cys Asn Gly Ile Ala Ala Val Gly Arg Trp Leu Ser Thr
1               5                   10                  15 aag ccc aag gtt atc ttc gtg ctc ggc gcc acc gcc acc ggc aag tcc      96
Lys Pro Lys Val Ile Phe Val Leu Gly Ala Thr Ala Thr Gly Lys Ser
            20                  25                  30 aag ctc gcc atc cgc ctc gcc gcg cgc ttc gac ggc gag gtc atc aac     144
Lys Leu Ala Ile Arg Leu Ala Ala Arg Phe Asp Gly Glu Val Ile Asn
        35                  40                  45 tcc gac aag atc cag gcg cac gac ggc ttc ccg gtc atc acc aac aag     192
Ser Asp Lys Ile Gln Ala His Asp Gly Phe Pro Val Ile Thr Asn Lys
50                  55                  60 gtc acc gac gag gag cgt gcc ggc gtc gcg cac cac ctc ctc ggc ggc     240
Val Thr Asp Glu Glu Arg Ala Gly Val Ala His His Leu Leu Gly Gly
65                  70                  75                  80 gtc agc ccc gac gcc gac ttc acc gcg gag gac ttc cgc cgc gag gcg     288
Val Ser Pro Asp Ala Asp Phe Thr Ala Glu Asp Phe Arg Arg Glu Ala
                85                  90                  95 gcc gcc gcc gtc gcc cgc gtc cac gcg gcc ggc cgc ctc ccc gtc gtc     336
Ala Ala Ala Val Ala Arg Val His Ala Ala Gly Arg Leu Pro Val Val
            100                 105                 110 gcc ggc ggg tcg aac atc tac gtc gag gcg ctc gtg gcc ggc ggc ggc     384
Ala Gly Gly Ser Asn Ile Tyr Val Glu Ala Leu Val Ala Gly Gly Gly
        115                 120                 125 ggc gcg ttc ctc gcg gcg tac gac tgc ctc ttc ctg tgg acc gac gtc     432
Gly Ala Phe Leu Ala Ala Tyr Asp Cys Leu Phe Leu Trp Thr Asp Val
    130                 135                 140 gcg ccg gac ctg ctg cgg tgg tac acg gcg gcg cgc gtg gac gac atg     480
Ala Pro Asp Leu Leu Arg Trp Tyr Thr Ala Ala Arg Val Asp Asp Met
145                 150                 155                 160 gtg cgg cgc ggg ctg gtt ggc gag gcc cgc gcc ggg ttc gac gcc ggg     528
Val Arg Arg Gly Leu Val Gly Glu Ala Arg Ala Gly Phe Asp Ala Gly
                165                 170                 175 gcg gac tac acc cgc ggc gtg cgc cgc gcc atc ggg cta ccc gag atg     576
Ala Asp Tyr Thr Arg Gly Val Arg Arg Ala Ile Gly Leu Pro Glu Met
            180                 185                 190 cac ggc tac ctg ctg gcg gag cgc gag ggc ggc gcc ggc gcc gag gac     624
His Gly Tyr Leu Leu Ala Glu Arg Glu Gly Gly Ala Gly Ala Glu Asp
        195                 200                 205 gac gac gac ctc ctc gcc ggc atg ctc gag gcc gcc gtg cgc gag atc     672
Asp Asp Asp Leu Leu Ala Gly Met Leu Glu Ala Ala Val Arg Glu Ile
    210                 215                 220 aag gac aac acg ttc cgc ctc acc gtg tcg cag gtg gcc aag atc cgg     720
Lys Asp Asn Thr Phe Arg Leu Thr Val Ser Gln Val Ala Lys Ile Arg
225                 230                 235                 240 cgc ctc agc gcg ctg ccc ggg tgg gac gtc cgg cgc gtg gac gcg acg     768
Arg Leu Ser Ala Leu Pro Gly Trp Asp Val Arg Arg Val Asp Ala Thr
                245                 250                 255 gcg gtg gtg gcg cgc atg gcg gag ggc gcg ccc cac ggc gag acg tgg     816
Ala Val Val Ala Arg Met Ala Glu Gly Ala Pro His Gly Glu Thr Trp
            260                 265                 270 agg gag gtg gtg tgg gag ccg tgc gag gag atg gtc agc cgc ttc ctc     864
Arg Glu Val Val Trp Glu Pro Cys Glu Glu Met Val Ser Arg Phe Leu
        275                 280                 285 gag acg ccc gcc gcc gcc gcc gcc gtc gtt gcc aac ggc aaa gtc gac     912
Glu Thr Pro Ala Ala Ala Ala Ala Val Val Ala Asn Gly Lys Val Asp
    290                 295                 300
```

```
gtg aac gtc ggc gac gcg gcc gcc ggc ttg cct gag gct gcc gcc gcc     960
Val Asn Val Gly Asp Ala Ala Ala Gly Leu Pro Glu Ala Ala Ala Ala
305                 310                 315                 320 gcc gtc gtt gcg gcg ggt gtg gtc                                     984
Ala Val Val Ala Ala Gly Val Val
                325

<210> SEQ ID NO 46
<211> LENGTH: 328
<212> TYPE: PRT
<213> ORGANISM: Oryza sativa

<400> SEQUENCE: 46

Met Glu His Cys Asn Gly Ile Ala Ala Val Gly Arg Trp Leu Ser Thr
1               5                   10                  15

Lys Pro Lys Val Ile Phe Val Leu Gly Ala Thr Ala Thr Gly Lys Ser
            20                  25                  30

Lys Leu Ala Ile Arg Leu Ala Ala Arg Phe Asp Gly Glu Val Ile Asn
        35                  40                  45

Ser Asp Lys Ile Gln Ala His Asp Gly Phe Pro Val Ile Thr Asn Lys
50                  55                  60

Val Thr Asp Glu Glu Arg Ala Gly Val Ala His Leu Leu Gly Gly
65                  70                  75                  80

Val Ser Pro Asp Ala Asp Phe Thr Ala Glu Asp Phe Arg Arg Glu Ala
                85                  90                  95

Ala Ala Ala Val Ala Arg Val His Ala Ala Gly Arg Leu Pro Val Val
            100                 105                 110

Ala Gly Gly Ser Asn Ile Tyr Val Glu Ala Leu Val Ala Gly Gly Gly
        115                 120                 125

Gly Ala Phe Leu Ala Ala Tyr Asp Cys Leu Phe Leu Trp Thr Asp Val
    130                 135                 140

Ala Pro Asp Leu Leu Arg Trp Tyr Thr Ala Ala Arg Val Asp Asp Met
145                 150                 155                 160

Val Arg Arg Gly Leu Val Gly Glu Ala Arg Ala Gly Phe Asp Ala Gly
                165                 170                 175

Ala Asp Tyr Thr Arg Gly Val Arg Arg Ala Ile Gly Leu Pro Glu Met
            180                 185                 190

His Gly Tyr Leu Leu Ala Glu Arg Glu Gly Ala Gly Ala Glu Asp
        195                 200                 205

Asp Asp Asp Leu Leu Ala Gly Met Leu Glu Ala Ala Val Arg Glu Ile
    210                 215                 220

Lys Asp Asn Thr Phe Arg Leu Thr Val Ser Gln Val Ala Lys Ile Arg
225                 230                 235                 240

Arg Leu Ser Ala Leu Pro Gly Trp Asp Val Arg Val Asp Ala Thr
                245                 250                 255

Ala Val Val Ala Arg Met Ala Glu Gly Ala Pro His Gly Glu Thr Trp
            260                 265                 270

Arg Glu Val Val Trp Glu Pro Cys Glu Glu Met Val Ser Arg Phe Leu
        275                 280                 285

Glu Thr Pro Ala Ala Ala Ala Val Val Ala Asn Gly Lys Val Asp
    290                 295                 300

Val Asn Val Gly Asp Ala Ala Ala Gly Leu Pro Glu Ala Ala Ala Ala
305                 310                 315                 320

Ala Val Val Ala Ala Gly Val Val
                325
```

<210> SEQ ID NO 47
<211> LENGTH: 4114
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT1 genomic sequence (006704_3)
<220> FEATURE:
<221> NAME/KEY: CDS
<222> LOCATION: (2001)...(2978)

<400> SEQUENCE: 47

```
tttgcttgca aggttttgtg tcgcaatgct agtttctttt tcttttttct tgttaatatc      60
cattttctt tttctttat caaaaaaaaa tatgtgggtg tagggtgga tctaggggga        120
aaaaagcagg ggctaaaaaa actagacaaa gctccaactc attttcggcc tttctgtatc    180
tttatcggaa aatttggag gctcaagggt ctctaataat ccatatatta gtagcgggcg     240
ctcgaaccct gtctccgtga tagatccata tatgggtg gttttgtttt gatctaaaaa      300
gattttttt tctttgtaat ccttatgttg agcgatagat attttatttt tacgttagat    360
atattagata tctaagttga ggctttttt aagggctaat attttcattt cacatagatc    420
tcaatgttat tataatttt ccatgtcata tataacttta gaccgaact aatgcatctt      480
gttttacct ttgacttta attacctttc aataggaccttt aaaagggatt agggagtcct    540
aattgccta ggctttgtct ttacccctg tatgatgtga acaccagaca taggttcaat     600
aggaatgaat agtttgcgga tacatatgag ataatgtttt gcgctatatg tcaaagttag   660
aaggtgggtga acataaaca aagttaaagt ttcactgaat aataactagc gacgatgaac    720
ataaagaaat tattgaagtt taccctcaag aagtagtaat attaatgatt gattttgtta    780
attttgctag ctagaatatg catacagcag cagatgttat catccttttt atttataacgt  840
actgtcatcc ttttctcctt tggtatagat tggtttatg aagttgatgg aaaattgacc    900
acagatgagt ttattattca ttcatgaacc gtgaacttct cttaaaaaaaa gtaaaataag   960
gaagttcaat gcgaataatc tatatgggg attaattact tgtcaatgct tttcatgata   1020
tttaatgttt tcgactgtaa gattaacaaa ttgtgcagag atgtattttt catgcatgat  1080
aatttggaag tgcacccaca ttgttccatg aacttgcatt gctagtttta tgttaaattc  1140
tcgttcacaa caaattaact agagacaatt aattatcatg atatataggt aatttagcat  1200
caaactgatc atttacaatc tgcattactg tttttgaaaa caaaataat aaaaaaatgc   1260
tatatcgtta caacggtggt ttatttact aacatcatca tgacatcaac atgggatcta   1320
ggtatcaata ctgttaccta tgggtatcat gtatgatacc ccgatattag atatggttcc  1380
tatgtttatc atgtctaatg ctagtatcat ataagtacca aatttgtgcc atgctggcgt  1440
tatggtgatg ccagaaataa agtattccat tctggaatgg tatagtgtct tctggtaatc  1500
cttatttaga aaatgtatta taaccattta aatatagtat atgttcccct tccatctcaa   1560
aatataaatg atttttggta gatgtaatct atagtcctta aaatgttagt agttctggtg   1620
gtgtccattc ccacaccatc tctactacta ccgtgtgagc cccacaatct atactattac   1680
attatctttt aacgagtcct ccccgttc accgttggct cttagtactt ggactaaata   1740
agtttttgtt aattgattta ataaatttaga aactcaattt gttgtccgtt acaaagcaca  1800
agctcttagc tatcctaata ttattaatct gaacaaactt atatcacatc catctaaaat  1860
ctcgtgtatt atattttggg acgggggagt aagaatgatc gagtgcacgt acatttagg   1920
```

```
                                                                -continued tcgtaaattt actatctttg caaaaagtaa ttaacgatgg cttatatacc tcttctccgg    1980
tgagcagctc accttcatca atg gag tac cac gtc ggc ggt gtc atc gga cag    2033
                      Met Glu Tyr His Val Gly Gly Val Ile Gly Gln
                       1               5                  10 tca ccc aag ccc aag gtc gtc ttc gtg ctc ggc gcc acc gcc acc ggc    2081
Ser Pro Lys Pro Lys Val Val Phe Val Leu Gly Ala Thr Ala Thr Gly
             15                  20                  25 aag tcc aag ctc gcc atc tcc atc gcc gag cgg ttc ggc ggc gag gtg    2129
Lys Ser Lys Leu Ala Ile Ser Ile Ala Glu Arg Phe Gly Gly Glu Val
         30                  35                  40 atc aac tcc gac aag atc cag gtg cac gac ggg ttc ccc atc atc acg    2177
Ile Asn Ser Asp Lys Ile Gln Val His Asp Gly Phe Pro Ile Ile Thr
     45                  50                  55 aac aag gtc acc gag gag gag cgc gcc ggc gtc ccc cac cac ctc ctc    2225
Asn Lys Val Thr Glu Glu Glu Arg Ala Gly Val Pro His His Leu Leu
 60                  65                  70                  75 ggc gtc ctc cac ccg gac gcc gac ttc acc gcc gag gac ttc cgg cgc    2273
Gly Val Leu His Pro Asp Ala Asp Phe Thr Ala Glu Asp Phe Arg Arg
                 80                  85                  90 gag gcg gcc gcc gcc gtc gcc cgc gtc ctc gcg gcg ggc cgc ctc ccc    2321
Glu Ala Ala Ala Ala Val Ala Arg Val Leu Ala Ala Gly Arg Leu Pro
             95                 100                 105 gtc gtg gcc ggc ggg tcg aac acc tac gtc gag gcg ctg gtg gag ggc    2369
Val Val Ala Gly Gly Ser Asn Thr Tyr Val Glu Ala Leu Val Glu Gly
         110                 115                 120 ggc ggc ggc gcg ttc cgc gcg gcg cac gac tgc ctc ttc ctg tgg acc    2417
Gly Gly Gly Ala Phe Arg Ala Ala His Asp Cys Leu Phe Leu Trp Thr
     125                 130                 135 gac gtc gcg ccg ggc ctg ctg cgg tgg tac acc gcg gcg cgc gtg gac    2465
Asp Val Ala Pro Gly Leu Leu Arg Trp Tyr Thr Ala Ala Arg Val Asp
140                 145                 150                 155 gac atg gtg cgg cgc ggg ctg gtg ggc gag gcg cgc gcc ggg ttc gtc    2513
Asp Met Val Arg Arg Gly Leu Val Gly Glu Ala Arg Ala Gly Phe Val
                 160                 165                 170 gac ggc gcc ggc gcc gcg gac tac tac acc cgc ggc gtg cgc cgc gcc    2561
Asp Gly Ala Gly Ala Ala Asp Tyr Tyr Thr Arg Gly Val Arg Arg Ala
             175                 180                 185 atc ggg atc ccg gag atg cac ggg tac ctc ctg gcc gag cgc tcg ggc    2609
Ile Gly Ile Pro Glu Met His Gly Tyr Leu Leu Ala Glu Arg Ser Gly
         190                 195                 200 ggc gag gcg gcc gac gac ggc gag ctc gcc gcc atg ctc gac ggc gcc    2657
Gly Glu Ala Ala Asp Asp Gly Glu Leu Ala Ala Met Leu Asp Gly Ala
     205                 210                 215 gtg cgc gag atc aag gcc aac acc tac cgc ctc gcc gcg acg cag gtg    2705
Val Arg Glu Ile Lys Ala Asn Thr Tyr Arg Leu Ala Ala Thr Gln Val
220                 225                 230                 235 gcg aag atc cgg cgg ctg agc gcg ctg gac ggg tgg gac gtg cgg cgc    2753
Ala Lys Ile Arg Arg Leu Ser Ala Leu Asp Gly Trp Asp Val Arg Arg
                 240                 245                 250 gtg gac gcg acg gtg gtg gtg gcg cgc atg gcg gag ggg gcg ccg cac    2801
Val Asp Ala Thr Val Val Val Ala Arg Met Ala Glu Gly Ala Pro His
             255                 260                 265 agg gag acg tgg gag gcg gtg gtg tgg aag ccg tgc gag gag atg gtc    2849
Arg Glu Thr Trp Glu Ala Val Val Trp Lys Pro Cys Glu Glu Met Val
         270                 275                 280 ggc cgc ttc ctc gag gcg tcc gcc gcc gtg gat gac gac gac aat gcc    2897
Gly Arg Phe Leu Glu Ala Ser Ala Ala Val Asp Asp Asp Asp Asn Ala
     285                 290                 295
```

| | |
|---|---|
| gcc tcc ggt tcg ccg gcg gcg ttg gca ccg atg acg gcg gcg tgt cgc<br>Ala Ser Gly Ser Pro Ala Ala Leu Ala Pro Met Thr Ala Ala Cys Arg<br>300                  305                  310                  315 | 2945 |
| ctg agg gcg cag ctg gtg cag ctg caa tac taa   ttagagtgga gtggcttggc<br>Leu Arg Ala Gln Leu Val Gln Leu Gln Tyr *<br>                  320                  325 | 2998 |
| gttggctagc gttagtgcta ccactataat taatatatat atagtgcaag cagatcgcgt | 3058 |
| ttgattagag tgacaattat atgtcgtcga aagtacgttt tgtgatggaa gtaacatcat | 3118 |
| ccagtcgcta taagtgggac ccatatgtca tcagtttaat taaagagatg attttttttg | 3178 |
| cggggaaatt aaagagatga ttaggaagaa ggttttcctt atttattcac agtggagtgc | 3238 |
| tattttacaa atagttctag tatataaata tagggagatg gattttcata attggagagg | 3298 |
| acatgcattc cctcgttttt ttataccacc tatatatata gaaaaaaatg ataaatataat | 3358 |
| taatacaaaa tatatcactt cacagcctcc atgttcaaat ttgtaaacaa aacaaattaa | 3418 |
| accgatacta attaatgtat gttcatagtt atatatattt gtatatttca tggtaatgat | 3478 |
| ggttttcttg cattttatat tataagatgt tttgattttt tttaaacttt taaaatttaa | 3538 |
| ttgattttat aggaaagcgt agcaacattt aatataacgc caaattaatt ttactaaatc | 3598 |
| cgacatctat agaaatgtta ctacatgcct ttatttttat aaatttgttt gaatttaaaa | 3658 |
| caatttgatt gaaaaaaaat tcaaacattg tataatataa aacaaaggaa gtatataatt | 3718 |
| aaggtattgt agttcgttgt tgcacgtgga atctcgtgtc tggaactcga tgatctttag | 3778 |
| ttccaagaga ggaagcaaag gtagcggacg gcagggttga tcgatggcga gtggcgagat | 3838 |
| ccaatgccga ctgcaaccgt gcaactaacc gccggcgccg ccgtctgatt cgctgcgaca | 3898 |
| agctgggctg ctgggcagca gctaagcaac cgagatcatc gagacggtct cagaatctga | 3958 |
| ttctccggac cggaccagac tcggattgga caaccagtag tttaatcgat cgatcgcctg | 4018 |
| tatatatatt ttgggttagt ttatcccgta cacatagaat cgattgatcg atcggcacta | 4078 |
| ctatacagcg agcgagagag attgatcggt cgagag | 4114 |

```
<210> SEQ ID NO 48
<211> LENGTH: 975
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT1 coding sequence (006704_3)
<220> FEATURE:
<221> NAME/KEY: CDS
<222> LOCATION: (1)...(975)

<400> SEQUENCE: 48
```

| | |
|---|---|
| atg gag tac cac gtc ggc ggt gtc atc gga cag tca ccc aag ccc aag<br>Met Glu Tyr His Val Gly Gly Val Ile Gly Gln Ser Pro Lys Pro Lys<br>1                  5                        10                  15 | 48 |
| gtc gtc ttc gtg ctc ggc gcc acc gcc acc ggc aag tcc aag ctc gcc<br>Val Val Phe Val Leu Gly Ala Thr Ala Thr Gly Lys Ser Lys Leu Ala<br>                  20                  25                  30 | 96 |
| atc tcc atc gcc gag cgg ttc ggc ggc gag gtg atc aac tcc gac aag<br>Ile Ser Ile Ala Glu Arg Phe Gly Gly Glu Val Ile Asn Ser Asp Lys<br>             35                  40                  45 | 144 |
| atc cag gtg cac gac ggg ttc ccc atc atc acg aac aag gtc acc gag<br>Ile Gln Val His Asp Gly Phe Pro Ile Ile Thr Asn Lys Val Thr Glu<br>50                   55                  60 | 192 |
| gag gag cgc gcc ggc gtc ccc cac cac ctc ctc ggc gtc ctc cac ccg<br>Glu Glu Arg Ala Gly Val Pro His His Leu Leu Gly Val Leu His Pro | 240 |

```
                65                  70                  75                  80
gac gcc gac ttc acc gcc gag gac ttc cgg cgc gag gcg gcc gcc gcc        288
Asp Ala Asp Phe Thr Ala Glu Asp Phe Arg Arg Glu Ala Ala Ala Ala
                    85                  90                  95 gtc gcc cgc gtc ctc gcg gcg ggc cgc ctc ccc gtc gtg gcc ggc ggg        336
Val Ala Arg Val Leu Ala Ala Gly Arg Leu Pro Val Val Ala Gly Gly
            100                 105                 110 tcg aac acc tac gtc gag gcg ctg gtg gag ggc ggc ggc gcg ttc            384
Ser Asn Thr Tyr Val Glu Ala Leu Val Glu Gly Gly Gly Ala Phe
        115                 120                 125 cgc gcg gcg cac gac tgc ctc ttc ctg tgg acc gac gtc gcg ccg ggc        432
Arg Ala Ala His Asp Cys Leu Phe Leu Trp Thr Asp Val Ala Pro Gly
    130                 135                 140 ctg ctg cgg tgg tac acc gcg gcg cgc gtg gac gac atg gtg cgg cgc        480
Leu Leu Arg Trp Tyr Thr Ala Ala Arg Val Asp Asp Met Val Arg Arg
145                 150                 155                 160 ggg ctg gtg ggc gag gcg cgc gcc ggg ttc gtc gac ggc gcc ggc gcc        528
Gly Leu Val Gly Glu Ala Arg Ala Gly Phe Val Asp Gly Ala Gly Ala
                165                 170                 175 gcg gac tac tac acc cgc ggc gtg cgc cgc gcc atc ggg atc ccg gag        576
Ala Asp Tyr Tyr Thr Arg Gly Val Arg Arg Ala Ile Gly Ile Pro Glu
            180                 185                 190 atg cac ggg tac ctc ctg gcc gag cgc tcg ggc ggc gag gcg gcc gac        624
Met His Gly Tyr Leu Leu Ala Glu Arg Ser Gly Gly Glu Ala Ala Asp
        195                 200                 205 gac ggc gag ctc gcc gcc atg ctc gac ggc gcc gtg cgc gag atc aag        672
Asp Gly Glu Leu Ala Ala Met Leu Asp Gly Ala Val Arg Glu Ile Lys
    210                 215                 220 gcc aac acc tac cgc ctc gcc gcg acg cag gtg gcg aag atc cgg cgg        720
Ala Asn Thr Tyr Arg Leu Ala Ala Thr Gln Val Ala Lys Ile Arg Arg
225                 230                 235                 240 ctg agc gcg ctg gac ggg tgg gac gtg cgg cgc gtg gac gcg acg gtg        768
Leu Ser Ala Leu Asp Gly Trp Asp Val Arg Arg Val Asp Ala Thr Val
                245                 250                 255 gtg gtg gcg cgc atg gcg gag ggg gcg ccg cac agg gag acg tgg gag        816
Val Val Ala Arg Met Ala Glu Gly Ala Pro His Arg Glu Thr Trp Glu
            260                 265                 270 gcg gtg gtg tgg aag ccg tgc gag gag atg gtc ggc cgc ttc ctc gag        864
Ala Val Val Trp Lys Pro Cys Glu Glu Met Val Gly Arg Phe Leu Glu
        275                 280                 285 gcg tcc gcc gcc gtg gat gac gac gac aat gcc gcc tcc ggt tcg ccg        912
Ala Ser Ala Ala Val Asp Asp Asp Asp Asn Ala Ala Ser Gly Ser Pro
    290                 295                 300 gcg gcg ttg gca ccg atg acg gcg gcg tgt cgc ctg agg gcg cag ctg        960
Ala Ala Leu Ala Pro Met Thr Ala Ala Cys Arg Leu Arg Ala Gln Leu
305                 310                 315                 320 gtg cag ctg caa tac                                                    975
Val Gln Leu Gln Tyr
                325

<210> SEQ ID NO 49
<211> LENGTH: 325
<212> TYPE: PRT
<213> ORGANISM: Oryza sativa

<400> SEQUENCE: 49

Met Glu Tyr His Val Gly Gly Val Ile Gly Gln Ser Pro Lys Pro Lys
1               5                   10                  15

Val Val Phe Val Leu Gly Ala Thr Ala Thr Gly Lys Ser Lys Leu Ala
            20                  25                  30
```

```
Ile Ser Ile Ala Glu Arg Phe Gly Gly Glu Val Ile Asn Ser Asp Lys
        35                  40                  45
Ile Gln Val His Asp Gly Phe Pro Ile Ile Thr Asn Lys Val Thr Glu
    50                  55                  60
Glu Glu Arg Ala Gly Val Pro His His Leu Leu Gly Val Leu His Pro
65                  70                  75                  80
Asp Ala Asp Phe Thr Ala Glu Asp Phe Arg Arg Glu Ala Ala Ala
                85                  90                  95
Val Ala Arg Val Leu Ala Ala Gly Arg Leu Pro Val Val Ala Gly Gly
                100                 105                 110
Ser Asn Thr Tyr Val Glu Ala Leu Val Glu Gly Gly Gly Ala Phe
                115                 120                 125
Arg Ala Ala His Asp Cys Leu Phe Leu Trp Thr Asp Val Ala Pro Gly
    130                 135                 140
Leu Leu Arg Trp Tyr Thr Ala Ala Arg Val Asp Asp Met Val Arg Arg
145                 150                 155                 160
Gly Leu Val Gly Glu Ala Arg Ala Gly Phe Val Asp Gly Ala Gly Ala
                165                 170                 175
Ala Asp Tyr Tyr Thr Arg Gly Val Arg Arg Ala Ile Gly Ile Pro Glu
                180                 185                 190
Met His Gly Tyr Leu Leu Ala Glu Arg Ser Gly Gly Glu Ala Ala Asp
            195                 200                 205
Asp Gly Glu Leu Ala Ala Met Leu Asp Gly Ala Val Arg Glu Ile Lys
    210                 215                 220
Ala Asn Thr Tyr Arg Leu Ala Ala Thr Gln Val Ala Lys Ile Arg Arg
225                 230                 235                 240
Leu Ser Ala Leu Asp Gly Trp Asp Val Arg Arg Val Asp Ala Thr Val
                245                 250                 255
Val Val Ala Arg Met Ala Glu Gly Ala Pro His Arg Glu Thr Trp Glu
                260                 265                 270
Ala Val Val Trp Lys Pro Cys Glu Glu Met Val Gly Arg Phe Leu Glu
                275                 280                 285
Ala Ser Ala Ala Val Asp Asp Asp Asn Ala Ala Ser Gly Ser Pro
                290                 295                 300
Ala Ala Leu Ala Pro Met Thr Ala Ala Cys Arg Leu Arg Ala Gln Leu
305                 310                 315                 320
Val Gln Leu Gln Tyr
            325

<210> SEQ ID NO 50
<211> LENGTH: 2599
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT5 genomic sequence (027814_1)
<220> FEATURE:
<221> NAME/KEY: CDS
<222> LOCATION: (1827)...(2579)

<400> SEQUENCE: 50
acctgacatc ataatacgaa caaatactgg cttgccaagt atgtggttaa caacgtgtaa      60
catagtacca atcatttagg gtggcaagac gtggcaacaa accaaacaag ccagcgagct     120
ccaggtgagt tattctgctc ttgcctcaag cccacaatcc aagttcgcac ttgatctttg     180
```

```
atctttggaa aggccatcat cgggagactg acatgatcc aacctctcgc ttttctctt      240 cccgctacag ccaccagggc aagcagcacc gccctgtcc aggctgattt cgcatgggtt      300
gctgatgatg gtcctcgacc tatcatccgg ctgggattat acatgatta ttaagtaata      360 gctaattttt ttaaaaaaaa atagattaat ttgatttttt taagtaactt tcgtatagaa      420 acctttata aaaacgtat cgtttaacag tttaaaaagc gtgcgtgcgg aaaacgagaa      480
agaggggttg ggaactcgaa ggaaagaaca cagcccgggtt gggaacttgt tgctgtcacc      540
ctactccctg atgaatcctc ttgtccaggt ttttgcatgg agtaggaagt aggaactatc      600
atatcaacct agcctactag tttctcaggc atcagtagcc cagtagtgga tgcacgaacg      660
aattttacct gttggggtg agaagctaga accgggcagg ggggaagga aggaccagca      720 acaagtggac ggatgatatg gaggctgatg gaaccgatcg tccggaggca acttgcaagc      780
aatgctacat ttgctcccgc agttgcgttg cacgacgtac tacatatgta accagaaaaa      840
tgccacgacg atgcagatcg atatatagtc aggcagcatt agcgtggtcg agtcccaac      900 gctcggcatt gcctcatcag ttaatccgca ctcgcctttt tgttagcggg acacgcatgc      960
gctgtgtgtg tgtgtgctcc cttcgatcgg gcacgagctg tgtgcggtgg catgggcgca     1020
tggcagcgac tggtcgaaac gcggccgcac gacggacacg ccgctcgatc ccccgcgcgg     1080
ctgccgtgct cccctctcg tctggatcac cggcggcgtg gcggctctc ttccacgagg     1140 catgagctcg gttttttttt acccttctgct cgcgacggag agggaaaagg ctgctgcttc     1200
ttattcttat tccctggagc gatcagcttt ttctccgccc ctcggaggtg aaaacaaagc     1260
aacgaatgga accatggaaa cgaagtgaag gagcgtgcct tcgcaatcat ggcctgaggc     1320
cctgagcggc tgagcccctg aggcctcctg agtatatata aaccaagcat ggtttgcctc     1380
ctgcattgcc cgtgtgaatg ccaatgatac agagcccccc aagagcagag caagcgcgag     1440
aacacacacc aacaacgcaa caaccacca ggcgtgcgcg tgcaagcgca aggcttgaaa     1500
cggagagaca cgaaaagcgc caaggtgttc gcccatcatt ataatcagct tataagggcg     1560
cgagcgaaac cgcacagttg tacacttgga ctcgcaaact agactctccg tctccttgcg     1620
ctgcgcgtta tatcggctct gcctatataa gtgtgctgag cgactgggg ctcggtgagt     1680 gttttgggtg ggccggcttt atgagcagtc tcggtttgaa gatccgcacc gtcgtccgct     1740
cacctatggc ggccgcggcc gtcgctggcg tcggaaggga tggtagcttc gcctcccaga     1800
agcggccacg tcgggttagt gtgaga atg gag aga agc aga gtc ggg gac ggt     1853
                               Met Glu Arg Ser Arg Val Gly Asp Gly
                                1               5 tgc tgc tgc tcc tgc tct ggc cgc ggc ggg gtg gcg tcc act acg gcg     1901
Cys Cys Cys Ser Cys Ser Gly Arg Gly Gly Val Ala Ser Thr Thr Ala
 10              15                  20                  25 gtc cgg ccg tcc acg ggg atg gtg gtg atc gtc ggc gcc acg ggc acg     1949
Val Arg Pro Ser Thr Gly Met Val Val Ile Val Gly Ala Thr Gly Thr
             30                  35                  40 ggg aag acc aag ctt tcc atc gac gcg gcg cag gag ctc gcc ggc gag     1997
Gly Lys Thr Lys Leu Ser Ile Asp Ala Ala Gln Glu Leu Ala Gly Glu
         45                  50                  55 gtg gtg aac gct gac aag att cag ctg tac gac ggc ctc gac gtc acc     2045
Val Val Asn Ala Asp Lys Ile Gln Leu Tyr Asp Gly Leu Asp Val Thr
     60                  65                  70 acg aac aag gtg tcg ctc gcc gac cgc cgg ggc gtc ccg cac cac ctc     2093
Thr Asn Lys Val Ser Leu Ala Asp Arg Arg Gly Val Pro His His Leu
 75                  80                  85 ctc ggc gca atc cgc gcc gag gcc ggg gag ctg ccg ccg tcg tcg ttc     2141
```

| | | | | | | | | | | | | | | | | |
|---|---|---|---|---|---|---|---|---|---|---|---|---|---|---|---|---|
| Leu | Gly | Ala | Ile | Arg | Ala | Glu | Ala | Gly | Glu | Leu | Pro | Pro | Ser | Ser | Phe | |
| 90 | | | | 95 | | | | | 100 | | | | | 105 | | |

| cgc | tcg | ctc | gcc | gcc | gcc | gcc | gcg | gcc | ggc | atc | gcg | tcg | cgc | ggg | cgc | 2189 |
|---|---|---|---|---|---|---|---|---|---|---|---|---|---|---|---|---|
| Arg | Ser | Leu | Ala | Ala | Ala | Ala | Ala | Ala | Gly | Ile | Ala | Ser | Arg | Gly | Arg | |
| | | | 110 | | | | | 115 | | | | | 120 | | | |

| gtg | ccg | gtc | gtg | gcc | ggc | ggg | tcc | aac | tcg | ctc | atc | cac | gcg | ctc | ctc | 2237 |
|---|---|---|---|---|---|---|---|---|---|---|---|---|---|---|---|---|
| Val | Pro | Val | Val | Ala | Gly | Gly | Ser | Asn | Ser | Leu | Ile | His | Ala | Leu | Leu | |
| | | | | 125 | | | | | 130 | | | | | 135 | | |

| gct | gac | ccc | atc | gat | gcc | gcg | ccg | cgt | gac | cct | ttc | gcg | gac | gcc | gat | 2285 |
|---|---|---|---|---|---|---|---|---|---|---|---|---|---|---|---|---|
| Ala | Asp | Pro | Ile | Asp | Ala | Ala | Pro | Arg | Asp | Pro | Phe | Ala | Asp | Ala | Asp | |
| | | | | 140 | | | | | 145 | | | | | 150 | | |

| gtc | ggg | tac | cgg | ccg | gcg | ctc | cgg | ttc | ccg | tgc | tgc | ctc | ctc | tgg | gtc | 2333 |
|---|---|---|---|---|---|---|---|---|---|---|---|---|---|---|---|---|
| Val | Gly | Tyr | Arg | Pro | Ala | Leu | Arg | Phe | Pro | Cys | Cys | Leu | Leu | Trp | Val | |
| | 155 | | | | | 160 | | | | | 165 | | | | | |

| gac | gtc | gac | gac | gat | gtt | ctc | gac | gaa | tac | ctc | gac | cgg | cgc | gtg | gac | 2381 |
|---|---|---|---|---|---|---|---|---|---|---|---|---|---|---|---|---|
| Asp | Val | Asp | Asp | Asp | Val | Leu | Asp | Glu | Tyr | Leu | Asp | Arg | Arg | Val | Asp | |
| 170 | | | | | 175 | | | | | 180 | | | | | 185 | |

| gac | atg | gtc | ggc | gag | ggg | atg | gtc | gag | gag | ctc | gag | gaa | tac | ttc | gcg | 2429 |
|---|---|---|---|---|---|---|---|---|---|---|---|---|---|---|---|---|
| Asp | Met | Val | Gly | Glu | Gly | Met | Val | Glu | Glu | Leu | Glu | Glu | Tyr | Phe | Ala | |
| | | | | 190 | | | | | 195 | | | | | 200 | | |

| acg | acg | tcg | gcc | tcg | gag | cgg | gcc | tcg | cac | gcc | ggg | ctg | ggc | aag | gcc | 2477 |
|---|---|---|---|---|---|---|---|---|---|---|---|---|---|---|---|---|
| Thr | Thr | Ser | Ala | Ser | Glu | Arg | Ala | Ser | His | Ala | Gly | Leu | Gly | Lys | Ala | |
| | | | 205 | | | | | 210 | | | | | 215 | | | |

| atc | ggc | gtg | ccg | gag | ctc | ggc | gac | tac | ttc | gcc | ggg | cgc | aag | agc | ctc | 2525 |
|---|---|---|---|---|---|---|---|---|---|---|---|---|---|---|---|---|
| Ile | Gly | Val | Pro | Glu | Leu | Gly | Asp | Tyr | Phe | Ala | Gly | Arg | Lys | Ser | Leu | |
| | | | 220 | | | | | 225 | | | | | 230 | | | |

| gac | gcg | gcg | ata | gac | gag | atc | aag | gcc | aac | acg | cgg | gtc | ctc | gcg | ggc | 2573 |
|---|---|---|---|---|---|---|---|---|---|---|---|---|---|---|---|---|
| Asp | Ala | Ala | Ile | Asp | Glu | Ile | Lys | Ala | Asn | Thr | Arg | Val | Leu | Ala | Gly | |
| | | 235 | | | | | 240 | | | | | 245 | | | | |

| cgc | cag | gtcggcaaga | tccgacgcat | | 2599 |
|---|---|---|---|---|---|
| Arg | Gln | | | | |
| 250 | | | | | |

<210> SEQ ID NO 51
<211> LENGTH: 773
<212> TYPE: DNA
<213> ORGANISM: Oryza sativa
<220> FEATURE:
<221> NAME/KEY: CDS
<222> LOCATION: (1)...(773)

<400> SEQUENCE: 51

| atg | gag | aga | agc | aga | gtc | ggg | gac | ggt | tgc | tgc | tgc | tcc | tgc | tct | ggc | 48 |
|---|---|---|---|---|---|---|---|---|---|---|---|---|---|---|---|---|
| Met | Glu | Arg | Ser | Arg | Val | Gly | Asp | Gly | Cys | Cys | Cys | Ser | Cys | Ser | Gly | |
| 1 | | | | 5 | | | | | 10 | | | | | 15 | | |

| cgc | ggc | ggg | gtg | gcg | tcc | act | acg | gcg | gtc | cgg | ccg | tcc | acg | ggg | atg | 96 |
|---|---|---|---|---|---|---|---|---|---|---|---|---|---|---|---|---|
| Arg | Gly | Gly | Val | Ala | Ser | Thr | Thr | Ala | Val | Arg | Pro | Ser | Thr | Gly | Met | |
| | | | 20 | | | | | 25 | | | | | 30 | | | |

| gtg | gtg | atc | gtc | ggc | gcc | acg | ggc | acg | ggg | aag | acc | aag | ctt | tcc | atc | 144 |
|---|---|---|---|---|---|---|---|---|---|---|---|---|---|---|---|---|
| Val | Val | Ile | Val | Gly | Ala | Thr | Gly | Thr | Gly | Lys | Thr | Lys | Leu | Ser | Ile | |
| | | | 35 | | | | | 40 | | | | | 45 | | | |

| gac | gcg | gcg | cag | gag | ctc | gcc | ggc | gag | gtg | gtg | aac | gct | gac | aag | att | 192 |
|---|---|---|---|---|---|---|---|---|---|---|---|---|---|---|---|---|
| Asp | Ala | Ala | Gln | Glu | Leu | Ala | Gly | Glu | Val | Val | Asn | Ala | Asp | Lys | Ile | |
| | 50 | | | | | 55 | | | | | 60 | | | | | |

| cag | ctg | tac | gac | ggc | ctc | gac | gtc | acc | acg | aac | aag | gtg | tcg | ctc | gcc | 240 |
|---|---|---|---|---|---|---|---|---|---|---|---|---|---|---|---|---|
| Gln | Leu | Tyr | Asp | Gly | Leu | Asp | Val | Thr | Thr | Asn | Lys | Val | Ser | Leu | Ala | |
| 65 | | | | | 70 | | | | | 75 | | | | | 80 | |

| gac | cgc | cgg | ggc | gtc | ccg | cac | cac | ctc | ctc | ggc | gca | atc | cgc | gcc | gag | 288 |
|---|---|---|---|---|---|---|---|---|---|---|---|---|---|---|---|---|
| Asp | Arg | Arg | Gly | Val | Pro | His | His | Leu | Leu | Gly | Ala | Ile | Arg | Ala | Glu | |
| | | | | 85 | | | | | 90 | | | | | 95 | | |

| gcc | ggg | gag | ctg | ccg | ccg | tcg | tcg | ttc | cgc | tcg | ctc | gcc | gcc | gcc | gcc | 336 |
|---|---|---|---|---|---|---|---|---|---|---|---|---|---|---|---|---|

```
Ala Gly Glu Leu Pro Pro Ser Ser Phe Arg Ser Leu Ala Ala Ala Ala
                100                 105                 110 gcg gcc ggc atc gcg tcg cgg ggg cgc gtg ccg gtc gtg gcc ggc ggg      384
Ala Ala Gly Ile Ala Ser Arg Gly Arg Val Pro Val Val Ala Gly Gly
                115                 120                 125 tcc aac tcg ctc atc cac gcg ctc ctc gct gac ccc atc gat gcc gcg      432
Ser Asn Ser Leu Ile His Ala Leu Leu Ala Asp Pro Ile Asp Ala Ala
            130                 135                 140 ccg cgt gac cct ttc gcg gac gcc gat gtc ggg tac cgg ccg gcg ctc      480
Pro Arg Asp Pro Phe Ala Asp Ala Asp Val Gly Tyr Arg Pro Ala Leu
145                 150                 155                 160 cgg ttc ccg tgc tgc ctc ctc tgg gtc gac gtc gac gac gat gtt ctc      528
Arg Phe Pro Cys Cys Leu Leu Trp Val Asp Val Asp Asp Asp Val Leu
                165                 170                 175 gac gaa tac ctc gac cgg cgc gtg gac gac atg gtc ggc gag ggg atg      576
Asp Glu Tyr Leu Asp Arg Arg Val Asp Asp Met Val Gly Glu Gly Met
            180                 185                 190 gtc gag gag ctc gag gaa tac ttc gcg acg acg tcg gcc tcg gag cgg      624
Val Glu Glu Leu Glu Glu Tyr Phe Ala Thr Thr Ser Ala Ser Glu Arg
        195                 200                 205 gcc tcg cac gcc ggg ctg ggc aag gcc atc ggc gtg ccg gag ctc ggc      672
Ala Ser His Ala Gly Leu Gly Lys Ala Ile Gly Val Pro Glu Leu Gly
210                 215                 220 gac tac ttc gcc ggg cgc aag agc ctc gac gcg gcg ata gac gag atc      720
Asp Tyr Phe Ala Gly Arg Lys Ser Leu Asp Ala Ala Ile Asp Glu Ile
225                 230                 235                 240 aag gcc aac acg cgg gtc ctc gcg ggc cgc cag gtc ggc aag atc cga      768
Lys Ala Asn Thr Arg Val Leu Ala Gly Arg Gln Val Gly Lys Ile Arg
                245                 250                 255 cgc at                                                               773
Arg

<210> SEQ ID NO 52
<211> LENGTH: 257
<212> TYPE: PRT
<213> ORGANISM: Oryza sativa

<400> SEQUENCE: 52

Met Glu Arg Ser Arg Val Gly Asp Gly Cys Cys Ser Cys Ser Gly
1               5                   10                  15

Arg Gly Gly Val Ala Ser Thr Thr Ala Val Arg Pro Ser Thr Gly Met
                20                  25                  30

Val Val Ile Val Gly Ala Thr Gly Thr Gly Lys Thr Lys Leu Ser Ile
            35                  40                  45

Asp Ala Ala Gln Glu Leu Ala Gly Glu Val Val Asn Ala Asp Lys Ile
    50                  55                  60

Gln Leu Tyr Asp Gly Leu Asp Val Thr Thr Asn Lys Val Ser Leu Ala
65                  70                  75                  80

Asp Arg Arg Gly Val Pro His His Leu Leu Gly Ala Ile Arg Ala Glu
                85                  90                  95

Ala Gly Glu Leu Pro Pro Ser Ser Phe Arg Ser Leu Ala Ala Ala Ala
                100                 105                 110

Ala Ala Gly Ile Ala Ser Arg Gly Arg Val Pro Val Val Ala Gly Gly
                115                 120                 125

Ser Asn Ser Leu Ile His Ala Leu Leu Ala Asp Pro Ile Asp Ala Ala
            130                 135                 140

Pro Arg Asp Pro Phe Ala Asp Ala Asp Val Gly Tyr Arg Pro Ala Leu
145                 150                 155                 160
```

```
Arg Phe Pro Cys Cys Leu Leu Trp Val Asp Val Asp Asp Val Leu
            165                 170                 175

Asp Glu Tyr Leu Asp Arg Arg Val Asp Asp Met Val Gly Glu Gly Met
        180                 185                 190

Val Glu Glu Leu Glu Glu Tyr Phe Ala Thr Thr Ser Ala Ser Glu Arg
        195                 200                 205

Ala Ser His Ala Gly Leu Gly Lys Ala Ile Gly Val Pro Glu Leu Gly
    210                 215                 220

Asp Tyr Phe Ala Gly Arg Lys Ser Leu Asp Ala Ala Ile Asp Glu Ile
225                 230                 235                 240

Lys Ala Asn Thr Arg Val Leu Ala Gly Arg Gln Val Gly Lys Ile Arg
            245                 250                 255

Arg

<210> SEQ ID NO 53
<211> LENGTH: 1284
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT7 genomic sequence (34911308 aka
      NM_192112)
<220> FEATURE:
<221> NAME/KEY: CDS
<222> LOCATION: (1)...(1284)

<400> SEQUENCE: 53 atg gca gcg act ggt cga aac gcg gcc gca cga cgg aca cgc cgc tcg      48
Met Ala Ala Thr Gly Arg Asn Ala Ala Ala Arg Arg Thr Arg Arg Ser
1               5                   10                  15 atc ccc cgc gcg gct gcc gtg ctc ccc ctc tcg tct gga tca ccg gcg      96
Ile Pro Arg Ala Ala Ala Val Leu Pro Leu Ser Ser Gly Ser Pro Ala
            20                  25                  30 gct gtg ctg agg cga ctg ggg ctc ggt gag tgt ttt ggg tgg gcc ggc     144
Ala Val Leu Arg Arg Leu Gly Leu Gly Glu Cys Phe Gly Trp Ala Gly
        35                  40                  45 ttt atg agc agt ctc ggt ttg aag atc cgc acc gtc gtc cgc tca cct     192
Phe Met Ser Ser Leu Gly Leu Lys Ile Arg Thr Val Val Arg Ser Pro
    50                  55                  60 atg gcg gcc gcg gcc gtc gct ggc gtc gga agg gat ggt agc ttc gcc     240
Met Ala Ala Ala Ala Val Ala Gly Val Gly Arg Asp Gly Ser Phe Ala
65                  70                  75                  80 tcc cag aag cgg cca cgt cgg gtt agt gtg aga atg gag aga agc aga     288
Ser Gln Lys Arg Pro Arg Arg Val Ser Val Arg Met Glu Arg Ser Arg
                85                  90                  95 gtc ggg gac ggt tgc tgc tgc tcc tgc tct ggc cgc ggc ggg gtg gcg     336
Val Gly Asp Gly Cys Cys Cys Ser Cys Ser Gly Arg Gly Gly Val Ala
            100                 105                 110 tcc act acg gcg gtc cgg ccg tcc acg ggg atg gtg gtg atc gtc ggc     384
Ser Thr Thr Ala Val Arg Pro Ser Thr Gly Met Val Val Ile Val Gly
        115                 120                 125 gcc acg ggc acg ggg aag acc aag ctt tcc atc gac gcg gcg cag gag     432
Ala Thr Gly Thr Gly Lys Thr Lys Leu Ser Ile Asp Ala Ala Gln Glu
    130                 135                 140 ctc gcc ggc gag gtg gtg aac gct gac aag att cag ctg tac gac ggc     480
Leu Ala Gly Glu Val Val Asn Ala Asp Lys Ile Gln Leu Tyr Asp Gly
145                 150                 155                 160 ctc gac gtc acc acg aac aag gtg tcg ctc gcc gac cgc cgg ggc gtc     528
Leu Asp Val Thr Thr Asn Lys Val Ser Leu Ala Asp Arg Arg Gly Val
```

|  |  |  |  |  |  |  |  |  |  |  |  |  |  |  |  |
|---|---|---|---|---|---|---|---|---|---|---|---|---|---|---|---|
|  |  | 165 |  |  |  | 170 |  |  |  | 175 |  |  |  |  |  |
| ccg | cac | cac | ctc | ctc | ggc | gca | atc | cgc | gcc | gag | gcc | ggg | gag | ctg | ccg | 576 |
| Pro | His | His | Leu | Leu | Gly | Ala | Ile | Arg | Ala | Glu | Ala | Gly | Glu | Leu | Pro |
|  |  | 180 |  |  |  |  | 185 |  |  |  | 190 |  |  |  |  |
| ccg | tcg | tcg | ttc | cgc | tcg | ctc | gcc | gcc | gcc | gcc | gcc | ggc | atc | gcg |  | 624 |
| Pro | Ser | Ser | Phe | Arg | Ser | Leu | Ala | Ala | Ala | Ala | Ala | Gly | Ile | Ala |
|  | 195 |  |  |  |  | 200 |  |  |  |  | 205 |  |  |  |  |
| tcg | cgc | ggg | cgc | gtg | ccg | gtc | gtg | gcc | ggc | ggg | tcc | aac | tcg | ctc | atc | 672 |
| Ser | Arg | Gly | Arg | Val | Pro | Val | Val | Ala | Gly | Gly | Ser | Asn | Ser | Leu | Ile |
| 210 |  |  |  |  | 215 |  |  |  |  | 220 |  |  |  |  |  |
| cac | gcc | ctc | ctc | gct | gac | ccc | atc | gat | gcc | gcg | ccg | cgt | gac | cct | ttc | 720 |
| His | Ala | Leu | Leu | Ala | Asp | Pro | Ile | Asp | Ala | Ala | Pro | Arg | Asp | Pro | Phe |
| 225 |  |  |  | 230 |  |  |  |  | 235 |  |  |  |  | 240 |  |
| gcg | gac | gcc | gat | gtc | ggg | tac | cgg | ccg | gcg | ctc | cgg | ttc | ccg | tgc | tgc | 768 |
| Ala | Asp | Ala | Asp | Val | Gly | Tyr | Arg | Pro | Ala | Leu | Arg | Phe | Pro | Cys | Cys |
|  |  |  |  | 245 |  |  |  |  | 250 |  |  |  |  | 255 |  |
| ctc | ctc | tgg | gtc | gac | gtc | gac | gac | gat | gtt | ctc | gac | gaa | tac | ctc | gac | 816 |
| Leu | Leu | Trp | Val | Asp | Val | Asp | Asp | Asp | Val | Leu | Asp | Glu | Tyr | Leu | Asp |
|  |  |  | 260 |  |  |  |  | 265 |  |  |  |  | 270 |  |  |
| cgg | cgc | gtg | gac | gac | atg | gtc | ggc | gag | ggg | atg | gtc | gag | gag | ctc | gag | 864 |
| Arg | Arg | Val | Asp | Asp | Met | Val | Gly | Glu | Gly | Met | Val | Glu | Glu | Leu | Glu |
|  | 275 |  |  |  |  | 280 |  |  |  |  | 285 |  |  |  |  |
| gaa | tac | ttc | gcg | acg | acg | tcg | gcc | tcg | gag | cgg | gcc | tcg | cac | gcc | ggg | 912 |
| Glu | Tyr | Phe | Ala | Thr | Thr | Ser | Ala | Ser | Glu | Arg | Ala | Ser | His | Ala | Gly |
| 290 |  |  |  |  | 295 |  |  |  |  | 300 |  |  |  |  |  |
| ctg | ggc | aag | gcc | atc | ggc | gtg | ccg | gag | ctc | ggc | gac | tac | ttc | gcc | ggg | 960 |
| Leu | Gly | Lys | Ala | Ile | Gly | Val | Pro | Glu | Leu | Gly | Asp | Tyr | Phe | Ala | Gly |
| 305 |  |  |  | 310 |  |  |  |  | 315 |  |  |  |  | 320 |  |
| cgc | aag | agc | ctc | gac | gcg | gcg | ata | gac | gag | atc | aag | gcc | aac | acg | cgg | 1008 |
| Arg | Lys | Ser | Leu | Asp | Ala | Ala | Ile | Asp | Glu | Ile | Lys | Ala | Asn | Thr | Arg |
|  |  |  |  | 325 |  |  |  |  | 330 |  |  |  |  | 335 |  |
| gtc | ctc | gcg | gcc | cgc | cag | gtc | ggc | aag | atc | cga | cgc | atg | gcc | gac | gtt | 1056 |
| Val | Leu | Ala | Ala | Arg | Gln | Val | Gly | Lys | Ile | Arg | Arg | Met | Ala | Asp | Val |
|  |  |  | 340 |  |  |  |  | 345 |  |  |  |  | 350 |  |  |
| tgg | ggc | tgg | ccc | atc | cgc | cgc | ctc | gac | gcc | acg | gcc | acc | atc | cgg | gcg | 1104 |
| Trp | Gly | Trp | Pro | Ile | Arg | Arg | Leu | Asp | Ala | Thr | Ala | Thr | Ile | Arg | Ala |
|  | 355 |  |  |  |  | 360 |  |  |  |  | 365 |  |  |  |  |
| cgg | ctc | tcc | ggc | gcc | ggc | cgc | gcc | gcc | gag | gcc | gcc | gcg | tgg | gag | cgc | 1152 |
| Arg | Leu | Ser | Gly | Ala | Gly | Arg | Ala | Ala | Glu | Ala | Ala | Ala | Trp | Glu | Arg |
| 370 |  |  |  |  | 375 |  |  |  |  | 380 |  |  |  |  |  |
| gac | gtg | cgc | ggg | cca | ggc | ctc | gcc | gcg | atg | cgt | cag | ttc | gtc | ggc | cgc | 1200 |
| Asp | Val | Arg | Gly | Pro | Gly | Leu | Ala | Ala | Met | Arg | Gln | Phe | Val | Gly | Arg |
| 385 |  |  |  | 390 |  |  |  |  | 395 |  |  |  |  | 400 |  |
| gcc | gac | ttc | aac | gcc | gca | gcg | gtc | gac | cag | cta | gcc | gcg | cgg | agt | cgg | 1248 |
| Ala | Asp | Phe | Asn | Ala | Ala | Ala | Val | Asp | Gln | Leu | Ala | Ala | Arg | Ser | Arg |
|  |  |  |  | 405 |  |  |  |  | 410 |  |  |  |  | 415 |  |
| agg | caa | tgc | ctt | cgc | ggt | ggc | atg | gtg | gcc | ggc | tga |  |  |  |  | 1284 |
| Arg | Gln | Cys | Leu | Arg | Gly | Gly | Met | Val | Ala | Gly | * |
|  | 420 |  |  |  |  | 425 |  |  |  |  |  |

<210> SEQ ID NO 54
<211> LENGTH: 427
<212> TYPE: PRT
<213> ORGANISM: Oryza sativa

<400> SEQUENCE: 54

Met Ala Ala Thr Gly Arg Asn Ala Ala Arg Arg Thr Arg Ser
1               5                   10                  15

Ile Pro Arg Ala Ala Ala Val Leu Pro Leu Ser Ser Gly Ser Pro Ala
            20                  25                  30

```
Ala Val Leu Arg Arg Leu Gly Leu Gly Glu Cys Phe Gly Trp Ala Gly
             35                  40                  45

Phe Met Ser Ser Leu Gly Leu Lys Ile Arg Thr Val Val Arg Ser Pro
 50                  55                  60

Met Ala Ala Ala Val Ala Gly Val Gly Arg Asp Gly Ser Phe Ala
 65                  70                  75                  80

Ser Gln Lys Arg Pro Arg Arg Val Ser Val Arg Met Glu Arg Ser Arg
                 85                  90                  95

Val Gly Asp Gly Cys Cys Cys Ser Cys Ser Gly Arg Gly Gly Val Ala
                100                 105                 110

Ser Thr Thr Ala Val Arg Pro Ser Thr Gly Met Val Val Ile Val Gly
            115                 120                 125

Ala Thr Gly Thr Gly Lys Thr Lys Leu Ser Ile Asp Ala Ala Gln Glu
        130                 135                 140

Leu Ala Gly Glu Val Val Asn Ala Asp Lys Ile Gln Leu Tyr Asp Gly
145                 150                 155                 160

Leu Asp Val Thr Thr Asn Lys Val Ser Leu Ala Asp Arg Arg Gly Val
                165                 170                 175

Pro His His Leu Leu Gly Ala Ile Arg Ala Glu Ala Gly Glu Leu Pro
            180                 185                 190

Pro Ser Ser Phe Arg Ser Leu Ala Ala Ala Ala Ala Gly Ile Ala
            195                 200                 205

Ser Arg Gly Arg Val Pro Val Val Ala Gly Gly Ser Asn Ser Leu Ile
        210                 215                 220

His Ala Leu Leu Ala Asp Pro Ile Asp Ala Ala Pro Arg Asp Pro Phe
225                 230                 235                 240

Ala Asp Ala Asp Val Gly Tyr Arg Pro Ala Leu Arg Phe Pro Cys Cys
                245                 250                 255

Leu Leu Trp Val Asp Val Asp Asp Val Leu Asp Glu Tyr Leu Asp
            260                 265                 270

Arg Arg Val Asp Asp Met Val Gly Glu Gly Met Val Glu Glu Leu Glu
        275                 280                 285

Glu Tyr Phe Ala Thr Thr Ser Ala Ser Glu Arg Ala Ser His Ala Gly
        290                 295                 300

Leu Gly Lys Ala Ile Gly Val Pro Glu Leu Gly Asp Tyr Phe Ala Gly
305                 310                 315                 320

Arg Lys Ser Leu Asp Ala Ala Ile Asp Glu Ile Lys Ala Asn Thr Arg
                325                 330                 335

Val Leu Ala Ala Arg Gln Val Gly Lys Ile Arg Arg Met Ala Asp Val
            340                 345                 350

Trp Gly Trp Pro Ile Arg Arg Leu Asp Ala Thr Ala Thr Ile Arg Ala
        355                 360                 365

Arg Leu Ser Gly Ala Gly Arg Ala Ala Glu Ala Ala Trp Glu Arg
        370                 375                 380

Asp Val Arg Gly Pro Gly Leu Ala Ala Met Arg Gln Phe Val Gly Arg
385                 390                 395                 400

Ala Asp Phe Asn Ala Ala Val Asp Gln Leu Ala Ala Arg Ser Arg
                405                 410                 415

Arg Gln Cys Leu Arg Gly Gly Met Val Ala Gly
            420                 425

<210> SEQ ID NO 55
<211> LENGTH: 5030
```

<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT6 genomic sequence (011783_3)
<220> FEATURE:
<221> NAME/KEY: CDS
<222> LOCATION: (1777)...(3031)

<400> SEQUENCE: 55

```
acggagacga caagccacgg gaggacgacg tcggctatcg acgagcttc ggggtgccct    60
aaggaaggag aagagaggga ttagagagag ggagatgaac cacggcgatc ggaaaccatg   120
gccgaaggcg gcggtggagg tggtgctcac ccgtgcgcga gggatgggg gctccggcga   180
cgaacttcga cggaggaggg gtggacgagg tggatctcgg ccacgcgaat cgaacgcgg    240
cgacggcgca agacggcggc gagcctagcg gcggctagcg gcggccggag tagcggaaaa   300
aaacggcggc aaggggttgc acgacgcggg gacgatgggg agcacgggag aggtcggcgt   360
aatgggaaa aagagagagg gggtgccggc gatgcttaaa aaggggagaga gagaaccgga   420
cgtggccggg aggggcggga atcgccggcc gacgtgggga gaggggagg agagagaggc   480
gggattcgat tttcgaatcc cggccatctc gggcgcgggc gcgagcggga gagagaggga   540
agtgggcccg ggagacgcgg cgcacgcgcg ggcgtggtcg acgtggcccg gggaaggcgg   600
agacgtgggc gcggcgacgg ttgcgggcgc ggcggcgcgc tgggatcggc gggaggaggg   660
agacgggccc gacaggtggg ccccacctgt cggcgacccc gagagaggag acagcggggc   720
ggcctggctg ccgggctggg cctcggcctg cggccggccc agcagagagg aggggggaagg   780
aaggagaaa tgggccgacg gcccatttcg caaaaggag gaaaagaga ggaaaaaaaa   840
agaaaagga aaaggatt tccctggaat aaaatattgc ttgctcaatt ttaattggtt     900
aaaattattt ctagagctct gaaaattcca ctaaaaatcc tgttaatgaa tttcgacatg   960
tagaactcaa gaaaaattcc acatgtcaaa tccgattatt atttgcatta tttccttagg  1020
gttttctcct gatttcacct gcatttttctt agggtcattt ataaaaatta caatttttggc 1080
ttgggaggaa aacttcgggg tgtgacacgc ctctccccgt aactccgatg ggaggagccc  1140
cacgagccgc tccaccatgg catcgactcc aaccgccccc tctcctccct cccaggctca  1200
ccggccgcct ctccccccct ttccagccgc ccactgccgc tgcccctct ctcttaggct    1260
ccctatgccg ccggcagcct cggagaaaga gtagagaaga tactcgaata ggagaaagaa  1320
aagagaaaag aaaagcaaaa agcagtgtgg gtcccacatt ttttcttctc acttacatgt  1380
gggtcccata aatttttta ttttttgctg acacgtcagc aaaaccagag atcaatactg    1440
tatagggacc ttttttacac agttttgtat agtttagggc cgagatttct ggttttgtgg  1500
ttagagggcc ttaaaaaagc tcgctgttaa gttgagggac ctccagtgaa cttattccaa  1560
aatagaatgt ccaattgggg cctgaaagcc caatacttgt ttgtttgttt tgggcctcta  1620
catctgcaca ggctctcttt cagaaatccc atccatctcc tcctctatcc tcttcccttc  1680
ccttccacac gaagccgccg cccgccggcc ggccgcccag aaccagaaag ctcctcctcc  1740
tcctcctccg cgcgccatca gatctcccag tgcggt atg cag tat gga tgc agg   1794
                                      Met Gln Tyr Gly Cys Arg
                                      1               5 cgc ccc gcc gtg tgg aag aga agt tgg tcc ccg gct gcc gcc gcc gcc    1842
Arg Pro Ala Val Trp Lys Arg Ser Trp Ser Pro Ala Ala Ala Ala Ala
        10                  15                  20 acc aag aac aag gtc atc gtc atc tca ggc ccc acc ggc gcc ggc aag    1890
```

```
                Thr Lys Asn Lys Val Ile Val Ile Ser Gly Pro Thr Gly Ala Gly Lys
                            25                  30                  35 acc agg ctc gcc ttg gac ctc gcc aag agg ctc tcc ggg gag atc atc        1938
Thr Arg Leu Ala Leu Asp Leu Ala Lys Arg Leu Ser Gly Glu Ile Ile
        40                  45                  50 agc gcc gac tcc gtc cag gtc tac cgg ggc ctc gac gtc ggc tcc gcc        1986
Ser Ala Asp Ser Val Gln Val Tyr Arg Gly Leu Asp Val Gly Ser Ala
 55                  60                  65                  70 aag ccc tcc tct tcc gac agg gcc gcc gtg ccg cac cac ctc atc gac        2034
Lys Pro Ser Ser Ser Asp Arg Ala Ala Val Pro His His Leu Ile Asp
                    75                  80                  85 atc ctc cac gcc tcc gac gac tac tcc gcc ggg gac ttc ttc cac gac        2082
Ile Leu His Ala Ser Asp Asp Tyr Ser Ala Gly Asp Phe Phe His Asp
                90                  95                 100 gcc cgc gca gca acc gac cac ctc ctc gcc cga gcc cgc gtc ccc att        2130
Ala Arg Ala Ala Thr Asp His Leu Leu Ala Arg Ala Arg Val Pro Ile
            105                 110                 115 gtc gcc gga ggg act ggc ctc tac ctc cgc tgg tac atc tat ggc aag        2178
Val Ala Gly Gly Thr Gly Leu Tyr Leu Arg Trp Tyr Ile Tyr Gly Lys
        120                 125                 130 ccc agt gtc ccg cag tct tcc atg gac gtc acc tcc gcc gtc tgg tcc        2226
Pro Ser Val Pro Gln Ser Ser Met Asp Val Thr Ser Ala Val Trp Ser
135                 140                 145                 150 gag ctc tcc cgc ttc cgg gac acc ggc cgc tgg gaa gaa gcc gtc gac        2274
Glu Leu Ser Arg Phe Arg Asp Thr Gly Arg Trp Glu Glu Ala Val Asp
                155                 160                 165 ctg gtt gcc aac gcc ggc gac ccc aaa gct cgg gac ctg tca gtc aac        2322
Leu Val Ala Asn Ala Gly Asp Pro Lys Ala Arg Asp Leu Ser Val Asn
            170                 175                 180 aac tgg tca agg tta agg aga agc ctt gag atc atc agg tct tca ggc        2370
Asn Trp Ser Arg Leu Arg Arg Ser Leu Glu Ile Ile Arg Ser Ser Gly
        185                 190                 195 tca cct ccc tct gcc ttc tcc ttg ccc tac aat gct tac aat ctc aat        2418
Ser Pro Pro Ser Ala Phe Ser Leu Pro Tyr Asn Ala Tyr Asn Leu Asn
200                 205                 210 cac cac cgt cgt ctc agt ctc acc aac caa gcc gat caa ccc acg gag        2466
His His Arg Arg Leu Ser Leu Thr Asn Gln Ala Asp Gln Pro Thr Glu
215                 220                 225                 230 ctg gag ctg gac tac gac ttc ctc tgc atc ttc ctc gcg tgc cca cgc        2514
Leu Glu Leu Asp Tyr Asp Phe Leu Cys Ile Phe Leu Ala Cys Pro Arg
                235                 240                 245 gtt gag ctc tac aga tca atc gat ctg agg tgc gaa gag atg ctg gcc        2562
Val Glu Leu Tyr Arg Ser Ile Asp Leu Arg Cys Glu Glu Met Leu Ala
            250                 255                 260 gac aca ggt ggc cta ctc tct gaa gcc tcc tgg ctc ctc gac atc ggc        2610
Asp Thr Gly Gly Leu Leu Ser Glu Ala Ser Trp Leu Leu Asp Ile Gly
        265                 270                 275 ttg agt cct ggc atg aac tcg gct acc tgc gca atc ggc tac agg caa        2658
Leu Ser Pro Gly Met Asn Ser Ala Thr Cys Ala Ile Gly Tyr Arg Gln
280                 285                 290 gcc atg gag tac ttg ctt cag tgt agg cac aac gga ggc agc agc tcc        2706
Ala Met Glu Tyr Leu Leu Gln Cys Arg His Asn Gly Gly Ser Ser Ser
295                 300                 305                 310 cca caa gag ttc ttg gag ttc ctg acc aag ttt cag act gcc tcc agg        2754
Pro Gln Glu Phe Leu Glu Phe Leu Thr Lys Phe Gln Thr Ala Ser Arg
                315                 320                 325 aac ttc tca aag agg cag atg aca tgg ttc cgc aac gag aag att tac        2802
Asn Phe Ser Lys Arg Gln Met Thr Trp Phe Arg Asn Glu Lys Ile Tyr
            330                 335                 340
```

```
cag tgg gtt gat gcc tcg cag cct ttc gac gcc att gcg cag ttt atc    2850
Gln Trp Val Asp Ala Ser Gln Pro Phe Asp Ala Ile Ala Gln Phe Ile
        345                 350                 355 tgt gat gct tac cat gac cgt gct gca agg ctg gtt cct gat tca ctg    2898
Cys Asp Ala Tyr His Asp Arg Ala Ala Arg Leu Val Pro Asp Ser Leu
    360                 365                 370 gaa atg aag agg gag agt tgc agg cac gag agc cgt gat ctc aag acc    2946
Glu Met Lys Arg Glu Ser Cys Arg His Glu Ser Arg Asp Leu Lys Thr
375                 380                 385                 390 tac cgt tct gag aac agg gtg ttc cgt ggg gat gat gat tgt tgc cac    2994
Tyr Arg Ser Glu Asn Arg Val Phe Arg Gly Asp Asp Asp Cys Cys His
                395                 400                 405 gtt ttg gat tgg atc aca agg aca cag agg aag tga c ctctactgct       3041
Val Leu Asp Trp Ile Thr Arg Thr Gln Arg Lys *
            410                 415 ctctcttgtt atctcttttc ccgccaggaa actatcctgc tgctgtgttt ggagatgtta  3101
caataggaaa tttcagcctt tttttgtcag aaaaatacag atacttgttt tgcaaatgtt  3161
ataccaaaag tgttttcaac tttggaattc aatgaaaatt cactagtgtt tcttcagcat  3221
atttctgtct gtattaactc tatgaaaaga agatatatga cattacagct tagagggtgt  3281
tttgcttgtg aatgtgagca tggagtttgc atggtctgaa actgaagttg gaagcatcac  3341
aaattttgtg agattcagag tactaaacag atgggagact tcacttcact tcacttgccg  3401
tgttacctgt atcactcttg ctcggttgtg gacgctgttt gtcaaccttc ttgtacttgt  3461
gctgcagcac ggcaatgtgg ttaatactaa tattttgta tctgaaatct cccgtagtgc   3521
ttagtgctgt atttgtcaaa gcattgtacc cattactgaa aagatgtgc aaaaccaaaa   3581 tgtgttgctg tctgcggtcg cattatcttc ctgctttccc ccaatcaaac actatctgca  3641
atttgcaatg gataagagat aaaaacaaaa catagcaaaa ggaagaaaaa gaaaacggcc  3701
gggagattga agatgacttt gttgggctac cagccatgtc tgatactctg atgcatcatg  3761
catatggtac tctcaagcaa ccaacgcaca agtggcagca gagtacatat aattctatcc  3821
ccttgtgtaa ggcaaccgtt ggcatctgat ctgagtatat tactacctcc gtattttaat  3881
gtatgacgcc gttgactttt cgacaacgtt tgaccattcg tttttattcta aaattttgtg  3941 taaatatgaa aatatttacg tcatgcttaa agaacatttg atgatgaatc aagtcataat  4001
aaaataaata ataattacat aaattttcg aataagacga atggtcaaac attgggaaaa  4061
aaagtcaacg tcatcataca ttaaaatatg gaggtagtac aacatattgt gccagaagaa  4121
gttcctctaa ttacccaaac tgacatggca tatgttgccc tgaaacatgt tgtaaggcaa  4181
ggtcaatgga ttcaattgga agtcagatta aggattaagt agttagcaca actgcaattg  4241
aaggaccaga atatatacaa ggttgaatga ttgcacgtgc tctggactag ctttctggtc  4301
agctctttgg acggtcacaa gctctgaata taacaactgg tgcactttct tgctgatcga  4361
tcattagtca gggatccaac gttgccaatg atctgtagca caactaagga gatcatcatc  4421
atatatatga tggtgcggtt gtaaccgcgt ctgcacctaa ctaaggaaaa agaaacatgt  4481
cgttttcggc tgtagcagag aaagttgcag gacaacccaa aatatgtata gccaacagaa  4541
atactgttcc aaatcttatg gttatatgca atgataccca ccaaacattt ggagggatg   4601 cactcgacat aatttgctct ccatgaaaaa ggcaggagag aaggaaaatg cagaaaagac  4661
agtgcaaaag cagtggtgtc atgtgtgtgc ccaccttgat gtaaagcacc agctcttata  4721
tagcttcaaa agcgtgaaga ttcttttgtca aacagcaagg taagtactag tgcttgtcaa   4781 tacttttga agaaaatagg cactccaagg agcagcattt gttttatgcc tacatgctta   4841
```

-continued

```
ctcttgctat acgagtacat atgagtagta catcatttca ggcctgcttg ctagagctgc    4901
aagaaggaag gagccgcaga tgctcacaag tcatgattaa ggattaatat taatgccgaa    4961
gcttttgcta ggtcttcatc ttttcctttt aaatttttt tggggggggga gatagagggg    5021 attgatctg                                                            5030
```

<210> SEQ ID NO 56
<211> LENGTH: 1254
<212> TYPE: DNA
<213> ORGANISM: Oryza sativa
<220> FEATURE:
<221> NAME/KEY: CDS
<222> LOCATION: (1)...(1254)
<220> FEATURE:
<221> NAME/KEY: misc_feature
<222> LOCATION: (0)...(0)
<223> OTHER INFORMATION: OsIPT6 coding sequence

<400> SEQUENCE: 56

```
atg cag tat gga tgc agg cgc ccc gcc gtg tgg aag aga agt tgg tcc     48
Met Gln Tyr Gly Cys Arg Arg Pro Ala Val Trp Lys Arg Ser Trp Ser
 1               5                  10                  15 ccg gct gcc gcc gcc gcc acc aag aac aag gtc atc gtc atc tca ggc     96
Pro Ala Ala Ala Ala Ala Thr Lys Asn Lys Val Ile Val Ile Ser Gly
             20                  25                  30 ccc acc ggc gcc ggc aag acc agg ctc gcc ttg gac ctc gcc aag agg    144
Pro Thr Gly Ala Gly Lys Thr Arg Leu Ala Leu Asp Leu Ala Lys Arg
         35                  40                  45 ctc tcc ggg gag atc atc agc gcc gac tcc gtc cag gtc tac cgg ggc    192
Leu Ser Gly Glu Ile Ile Ser Ala Asp Ser Val Gln Val Tyr Arg Gly
     50                  55                  60 ctc gac gtc ggc tcc gcc aag ccc tcc tct tcc gac agg gcc gcc gtg    240
Leu Asp Val Gly Ser Ala Lys Pro Ser Ser Ser Asp Arg Ala Ala Val
 65                  70                  75                  80 ccg cac cac ctc atc gac atc ctc cac gcc tcc gac gac tac tcc gcc    288
Pro His His Leu Ile Asp Ile Leu His Ala Ser Asp Asp Tyr Ser Ala
                 85                  90                  95 ggg gac ttc ttc cac gac gcc cgc gca gca acc gac cac ctc ctc gcc    336
Gly Asp Phe Phe His Asp Ala Arg Ala Ala Thr Asp His Leu Leu Ala
            100                 105                 110 cga gcc cgc gtc ccc att gtc gcc gga ggg act ggc ctc tac ctc cgc    384
Arg Ala Arg Val Pro Ile Val Ala Gly Gly Thr Gly Leu Tyr Leu Arg
        115                 120                 125 tgg tac atc tat ggc aag ccc agt gtc ccg cag tct tcc atg gac gtc    432
Trp Tyr Ile Tyr Gly Lys Pro Ser Val Pro Gln Ser Ser Met Asp Val
    130                 135                 140 acc tcc gcc gtc tgg tcc gag ctc tcc cgc ttc cgg gac acc ggc cgc    480
Thr Ser Ala Val Trp Ser Glu Leu Ser Arg Phe Arg Asp Thr Gly Arg
145                 150                 155                 160 tgg gaa gaa gcc gtc gac ctg gtt gcc aac gcc ggc gac ccc aaa gct    528
Trp Glu Glu Ala Val Asp Leu Val Ala Asn Ala Gly Asp Pro Lys Ala
                165                 170                 175 cgg gac ctg tca gtc aac aac tgg tca agg tta agg aga agc ctt gag    576
Arg Asp Leu Ser Val Asn Asn Trp Ser Arg Leu Arg Arg Ser Leu Glu
            180                 185                 190 atc atc agg tct tca ggc tca cct ccc tct gcc ttc tcc ttg ccc tac    624
Ile Ile Arg Ser Ser Gly Ser Pro Pro Ser Ala Phe Ser Leu Pro Tyr
        195                 200                 205 aat gct tac aat ctc aat cac cac cgt cgt ctc agt ctc acc aac caa    672
Asn Ala Tyr Asn Leu Asn His His Arg Arg Leu Ser Leu Thr Asn Gln
    210                 215                 220
```

```
gcc gat caa ccc acg gag ctg gag ctg gac tac gac ttc ctc tgc atc        720
Ala Asp Gln Pro Thr Glu Leu Glu Leu Asp Tyr Asp Phe Leu Cys Ile
225                 230                 235                 240 ttc ctc gcg tgc cca cgc gtt gag ctc tac aga tca atc gat ctg agg        768
Phe Leu Ala Cys Pro Arg Val Glu Leu Tyr Arg Ser Ile Asp Leu Arg
                245                 250                 255 tgc gaa gag atg ctg gcc gac aca ggt ggc cta ctc tct gaa gcc tcc        816
Cys Glu Glu Met Leu Ala Asp Thr Gly Gly Leu Leu Ser Glu Ala Ser
            260                 265                 270 tgg ctc ctc gac atc ggc ttg agt cct ggc atg aac tcg gct acc tgc        864
Trp Leu Leu Asp Ile Gly Leu Ser Pro Gly Met Asn Ser Ala Thr Cys
        275                 280                 285 gca atc ggc tac agg caa gcc atg gag tac ttg ctt cag tgt agg cac        912
Ala Ile Gly Tyr Arg Gln Ala Met Glu Tyr Leu Leu Gln Cys Arg His
    290                 295                 300 aac gga ggc agc agc tcc cca caa gag ttc ttg gag ttc ctg acc aag        960
Asn Gly Gly Ser Ser Ser Pro Gln Glu Phe Leu Glu Phe Leu Thr Lys
305                 310                 315                 320 ttt cag act gcc tcc agg aac ttc tca aag agg cag atg aca tgg ttc       1008
Phe Gln Thr Ala Ser Arg Asn Phe Ser Lys Arg Gln Met Thr Trp Phe
                325                 330                 335 cgc aac gag aag att tac cag tgg gtt gat gcc tcg cag cct ttc gac       1056
Arg Asn Glu Lys Ile Tyr Gln Trp Val Asp Ala Ser Gln Pro Phe Asp
            340                 345                 350 gcc att gcg cag ttt atc tgt gat gct tac cat gac cgt gct gca agg       1104
Ala Ile Ala Gln Phe Ile Cys Asp Ala Tyr His Asp Arg Ala Ala Arg
        355                 360                 365 ctg gtt cct gat tca ctg gaa atg aag agg gag agt tgc agg cac gag       1152
Leu Val Pro Asp Ser Leu Glu Met Lys Arg Glu Ser Cys Arg His Glu
    370                 375                 380 agc cgt gat ctc aag acc tac cgt tct gag aac agg gtg ttc cgt ggg       1200
Ser Arg Asp Leu Lys Thr Tyr Arg Ser Glu Asn Arg Val Phe Arg Gly
385                 390                 395                 400 gat gat gat tgt tgc cac gtt ttg gat tgg atc aca agg aca cag agg       1248
Asp Asp Asp Cys Cys His Val Leu Asp Trp Ile Thr Arg Thr Gln Arg
                405                 410                 415 aag tga                                                                1254
Lys *

<210> SEQ ID NO 57
<211> LENGTH: 417
<212> TYPE: PRT
<213> ORGANISM: Oryza sativa

<400> SEQUENCE: 57

Met Gln Tyr Gly Cys Arg Arg Pro Ala Val Trp Lys Arg Ser Trp Ser
1               5                   10                  15

Pro Ala Ala Ala Ala Thr Lys Asn Lys Val Ile Val Ile Ser Gly
            20                  25                  30

Pro Thr Gly Ala Gly Lys Thr Arg Leu Ala Leu Asp Leu Ala Lys Arg
        35                  40                  45

Leu Ser Gly Glu Ile Ile Ser Ala Asp Ser Val Gln Val Tyr Arg Gly
    50                  55                  60

Leu Asp Val Gly Ser Ala Lys Pro Ser Ser Asp Arg Ala Ala Val
65                  70                  75                  80

Pro His His Leu Ile Asp Ile Leu His Ala Ser Asp Tyr Ser Ala
                85                  90                  95

Gly Asp Phe Phe His Asp Ala Arg Ala Ala Thr Asp His Leu Leu Ala
```

```
                100                 105                 110
Arg Ala Arg Val Pro Ile Val Ala Gly Gly Thr Gly Leu Tyr Leu Arg
            115                 120                 125

Trp Tyr Ile Tyr Gly Lys Pro Ser Val Pro Gln Ser Ser Met Asp Val
130                 135                 140

Thr Ser Ala Val Trp Ser Glu Leu Ser Arg Phe Arg Asp Thr Gly Arg
145                 150                 155                 160

Trp Glu Glu Ala Val Asp Leu Val Ala Asn Ala Gly Asp Pro Lys Ala
            165                 170                 175

Arg Asp Leu Ser Val Asn Asn Trp Ser Arg Leu Arg Arg Ser Leu Glu
            180                 185                 190

Ile Ile Arg Ser Ser Gly Ser Pro Ser Ala Phe Ser Leu Pro Tyr
            195                 200                 205

Asn Ala Tyr Asn Leu Asn His His Arg Arg Leu Ser Leu Thr Asn Gln
            210                 215                 220

Ala Asp Gln Pro Thr Glu Leu Glu Leu Asp Tyr Asp Phe Leu Cys Ile
225                 230                 235                 240

Phe Leu Ala Cys Pro Arg Val Glu Leu Tyr Arg Ser Ile Asp Leu Arg
            245                 250                 255

Cys Glu Glu Met Leu Ala Asp Thr Gly Gly Leu Leu Ser Glu Ala Ser
            260                 265                 270

Trp Leu Leu Asp Ile Gly Leu Ser Pro Gly Met Asn Ser Ala Thr Cys
            275                 280                 285

Ala Ile Gly Tyr Arg Gln Ala Met Glu Tyr Leu Leu Gln Cys Arg His
            290                 295                 300

Asn Gly Gly Ser Ser Ser Pro Gln Glu Phe Leu Glu Phe Leu Thr Lys
305                 310                 315                 320

Phe Gln Thr Ala Ser Arg Asn Phe Ser Lys Arg Gln Met Thr Trp Phe
            325                 330                 335

Arg Asn Glu Lys Ile Tyr Gln Trp Val Asp Ala Ser Gln Pro Phe Asp
            340                 345                 350

Ala Ile Ala Gln Phe Ile Cys Asp Ala Tyr His Asp Arg Ala Ala Arg
            355                 360                 365

Leu Val Pro Asp Ser Leu Glu Met Lys Arg Glu Ser Cys Arg His Glu
            370                 375                 380

Ser Arg Asp Leu Lys Thr Tyr Arg Ser Glu Asn Arg Val Phe Arg Gly
385                 390                 395                 400

Asp Asp Asp Cys Cys His Val Leu Asp Trp Ile Thr Arg Thr Gln Arg
            405                 410                 415

Lys

<210> SEQ ID NO 58
<211> LENGTH: 8306
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT10 genomic sequence (011410_2)
<220> FEATURE:
<221> NAME/KEY: exon
<222> LOCATION: (2001)...(2675)
<220> FEATURE:
<221> NAME/KEY: exon
<222> LOCATION: (3415)...(3438)
<220> FEATURE:
<221> NAME/KEY: exon
<222> LOCATION: (3922)...(4065)
```

```
<220> FEATURE:
<221> NAME/KEY: exon
<222> LOCATION: (5392)...(6306)

<400> SEQUENCE: 58
tagagacata tgggaagatc tctcaccgag aaactgatcc atgagtttaa gcaaaactgg      60
tcattataat aaagaaaaat ctacaaaatt actgttgtta attcccttga actactgtca     120
tcaagaaaga ttggttgatg atggacatgt ccgcagcaat ggagggtcac cgcgtcgtct     180
ccatcggcag cgagatctgc gagcaggatc acgccggcgg cgaccagcgc tccaccgccg     240
gcgacgatgg cgacggcgac ggtgacggcc cttacgtctc cctcttcgag ctcgcgccca     300
tcgtggcgcg cgcaccgcag gacgaggacg gacacggcca ggaagacagc catgcccaag     360
aggtgttcga tgacctgccg gccgagctgc ggcgcgacgg cgacggcgcg ctgaccgtgg     420
gcgggctcgc agcggcgctc cgggcgcagc ggagggagct ggaggccgtt cgcgccgagc     480
tcgacgcgga gcggcgcgcg ggcgcggagg cggcggagta ccagcggcag ctggaggagc     540 aggggggagtt cgaccgggag gcggtgcgcc tcgccatgca gctcgtccac gaggccgaga     600
cggagaagca cgccctgcag caccagctcg acgcgttccg ggtcaaggcc cagctctacg     660
actacgaggc cgccgccacc gccgccgcca ggaccacga cgcggccggc gacggcggcg     720
gcggcggcaa caactaccag tcgctggtgg acttcttgcc ggggtcggtg ttctcctcct     780
cgccggacct ggccaacctg ctcaagtctc acaccgaggg caatggcggc ggccgtcgac     840
tgaccgacgc gccggtgccg gtggtcaccg aggtggttga ggaagaagag gaagaggagg     900
aggaggagga ggaggaagtc gccgtcgcgg ccatcggtgg cgtggattcg aacgggaacg     960
gtggtgctgc cgccaccatc gccatcgccg gcgattcttt gcaggaagga agcagtgatc    1020
acctcgaacc cacagaagtg tcaccgcaac ggtgaattgt gaatcttggg attaatacaa    1080
ccttgtcaat atatacatat catgtaatta tatttgacta gccacatgtg cccgcgcttc    1140
gttgcggatc atgaatttgt aaattaccgt agtaaagaaa gttttttcta atatgtatac    1200
tgatccattg tttaaatggc tgcaatatat tttattactt aatgatacccc cacgcgttgt    1260 tgcagaaaat tctcaaattt tagttattgg gtagaatgta caacctaatg ctaaaaagtt    1320
agagaaacaa aatgattttt tggaccaata attgtgtgaa tagcgtaagt caaattctaa    1380
aaataattta ggtaacacat tttagcagaa acttcaaaag atgtacatac tttgaggtca    1440
tgagttaaca tacaatgttg tactgtatta ttcatcaaat attgtcacaa tgtagcttac    1500
tcatagatat aagattgtat gtatctagtg agggacaatt tatattgttc actaacatct    1560
aatattgttc tcggaatggt atccagagaa atttttatga tttagaataa aatggaacaa    1620
tgttgtataa atctataaaa atataattgc ttaattattt atatgcttag atttggcacc    1680
tctaaatgtg gcctaactac cattggacca cagtaagtag gggctcataa agatgcatcc    1740
cctataaaag ccaagggaca ccgagagtcc tctacgaaag aattctaccc ttcccattag    1800
gacagtcaaa caccttattg ctactccaat cttcctttca gtatggagaa ctcctcaaag    1860
aaaacccaag agttcttccc taaggtgggg aatggaggtt atgctgagca gctggatctc    1920
ttgctgaagc agcttcgttt tcctaacaac cgatccacca tgcggagcaa gtgatcaaag    1980
gattccagaa ggattggacg atgaagatct acattcaagc cagggaagag aagtgtcaag    2040
gacatgtgtt caagtcccgc caccttcgag ccaacaaaga ggcagcactc caggatgcgt    2100
cgcgtgaggc attcatgcgt ctatgtaaga tctacagcat cgaggttgcg agtactccgt    2160
tctttctaca tccattccgt gaatgcggtg accgccgctg ccatattcgg aaatttaggg    2220
```

```
gctttgagga gcactctccc atccacttct ccatgtggat gtgggctgca gacgaggcct   2280
atgaggaggc cttagaggaa ttagatatgc ttcggtcaaa gattgccggc tgggaggagc   2340
ggtacaacca ccttgctaaa gaacacacca ctcgtggaca actattggaa gcaatcaagc   2400
ttcgcctcca gtggtatttt cgaacccat ctcaagctca aatccaacgg actttgtcac   2460
caccaccaca aagagtgaca agaagtgatg gtgaggacta tagtcaaatc aatgcacagc   2520
aggcatgtct ggaaaggtcc gaagttaaac ttgatagggc aacttcacaa gactatctgc   2580
aaggatacaa gcccccatca gaatccctcg acgctattgt ttggcctctt gttgaaggga   2640
agcatgacaa tacaagcagc ggtaggagga atgaggtaaa ggaaactgct cacaataacc   2700
aagggaccct gttgggctag tcctcggaaa gagagttgga ccagctacat atctagaaga   2760
ccacaatgta agtgacaggg ctatatcttg tcacgtagga gtagcatgtg ggtgggagtt   2820
ggaccaattt cacatatagg agaccgctat gtaagtgaca ggttatagcc tgtcacctag   2880
cagtactatg tgggtggtca agatcaccta tcaagtgtgc ttgtctatgc ctagttgtga   2940
cctaccagtt agagtagtat gtgagggtgg tagtaagatt gtattcccctt tgtccagttg   3000 tgggtggaca agctaggcgg atagtctagt gtgtttgtgt atgcgtggtt gtgatgcttt   3060
tgtgcttggc ccgaggacaa tgagcaatat ttgcttaaaa gtgcttgttt cttctgcaa    3120 tgctactttg ttttcatgat catgcaagtt acctaaatac atgtgaattg ttctagttga   3180
tgggatctat tgcgatagaa tcaaatgatt tccaattgta tagtaacgga gctagcaaca   3240
gtaatataac cattttgacc aggatggttc aaaagtaaac catatagaaa aggagttgtt   3300
tattaaatat atgtattgta tcaactaaaa tagtacacaa tggccaataa ttttgcaatg   3360
aatttagttg ataattggca tggtatggtt tttttttttt tttgcttttt gcagaaggca   3420
tgggaaatgg caaaacaagt aaatatatta caaagtaatt tctaacgatt gttagtaacc   3480
ggaagatggt tggtattaga ttaccaagtt tggaagtatt attttaccag agaacgtata   3540
agtaacatgt atattgttcg aagtgcccac atttgaattt acattcgatg aaggattgtt   3600
atgtaatttt tccttgaaaa atgtgcaaaa gcacatgttt acaaatcatc accatatctt   3660
aagatgaaag taggcataag gtttaaaaag tcaaggtaa ttattaggtt tatttttttg    3720
ttatgcttac acacgtattg acgatacaaa ggtttgagcc attaactctg atgcctaaaa   3780
atatcttcaa agaaaaaaaa tcgatcacaa ttgcttgaat aatagtaaga gtatacctaa   3840
ctgaatttgg ggcccaccaa tataattacc gtacacatcc aactgcacat ggattgatag   3900
gccaaattac tataattgga ggtgcctaga ggaaggattt atgctttggt ctataaacat   3960
caagacaata ttggactggt ccttgaaaag agagttggac cagctgcaca tctaggagac   4020
cgctatgtaa gtgacagggt catatcacat ctaggagacc tctatgtaag tgacagggtc   4080
atatgttgtc acctaggagt agtatgtggg taagagttgg accaacttca catataggta   4140
accgctatgt aagtgatagg gtcatagcct gtcacctagc agcactatgt gggtgatcaa   4200
aatggcctct ctggtgtgct tgtctatgcc taattgtaat gcttttgtgc ttggctcgag   4260
gccaatgagt aatgtatgct tgaactgcta tgtaagcgac agggtcatag cctattagtt   4320
agagtagtag gtgagggtgg taataaaatt gtattcccctt tgtctagtta tgggtggaca   4380
aggtgggtaa tctagtgtgt ttgtgtatgc gtggttgtga tgcttttgtg cttggcccga   4440
ggataatgag caatatttgc ttaaagttgc atgttttctt ctccaatgca ggtttgtttt   4500
catgagcatg caaattatct aaatacatgt gaattgttct agttgatggg atctattgcg   4560
```

```
atagaatcaa atggcctcta atcgtatagt aacagagcta gcaacagtaa tataaccatc    4620
ttaaccagga tggttcaaaa gcaaaccata tataaaagga gttgtttatt aaatatatgt    4680
attgtatcaa ccggaatatt acacaagggc taataatttt gcaatgaatt tatttgataa    4740
ttggcattgt atggctattt tgttttttgc attttgcgga aggcatgaga aatgccaaaa    4800
caagtaaata tagagcaaag tattttacaa cgattgttag taagtatttt tgaggtagat    4860
ggttggtatt atattaccaa gtttcaaagt attcttttac cagagaacat ataagtaaca    4920
tatgtatgat ttgaattgcc cacatttgaa tttactttcg atgaaggatt gatacggatt    4980
tttttttcctt gaaaaatgtg taaaagcaca tgtttacaaa tcatcaccat attaagatga    5040
aagtaggcat attgtttaaa aagttaaagg agcttatcag gtttaatttg ttttatgctt    5100
acacacgtat tgaggataca attttaaggg ttgagccgtt aactcttatg ccaaaaatat    5160
ctccaaagaa aaaaaatcga tcacaattgc ttggataatt gtatgagtat atctaattga    5220
atttgggccc catcaagatg attaccatac acattcaact gtacatggat tgatatgcca    5280
aattccggta agtggaggtg ccaagaggaa ggaggaagga tttatgcttt gatctagaaa    5340
catcaaggcg gcacactttc ccctttccta tatactgagg aactcttcca ggtaatacga    5400
acccttagct actttccttt catgctcaat tttcacccct tcttgtgattg cttcctcaat   5460
atgctgggaa acaagttagt agtgattatt ggtgccacgg gaactggaaa aacaagactc    5520
tcaattgaga ttgccaaggc gattggtggg gaagtggtaa atggtgacaa gatgcaaatt    5580
tatgatggcc tggatattac gacaaacaag gttctttac aagatcgatg cggcatacct     5640
catcacctta ttgcgtccat ccctcacaac gcaggtgatt ttcctgtgtc attttttcga    5700
tatgctgcaa aaaccacaat aaactgcatt gccagacgtg gtcacacacc gattgtggtg    5760
ggtggatcta actcacttat ccatggtctc cttgttgaca attttgatttt gtctattgtg   5820
gatccttttg ggcaattgga ggttagctat cagccgacgc ctcaatggca atgttgtttt    5880
ctatgggttc atgttaatga ggtgattctt aatgagtatt tgaaacgtcg tgttgacggc    5940
atggttgatg ctgggttagt tgaggaaatt gaagaatatt ttgacacatt atcagttaat    6000
ggacatgttc catatgtggg attagggaag gccattggtg ttccagagct aagcgagtat    6060
tttactggac gggtgagttg tagtgatgct cttttctatga tgaagaccaa tacacagatt    6120
cttgcacgat ctcaagtcac aaagattcat cgcatggttg atgtgtgggg atggcatgtt    6180
catgcccttg attgtactga aactattcta gcacatctta ctggatcaaa taagtatatg    6240
gaggatttgg tgtggaaacg tgatgtaagt gactctggac ttgctgctat acaagatttt    6300
ctgtgataat atcagaagat gggaagctag tttctcaaac acatcggcta ttgattttgt    6360
ctacaataat ggtttaatcg tctggcttgc ttagtaattt tacagatcat ggcatactaa    6420
gttaacttgg atcatttttgg gtgtgtttgg aaggagcaaa cgtcaattgg tgtatatgaa    6480
attacttgga ggccttttgt accttaaaca cttggatgcc ttttatttta cataatagtt    6540
atatatagtt gttgttcata atttttttgat gtcatcaata ttcatacgtg gtgatgcaat    6600
tcttattgat tatctctaat agatatgatg tcgtgccaac aaaaacaaca aacatggaag    6660
tcacaaatag tcatataaga aaataataga gggttcccag ttgttcatgc accaagctta    6720
atacaaatag gaaataaaca tgatagtcca atgacaatgg accaagttta gagtagcacc    6780
acacacaatg cttgttcact tactgataca acataaataa taaagagtta agtatgacaa    6840
cacaaaaaac atcccctgca acaaagagcc cacatagaga gtatacataa aatccaaaaa    6900
caatgttttt gttaaatctc tggttgggaa gtaattattt gtcattacag tcgaaatttt    6960
```

-continued

```
caaacttgaa aacttaacca taggaatttt tggagagccc agcctttgag gatggactta      7020
gaatttggag gaaattttct aagaggttga taaacccaaa cctcaagatt caaatatttg      7080
gatcaagact tttgggcttg ggatttggtg tttgaagaaa cagcgggatt tgagagtact      7140
ggcacataat cctaaataca ctcaaagaat caaaagattt taaacatagg tttcaaataa      7200
aaaaaatcaa ccgaggcaaa acccaaggcg ttgcaatcct accccctatt aatagaatct      7260
cgtcttgaga tttcggccaa agaagggtag cagaatgttg ttgtggctcc tgttcagtga      7320
taggctcaat accagggaca tgttggatag aagacattgt gcaaggaag atgatgatct      7380 aacatgtgtt gtgtgtaatg gtgagtgtag agaaactcgg cttcatctct tttctgccta      7440
ccctagcatc agatgtaggc aacacttggg aattgaatgg aaacataacc tggaattttt      7500
cccaacggtt gttctcgcga gattgaggtt tggtcggaga ggttttctgg aaatattttt      7560
tatagcctca tggcatattt ggaaacagag aaagaggctt attttccaaa atatcctgcc      7620
tatgttccag tcttggaggt tgcttttttgt gaatgaagtt cttctacata tgtgtagaat      7680
gaaggatcct ctaaaacaat ctgttttga ttggttacaa accttatagg ttttgagttt      7740
tccctgtaat tgtttaatg aaaatacact gctaggcaaa gccctggcag tatttgcagt      7800
taaaaaaata gggtccttga aatgatacat ggtctatgtg ctgacctttt cctttggtga      7860
ttgaggcatt cctatcccat cttttactga gtgatacatg ggccactgtt tgacccaaaa      7920
tttttgaact caagtgtcga ctctgaactg atactgtctt tgttgagaat ctaaagttct      7980
tctttggtgt cagtgctggt gttgttatgt cctgatcggg caataatggg gacctctatt      8040
tggacgtgtt gtggccatat cctgcatcct tgccggttgt tatgatagtc attcggggta      8100
ttcgagatca tttctcagcc tctatacatg ttcaccaaca tactttttt ttacctcgtg      8160 cacttgggta cccatttcat tgagcgcacc cttatcttcg ggggcccatc tctgtctcct      8220
tggagtggtt ttggtcgtgc acgcgggtgt ggcgagtgga ggcggtgtag ctcgggcgag      8280
gcgaaaaaat ggagcggagg ttcgac                                          8306
```

```
<210> SEQ ID NO 59
<211> LENGTH: 585
<212> TYPE: PRT
<213> ORGANISM: Oryza sativa
<220> FEATURE:
<221> NAME/KEY: CHAIN
<222> LOCATION: (0)...(0)
<223> OTHER INFORMATION: OsIPT10 amino acid sequence (011410_2)

<400> SEQUENCE: 59

Met Lys Ile Tyr Ile Gln Ala Arg Glu Glu Lys Cys Gln Gly His Val
1               5                   10                  15

Phe Lys Ser Arg His Leu Arg Ala Asn Lys Glu Ala Ala Leu Gln Asp
            20                  25                  30

Ala Ser Arg Glu Ala Phe Met Arg Leu Cys Lys Ile Tyr Ser Ile Glu
        35                  40                  45

Val Ala Ser Thr Pro Phe Phe Leu His Pro Phe Arg Glu Cys Gly Asp
    50                  55                  60

Arg Arg Cys His Ile Arg Lys Phe Arg Gly Phe Glu Glu His Ser Pro
65                  70                  75                  80

Ile His Phe Ser Met Trp Met Trp Ala Ala Asp Glu Ala Tyr Glu Glu
                85                  90                  95

Ala Leu Glu Glu Leu Asp Met Leu Arg Ser Lys Ile Ala Gly Trp Glu
            100                 105                 110
```

-continued

Glu Arg Tyr Asn His Leu Ala Lys Glu His Thr Thr Arg Gly Gln Leu
    115                 120                 125

Leu Glu Ala Ile Lys Leu Arg Leu Gln Trp Tyr Phe Arg Thr Pro Ser
130                 135                 140

Gln Ala Gln Ile Gln Arg Thr Leu Ser Pro Pro Gln Arg Val Thr
145                 150                 155                 160

Arg Ser Asp Gly Glu Asp Tyr Ser Gln Ile Asn Ala Gln Gln Ala Cys
                165                 170                 175

Leu Glu Arg Ser Glu Val Lys Leu Asp Arg Ala Thr Ser Gln Asp Tyr
            180                 185                 190

Leu Gln Gly Tyr Lys Pro Pro Ser Glu Ser Leu Asp Ala Ile Val Trp
        195                 200                 205

Pro Leu Val Glu Gly Lys His Asp Asn Thr Ser Ser Gly Arg Arg Asn
    210                 215                 220

Glu Lys Ala Trp Glu Met Ala Lys Gln Val Pro Arg Gly Arg Ile Tyr
225                 230                 235                 240

Ala Leu Val Tyr Lys His Gln Asp Asn Ile Gly Leu Val Leu Glu Lys
                245                 250                 255

Arg Val Gly Pro Ala Ala His Leu Gly Asp Arg Tyr Val Ser Asp Arg
            260                 265                 270

Val Ile Ser His Leu Gly Asp Leu Tyr Val Ile Arg Thr Leu Ser Tyr
        275                 280                 285

Phe Pro Phe Met Leu Asn Phe His Pro Ser Cys Asp Cys Phe Leu Asn
    290                 295                 300

Met Leu Gly Asn Lys Leu Val Val Ile Ile Gly Ala Thr Gly Thr Gly
305                 310                 315                 320

Lys Thr Arg Leu Ser Ile Glu Ile Ala Lys Ala Ile Gly Gly Glu Val
                325                 330                 335

Val Asn Gly Asp Lys Met Gln Ile Tyr Asp Gly Leu Asp Ile Thr Thr
            340                 345                 350

Asn Lys Val Ser Leu Gln Asp Arg Cys Gly Ile Pro His His Leu Ile
        355                 360                 365

Ala Ser Ile Pro His Asn Ala Gly Asp Phe Pro Val Ser Phe Arg
    370                 375                 380

Tyr Ala Ala Lys Thr Thr Ile Asn Cys Ile Ala Arg Arg Gly His Thr
385                 390                 395                 400

Pro Ile Val Val Gly Gly Ser Asn Ser Leu Ile His Gly Leu Leu Val
                405                 410                 415

Asp Asn Phe Asp Leu Ser Ile Val Asp Pro Phe Gly Gln Leu Glu Val
            420                 425                 430

Ser Tyr Gln Pro Thr Pro Gln Trp Gln Cys Cys Phe Leu Trp Val His
        435                 440                 445

Val Asn Glu Val Ile Leu Asn Glu Tyr Leu Lys Arg Arg Val Asp Gly
    450                 455                 460

Met Val Asp Ala Gly Leu Val Glu Glu Ile Glu Tyr Phe Asp Thr
465                 470                 475                 480

Leu Ser Val Asn Gly His Val Pro Tyr Val Gly Leu Gly Lys Ala Ile
                485                 490                 495

Gly Val Pro Glu Leu Ser Glu Tyr Phe Thr Gly Arg Val Ser Cys Ser
            500                 505                 510

Asp Ala Leu Ser Met Met Lys Thr Asn Thr Gln Ile Leu Ala Arg Ser
        515                 520                 525

```
Gln Val Thr Lys Ile His Arg Met Val Asp Val Trp Gly Trp His Val
        530                 535                 540

His Ala Leu Asp Cys Thr Glu Thr Ile Leu Ala His Leu Thr Gly Ser
545                 550                 555                 560

Asn Lys Tyr Met Glu Asp Leu Val Trp Lys Arg Asp Val Ser Asp Ser
                565                 570                 575

Gly Leu Ala Ala Ile Gln Asp Phe Leu
        580                 585

<210> SEQ ID NO 60
<211> LENGTH: 7608
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT9 genomic sequence (005021_3)
<220> FEATURE:
<221> NAME/KEY: exon
<222> LOCATION: (2001)...(3079)
<220> FEATURE:
<221> NAME/KEY: exon
<222> LOCATION: (3322)...(3390)
<220> FEATURE:
<221> NAME/KEY: exon
<222> LOCATION: (4363)...(4436)
<220> FEATURE:
<221> NAME/KEY: exon
<222> LOCATION: (5516)...(5608)

<400> SEQUENCE: 60
```

| | | | | | |
|---|---|---|---|---|---|
| taatgttatg | atctgctcgc | tccatttaaa | agtcttaagc | atatttttta | tattttttaa | 60 |
| taaatgagat | ggtcatattt | atattcaaga | cttaaatgta | gagattatct | tttcatattg | 120 |
| tcgcagtgct | aaattaaatt | attgatccga | acccaagtag | ttatcttaat | atatatttat | 180 |
| atgttgtata | tattagtgta | gcttttttta | atttgttaca | tgtgcattga | gttgattttt | 240 |
| tcatggtttt | gattatagaa | aatgagaaaa | ttgtaatatt | gtgacctaaa | ttttttggat | 300 |
| agagggagta | tgaccggtga | aatctccaaa | actactgcag | ggtaggagta | ctcgtagtac | 360 |
| ttctaaccag | cctgaccaca | ttcaaacgca | cagtagtaca | gtacttggag | gacattcaag | 420 |
| tcacagtaca | caaatgtttc | cagcacaata | aaactacttg | gaacagtact | gtgggcagca | 480 |
| gctctttgca | ggccgcaggc | gagtacagat | ggaccctcat | cgaaacgaaa | cgaaacccat | 540 |
| gccaagaacc | tgcgtgctct | tgatgagcc | agtcattcct | cgaggcatct | tttcatcaga | 600 |
| tcagaattca | gagcctcgcg | agaaagaaag | gctgggccaa | tcctgcagct | gcacagatcc | 660 |
| cagcagctgc | agctgtagct | gtagtagtag | ctgtagtcga | tcgacagtgt | ccgagccaat | 720 |
| ccatcgccgc | aaacaagcca | aggggaagaa | atatatatag | ccctggccac | gtactacgta | 780 |
| ctagcctctg | ccgatctgcc | atgggcgcta | gtatagccat | gtgaccgtgc | gagagtgcaa | 840 |
| gtgatgggta | cagacgttgt | tagcaccaat | ctgggaggct | tatctccaaa | cccccaaatt | 900 |
| ctctccattc | cattgccgtc | cgtcgtgtgg | ctgccgcacg | ctggagggc | agcggcaatc | 960 |
| gctagattta | cgagggtccc | acggcgcagt | ggcacgacga | cgcagcaccg | tccgggattt | 1020 |
| tcaacggcac | ccgaacctgg | gcgtatcaat | cgctttgtct | cccggaaaag | agaacgacat | 1080 |
| gggatcgtat | taccccaagc | gtcgccgatg | atcgccaaaa | gtcaaaaaaa | cgtatcaccg | 1140 |
| tccaccgacc | gaaccgaggt | cgctaccacg | tactaccagt | agtagtagta | gtagtacgcg | 1200 |
| gactcgcgac | cagccagccg | ctcggttgt | ctcctctttt | tttttttct | tgccgggatg | 1260 |
| ggagcgtgca | ccggtggctg | cactcaccgt | caccggccag | tagtctaggc | gacacacgaa | 1320 |

```
gcggcggcct gcgtcgccga aaggcgggg aaaaccccga aaatacagga gaattctgcg    1380
tttcccgcgg gcgcgagagc ccgcgacccc gcgcacggtg agacagggac cacgaccccg    1440
cgcgaactcc cccttcaggt ggacgaccaa cccagcccag ccagccgcgc gggggtttgt    1500
agctttgccg aatccaacgc ttgcacacac caccgcggcg ccgtatgccg ggtccccac     1560
ttgcattcca cccggtcgtc gcgtcgcgtg atcgcgtcac gtcccggcgc gccaggatac    1620
gggtgcttgg ctccgcctcc ggcttattat ttaagcacgc gacgccgcgg ccatgtctag    1680
tctcctcggc tgctactact actgcgttgt gcgcacaatg ccaagcgacc cactactgcc    1740
ctgcgtctgc gtgtgccgcg tatccgcaca agccaaagag aattttagg cgggtagaaa     1800
caaaaatcag acccagtttc gcgcaaaaaa aaaacaaaga gaagcccggg ggtaagagag    1860
agagagagaa tttgagagat gtgagacgga agcaacaagc acatgagcgt tttgtgatta    1920
ggaacggaca aaacaaggtc ataaggcggc ctaatcagga ttggaggaga ggtctagtct    1980
cccttctag tttcccctac atgaccagcg ttgccaccag gattgccacg ctcgtgcggg     2040
ccgcggcggc ggcgagccgg ccattgcggc tccaccgccg gccggcggc gaggatacga     2100
ggatggtggt gatcgtcggc gccacgggca ccgggaagac caagctgtcc atcgacgccg    2160
ccaaggtgat cggcggcgag gttgtcaacg ccgacaagat tcagctctat gacggcctcg    2220
acgtgaccac caacaaggtg agcctcgccg accgccgcgg cgtgccgcac cacctcctcg    2280
gagccatccg ccccgaggcc ggcgagctcc cgccgtcgtc cttccggtcc ctcgccgccg    2340
ccacggccgc gtcgatcgcg gcgaggcggc tcgtgccggt catcgccggt gggtcgaact    2400
ccctcatcca cgccctcctc gccgaccact tcgacgcctc cgctggcgat cccttctccc    2460
ccgccgccgc cttccgccac taccgccggg cgctccggtt cccgtgctgc ctgctctggg    2520
tccacgtcga tgaggcgctc ctcgacgagt acctcgaccg ccgcgtggac gacatggtgg    2580
acgctggcat ggtcgaggag ctccgggagt acttcgccac gacaaccgcc gcggagcgcg    2640
ccgcgcactc cgggctgggc aaggccatcg gcgtccccga gctcggcgac tacttcgccg    2700
ggcgcaagac cttctccgag gcgatcgacg acatcaaagc caacaccgc gtcctcgccg     2760
ccgcgcaggt gtccaagatc cgccgcatgt ccgacgcctg gggctggccc atccaccgcc    2820
tcgacgcctc cgacacagtc cgccgccagg tcacgcgggc gggctccgcc gccgagtccg    2880
cctcctggga gcgcgacgtg cgcggcccag gcctcgccac catccgcagc ttcctcgccg    2940
atcagtcacc gccaccgcgc agcgagggca ccaacgacta cctgtacgcc atggagacgg    3000
aaccagagcc gccgccgccg ccgacgttgc cgccgcggct gctccggttg ccgcggatgc    3060
agtactgcga catggtgggg tgagctcgcc gccgccgccg ccgccgccgc acggcgccgc    3120
agtcacttca ttgaaggctt ttgggggttc gagggtttag gccgccaatt ttccagtgtc    3180
ccggcggcgc ccttctctga cactgctcgg tgggcccaga aaaagcagcc agtgacatag    3240
aaagaagaga caaaggtaat taacgtagag agagagaagc taagctatgc aactgatgag    3300
aagtgttctt cttcattgca gcagaatttg tgtactcttt cttggagagg tggtgattca    3360
tcacatcgct ctcctcctaa ccgcggcact gtatgtatgt agtgagtagt actaatcatc    3420
taattatcca ccgtgttcag aattttgaga cagataatga gtacagtcta gtatatgatt    3480
tttcatcagt gtttgttgca gtgcaacggg tgacctgctc tatttccgga gctgaatttt    3540
ttttggtttg gttttgtttg ttttgtttgt ttaattaatc ctcctcctcc tcctgctgct    3600
gctgctagta gtagtagttt gaggtggcta atgccatggt ggatgcttga catgttccat    3660
```

```
ccatttttcca gctggttgtt gttgggatga ttggatgggt aatgccacgc ttagtgtgtg    3720
atttctgatc gagggggaga aggattgtgt tgggcgtgtg ggttggtgcc tggtgttctt    3780
gctgttgcca gctaggaaca aacaaattcg tccccgtctc ctactctttt ttctttcttt    3840 ctttcttttct ttcttttcttt ctttctgttt ttttttcctt ttacccctcc tctccagttt    3900
tcccgtacgg tcaaagagct ggaattcagt ggcattacga ttttcactct cttttggatt    3960
gttttctttc ttgtttggat tctacagcag cagtctaccg catcagattt tcagcatcgt    4020
tttatactgt cgcggacttc aggcattgga tactcgcttc cagaagtttc tggtcatttt    4080
tttctttttc tttttcaaaa aaaattgcac ttcacatggt cggttggtac gcgtatgtgt    4140
acgttgtatg cagagttgta cattgtttta tgcgtatgta taccttgtag gcgacacgtc    4200
cgacataagc caggcttttt atacactgtc atcgatcacc tgccctcaaa tcgccatgat    4260
tagcagcaat gcaagtactg tgttttgctc gaagcggttc tactgtaata taatgtcgca    4320
gtactatacc actgctctat ggtactgtac tccctatttc agtatactcc agtccagtac    4380
ttttgcctgt accatcgctg cagtgtacga atgccaagtc tcctggataa tcgcaagtaa    4440
gcagattctt ggggacggct cggcccaaat agaatgcagc atcgcaaccc tgaagaagcc    4500
cagcaactgc cgtcaagctg tcatacggct atttcactac tcctttcatt tcatcctaaa    4560
atatactccc tccgtttcac aatgtaagtt attctagcat tttccacatt tatattgatg    4620
ttagaaagtg aaacggagga agtaaagaat tatacccttt aaatttatat gaaaatataa    4680
gtaattttgt aatcccaaga cagtacttta ttcctcactt atcatctttt atatagttta    4740 ttttcactt atcaccttttt gtattgatgg atttcccgtc taatcacttt tttactactt    4800
tgttcttcca accatttgta tcgtgatttg ttcttttact attatcttaa tttttgtaaa    4860
aacaaatagt agaatccctt atattcacgg acggaaggag tacttcctta ctagtcagaa    4920
gggattgaac cggactacta gttgtggtta acaacagaat gatagacctg cgtttgggct    4980
ccgtcatcat tagcttttttg cattttttact tctgcttatt gaaatataac tggccaattt    5040
agtttgaaaa agaaaaaaga actgacgagc aaatgcaccg ttatttgagc caatagactg    5100
acagagtatc agacagttta agtgtgctgg gccgcgtcag ccttggccaa caatttcata    5160
tcctctgatc gtctcatcca atagtaggaa aggatgttca caagagtgtt caagctacgc    5220
tctaacttta ccacatgaag gattcagata tcagaactcg tcactgtttc ttgacatgat    5280
caaatttcgt ttgtaaaact gtgcaatatc acttccaggc tttgcctccg gcctatttg    5340 caggattgct gtactggatg agacagtcaa ggtatgggcc agactaacga aagggcctct    5400
cagtctcatc cccagccttt catgtactgc aatgtggaac atcaactgta attacagaac    5460
acttgttgta catctgaggg aatgttttgt gctgttcttc ccaatccaat tgcaggagtt    5520
agatatttgg aagcttaaga tagccaatgg atttctaaaa attacaatgt gtctgaaaga    5580
ttggtcaggc tatccccttg gagtgtgatc ttgatgtcgt gtgctgcatg ccacacgttc    5640
agagaaacat tccccacgtt ggatttttg aaggttctca catcaccaaa tgaggcattc    5700
agaaagtaca gtaaagtcac atctcgagga tgacaaaaga cgttcaaagg ataattgggt    5760
agggagttgg cacaaatgta cactatctca tcaacgcagt tctgcactag tttgaacaaa    5820
cacactctct tgtgcgatta caacaccagc gacatgtcca tgaaaaagaa gagaacggac    5880
acgtccaaaa ggcactcaac aatattgctt tcgccaaaat tcatatgaat taatccagca    5940
gatattttaa acatgatcag tatataggta tgctaataat tactagtttc agttagtcag    6000
tagccacaag aatctggact atggagaact ggaacggctg gaagggcgca ctgatcatgc    6060
```

-continued

```
atcaagccac tcaagagtga agaacatcat ctagctctag ccaaacggca ctacctgtca    6120
ggaacaaagc ctggagatac tgatggttca gccaaaaaag ataagcattt tacctgaaaa    6180
ataactcata aacctaacat ggaatttctg aaatttgatg tccacaggac cacagcagaa    6240
gtaaaatgac tacttgtacc accattctgc gtctgcaaga gtaaaacatt gacactacag    6300
gctggatgga gacccgcatc agacatataa tgcaaccac tggaaccaaa tcaaccaatt     6360
atgtgcaaca tgtaaaattg taaatcgtga acatgaagca ctattaagtt ttaactcttg    6420
atttacaaaa taaaaaatca atcataggaa atgatcagac agacaaaatt gaagtcccag    6480
ggcatactgt caatcaaata atccaataac accagctccg aacacaaccg tgcataactt    6540
aaaaacctga ttaccgactc accatggatg tcatcagaat actaaattag tgcataatta    6600
gattgctaag tgagtatgga aaaggacac aatgcaacaa tcaagcagtc tttcagctcc     6660
tgcatagtgc acacaggtac acaactggtg ttccatatgt caagaacgat aagcagaagt    6720
tcaaattatt aatgcactta gcaaatcgtt ctaataagca gtgtcaggat atgactagtg    6780
aacacttcgt ctcctccaaa agtgcaaaac agagatcaga cgaaaacag aagtatcagc     6840
attcgagaag caagaatgat gtgcaccagc ttttgcaaac aacagaatat tgcaaaatga    6900
acaaatatat tgaacaaagg tatatgtaaa aatgaacaac taattctgga agaggtaatt    6960
aatgccagct aagacctttc ttaattgaaa attggcaatg attttgccgt tctgttaaaa    7020
aaaattaatg cgagctatac ttacaagcag gagattataa caaagcgcac ccttgataac    7080
tagtttgatt tcctacctga atttcactag ctgagatttc tttttctctt ttcaaaccac    7140
tttgttgcac cccaagtaca ctttcatttt cttcggtatc aatgtccaac tcaagacatg    7200
atatatgccc tgcagagaaa ccaaagctgc atctttttcc ctctatctac aatgcagaaa    7260
gtagagctta atacaaggaa atatcatcct cactaacact acaaaaccac atagtgatat    7320
catagccaac aacttgcaga gttgaagcga tttgcaccga agaaatatt tcacagactg     7380
aaaccatgta tataacatga cagctaacca acatcacac cacatatgcc acagggcaca     7440
aacatcgcat acgattccac ctttcttcta attagaaaac ctattcacaa tcaaccataa    7500
aatctatatc catcctctga tctagaagaa ccaacataat tattggatgg acatgttagc    7560
cgtcagaaga aaaaaagca aaacatggga acatctgaaa agttgctc                   7608
```

<210> SEQ ID NO 61
<211> LENGTH: 455
<212> TYPE: PRT
<213> ORGANISM: Oryza sativa
<220> FEATURE:
<221> NAME/KEY: CHAIN
<222> LOCATION: (0)...(0)
<223> OTHER INFORMATION: OsIPT9 amino acidi (005021_3)

<400> SEQUENCE: 61

```
Met Thr Ser Val Ala Thr Arg Ile Ala Thr Leu Val Arg Ala Ala Ala
  1               5                  10                  15

Ala Ala Ser Arg Pro Leu Arg Leu His Arg Arg Pro Gly Gly Glu Asp
             20                  25                  30

Thr Arg Met Val Val Ile Val Gly Ala Thr Gly Thr Gly Lys Thr Lys
         35                  40                  45

Leu Ser Ile Asp Ala Ala Lys Val Ile Gly Gly Glu Val Val Asn Ala
     50                  55                  60

Asp Lys Ile Gln Leu Tyr Asp Gly Leu Asp Val Thr Thr Asn Lys Val
 65                  70                  75                  80
```

```
Ser Leu Ala Asp Arg Arg Gly Val Pro His His Leu Gly Ala Ile
             85                  90                  95

Arg Pro Glu Ala Gly Glu Leu Pro Pro Ser Ser Phe Arg Ser Leu Ala
            100                 105                 110

Ala Ala Thr Ala Ala Ser Ile Ala Ala Arg Arg Leu Val Pro Val Ile
        115                 120                 125

Ala Gly Gly Ser Asn Ser Leu Ile His Ala Leu Leu Ala Asp His Phe
    130                 135                 140

Asp Ala Ser Ala Gly Asp Pro Phe Ser Pro Ala Ala Ala Phe Arg His
145                 150                 155                 160

Tyr Arg Pro Ala Leu Arg Phe Pro Cys Cys Leu Leu Trp Val His Val
                165                 170                 175

Asp Glu Ala Leu Leu Asp Glu Tyr Leu Asp Arg Arg Val Asp Asp Met
            180                 185                 190

Val Asp Ala Gly Met Val Glu Glu Leu Arg Glu Tyr Phe Ala Thr Thr
        195                 200                 205

Thr Ala Ala Glu Arg Ala Ala His Ser Gly Leu Gly Lys Ala Ile Gly
    210                 215                 220

Val Pro Glu Leu Gly Asp Tyr Phe Ala Gly Arg Lys Thr Phe Ser Glu
225                 230                 235                 240

Ala Ile Asp Asp Ile Lys Ala Asn Thr Arg Val Leu Ala Ala Ala Gln
                245                 250                 255

Val Ser Lys Ile Arg Arg Met Ser Asp Ala Trp Gly Trp Pro Ile His
            260                 265                 270

Arg Leu Asp Ala Ser Asp Thr Val Arg Ala Arg Leu Thr Arg Ala Gly
        275                 280                 285

Ser Ala Ala Glu Ser Ala Ser Trp Glu Arg Asp Val Arg Gly Pro Gly
    290                 295                 300

Leu Ala Thr Ile Arg Ser Phe Leu Ala Asp Gln Ser Pro Pro Arg
305                 310                 315                 320

Ser Glu Gly Thr Asn Asp Tyr Leu Tyr Ala Met Glu Thr Glu Pro Glu
                325                 330                 335

Pro Pro Pro Pro Thr Leu Pro Pro Arg Leu Leu Arg Leu Pro Arg
            340                 345                 350

Met Gln Tyr Cys Asp Met Val Gly Arg Ile Cys Val Leu Phe Leu Gly
        355                 360                 365

Glu Val Val Ile His His Ile Ala Leu Leu Leu Thr Ala Ala Leu Ile
370                 375                 380

Leu Gln Ser Ser Thr Phe Ala Cys Thr Ile Ala Ala Val Tyr Glu Cys
385                 390                 395                 400

Gln Val Ser Trp Ile Ile Ala Ser Phe Ala Ser Gly Leu Phe Cys Arg
                405                 410                 415

Ile Ala Val Leu Asp Glu Thr Val Lys Glu Leu Asp Ile Trp Lys Leu
            420                 425                 430

Lys Ile Ala Asn Gly Phe Leu Lys Ile Thr Met Cys Leu Lys Asp Trp
        435                 440                 445

Ser Gly Tyr Pro Leu Gly Val
    450                 455

<210> SEQ ID NO 62
<211> LENGTH: 5075
<212> TYPE: DNA
<213> ORGANISM: Oryza sativa
<220> FEATURE:
```

```
<221> NAME/KEY: misc_feature
<222> LOCATION: (0)...(0)
<223> OTHER INFORMATION: OsIPT3 genomic sequence (002374_2)
<220> FEATURE:
<221> NAME/KEY: exon
<222> LOCATION: (2001)...(2503)
<220> FEATURE:
<221> NAME/KEY: exon
<222> LOCATION: (2544)...(3075)

<400> SEQUENCE: 62
```

| | | | | | |
|---|---|---|---|---|---|
| atataaaaaa | cgaaaaattg | tacttaaagt | actttggata | ataaagtaag | tcaaaaaaat | 60 |
| aataattcta | tttttttaaat | aagacgagtg | gtcaaacagt | gaaaaaaaac | tcaaaatccg | 120 |
| ttatattacg | gaacggagga | agtagcttac | acggtgtagt | acagtggcag | cagtacgtcg | 180 |
| tctgttggct | ctggtcaact | gtaccgttat | atataaagtg | tcactcactt | tgagagaaaa | 240 |
| agaggcatca | tgacacgggc | accaccattt | gtatggatac | gtaactacca | tccatatata | 300 |
| tgcatatcag | tgtcgaatgc | aatcagctca | tctcgatcca | gtctccaatt | tcaaaagaga | 360 |
| agatgtttga | aattttaaca | ttttagtttc | ttttttgaaa | atttactaca | caaatatact | 420 |
| tcttaaaaaa | actaattcta | tatacctcgc | ctcaaaaaaa | atctctaaat | tgatttgtct | 480 |
| gctcaagcta | gtctcttttt | aaaaaatgaa | taagacaact | ccattgttca | gatagcccaa | 540 |
| cacagttgaa | ctgctagcta | ctccctccat | cccataatat | aagggatttt | gagttttttac | 600 |
| ttgtaacgtt | tgatcactcg | tcttattcaa | attttttttaa | aactattatt | tattttattt | 660 |
| gtgacttact | ttattatcta | cagaactttta | agcacaactt | ttcgtctttt | atatttgaaa | 720 |
| aaaaatttga | atgagacgag | tggtcaaacg | ttgcaatcaa | aaactcaaaa | tcccttatat | 780 |
| tgtgggacgg | agggagaacc | aaattacaaa | caatgtctgg | gaatccttca | agccaaacaa | 840 |
| agtgactttg | tagacctaga | gatgcgtcaa | ttttagcaag | ctcatgggta | acacgattat | 900 |
| gttctctagg | acaattcata | acttgataga | caaaaaaaaa | tcattgtaag | cgcataaatt | 960 |
| tggcctatct | aatgataaca | acttttactc | ttgatcagac | agcaagagtt | tttttttatt | 1020 |
| gacaaaattt | aggcatatta | tctgaaaacc | ccaggtggcc | gcgtgtggcc | gcgcgcgtcc | 1080 |
| gcggcgtgct | tcttctgaat | gctcacaatg | acgccatcct | catcagccgc | tgcggagcac | 1140 |
| tccaccaagg | tcagcatcct | cgacgcaccg | gcgcagcgta | cgtctcatgc | atgcatcctt | 1200 |
| tatcgtacaa | gaactattac | tccatccggt | ttcatattcc | taacatttta | aacaaggtta | 1260 |
| aggacgttaa | ggtctcttttt | agaattttgc | actatcaata | actacaccag | cggcatacat | 1320 |
| agattactct | taaaaagcac | tatcaataaa | gtaatatttt | atttattcac | tgtatatata | 1380 |
| ttataataga | aaactataac | taaagaaatg | ttttggcgat | cgtgcatgtg | gaaaatataa | 1440 |
| tttgttgtat | tattgtagtg | actctctcac | agatatatat | agagtatatg | tgagatagag | 1500 |
| atttagagta | caatacaaat | tttaaaacag | atttatttct | agaactacat | ttatctataa | 1560 |
| taatattcta | tctctagaat | tctatcttat | ctctataatt | tatatttaaa | ctttcctccg | 1620 |
| aacatttatt | ttaagaagaa | attattagcg | tattgggaat | tgaacgcggg | attttttaggg | 1680 |
| ttgaaaccac | atacctcttg | tcactgcact | atcaaatgca | tctcagagca | ctgcagcatg | 1740 |
| atcactaaac | tccctctccc | cctaacgact | gcaaggcgcc | gcgtcctcca | acccacagtg | 1800 |
| tgggtgatcg | cccttcacat | tccagagcgc | cctctccccc | cctataaata | ccccactgcc | 1860 |
| agcctcatct | tcctccacag | catccatcgc | aaaatccacc | tcagctagct | acccaagcgc | 1920 |
| acgcgccacc | gcccgcgcgc | gagctgagct | aacgatcaac | accggtcgaa | cacctagcga | 1980 |
| gcatcaccac | catcatcacc | atgcaggcgt | acatggcggt | cgccgccgct | ccggcgccac | 2040 |

```
cggcctcgct gacgctgctg ccgcgcacca ccaccgtcat cagggacagg gagcgcttcg    2100
acgcggccgt cccggtggcg ccgctcgtgc tgaggcatgg cgccggcgtc aagcacaagg    2160
ccgtcgtggt gatgggcgcc acgggcaccg ggaagtcacg cctcgccgtc gacctcgccc    2220
tgcggttcgg cggcgaggtc atcaactccg acaagatgca gatacattcc gggttggatg    2280
tggtgacgaa caaggtgacc gaggaggagt gcgccggcgt gccgcaccac ctgatcggcg    2340
tggcgcgccc cgacgacgag ttcacggccg ccgacttccg ccgcgaggcg gcgcgcgccg    2400
cggcggggc ggttgagagg gggaggttgc ccatcatcgc cggggggtcc aactcctacg    2460
tcgaggagct cgtcgaaggc gacggccgcg cgttccggga gcggtacgag tgctgcttcc    2520
tctgggtcga cgtggatctc gaggtgctcc gcggtttcgt cgcccgccgc gtcgacgaga    2580
tgtgccggcg aggcctcgtc cgggaggtgg ccgcagcgtt cgaccgcgc cgcaccgact    2640
actcccaggg gcatctggcg cgccatcggc gtgccggagc tcgacgcgta cctccgctcc    2700
cgcggcgacg gcgccgacga ggaggagcgg gcgcgcatgc tcgccgcggc cgtcgcggag    2760
atcaagtcga acacgttccg gctcgcgtgc cgccagcacc gcaagatcga gaggctggac    2820
cgcatgtggc gcgcccgccg cgtcgacgcc acggaggtgt tcaggaggcg cggccacgcc    2880
gccgacgacg cgtggcagcg gctcgtcgcc gcgccgtgca tcgacgccgt ccggtcattc    2940
ctcttcgagg accaagaacg cagcagcatc gccgccggca aacctcccct cttcgccgcc    3000
ggcaaggcca cttcaggcaa catctccgtc ttcgcctccg cggccgccgc catggcggcg    3060
gccgctgcaa tctgagaagc gcaggcacca acctacttac atacacatac atgaccaaac    3120
acaaaaacgc agagcaccat gccactctca agacattcag gctgctgcca atcgccattg    3180
ccgatcaaat tcagagctcg tcagtcggat caaacgatga aggctgctgc ttctgcggtc    3240
aacatctcga tgacctgcca attgcaatgc aaagcaagat tgttcatata ctggtaactg    3300
gttgactcct ttttgttttt gctgggtttc tttgtgatat gaggagattg atgaattgcg    3360
cgcgagaatg taacttatga gttttgagtt ttttttttctt tttggtttct cctctgatt   3420
tgggtgtgta acagtaggag taaaaactaa aaagtattga cttggatgtt aattggggga    3480
ttgatgtaat agcctctcct tgtaacatag aaatcatgag ctgaaataat taaatcgttg    3540
agaccttgca aagaaaaagg gggaaaaaca aagaaggaa tcttgtgaaa ggggaatatt    3600
tggcagtctt tatcgtaata tatcaacttt ttcaaggtct tcactgagct ttgctattga    3660
gaatctcact tgccgcgcac ttcaatagtc tatgactatg ctctacactg tccttgttct    3720
taattcgaga ccgcatactt tgagtgacat gttgtgggta tgagtaaaac tcggtggcac    3780
gcaatactaa tttttctta catgaaaact tataattcgc acaatttgt gtcaaaaaaa    3840
aattcgcgca atcctttgc gcattcccta taaaaactta taaattgtct gtatttataa    3900
ttttatttt cttacgttct ctatttcatt cagaaaactc ctggccaatc accatgacag    3960
gtgatacatg caacatttgg cctggaaaac tagtggcagt cagccagtca ttcctcttgt    4020
gcaatgtgtg gctctatgct gtatctgtct gtggatacaa gttggcatct gcatcagttc    4080
tggttgcttc tttgacatca tattcccaag tcttgtttct tggtcatgga gacactctca    4140
tgcatgattg ggaactgggt attagttagg gcagtgcttg catgtcaaag gtcaagccca    4200
tcatcttctt gttcaaagtc aacttcacat tctgaatgca tatgcacatt tttacaagga    4260
taagcttgat ttaacacata ttttagagtt cacttgaaca ttgtcaaact ctttcgtaga    4320
atgcagtggt gatctctctg gatagtatgg agaccagaag actcagcgat catcggttca    4380
```

-continued

```
gaatattata taagattcag aaggtcaaca tgaacaaata tttatatgaa atagtaaaat    4440
tggtcaggta aatgataact ttgacttaat cctactacag ttagacagtc aaaatggcat    4500
ttcttgatgc tacattttt ttctacatgg attgacaaaa acgaatgaac gaatcagagt    4560
tatttgacca atttatcaaa ttatgtcaag tggatgatca gagaataaga tctgaatatc    4620
gcgataggaa tgaaatcttt ggtcaagggt caatgtgcag ttcctgcatt tccttcccca    4680
aatcaaacct agaactggtt gacacttgac agagaatgca acgactctgt ttttgtttc    4740 attttttgg aagattcttc tatgaacact ggctctttga ccaactgcct acatatctct    4800
actgatacat gagtgatcag taataatttc tgttgtacaa tgttttctat agcattctga    4860
tttgccaata ataattaaca aagtcaaaag cttttttttt tctgaaggag aaagtcaaac    4920
tgttcttctc aaatacagag tccaacttgc aacatggtga acaaaacaaa aggaggaaaa    4980
tacgaaagga atcagcaaat agctaacaag ctgatcattg agcaatgaga aaaatatcac    5040
atttaataaa ggtttaaagt caacactaga gcttg                               5075
```

<210> SEQ ID NO 63
<211> LENGTH: 344
<212> TYPE: PRT
<213> ORGANISM: Oryza sativa
<220> FEATURE:
<221> NAME/KEY: CHAIN
<222> LOCATION: (0)...(0)
<223> OTHER INFORMATION: OsIPT3 amino acid sequence (002374_2)

<400> SEQUENCE: 63

```
Met Gln Ala Tyr Met Ala Val Ala Ala Pro Ala Pro Pro Ala Ser
 1               5                  10                  15

Leu Thr Leu Leu Pro Arg Thr Thr Thr Val Ile Arg Asp Arg Glu Arg
             20                  25                  30

Phe Asp Ala Ala Val Pro Val Ala Pro Leu Val Leu Arg His Gly Ala
         35                  40                  45

Gly Val Lys His Lys Ala Val Val Val Met Gly Ala Thr Gly Thr Gly
     50                  55                  60

Lys Ser Arg Leu Ala Val Asp Leu Ala Leu Arg Phe Gly Gly Glu Val
 65                  70                  75                  80

Ile Asn Ser Asp Lys Met Gln Ile His Ser Gly Leu Asp Val Val Thr
                 85                  90                  95

Asn Lys Val Thr Glu Glu Glu Cys Ala Gly Val Pro His His Leu Ile
            100                 105                 110

Gly Val Ala Arg Pro Asp Asp Glu Phe Thr Ala Ala Asp Phe Arg Arg
        115                 120                 125

Glu Ala Ala Arg Ala Ala Ala Gly Ala Val Glu Arg Gly Arg Leu Pro
    130                 135                 140

Ile Ile Ala Gly Gly Ser Asn Ser Tyr Val Glu Glu Leu Val Glu Gly
145                 150                 155                 160

Asp Gly Arg Ala Phe Arg Glu Arg Cys Ser Ala Val Ser Ser Pro Ala
                165                 170                 175

Ala Ser Thr Arg Cys Ala Gly Glu Ala Ser Ser Gly Arg Trp Pro Gln
            180                 185                 190

Arg Ser Thr Arg Ala Ala Pro Thr Thr Pro Arg Gly Ile Trp Arg Ala
        195                 200                 205

Ile Gly Val Pro Glu Leu Asp Ala Tyr Leu Arg Ser Arg Gly Asp Gly
    210                 215                 220

Ala Asp Glu Glu Glu Arg Ala Arg Met Leu Ala Ala Ala Val Ala Glu
```

|     |     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- | --- |

Ile Lys Ser Asn Thr Phe Arg Leu Ala Cys Arg Gln His Arg Lys Ile
            245                 250                 255

Glu Arg Leu Asp Arg Met Trp Arg Ala Arg Arg Val Asp Ala Thr Glu
            260                 265                 270

Val Phe Arg Arg Gly His Ala Ala Asp Asp Ala Trp Gln Arg Leu
            275                 280                 285

Val Ala Ala Pro Cys Ile Asp Ala Val Arg Ser Phe Leu Phe Glu Asp
290                 295                 300

Gln Glu Arg Ser Ser Ile Ala Ala Gly Lys Pro Pro Leu Phe Ala Ala
305                 310                 315                 320

Gly Lys Ala Thr Ser Gly Asn Ile Ser Val Phe Ala Ser Ala Ala Ala
            325                 330                 335

Ala Met Ala Ala Ala Ala Ala Ile
            340

<210> SEQ ID NO 64
<211> LENGTH: 4777
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT4 genomic sequence (000911_6)
<220> FEATURE:
<221> NAME/KEY: CDS
<222> LOCATION: (1734)...(2778)

<400> SEQUENCE: 64

```
gaacagagat taagtgatta acacatacga gaggcaagat gatggacaca cccacaggat     60
cgcctgccga tcgatggcac gccgtccgac caggtcgatg gagacccaga agccggccaa    120
caactaatgc catagaaaaa ttttacagcc tagagacaaa catatttgaa aaaattttag    180
atatatattt tcaaaccata gagtttcccg gatggttatg gatccacccc tgcaacagg    240
acaagtcatc tagatggaga gtaaaaagtc gcgcgaggac gaagctgatg aacctcgtct    300
tttttttct taacctgaaa acaactagt atgtacaact aaagttgcat ttagggttat    360
tatatccttg ttagtattga tttcaaatga agttatcag tggtaaataa gaaaaagttg    420
tacaagaata tctggaatgg cttcattgcc tttaataatt gacaatgaca atcaagaaaa    480
gaaaaaaaaa gataacattt ctaggtgttc acaaactcac gaagagtgtc gacaagtttg    540
caacaacatg tatttgaaat cggagaaagt actctctcta tactaaaata ttttttttt    600
aaattttatc atttgttcta aaataaattt acttttatca ccttatttac cctaattgat    660
gcaccaattg aaagcttatt atttaaatat ctcttaccta cctatccact aatatactat    720
actttcttat taactagata atgtatcgca ctttgctatg agatatatgt tagttattga    780
agatacaata aaataatttg gattgaaata ttatgaaaat gatttgagaa tgatgattta    840
gcatgtgtat gtttagtttt agaatgaaat aagttgtaga tataattact acgtgcttgc    900
atgttgaact ttgtgtgttt tataggttga tgtggcatgc ttgcatgcag attttaggag    960
tgctaataaa tactccctat atttgcatgt tgagttttag gtgtttagtg gatattagct   1020
ttatacaaag aagagataaa gagcacttcg tttttttcct ctgataattt gaaatccatt   1080
ggctaaagat gaagttattt tagatggagg tagtacttt tttatctgat agtgcactac   1140
atctctctac cttgtgcatt tgttttcatt cttgtttttc attcttgtgg tcctctacat   1200
aaaagatgtt acgtagtctc tatcgacact aaggatttct ttggagaagc ttctagcagc   1260
```

-continued

```
tacaactata ttaaaaatct ctaactttt gctatatatt ttgaatctct agctccctaa    1320
gcagtataga ttctcgctcc aaattttaag agttagtaca tgtaaaattt agaaataaac    1380
tagtagctaa aagcagcgga gcttcgatct ctcaagattc tcataagtta tttcttagaa    1440
tctataattc cccaaatata gcatatatgt ttttagtaga tggctaaact tatactttat    1500
gcctcaaatt aaaactcgtt aattctgttg agtatctttg ttgtttgttc tccacttggt    1560
tttggttagc taactccata taatacaca tccaaacaca cccacaagac agcaaccaac     1620
tccaagcttg ctaactaaca aagcatcttg aattcctctt gaccaagtag ttaagtagct    1680
aagctaatta gtggtctaac tttgaacaca acacaacaaa acacacacac atc atg      1736
                                                              Met
                                                               1 gcc acg tca cta tcc ttg gcg ccc aaa ccc gcc gcc gtc gcc gtc gcc    1784
Ala Thr Ser Leu Ser Leu Ala Pro Lys Pro Ala Ala Val Ala Val Ala
          5              10                  15 gcc gcc gcc atc ccg agg ctt gtt ccg ccg ccg tct atc gac atg tcg    1832
Ala Ala Ala Ile Pro Arg Leu Val Pro Pro Pro Ser Ile Asp Met Ser
         20              25                  30 gcg ctg tcg ccg ccg ccg ccg ctc gtc agc gtc agc agg agc atg gta    1880
Ala Leu Ser Pro Pro Pro Pro Leu Val Ser Val Ser Arg Ser Met Val
     35              40                  45 gcg aag cac aag gcc gtg gtt gtg atg ggc gcg acg ggg acg ggg aag    1928
Ala Lys His Lys Ala Val Val Val Met Gly Ala Thr Gly Thr Gly Lys
 50              55                  60                  65 acg cgg ctc gcc gtc gac ctc gcg ctc cag ttc ggc ggc gag gtg atc    1976
Thr Arg Leu Ala Val Asp Leu Ala Leu Gln Phe Gly Gly Glu Val Ile
             70                  75                  80 aac gcc gac aag ctg cag ctg cac cgg ggg ctc gac gtg gcc acc aac    2024
Asn Ala Asp Lys Leu Gln Leu His Arg Gly Leu Asp Val Ala Thr Asn
         85                  90                  95 aag gcc acc gcc gac gag cgc gcc ggc gtg ccg cac cac ctg atc ggg    2072
Lys Ala Thr Ala Asp Glu Arg Ala Gly Val Pro His His Leu Ile Gly
        100                 105                 110 gtg gcg cac ccg gac gag gag ttc acg gcc gcg gac ttc cgc cgc gcc    2120
Val Ala His Pro Asp Glu Glu Phe Thr Ala Ala Asp Phe Arg Arg Ala
    115                 120                 125 gcg tcg cgc gcc gcc gcc gcg gtc gcc gcg cgc ggc gcg ctg ccc atc    2168
Ala Ser Arg Ala Ala Ala Ala Val Ala Ala Arg Gly Ala Leu Pro Ile
130                 135                 140                 145 atc gcc ggc ggc tcc aac tcc tac atc gag gag ctc gtc gac ggc gac    2216
Ile Ala Gly Gly Ser Asn Ser Tyr Ile Glu Glu Leu Val Asp Gly Asp
                150                 155                 160 cgc cgc gcg ttc cgc gac cgg tac gac tgc tgc ttc ctg tgg gtg gac    2264
Arg Arg Ala Phe Arg Asp Arg Tyr Asp Cys Cys Phe Leu Trp Val Asp
            165                 170                 175 gtg cag ctc ccc gtg ctc cac ggc ttc gtc ggc cgc cgc gtc gac gac    2312
Val Gln Leu Pro Val Leu His Gly Phe Val Gly Arg Arg Val Asp Asp
        180                 185                 190 atg tgc ggc cgc ggg atg gtc gcc gag atc gag gcg gcg ttc gac ccg    2360
Met Cys Gly Arg Gly Met Val Ala Glu Ile Glu Ala Ala Phe Asp Pro
    195                 200                 205 gac cgc acc gac tac tcc cgc ggc gtc tgg cgc gcc atc ggc gtg ccg    2408
Asp Arg Thr Asp Tyr Ser Arg Gly Val Trp Arg Ala Ile Gly Val Pro
210                 215                 220                 225 gag ctc gac gcg tac ctc cgc tcg tgc gcc gcc gcc ggc ggc gag gag    2456
Glu Leu Asp Ala Tyr Leu Arg Ser Cys Ala Ala Ala Gly Gly Glu Glu
                230                 235                 240
```

| | |
|---|---|
| gaa cgc gcg cgg ctg ctg gcc aat gcc atc gag gac atc aag gcg aac<br>Glu Arg Ala Arg Leu Leu Ala Asn Ala Ile Glu Asp Ile Lys Ala Asn<br>245 250 255 | 2504 |
| acc cgc tgg ctg tcg tgc cgg cag cgc gcc aag atc gtg agg cta gac<br>Thr Arg Trp Leu Ser Cys Arg Gln Arg Ala Lys Ile Val Arg Leu Asp<br>260 265 270 | 2552 |
| cgc cta tgg cga atc cgc cgc gtg gac gcc acg gag gcg ttc cgg cgg<br>Arg Leu Trp Arg Ile Arg Arg Val Asp Ala Thr Glu Ala Phe Arg Arg<br>275 280 285 | 2600 |
| cgc ggc ggc gcc gcc aac gag gcg tgg gag cgg cac gtc gcc gcg ccg<br>Arg Gly Gly Ala Ala Asn Glu Ala Trp Glu Arg His Val Ala Ala Pro<br>290 295 300 305 | 2648 |
| agc att gac acc gtg cga tcc ttc ctc cac ggc gaa ttc acc acc gcc<br>Ser Ile Asp Thr Val Arg Ser Phe Leu His Gly Glu Phe Thr Thr Ala<br>310 315 320 | 2696 |
| gcc gaa act acg gcg gcg ccg gtg cca cca ccg ccg ttc ctc ccc atg<br>Ala Glu Thr Thr Ala Ala Pro Val Pro Pro Pro Pro Phe Leu Pro Met<br>325 330 335 | 2744 |
| ttt gct ctc gcc gcg gcg ggc gcc ggc gtc taa g ctcagctcag<br>Phe Ala Leu Ala Ala Ala Gly Ala Gly Val *<br>340 345 | 2788 |
| ctcgaaacga cagtaaaaat tttaaaaaac ttgcagagat ggatggggag cttaataagt | 2848 |
| gtgaagtgaa ggtaattaag aagaaattaa ccactgtttg atgtaatgac attgatattg | 2908 |
| accaggccaa aaaagggaga gaaaagagc agcagatgtg gaggagtgta ccatctgtgg | 2968 |
| actgagagtg acccttccga ttagggatgg acattggtcg atccacaaga acttcttgac | 3028 |
| ccactctgat tcagctaaat gaactaattt atacgattgg agttttgaaa ataaatttag | 3088 |
| ttcatatagc taaactagga tggttaagga gtattcgtgg gtcggcccac tctaaccct | 3148 |
| agctactttg gatcacagga ttttatggcg gtattttcac tttacaaatt agtatgagat | 3208 |
| ctttataagg ttgttgtgca ttgcatatgt aaatgcgatg gtctagtagg gtatgaatgt | 3268 |
| cgggcctctg tatgattctg ttgagagtga ttaatattag ttttttcttg ttatttattt | 3328 |
| gaactacaat aaaaaaatac ggttgtgtga ttgagctagt gttacccaac cttcaccta | 3388 |
| attctgctta ttctggattg tttattcatc ttacttggaa atattaattt gtgagtgaga | 3448 |
| tgatctgatg atgaatgtaa taattatttg aggtgattga gtattgatct tgttatctat | 3508 |
| atattgtgtt ttgtattatc agattataca actagctagt ttttttttcaa ttgatcgaga | 3568 |
| tatataactc ctatagctag ttgacctata tgggaagcta ggctagctag cttgtctgta | 3628 |
| ttgctaacat aaatgtgaat acatgataat tacatgttga ttgaaataac tctcagataa | 3688 |
| agaaactaat taaataagct agtagtgcac atgattttga taatgaaggc aaatttggct | 3748 |
| aatgtgcact gcgctggttg atattttctg atagtaatca agaatatatt ggtgctagtg | 3808 |
| ggcaccatga atttgtgcca gttgctaaca caaatggatc gaggccagct aacaagaata | 3868 |
| tataaaacac ctgagcttca accttagtag catgcatgca gttgatttaa ttatcatcat | 3928 |
| tgtaatatct tgtaatatga cctttcaac ttaatcatga aaaaaattc cttcaagaaa | 3988 |
| ctagtaagtg acatcgttgc acatctggag aagtccatcg atcaacttga agtgcattca | 4048 |
| cagttgcaca agctaaatct gaattatggt tcctaggcta atatataatt cgaaaatacc | 4108 |
| ttctttgaaa aaaactaac acaacttttg gtaaatatga aatgcatag catggtatta | 4168 |
| aaattttcag aatattcaat attaaattta taccacttct taaccaattt aattagttct | 4228 |
| gctggtttca tgaatatttt taggcatatt ctgagtggat aaaaatatta aaatctaggc | 4288 |
| agtgatataa aataatttat caataatatc gttcattaaa ttaataattt tgcagtgtgg | 4348 |

```
aagaaggtga tgctgtaatg catgaggaaa aatgggtccc cctatcctcc ggtaagaaaa    4408
ttccttaaga taaagcatca tatataaata tgttgattta gaaatataaa taattttaaa    4468
ttgtagccaa ttatatacac atatccgata caaattctaa caataattat taggttggta    4528
aaatgaattc atcagacata tattagccgt cggacatatg ttgtggttag tttatgtttc    4588
agtaagcttt taaacaaaat aggcgaattc taagagattg catgaaaacc accttttga    4648 aacaaagtaa agcctataaa ccaccttagc ccgatcgaca tgttctaatg aatgagctat    4708
ggctacaaat atataactgt tctattagga accatattct ggaaatatat taaattaagt    4768
tccctctttt                                                          4777

<210> SEQ ID NO 65
<211> LENGTH: 1044
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT4 coding sequence (000911_6)
<220> FEATURE:
<221> NAME/KEY: CDS
<222> LOCATION: (1)...(1044)

<400> SEQUENCE: 65
```

| | | | | | | | | | | | | | | | | |
|---|---|---|---|---|---|---|---|---|---|---|---|---|---|---|---|---|
| atg | gcc | acg | tca | cta | tcc | ttg | gcg | ccc | aaa | ccc | gcc | gcc | gtc | gcc | gtc | 48 |
| Met | Ala | Thr | Ser | Leu | Ser | Leu | Ala | Pro | Lys | Pro | Ala | Ala | Val | Ala | Val | |
| 1 | | | | 5 | | | | | 10 | | | | | 15 | | |
| gcc | gcc | gcc | gcc | atc | ccg | agg | ctt | gtt | ccg | ccg | ccg | tct | atc | gac | atg | 96 |
| Ala | Ala | Ala | Ala | Ile | Pro | Arg | Leu | Val | Pro | Pro | Pro | Ser | Ile | Asp | Met | |
| | | | 20 | | | | | 25 | | | | | 30 | | | |
| tcg | gcg | ctg | tcg | ccg | ccg | ccg | ctc | gtc | agc | gtc | agc | agg | agc | atg | | 144 |
| Ser | Ala | Leu | Ser | Pro | Pro | Pro | Leu | Val | Ser | Val | Ser | Arg | Ser | Met | | |
| | | 35 | | | | | 40 | | | | | 45 | | | | |
| gta | gcg | aag | cac | aag | gcc | gtg | gtt | gtg | atg | ggc | gcg | acg | ggg | acg | ggg | 192 |
| Val | Ala | Lys | His | Lys | Ala | Val | Val | Val | Met | Gly | Ala | Thr | Gly | Thr | Gly | |
| | 50 | | | | | 55 | | | | | 60 | | | | | |
| aag | acg | cgg | ctc | gcc | gtc | gac | ctc | gcg | ctc | cag | ttc | ggc | ggc | gag | gtg | 240 |
| Lys | Thr | Arg | Leu | Ala | Val | Asp | Leu | Ala | Leu | Gln | Phe | Gly | Gly | Glu | Val | |
| 65 | | | | | 70 | | | | | 75 | | | | | 80 | |
| atc | aac | gcc | gac | aag | ctg | cag | ctg | cac | cgg | ggg | ctc | gac | gtg | gcc | acc | 288 |
| Ile | Asn | Ala | Asp | Lys | Leu | Gln | Leu | His | Arg | Gly | Leu | Asp | Val | Ala | Thr | |
| | | | | 85 | | | | | 90 | | | | | 95 | | |
| aac | aag | gcc | acc | gcc | gac | gag | cgc | gcc | ggc | gtg | ccg | cac | cac | ctg | atc | 336 |
| Asn | Lys | Ala | Thr | Ala | Asp | Glu | Arg | Ala | Gly | Val | Pro | His | His | Leu | Ile | |
| | | | 100 | | | | | 105 | | | | | 110 | | | |
| ggg | gtg | gcg | cac | ccg | gac | gag | gag | ttc | acg | gcc | gcg | gac | ttc | cgc | cgc | 384 |
| Gly | Val | Ala | His | Pro | Asp | Glu | Glu | Phe | Thr | Ala | Ala | Asp | Phe | Arg | Arg | |
| | | 115 | | | | | 120 | | | | | 125 | | | | |
| gcc | gcg | tcg | cgc | gcc | gcc | gcc | gcg | gtc | gcc | gcg | cgc | ggc | gcg | ctg | ccc | 432 |
| Ala | Ala | Ser | Arg | Ala | Ala | Ala | Ala | Val | Ala | Ala | Arg | Gly | Ala | Leu | Pro | |
| | 130 | | | | | 135 | | | | | 140 | | | | | |
| atc | atc | gcc | ggc | ggc | tcc | aac | tcc | tac | atc | gag | gag | ctc | gtc | gac | ggc | 480 |
| Ile | Ile | Ala | Gly | Gly | Ser | Asn | Ser | Tyr | Ile | Glu | Glu | Leu | Val | Asp | Gly | |
| 145 | | | | | 150 | | | | | 155 | | | | | 160 | |
| gac | cgc | cgc | gcg | ttc | cgc | gac | cgg | tac | gac | tgc | tgc | ttc | ctg | tgg | gtg | 528 |
| Asp | Arg | Arg | Ala | Phe | Arg | Asp | Arg | Tyr | Asp | Cys | Cys | Phe | Leu | Trp | Val | |
| | | | | 165 | | | | | 170 | | | | | 175 | | |
| gac | gtg | cag | ctc | ccc | gtg | ctc | cac | ggc | ttc | gtc | ggc | cgc | cgc | gtc | gac | 576 |
| Asp | Val | Gln | Leu | Pro | Val | Leu | His | Gly | Phe | Val | Gly | Arg | Arg | Val | Asp | |
| | | | 180 | | | | | 185 | | | | | 190 | | | |

-continued

| | | |
|---|---|---|
| gac atg tgc ggc cgc ggg atg gtc gcc gag atc gag gcg gcg ttc gac<br>Asp Met Cys Gly Arg Gly Met Val Ala Glu Ile Glu Ala Ala Phe Asp<br>                 195                              200                          205 | 624 |
| ccg gac cgc acc gac tac tcc cgc ggc gtc tgg cgc gcc atc ggc gtg<br>Pro Asp Arg Thr Asp Tyr Ser Arg Gly Val Trp Arg Ala Ile Gly Val<br>210                               215                              220 | 672 |
| ccg gag ctc gac gcg tac ctc cgc tcg tgc gcc gcc gcc ggc ggc gag<br>Pro Glu Leu Asp Ala Tyr Leu Arg Ser Cys Ala Ala Ala Gly Gly Glu<br>225                               230                              240 | 720 |
| gag gaa cgc gcg cgg ctg ctg gcc aat gcc atc gag gac atc aag gcg<br>Glu Glu Arg Ala Arg Leu Leu Ala Asn Ala Ile Glu Asp Ile Lys Ala<br>                          245                              250                          255 | 768 |
| aac acc cgc tgg ctg tcg tgc cgg cag cgc gcc aag atc gtg agg cta<br>Asn Thr Arg Trp Leu Ser Cys Arg Gln Arg Ala Lys Ile Val Arg Leu<br>                 260                              265                              270 | 816 |
| gac cgc cta tgg cga atc cgc cgc gtg gac gcc acg gag gcg ttc cgg<br>Asp Arg Leu Trp Arg Ile Arg Arg Val Asp Ala Thr Glu Ala Phe Arg<br>                 275                              280                              285 | 864 |
| cgg cgc ggc ggc gcc gcc aac gag gcg tgg gag cgg cac gtc gcc gcg<br>Arg Arg Gly Gly Ala Ala Asn Glu Ala Trp Glu Arg His Val Ala Ala<br>               290                              295                             300 | 912 |
| ccg agc att gac acc gtg cga tcc ttc ctc cac ggc gaa ttc acc acc<br>Pro Ser Ile Asp Thr Val Arg Ser Phe Leu His Gly Glu Phe Thr Thr<br>305                             310                              315                          320 | 960 |
| gcc gcc gaa act acg gcg gcg ccg gtg ccg cca ccg ccg ttc ctc ccc<br>Ala Ala Glu Thr Thr Ala Ala Pro Val Pro Pro Pro Pro Phe Leu Pro<br>                          325                              330                          335 | 1008 |
| atg ttt gct ctc gcc gcg gcg ggc gcc ggc gtc taa<br>Met Phe Ala Leu Ala Ala Ala Gly Ala Gly Val *<br>               340                              345 | 1044 |

<210> SEQ ID NO 66
<211> LENGTH: 347
<212> TYPE: PRT
<213> ORGANISM: Oryza sativa

<400> SEQUENCE: 66

Met Ala Thr Ser Leu Ser Leu Ala Pro Lys Pro Ala Ala Val Ala Val
1               5                   10                  15

Ala Ala Ala Ile Pro Arg Leu Val Pro Pro Ser Ile Asp Met
            20                  25                  30

Ser Ala Leu Ser Pro Pro Pro Leu Val Ser Val Ser Arg Ser Met
            35                  40                  45

Val Ala Lys His Lys Ala Val Val Met Gly Ala Thr Gly Thr Gly
        50                  55                  60

Lys Thr Arg Leu Ala Val Asp Leu Ala Leu Gln Phe Gly Gly Glu Val
65                  70                  75                  80

Ile Asn Ala Asp Lys Leu Gln Leu His Arg Gly Leu Asp Val Ala Thr
                85                  90                  95

Asn Lys Ala Thr Ala Asp Glu Arg Ala Gly Val Pro His His Leu Ile
            100                 105                 110

Gly Val Ala His Pro Asp Glu Glu Phe Thr Ala Ala Asp Phe Arg Arg
        115                 120                 125

Ala Ala Ser Arg Ala Ala Ala Val Ala Ala Arg Gly Ala Leu Pro
    130                 135                 140

Ile Ile Ala Gly Gly Ser Asn Ser Tyr Ile Glu Glu Leu Val Asp Gly
145                 150                 155                 160

```
Asp Arg Arg Ala Phe Arg Asp Arg Tyr Asp Cys Cys Phe Leu Trp Val
            165                 170                 175
Asp Val Gln Leu Pro Val Leu His Gly Phe Val Gly Arg Arg Val Asp
        180                 185                 190
Asp Met Cys Gly Arg Gly Met Val Ala Glu Ile Glu Ala Ala Phe Asp
        195                 200                 205
Pro Asp Arg Thr Asp Tyr Ser Arg Gly Val Trp Arg Ala Ile Gly Val
        210                 215                 220
Pro Glu Leu Asp Ala Tyr Leu Arg Ser Cys Ala Ala Gly Gly Glu
225                 230                 235                 240
Glu Glu Arg Ala Arg Leu Leu Ala Asn Ala Ile Glu Asp Ile Lys Ala
                245                 250                 255
Asn Thr Arg Trp Leu Ser Cys Arg Gln Arg Ala Lys Ile Val Arg Leu
                260                 265                 270
Asp Arg Leu Trp Arg Ile Arg Arg Val Asp Ala Thr Glu Ala Phe Arg
                275                 280                 285
Arg Arg Gly Gly Ala Ala Asn Glu Ala Trp Glu Arg His Val Ala Ala
            290                 295                 300
Pro Ser Ile Asp Thr Val Arg Ser Phe Leu His Gly Glu Phe Thr Thr
305                 310                 315                 320
Ala Ala Glu Thr Thr Ala Ala Pro Val Pro Pro Pro Phe Leu Pro
                325                 330                 335
Met Phe Ala Leu Ala Ala Ala Gly Ala Gly Val
                340                 345

<210> SEQ ID NO 67
<211> LENGTH: 484
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 3, 4, 5, 6, 7, 8, 9, 10, 11, 12, 13, 14, 15, 16, 17, 18,
      19, 20, 21, 22, 23, 24, 25, 26, 27, 28, 29, 30, 31, 32,
      33, 34, 35, 36, 37, 38, 39, 40, 41, 42, 43, 44, 45, 46,
      47, 48, 49, 50, 51, 52, 53, 54, 55, 56, 57, 58, 59, 60,
      61, 62
<223> OTHER INFORMATION: Xaa = Any Amino Acid
<220> FEATURE:
<221> NAME/KEY: VARIANT
<222> LOCATION: 63, 64, 65, 66, 67, 68, 69, 70, 71, 72, 73, 74, 75, 76,
      77, 78, 79, 80, 81, 82, 83, 84, 85, 86, 87, 88, 89, 90, 92,
      114, 116, 117, 145, 148, 157, 159, 172, 173, 176, 180, 182,
      183, 204, 205, 206, 207, 209, 210, 211, 212, 213, 214
<223> OTHER INFORMATION: Xaa = Any Amino Acid
<220> FEATURE:
<221> NAME/KEY: VARIANT
<222> LOCATION: 215, 216, 217, 218, 219, 220, 221, 222, 223, 224, 225,
      226, 227, 228, 229, 230, 231, 232, 233, 234, 235, 236, 237, 238,
      239, 240, 241, 242, 243, 244, 245, 246, 247, 248, 249, 250,
      251, 252, 253, 254, 255, 256, 257, 258, 259, 260, 261
<223> OTHER INFORMATION: Xaa = Any Amino Acid
<220> FEATURE:
<221> NAME/KEY: VARIANT
<222> LOCATION: 262, 263, 264, 265, 266, 267, 268, 269, 270, 271, 272,
      273, 274, 275, 276, 277, 278, 279, 280, 281, 282, 283, 284, 285,
      286, 287, 288, 289, 290, 291, 292, 293, 294, 295, 296, 297,
      298, 299, 300, 301, 302, 303, 304, 305, 306, 319, 320
<223> OTHER INFORMATION: Xaa = Any Amino Acid
<220> FEATURE:
<221> NAME/KEY: VARIANT
<222> LOCATION: 321, 324, 325, 328, 333, 336, 339, 340, 347, 352, 353,
      354, 356, 357, 358, 359, 360, 361, 362, 363, 364, 365, 366, 369,
      383, 384, 385, 386, 387, 388, 389, 390, 391, 392, 393, 394,
      395, 396, 397, 398, 399, 400, 401, 402, 403, 406, 409
<223> OTHER INFORMATION: Xaa = Any Amino Acid
```

```
<220> FEATURE:
<221> NAME/KEY: VARIANT
<222> LOCATION: 413, 416, 417, 420, 424, 427, 430, 431, 432, 433, 436,
      438, 439, 446, 448, 449, 450, 451, 452, 453, 454, 455, 456, 457,
      458, 459, 460, 461, 462, 463, 464, 465, 467, 471, 473, 474
      476, 478, 479, 482
<223> OTHER INFORMATION: Xaa = Any Amino Acid

<400> SEQUENCE: 67

Ser Ser Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa
 65              70                  75                  80

Xaa Xaa Xaa Xaa Xaa Xaa Xaa Xaa Lys Xaa Lys Val Val Val
             85                  90                  95

Ile Met Gly Ala Thr Gly Thr Gly Lys Ser Arg Leu Ser Ile Asp Leu
            100                 105                 110

Ala Xaa Arg Xaa Xaa Phe Gly Gly Glu Val Ile Asn Ser Asp Lys Ile
        115                 120                 125

Gln Val Tyr Ala Asp Gly Leu Asp Val Ala Thr Asn Lys Val Thr Leu
    130                 135                 140

Xaa Glu Arg Xaa Gly Val Pro His His Leu Leu Gly Xaa Ile Xaa Pro
145                 150                 155                 160

Glu Ala Gly Glu Leu Thr Ala Ser Asp Phe Arg Xaa Xaa Ala Ala Xaa
                165                 170                 175

Ala Ile Ala Xaa Ile Xaa Xaa Ala Arg Gly Arg Leu Pro Ile Val Ala
            180                 185                 190

Gly Gly Ser Asn Ser Tyr Ile His Ala Leu Leu Xaa Xaa Xaa Xaa Asp
        195                 200                 205

Xaa Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa
    275                 280                 285

Xaa Xaa Xaa Xaa Xaa Xaa Xaa Xaa Xaa Xaa Xaa Xaa
290                 295                 300

Xaa Xaa Leu Arg Tyr Asp Cys Cys Phe Leu Trp Val Asp Val Xaa Xaa
305                 310                 315                 320

Xaa Val Leu Xaa Xaa Tyr Leu Xaa Arg Arg Val Asp Xaa Met Val Xaa
                325                 330                 335

Asp Ser Xaa Xaa Gly Leu Val Glu Glu Leu Xaa Glu Phe Phe Asp Xaa
            340                 345                 350

Xaa Xaa Ala Xaa Xaa Xaa Xaa Xaa Xaa Xaa Xaa Xaa Xaa Gly Ile
        355                 360                 365
```

```
Xaa Lys Ala Ile Gly Val Pro Glu Leu Asp Glu Tyr Phe Arg Xaa Xaa
    370                 375                 380

Xaa Xaa Xaa Xaa Xaa Xaa Xaa Xaa Xaa Xaa Xaa Xaa Xaa Xaa Xaa Xaa
    385                 390                 395                 400

Xaa Xaa Xaa Leu Asp Xaa Ala Val Xaa Glu Ile Lys Xaa Asn Thr Xaa
                405                 410                 415

Xaa Leu Ala Xaa Arg Gln Val Xaa Lys Ile Xaa Arg Leu Xaa Xaa Xaa
                420                 425                 430

Xaa Gly Trp Xaa Ile Xaa Xaa Arg Val Asp Ala Thr Glu Xaa Phe Xaa
                435                 440                 445

Xaa Xaa Xaa Xaa Xaa Xaa Xaa Xaa Xaa Xaa Xaa Xaa Xaa Xaa Xaa Xaa
    450                 455                 460

Xaa Glu Xaa Trp Glu Arg Xaa Val Xaa Xaa Pro Xaa Val Xaa Xaa Val
    465                 470                 475                 480

Arg Xaa Phe Leu

<210> SEQ ID NO 68
<211> LENGTH: 8
<212> TYPE: PRT
<213> ORGANISM: Artificial Sequence
<220> FEATURE:
<223> OTHER INFORMATION: consensus sequence for ATP binding domain
<220> FEATURE:
<221> NAME/KEY: VARIANT
<222> LOCATION: (1)...(1)
<223> OTHER INFORMATION: amino acid at position 1 can also be a G
<220> FEATURE:
<221> NAME/KEY: VARIANT
<222> LOCATION: (8)...(8)
<223> OTHER INFORMATION: amino acid at position 8 can also be a T
<220> FEATURE:
<221> NAME/KEY: VARIANT
<222> LOCATION: (2)...(5)
<223> OTHER INFORMATION: amino acid residues at positions 2 to 5 can be
      any amino acid
<220> FEATURE:
<221> NAME/KEY: VARIANT
<222> LOCATION: 2, 3, 4, 5
<223> OTHER INFORMATION: Xaa = Any Amino Acid

<400> SEQUENCE: 68

Ala Xaa Xaa Xaa Xaa Gly Lys Ser
 1               5

<210> SEQ ID NO 69
<211> LENGTH: 1035
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT3 coding sequence
<220> FEATURE:
<221> NAME/KEY: CDS
<222> LOCATION: (1)...(1035)

<400> SEQUENCE: 69 atg cag gcg tac atg gcg gtc gcc gcc gct ccg gcg cca ccg gcc tcg      48
Met Gln Ala Tyr Met Ala Val Ala Ala Ala Pro Ala Pro Pro Ala Ser
 1               5                  10                  15 ctg acg ctg ctg ccg cgc acc acc acc gtc atc agg gac agg gag cgc      96
Leu Thr Leu Leu Pro Arg Thr Thr Thr Val Ile Arg Asp Arg Glu Arg
                20                  25                  30 ttc gac gcg gcc gtc ccg gtg gcg ccg ctc gtg ctg agg cat ggc gcc     144
Phe Asp Ala Ala Val Pro Val Ala Pro Leu Val Leu Arg His Gly Ala
            35                  40                  45
```

```
ggc gtc aag cac aag gcc gtc gtg gtg atg ggc gcc acg ggc acc ggg      192
Gly Val Lys His Lys Ala Val Val Val Met Gly Ala Thr Gly Thr Gly
 50                  55                  60 aag tca cgc ctc gcc gtc gac ctc gcc ctg cgg ttc ggc ggc gag gtc      240
Lys Ser Arg Leu Ala Val Asp Leu Ala Leu Arg Phe Gly Gly Glu Val
 65                  70                  75                  80 atc aac tcc gac aag atg cag ata cat tcc ggg ttg gat gtg gtg acg      288
Ile Asn Ser Asp Lys Met Gln Ile His Ser Gly Leu Asp Val Val Thr
                 85                  90                  95 aac aag gtg acc gag gag gag tgc gcc ggc gtg ccg cac cac ctg atc      336
Asn Lys Val Thr Glu Glu Glu Cys Ala Gly Val Pro His His Leu Ile
            100                 105                 110 ggc gtg gcg cgc ccc gac gac gag ttc acg gcc gcc gac ttc cgc cgc      384
Gly Val Ala Arg Pro Asp Asp Glu Phe Thr Ala Ala Asp Phe Arg Arg
        115                 120                 125 gag gcg gcg cgc gcc gcg gcg ggg gcg gtt gag agg ggg agg ttg ccc      432
Glu Ala Ala Arg Ala Ala Ala Gly Ala Val Glu Arg Gly Arg Leu Pro
    130                 135                 140 atc atc gcc ggg ggg tcc aac tcc tac gtc gag gag ctc gtc gaa ggc      480
Ile Ile Ala Gly Gly Ser Asn Ser Tyr Val Glu Glu Leu Val Glu Gly
145                 150                 155                 160 gac ggc cgc gcg ttc cgg gag cgg tgc tcc gcg gtt tcg tcg ccc gcc      528
Asp Gly Arg Ala Phe Arg Glu Arg Cys Ser Ala Val Ser Ser Pro Ala
                165                 170                 175 gcg tcg acg aga tgt gcc ggc gag gcc tcg tcc ggg agg tgg ccg cag      576
Ala Ser Thr Arg Cys Ala Gly Glu Ala Ser Ser Gly Arg Trp Pro Gln
            180                 185                 190 cgt tcg acc cgc gcc gca ccg act act ccc agg ggc atc tgg cgc gcc      624
Arg Ser Thr Arg Ala Ala Pro Thr Thr Pro Arg Gly Ile Trp Arg Ala
        195                 200                 205 atc ggc gtg ccg gag ctc gac gcg tac ctc cgc tcc cgc ggc gac ggc      672
Ile Gly Val Pro Glu Leu Asp Ala Tyr Leu Arg Ser Arg Gly Asp Gly
    210                 215                 220 gcc gac gag gag gag cgg gcg cgc atg ctc gcc gcg gcc gtc gcg gag      720
Ala Asp Glu Glu Glu Arg Ala Arg Met Leu Ala Ala Ala Val Ala Glu
225                 230                 235                 240 atc aag tcg aac acg ttc cgg ctc gcg tgc cgc cag cac cgc aag atc      768
Ile Lys Ser Asn Thr Phe Arg Leu Ala Cys Arg Gln His Arg Lys Ile
                245                 250                 255 gag agg ctg gac cgc atg tgg cgc gcc cgc cgc gtc gac gcc acg gag      816
Glu Arg Leu Asp Arg Met Trp Arg Ala Arg Arg Val Asp Ala Thr Glu
            260                 265                 270 gtg ttc agg agg cgc ggc cac gcc gcc gac gac gcg tgg cag cgg ctc      864
Val Phe Arg Arg Arg Gly His Ala Ala Asp Asp Ala Trp Gln Arg Leu
        275                 280                 285 gtc gcc gcg ccg tgc atc gac gcc gtc cgg tca ttc ctc ttc gag gac      912
Val Ala Ala Pro Cys Ile Asp Ala Val Arg Ser Phe Leu Phe Glu Asp
    290                 295                 300 caa gaa cgc agc agc atc gcc gcc ggc aaa cct ccc ctc ttc gcc gcc      960
Gln Glu Arg Ser Ser Ile Ala Ala Gly Lys Pro Pro Leu Phe Ala Ala
305                 310                 315                 320 ggc aag gcc act tca ggc aac atc tcc gtc ttc gcc tcc gcg gcc gcc     1008
Gly Lys Ala Thr Ser Gly Asn Ile Ser Val Phe Ala Ser Ala Ala Ala
                325                 330                 335 gcc atg gcg gcg gcc gct gca atc tga                                 1035
Ala Met Ala Ala Ala Ala Ile *
            340

<210> SEQ ID NO 70
```

<211> LENGTH: 1284
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT7 coding sequence
<220> FEATURE:
<221> NAME/KEY: CDS
<222> LOCATION: (1)...(1284)

<400> SEQUENCE: 70

```
atg gca gcg act ggt cga aac gcg gcc gca cga cgg aca cgc cgc tcg      48
Met Ala Ala Thr Gly Arg Asn Ala Ala Ala Arg Arg Thr Arg Arg Ser
1               5                   10                  15 atc ccc cgc gcg gct gcc gtg ctc ccc ctc tcg tct gga tca ccg gcg      96
Ile Pro Arg Ala Ala Ala Val Leu Pro Leu Ser Ser Gly Ser Pro Ala
                20                  25                  30 gct gtg ctg agg cga ctg ggg ctc ggt gag tgt ttt ggg tgg gcc ggc     144
Ala Val Leu Arg Arg Leu Gly Leu Gly Glu Cys Phe Gly Trp Ala Gly
            35                  40                  45 ttt atg agc agt ctc ggt ttg aag atc cgc acc gtc gtc cgc tca cct     192
Phe Met Ser Ser Leu Gly Leu Lys Ile Arg Thr Val Val Arg Ser Pro
        50                  55                  60 atg gcg gcc gcg gcc gtc gct ggc gtc gga agg gat ggt agc ttc gcc     240
Met Ala Ala Ala Ala Val Ala Gly Val Gly Arg Asp Gly Ser Phe Ala
65                  70                  75                  80 tcc cag aag cgg cca cgt cgg gtt agt gtg aga atg gag aga agc aga     288
Ser Gln Lys Arg Pro Arg Arg Val Ser Val Arg Met Glu Arg Ser Arg
                85                  90                  95 gtc ggg gac ggt tgc tgc tgc tcc tgc tct ggc cgc ggc ggg gtg gcg     336
Val Gly Asp Gly Cys Cys Cys Ser Cys Ser Gly Arg Gly Gly Val Ala
                100                 105                 110 tcc act acg gcg gtc cgg ccg tcc acg ggg atg gtg gtg atc gtc ggc     384
Ser Thr Thr Ala Val Arg Pro Ser Thr Gly Met Val Val Ile Val Gly
            115                 120                 125 gcc acg ggc acg ggg aag acc aag ctt tcc atc gac gcg gcg cag gag     432
Ala Thr Gly Thr Gly Lys Thr Lys Leu Ser Ile Asp Ala Ala Gln Glu
        130                 135                 140 ctc gcc ggc gag gtg gtg aac gct gac aag att cag ctg tac gac ggc     480
Leu Ala Gly Glu Val Val Asn Ala Asp Lys Ile Gln Leu Tyr Asp Gly
145                 150                 155                 160 ctc gac gtc acc acg aac aag gtg tcg ctc gcc gac cgc cgg ggc gtc     528
Leu Asp Val Thr Thr Asn Lys Val Ser Leu Ala Asp Arg Arg Gly Val
                165                 170                 175 ccg cac cac ctc ctc ggc gca atc cgc gcc gag gcc ggg gag ctg ccg     576
Pro His His Leu Leu Gly Ala Ile Arg Ala Glu Ala Gly Glu Leu Pro
            180                 185                 190 ccg tcg tcg ttc cgc tcg ctc gcc gcc gcc gcg gcc ggc atc gcg         624
Pro Ser Ser Phe Arg Ser Leu Ala Ala Ala Ala Ala Gly Ile Ala
        195                 200                 205 tcg cgc ggg cgc gtg ccg gtc gtg gcc ggc ggg tcc aac tcg ctc atc     672
Ser Arg Gly Arg Val Pro Val Val Ala Gly Gly Ser Asn Ser Leu Ile
    210                 215                 220 cac gcg ctc ctc gct gac ccc atc gat gcc gcg ccg cgt gac cct ttc     720
His Ala Leu Leu Ala Asp Pro Ile Asp Ala Ala Pro Arg Asp Pro Phe
225                 230                 235                 240 gcg gac gcc gat gtc ggg tac cgg ccg gcg ctc cgg ttc ccg tgc tgc     768
Ala Asp Ala Asp Val Gly Tyr Arg Pro Ala Leu Arg Phe Pro Cys Cys
                245                 250                 255 ctc ctc tgg gtc gac gtc gac gac gat gtt ctc gac gaa tac ctc gac     816
Leu Leu Trp Val Asp Val Asp Asp Asp Val Leu Asp Glu Tyr Leu Asp
```

```
cgg cgc gtg gac gac atg gtc ggc gag ggg atg gtc gag gag ctc gag      864
Arg Arg Val Asp Asp Met Val Gly Glu Gly Met Val Glu Glu Leu Glu
            275                 280                 285 gaa tac ttc gcg acg acg tcg gcc tcg gag cgg gcc tcg cac gcc ggg      912
Glu Tyr Phe Ala Thr Thr Ser Ala Ser Glu Arg Ala Ser His Ala Gly
        290                 295                 300 ctg ggc aag gcc atc ggc gtg ccg gag ctc ggc gac tac ttc gcc ggg      960
Leu Gly Lys Ala Ile Gly Val Pro Glu Leu Gly Asp Tyr Phe Ala Gly
305                 310                 315                 320 cgc aag agc ctc gac gcg gcg ata gac gag atc aag gcc aac acg cgg     1008
Arg Lys Ser Leu Asp Ala Ala Ile Asp Glu Ile Lys Ala Asn Thr Arg
                325                 330                 335 gtc ctc gcg gcc cgc cag gtc ggc aag atc cga cgc atg gcc gac gtt     1056
Val Leu Ala Ala Arg Gln Val Gly Lys Ile Arg Arg Met Ala Asp Val
            340                 345                 350 tgg ggc tgg ccc atc cgc cgc ctc gac gcc acg gcc acc atc cgg gcg     1104
Trp Gly Trp Pro Ile Arg Arg Leu Asp Ala Thr Ala Thr Ile Arg Ala
        355                 360                 365 cgg ctc tcc ggc gcc ggc cgc gcc gcc gag gcc gcc gcg tgg gag cgc     1152
Arg Leu Ser Gly Ala Gly Arg Ala Ala Glu Ala Ala Ala Trp Glu Arg
370                 375                 380 gac gtg cgc ggg cca ggc ctc gcc gcg atg cgt cag ttc gtc ggc cgc     1200
Asp Val Arg Gly Pro Gly Leu Ala Ala Met Arg Gln Phe Val Gly Arg
                385                 390                 395                 400 gcc gac ttc aac gcc gca gcg gtc gac cag cta gcc gcg cgg agt cgg     1248
Ala Asp Phe Asn Ala Ala Ala Val Asp Gln Leu Ala Ala Arg Ser Arg
            405                 410                 415 agg caa tgc ctt cgc ggt ggc atg gtg gcc ggc tga                     1284
Arg Gln Cys Leu Arg Gly Gly Met Val Ala Gly  *
        420                 425
```

<210> SEQ ID NO 71
<211> LENGTH: 1353
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT8 coding sequence
<220> FEATURE:
<221> NAME/KEY: CDS
<222> LOCATION: (1)...(1353)

<400> SEQUENCE: 71

```
atg gcc cac ctc gcg gcc tct gcc gcc ccg ctt cca agc gct gac ccc       48
Met Ala His Leu Ala Ala Ser Ala Ala Pro Leu Pro Ser Ala Asp Pro
 1               5                  10                  15 gac gcc ggc gag gag tcc tcc cac tct ccg ccg ccg gag aag ggg           96
Asp Ala Gly Glu Glu Ser Ser His Ser Pro Pro Pro Glu Lys Gly
            20                  25                  30 ctg agg aag gtg gtg gtg gtg atg ggc gcg act ggc gcc ggc aag tcg     144
Leu Arg Lys Val Val Val Val Met Gly Ala Thr Gly Ala Gly Lys Ser
        35                  40                  45 cgg ctg gcc gtc gac ctc gcg agc cac ttc gcc ggc gtc gag gtg gtc     192
Arg Leu Ala Val Asp Leu Ala Ser His Phe Ala Gly Val Glu Val Val
    50                  55                  60 agc gcc gac tcc atg caa gtc tac ggt ggg ctc gat gtc ctc acc aac     240
Ser Ala Asp Ser Met Gln Val Tyr Gly Gly Leu Asp Val Leu Thr Asn
65                  70                  75                  80 aag gtc ccc ctc cac gag cag aaa ggc gtt cct cac cat ctc ctg agc     288
Lys Val Pro Leu His Glu Gln Lys Gly Val Pro His His Leu Leu Ser
```

```
                       85                  90                  95
gtg att gat ccc tct gtg gag ttc act tgc cgc gat ttc cgc gac cat    336
Val Ile Asp Pro Ser Val Glu Phe Thr Cys Arg Asp Phe Arg Asp His
            100                 105                 110 gct gtg ccg att ata gaa ggt ata ttg gat cgt ggc ctc cct gtt        384
Ala Val Pro Ile Ile Glu Gly Ile Leu Asp Arg Gly Leu Pro Val
        115                 120                 125 att gtt ggt ggt aca aac ttc tac atc cag gct ctt gtt agc cca ttc    432
Ile Val Gly Gly Thr Asn Phe Tyr Ile Gln Ala Leu Val Ser Pro Phe
130                 135                 140 ctc ttt gat gat atg gca cag gat att gag ggt ctt act tta aat gac    480
Leu Phe Asp Asp Met Ala Gln Asp Ile Glu Gly Leu Thr Leu Asn Asp
145                 150                 155                 160 cac cta gat gag ata ggg ctt gat aat gat gat gaa gcc ggt ctg tat    528
His Leu Asp Glu Ile Gly Leu Asp Asn Asp Asp Glu Ala Gly Leu Tyr
                165                 170                 175 gaa cat ttg aag aag att gat cct gtt gct gca caa agg ata cac ccg    576
Glu His Leu Lys Lys Ile Asp Pro Val Ala Ala Gln Arg Ile His Pro
            180                 185                 190 aac aac cat cga aaa ata aaa cgc tac ctt gag ttg tat gaa tcc aca    624
Asn Asn His Arg Lys Ile Lys Arg Tyr Leu Glu Leu Tyr Glu Ser Thr
        195                 200                 205 ggt gcc cta cct agt gat ctt ttc caa ggg caa gcc aca gag gac aga    672
Gly Ala Leu Pro Ser Asp Leu Phe Gln Gly Gln Ala Thr Glu Asp Arg
210                 215                 220 agt ggg gtc gac cta gta act cca gat ttg act gtt gtt tct tgt gat    720
Ser Gly Val Asp Leu Val Thr Pro Asp Leu Thr Val Val Ser Cys Asp
225                 230                 235                 240 gct gat ctt cat gtt ctg gat cgt tat gtc aat gaa agg gtc gac tgc    768
Ala Asp Leu His Val Leu Asp Arg Tyr Val Asn Glu Arg Val Asp Cys
                245                 250                 255 atg att gat gat ggc ctg cta gat gaa gtg tgt aac ata tat gat cga    816
Met Ile Asp Asp Gly Leu Leu Asp Glu Val Cys Asn Ile Tyr Asp Arg
            260                 265                 270 gag gcc act tat acc caa ggg ctg cgg cag gcc att ggt gtt cgt gaa    864
Glu Ala Thr Tyr Thr Gln Gly Leu Arg Gln Ala Ile Gly Val Arg Glu
        275                 280                 285 ttt gat gag ttt ttc aga ttt tat ttt gca agg aag gaa acc ggt ctc    912
Phe Asp Glu Phe Phe Arg Phe Tyr Phe Ala Arg Lys Glu Thr Gly Leu
290                 295                 300 cat gat gat aac ctg aag ggc tta ttg gat gaa gca gtc tca caa cta    960
His Asp Asp Asn Leu Lys Gly Leu Leu Asp Glu Ala Val Ser Gln Leu
305                 310                 315                 320 aaa gca aac act cgc aga ctt gtt cga cgt caa aga cga agg ctg cat    1008
Lys Ala Asn Thr Arg Arg Leu Val Arg Arg Gln Arg Arg Arg Leu His
                325                 330                 335 cgg ttg aat aaa tat ttt gag tgg aac ttg cgt cat att gat gca aca    1056
Arg Leu Asn Lys Tyr Phe Glu Trp Asn Leu Arg His Ile Asp Ala Thr
            340                 345                 350 gaa gct ttc tat ggt gcc act gct gac tca tgg aac atg aaa gtt gtg    1104
Glu Ala Phe Tyr Gly Ala Thr Ala Asp Ser Trp Asn Met Lys Val Val
        355                 360                 365 aaa cct tgc gtg gat att gtt aga gat ttc ttg tct gat gat aca att    1152
Lys Pro Cys Val Asp Ile Val Arg Asp Phe Leu Ser Asp Asp Thr Ile
370                 375                 380 ttg gca agc aga gat ggt tct agt gta act gga agc cct agg atg tct    1200
Leu Ala Ser Arg Asp Gly Ser Ser Val Thr Gly Ser Pro Arg Met Ser
385                 390                 395                 400 tca aga gag ttg tgg act caa tat gtt tgt gag gcc tgt gat aac cgg    1248
```

| | | | | | | | | | | | | | | | | |
|---|---|---|---|---|---|---|---|---|---|---|---|---|---|---|---|---|
| Ser | Arg | Glu | Leu | Trp | Thr | Gln | Tyr | Val | Cys | Glu | Ala | Cys | Asp | Asn | Arg | |
| | | | | 405 | | | | 410 | | | | 415 | | | | |

```
gta ctt cgg gga acg cat gag tgg gag caa cac aag caa ggc cga tgc    1296
Val Leu Arg Gly Thr His Glu Trp Glu Gln His Lys Gln Gly Arg Cys
            420                 425                 430 cac cgt aaa aga gta caa cgt ttg aaa cag aag gct agt aca gtg ata    1344
His Arg Lys Arg Val Gln Arg Leu Lys Gln Lys Ala Ser Thr Val Ile
        435                 440                 445 tca tta tag                                                        1353
Ser Leu *
    450

<210> SEQ ID NO 72
<211> LENGTH: 1368
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT9 coding sequence
<220> FEATURE:
<221> NAME/KEY: CDS
<222> LOCATION: (1)...(1368)

<400> SEQUENCE: 72 atg acc agc gtt gcc acc agg att gcc acg ctc gtg cgg gcc gcg gcg    48
Met Thr Ser Val Ala Thr Arg Ile Ala Thr Leu Val Arg Ala Ala Ala
1               5                   10                  15 gcg gcg agc cgg cca ttg cgg ctc cac cgc cgg ccc ggc ggc gag gat    96
Ala Ala Ser Arg Pro Leu Arg Leu His Arg Arg Pro Gly Gly Glu Asp
            20                  25                  30 acg agg atg gtg gtg atc gtc ggc gcc acg ggc acc ggg aag acc aag    144
Thr Arg Met Val Val Ile Val Gly Ala Thr Gly Thr Gly Lys Thr Lys
        35                  40                  45 ctg tcc atc gac gcc gcc aag gtg atc ggc ggc gag gtt gtc aac gcc    192
Leu Ser Ile Asp Ala Ala Lys Val Ile Gly Gly Glu Val Val Asn Ala
    50                  55                  60 gac aag att cag ctc tat gac ggc ctc gac gtg acc acc aac aag gtg    240
Asp Lys Ile Gln Leu Tyr Asp Gly Leu Asp Val Thr Thr Asn Lys Val
65                  70                  75                  80 agc ctc gcc gac cgc cgc ggc gtg ccg cac cac ctc ctc gga gcc atc    288
Ser Leu Ala Asp Arg Arg Gly Val Pro His His Leu Leu Gly Ala Ile
                85                  90                  95 cgc ccc gag gcc ggc gag ctc ccg ccg tcg tcc ttc cgg tcc ctc gcc    336
Arg Pro Glu Ala Gly Glu Leu Pro Pro Ser Ser Phe Arg Ser Leu Ala
            100                 105                 110 gcc gcc acg gcc gcg tcg atc gcg gcg agg cgg ctc gtg ccg gtc atc    384
Ala Ala Thr Ala Ala Ser Ile Ala Ala Arg Arg Leu Val Pro Val Ile
        115                 120                 125 gcc ggt ggg tcg aac tcc ctc atc cac gcc ctc ctc gcc gac cac ttc    432
Ala Gly Gly Ser Asn Ser Leu Ile His Ala Leu Leu Ala Asp His Phe
    130                 135                 140 gac gcc tcc gct ggc gat ccc ttc tcc ccc gcc gcc gcc ttc cgc cac    480
Asp Ala Ser Ala Gly Asp Pro Phe Ser Pro Ala Ala Ala Phe Arg His
145                 150                 155                 160 tac cgc ccg gcg ctc cgg ttc ccg tgc tgc ctg ctc tgg gtc cac gtc    528
Tyr Arg Pro Ala Leu Arg Phe Pro Cys Cys Leu Leu Trp Val His Val
                165                 170                 175 gat gag gcg ctc ctc gac gag tac ctc gac cgc cgc gtg gac gac atg    576
Asp Glu Ala Leu Leu Asp Glu Tyr Leu Asp Arg Arg Val Asp Asp Met
            180                 185                 190 gtg gac gct ggc atg gtc gag gag ctc cgg gag tac ttc gcc acg aca    624
Val Asp Ala Gly Met Val Glu Glu Leu Arg Glu Tyr Phe Ala Thr Thr
```

```
Val Asp Ala Gly Met Val Glu Glu Leu Arg Glu Tyr Phe Ala Thr Thr
            195                 200                 205 acc gcc gcg gag cgc gcc gcg cac tcc ggg ctg ggc aag gcc atc ggc      672
Thr Ala Glu Arg Ala Ala His Ser Gly Leu Gly Lys Ala Ile Gly
    210                 215                 220 gtc ccc gag ctc ggc gac tac ttc gcc ggg cgc aag acc ttc tcc gag      720
Val Pro Glu Leu Gly Asp Tyr Phe Ala Gly Arg Lys Thr Phe Ser Glu
225                 230                 235                 240 gcg atc gac gac atc aaa gcc aac acc cgc gtc ctc gcc gcc gcg cag      768
Ala Ile Asp Asp Ile Lys Ala Asn Thr Arg Val Leu Ala Ala Ala Gln
                245                 250                 255 gtg tcc aag atc cgc cgc atg tcc gac gcc tgg ggc tgg ccc atc cac      816
Val Ser Lys Ile Arg Arg Met Ser Asp Ala Trp Gly Trp Pro Ile His
        260                 265                 270 cgc ctc gac gcc tcc gac aca gtc cgc gcc agg ctc acg cgg gcg ggc      864
Arg Leu Asp Ala Ser Asp Thr Val Arg Ala Arg Leu Thr Arg Ala Gly
    275                 280                 285 tcc gcc gcc gag tcc gcc tcc tgg gag cgc gac gtg cgc ggc cca ggc      912
Ser Ala Ala Glu Ser Ala Ser Trp Glu Arg Asp Val Arg Gly Pro Gly
290                 295                 300 ctc gcc acc atc cgc agc ttc ctc gcc gat cag tca ccg cca ccg cgc      960
Leu Ala Thr Ile Arg Ser Phe Leu Ala Asp Gln Ser Pro Pro Pro Arg
305                 310                 315                 320 agc gag ggc acc aac gac tac ctg tac gcc atg gag acg gaa cca gag     1008
Ser Glu Gly Thr Asn Asp Tyr Leu Tyr Ala Met Glu Thr Glu Pro Glu
                325                 330                 335 ccg ccg ccg ccg ccg acg ttg ccg ccg cgg ctg ctc cgg ttg ccg cgg     1056
Pro Pro Pro Pro Pro Thr Leu Pro Pro Arg Leu Leu Arg Leu Pro Arg
        340                 345                 350 atg cag tac tgc gac atg gtg ggc aga att tgt gta ctc ttt ctt gga     1104
Met Gln Tyr Cys Asp Met Val Gly Arg Ile Cys Val Leu Phe Leu Gly
    355                 360                 365 gag gtg gtg att cat cac atc gct ctc ctc cta acc gcg gca ctt ata     1152
Glu Val Val Ile His His Ile Ala Leu Leu Leu Thr Ala Ala Leu Ile
370                 375                 380 ctc cag tcc agt act ttt gcc tgt acc atc gct gca gtg tac gaa tgc     1200
Leu Gln Ser Ser Thr Phe Ala Cys Thr Ile Ala Ala Val Tyr Glu Cys
385                 390                 395                 400 caa gtc tcc tgg ata atc gca agc ttt gcc tcc ggc cta ttt tgc agg     1248
Gln Val Ser Trp Ile Ile Ala Ser Phe Ala Ser Gly Leu Phe Cys Arg
                405                 410                 415 att gct gta ctg gat gag aca gtc aag gag tta gat att tgg aag ctt     1296
Ile Ala Val Leu Asp Glu Thr Val Lys Glu Leu Asp Ile Trp Lys Leu
        420                 425                 430 aag ata gcc aat gga ttt cta aaa att aca atg tgt ctg aaa gat tgg     1344
Lys Ile Ala Asn Gly Phe Leu Lys Ile Thr Met Cys Leu Lys Asp Trp
    435                 440                 445 tca ggc tat ccc ctt gga gtg tga                                      1368
Ser Gly Tyr Pro Leu Gly Val *
450                 455

<210> SEQ ID NO 73
<211> LENGTH: 1758
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT10 coding sequence
<220> FEATURE:
<221> NAME/KEY: CDS
<222> LOCATION: (1)...(1758)
```

<400> SEQUENCE: 73

```
atg aag atc tac att caa gcc agg gaa gag aag tgt caa gga cat gtg      48
Met Lys Ile Tyr Ile Gln Ala Arg Glu Glu Lys Cys Gln Gly His Val
 1               5                  10                  15 ttc aag tcc cgc cac ctt cga gcc aac aaa gag gca gca ctc cag gat      96
Phe Lys Ser Arg His Leu Arg Ala Asn Lys Glu Ala Ala Leu Gln Asp
             20                  25                  30 gcg tcg cgt gag gca ttc atg cgt cta tgt aag atc tac agc atc gag     144
Ala Ser Arg Glu Ala Phe Met Arg Leu Cys Lys Ile Tyr Ser Ile Glu
         35                  40                  45 gtt gcg agt act ccg ttc ttt cta cat cca ttc cgt gaa tgc ggt gac     192
Val Ala Ser Thr Pro Phe Phe Leu His Pro Phe Arg Glu Cys Gly Asp
     50                  55                  60 cgc cgc tgc cat att cgg aaa ttt agg ggc ttt gag gag cac tct ccc     240
Arg Arg Cys His Ile Arg Lys Phe Arg Gly Phe Glu Glu His Ser Pro
 65                  70                  75                  80 atc cac ttc tcc atg tgg atg tgg gct gca gac gag gcc tat gag gag     288
Ile His Phe Ser Met Trp Met Trp Ala Ala Asp Glu Ala Tyr Glu Glu
                 85                  90                  95 gcc tta gag gaa tta gat atg ctt cgg tca aag att gcc ggc tgg gag     336
Ala Leu Glu Glu Leu Asp Met Leu Arg Ser Lys Ile Ala Gly Trp Glu
            100                 105                 110 gag cgg tac aac cac ctt gct aaa gaa cac acc act cgt gga caa cta     384
Glu Arg Tyr Asn His Leu Ala Lys Glu His Thr Thr Arg Gly Gln Leu
        115                 120                 125 ttg gaa gca atc aag ctt cgc ctc cag tgg tat ttt cga acc cca tct     432
Leu Glu Ala Ile Lys Leu Arg Leu Gln Trp Tyr Phe Arg Thr Pro Ser
    130                 135                 140 caa gct caa atc caa cgg act ttg tca cca cca cca caa aga gtg aca     480
Gln Ala Gln Ile Gln Arg Thr Leu Ser Pro Pro Pro Gln Arg Val Thr
145                 150                 155                 160 aga agt gat ggt gag gac tat agt caa atc aat gca cag cag gca tgt     528
Arg Ser Asp Gly Glu Asp Tyr Ser Gln Ile Asn Ala Gln Gln Ala Cys
                165                 170                 175 ctg gaa agg tcc gaa gtt aaa ctt gat agg gca act tca caa gac tat     576
Leu Glu Arg Ser Glu Val Lys Leu Asp Arg Ala Thr Ser Gln Asp Tyr
            180                 185                 190 ctg caa gga tac aag ccc cca tca gaa tcc ctc gac gct att gtt tgg     624
Leu Gln Gly Tyr Lys Pro Pro Ser Glu Ser Leu Asp Ala Ile Val Trp
        195                 200                 205 cct ctt gtt gaa ggg aag cat gac aat aca agc agc ggt agg agg aat     672
Pro Leu Val Glu Gly Lys His Asp Asn Thr Ser Ser Gly Arg Arg Asn
    210                 215                 220 gag aag gca tgg gaa atg gca aaa caa gtg cct aga gga agg att tat     720
Glu Lys Ala Trp Glu Met Ala Lys Gln Val Pro Arg Gly Arg Ile Tyr
225                 230                 235                 240 gct ttg gtc tat aaa cat caa gac aat att gga ctg gtc ctt gaa aag     768
Ala Leu Val Tyr Lys His Gln Asp Asn Ile Gly Leu Val Leu Glu Lys
                245                 250                 255 aga gtt gga cca gct gca cat cta gga gac cgc tat gta agt gac agg     816
Arg Val Gly Pro Ala Ala His Leu Gly Asp Arg Tyr Val Ser Asp Arg
            260                 265                 270 gtc ata tca cat cta gga gac ctc tat gta ata cga acc ctt agc tac     864
Val Ile Ser His Leu Gly Asp Leu Tyr Val Ile Arg Thr Leu Ser Tyr
        275                 280                 285 ttt cct ttc atg ctc aat ttt cac cct tct tgt gat tgc ttc ctc aat     912
Phe Pro Phe Met Leu Asn Phe His Pro Ser Cys Asp Cys Phe Leu Asn
    290                 295                 300
```

| | | |
|---|---|---|
| atg ctg gga aac aag tta gta gtg att att ggt gcc acg gga act gga<br>Met Leu Gly Asn Lys Leu Val Val Ile Ile Gly Ala Thr Gly Thr Gly<br>305                   310                   315                  320 | 960 |
| aaa aca aga ctc tca att gag att gcc aag gcg att ggt ggg gaa gtg<br>Lys Thr Arg Leu Ser Ile Glu Ile Ala Lys Ala Ile Gly Gly Glu Val<br>                  325                  330                  335 | 1008 |
| gta aat ggt gac aag atg caa att tat gat ggc ctg gat att acg aca<br>Val Asn Gly Asp Lys Met Gln Ile Tyr Asp Gly Leu Asp Ile Thr Thr<br>340                   345                   350 | 1056 |
| aac aag gtt tct tta caa gat cga tgc ggc ata cct cat cac ctt att<br>Asn Lys Val Ser Leu Gln Asp Arg Cys Gly Ile Pro His His Leu Ile<br>                  355                  360                  365 | 1104 |
| gcg tcc atc cct cac aac gca ggt gat ttt cct gtg tca ttt ttt cga<br>Ala Ser Ile Pro His Asn Ala Gly Asp Phe Pro Val Ser Phe Phe Arg<br>370                   375                   380 | 1152 |
| tat gct gca aaa acc aca ata aac tgc att gcc aga cgt ggt cac aca<br>Tyr Ala Ala Lys Thr Thr Ile Asn Cys Ile Ala Arg Arg Gly His Thr<br>385                   390                   395                  400 | 1200 |
| ccg att gtg gtg ggt gga tct aac tca ctt atc cat ggt ctc ctt gtt<br>Pro Ile Val Val Gly Gly Ser Asn Ser Leu Ile His Gly Leu Leu Val<br>                  405                  410                  415 | 1248 |
| gac aat ttt gat ttg tct att gtg gat cct ttt ggg caa ttg gag gtt<br>Asp Asn Phe Asp Leu Ser Ile Val Asp Pro Phe Gly Gln Leu Glu Val<br>420                   425                   430 | 1296 |
| agc tat cag ccg acg cct caa tgg caa tgt tgt ttt cta tgg gtt cat<br>Ser Tyr Gln Pro Thr Pro Gln Trp Gln Cys Cys Phe Leu Trp Val His<br>                  435                  440                  445 | 1344 |
| gtt aat gag gtg att ctt aat gag tat ttg aaa cgt cgt gtt gac ggc<br>Val Asn Glu Val Ile Leu Asn Glu Tyr Leu Lys Arg Arg Val Asp Gly<br>450                   455                   460 | 1392 |
| atg gtt gat gct ggg tta gtt gag gaa att gaa gaa tat ttt gac aca<br>Met Val Asp Ala Gly Leu Val Glu Glu Ile Glu Glu Tyr Phe Asp Thr<br>465                   470                   475                  480 | 1440 |
| tta tca gtt aat gga cat gtt cca tat gtg gga tta ggg aag gcc att<br>Leu Ser Val Asn Gly His Val Pro Tyr Val Gly Leu Gly Lys Ala Ile<br>                  485                  490                  495 | 1488 |
| ggt gtt cca gag cta agc gag tat ttt act gga cgg gtg agt tgt agt<br>Gly Val Pro Glu Leu Ser Glu Tyr Phe Thr Gly Arg Val Ser Cys Ser<br>500                   505                   510 | 1536 |
| gat gct ctt tct atg atg aag acc aat aca cag att ctt gca cga tct<br>Asp Ala Leu Ser Met Met Lys Thr Asn Thr Gln Ile Leu Ala Arg Ser<br>                  515                  520                  525 | 1584 |
| caa gtc aca aag att cat cgc atg gtt gat gtg tgg gga tgg cat gtt<br>Gln Val Thr Lys Ile His Arg Met Val Asp Val Trp Gly Trp His Val<br>530                   535                   540 | 1632 |
| cat gcc ctt gat tgt act gaa act att cta gca cat ctt act gga tca<br>His Ala Leu Asp Cys Thr Glu Thr Ile Leu Ala His Leu Thr Gly Ser<br>545                   550                   555                  560 | 1680 |
| aat aag tat atg gag gat ttg gtg tgg aaa cgt gat gta agt gac tct<br>Asn Lys Tyr Met Glu Asp Leu Val Trp Lys Arg Asp Val Ser Asp Ser<br>                  565                  570                  575 | 1728 |
| gga ctt gct gct ata caa gat ttt ctg tga<br>Gly Leu Ala Ala Ile Gln Asp Phe Leu *<br>580                   585 | 1758 |

<210> SEQ ID NO 74
<211> LENGTH: 1773
<212> TYPE: DNA
<213> ORGANISM: Oryza sativa
<220> FEATURE:
<221> NAME/KEY: misc_feature
<222> LOCATION: (0)...(0)
<223> OTHER INFORMATION: OsIPT11 coding sequence
<220> FEATURE:
<221> NAME/KEY: CDS
<222> LOCATION: (1)...(1773)

<400> SEQUENCE: 74

| | | | | | | | | | | | | | | | | |
|---|---|---|---|---|---|---|---|---|---|---|---|---|---|---|---|---|
| atg | gag | aac | tcc | tca | aag | aaa | acc | caa | gag | ttc | ttc | cct | aaa | ggt | ggg | 48 |
| Met | Glu | Asn | Ser | Ser | Lys | Lys | Thr | Gln | Glu | Phe | Phe | Pro | Lys | Gly | Gly | |
| 1 | | | | 5 | | | | | 10 | | | | | 15 | | |

| aat | gga | ggt | tat | gct | gag | cag | ctg | gag | ctc | ttg | ctg | aag | cag | ctt | cgt | 96 |
|---|---|---|---|---|---|---|---|---|---|---|---|---|---|---|---|---|
| Asn | Gly | Gly | Tyr | Ala | Glu | Gln | Leu | Glu | Leu | Leu | Leu | Lys | Gln | Leu | Arg | |
| | | | 20 | | | | | 25 | | | | | 30 | | | |

| ttt | cct | aac | aag | ccg | atc | cac | cat | gcg | gag | caa | gtg | atc | aaa | gga | ttc | 144 |
|---|---|---|---|---|---|---|---|---|---|---|---|---|---|---|---|---|
| Phe | Pro | Asn | Lys | Pro | Ile | His | His | Ala | Glu | Gln | Val | Ile | Lys | Gly | Phe | |
| | 35 | | | | | 40 | | | | | 45 | | | | | |

| cgg | aag | gat | tgg | acg | atg | aag | atc | tac | att | caa | gcc | agg | gaa | gag | aag | 192 |
|---|---|---|---|---|---|---|---|---|---|---|---|---|---|---|---|---|
| Arg | Lys | Asp | Trp | Thr | Met | Lys | Ile | Tyr | Ile | Gln | Ala | Arg | Glu | Glu | Lys | |
| 50 | | | | | 55 | | | | | 60 | | | | | | |

| tgt | caa | gga | cat | gtg | ttc | aag | tcc | cgc | cac | ctt | cga | gcc | aac | aaa | gag | 240 |
|---|---|---|---|---|---|---|---|---|---|---|---|---|---|---|---|---|
| Cys | Gln | Gly | His | Val | Phe | Lys | Ser | Arg | His | Leu | Arg | Ala | Asn | Lys | Glu | |
| 65 | | | | | 70 | | | | | 75 | | | | | 80 | |

| gca | gca | ctc | cag | gat | gcg | tcg | cgt | gag | gca | ttc | atg | cgt | cta | tgt | aag | 288 |
|---|---|---|---|---|---|---|---|---|---|---|---|---|---|---|---|---|
| Ala | Ala | Leu | Gln | Asp | Ala | Ser | Arg | Glu | Ala | Phe | Met | Arg | Leu | Cys | Lys | |
| | | | | 85 | | | | | 90 | | | | | 95 | | |

| atc | tac | agc | atc | gag | gtt | gca | agt | act | ccg | ttc | ttt | cta | cat | cca | ttc | 336 |
|---|---|---|---|---|---|---|---|---|---|---|---|---|---|---|---|---|
| Ile | Tyr | Ser | Ile | Glu | Val | Ala | Ser | Thr | Pro | Phe | Phe | Leu | His | Pro | Phe | |
| | | | 100 | | | | | 105 | | | | | 110 | | | |

| cgt | gaa | tgc | ggt | gac | cgc | cgc | tgc | cat | att | cgg | aaa | ttt | agg | ggc | ttt | 384 |
|---|---|---|---|---|---|---|---|---|---|---|---|---|---|---|---|---|
| Arg | Glu | Cys | Gly | Asp | Arg | Arg | Cys | His | Ile | Arg | Lys | Phe | Arg | Gly | Phe | |
| | | 115 | | | | | 120 | | | | | 125 | | | | |

| gag | gag | cag | tcg | ccc | atc | cac | ttc | tcc | atg | tgg | atg | tgg | gct | gca | gac | 432 |
|---|---|---|---|---|---|---|---|---|---|---|---|---|---|---|---|---|
| Glu | Glu | Gln | Ser | Pro | Ile | His | Phe | Ser | Met | Trp | Met | Trp | Ala | Ala | Asp | |
| 130 | | | | | 135 | | | | | 140 | | | | | | |

| gag | gcc | tat | gag | gag | gcc | tta | gag | gaa | tta | gat | atg | ctt | cgg | tca | aag | 480 |
|---|---|---|---|---|---|---|---|---|---|---|---|---|---|---|---|---|
| Glu | Ala | Tyr | Glu | Glu | Ala | Leu | Glu | Glu | Leu | Asp | Met | Leu | Arg | Ser | Lys | |
| 145 | | | | | 150 | | | | | 155 | | | | | 160 | |

| atc | gcc | ggc | tgg | gag | gag | cgg | tac | aac | cac | ctt | gct | aaa | gaa | cac | acc | 528 |
|---|---|---|---|---|---|---|---|---|---|---|---|---|---|---|---|---|
| Ile | Ala | Gly | Trp | Glu | Glu | Arg | Tyr | Asn | His | Leu | Ala | Lys | Glu | His | Thr | |
| | | | | 165 | | | | | 170 | | | | | 175 | | |

| act | cgt | gga | caa | cta | ttg | gaa | gca | atc | aag | ctt | cgc | ctc | cag | tgg | tat | 576 |
|---|---|---|---|---|---|---|---|---|---|---|---|---|---|---|---|---|
| Thr | Arg | Gly | Gln | Leu | Leu | Glu | Ala | Ile | Lys | Leu | Arg | Leu | Gln | Trp | Tyr | |
| | | | 180 | | | | | 185 | | | | | 190 | | | |

| ttt | cga | acc | cca | tct | caa | gct | cat | atc | caa | cgg | act | ttg | cca | cca | cca | 624 |
|---|---|---|---|---|---|---|---|---|---|---|---|---|---|---|---|---|
| Phe | Arg | Thr | Pro | Ser | Gln | Ala | His | Ile | Gln | Arg | Thr | Leu | Pro | Pro | Pro | |
| | | 195 | | | | | 200 | | | | | 205 | | | | |

| cca | caa | aga | gtg | aca | aga | agt | gat | ggt | gag | gac | tat | agt | caa | atc | aat | 672 |
|---|---|---|---|---|---|---|---|---|---|---|---|---|---|---|---|---|
| Pro | Gln | Arg | Val | Thr | Arg | Ser | Asp | Gly | Glu | Asp | Tyr | Ser | Gln | Ile | Asn | |
| 210 | | | | | 215 | | | | | 220 | | | | | | |

| gca | cat | cag | gca | tgt | ctg | gaa | agg | tcc | gaa | gtt | aaa | ctt | gat | agg | gca | 720 |
|---|---|---|---|---|---|---|---|---|---|---|---|---|---|---|---|---|
| Ala | His | Gln | Ala | Cys | Leu | Glu | Arg | Ser | Glu | Val | Lys | Leu | Asp | Arg | Ala | |
| 225 | | | | | 230 | | | | | 235 | | | | | 240 | |

| act | tca | caa | gac | tat | ctg | caa | gga | tac | aag | ccc | cca | tca | gaa | tcc | ctc | 768 |
|---|---|---|---|---|---|---|---|---|---|---|---|---|---|---|---|---|
| Thr | Ser | Gln | Asp | Tyr | Leu | Gln | Gly | Tyr | Lys | Pro | Pro | Ser | Glu | Ser | Leu | |
| | | | | 245 | | | | | 250 | | | | | 255 | | |

| gac | gct | att | gtt | tgg | cct | ctt | gtt | gaa | ggg | aag | cat | gac | aat | aca | agc | 816 |
|---|---|---|---|---|---|---|---|---|---|---|---|---|---|---|---|---|
| Asp | Ala | Ile | Val | Trp | Pro | Leu | Val | Glu | Gly | Lys | His | Asp | Asn | Thr | Ser | |
| | | | 260 | | | | | 265 | | | | | 270 | | | |

| agt | ggt | agg | agg | aat | gag | aag | gca | tgg | gaa | atg | gca | aaa | caa | gta | ata | 864 |
|---|---|---|---|---|---|---|---|---|---|---|---|---|---|---|---|---|
| Ser | Gly | Arg | Arg | Asn | Glu | Lys | Ala | Trp | Glu | Met | Ala | Lys | Gln | Val | Ile | |
| | 275 | | | | | 280 | | | | | 285 | | | | | |

```
cga acc ctt agc tac ttt cct ttc atg ctc aat ttt cac cct tct tgt       912
Arg Thr Leu Ser Tyr Phe Pro Phe Met Leu Asn Phe His Pro Ser Cys
    290             295                 300 gat tgc ttc ctc aat atg ctg gga aac aag tta gta gtg att att ggt       960
Asp Cys Phe Leu Asn Met Leu Gly Asn Lys Leu Val Val Ile Ile Gly
305             310                 315                 320 gcc acg gga act gga aaa aca aga ctc tca att gag ata gcc aag gcg      1008
Ala Thr Gly Thr Gly Lys Thr Arg Leu Ser Ile Glu Ile Ala Lys Ala
                325                 330                 335 att ggt ggg gaa gtg gta aat gct gac aag atg caa att tac gat ggc      1056
Ile Gly Gly Glu Val Val Asn Ala Asp Lys Met Gln Ile Tyr Asp Gly
            340                 345                 350 ctg gat att acg aca aac aag gtt tct tta caa gat cga tgc ggc ata      1104
Leu Asp Ile Thr Thr Asn Lys Val Ser Leu Gln Asp Arg Cys Gly Ile
        355                 360                 365 cct cat cac ctt att gcg tcc atc cct cgc aac gca ggt gat ttt cct      1152
Pro His His Leu Ile Ala Ser Ile Pro Arg Asn Ala Gly Asp Phe Pro
    370                 375                 380 gtg tca ttt ttt cga tct gct gca aaa acc aca ata aac tgc att gcc      1200
Val Ser Phe Phe Arg Ser Ala Ala Lys Thr Thr Ile Asn Cys Ile Ala
385             390                 395                 400 aga cgt ggt cac aca ccg att gtg gtg ggt gga tct aac tca ctt atc      1248
Arg Arg Gly His Thr Pro Ile Val Val Gly Gly Ser Asn Ser Leu Ile
                405                 410                 415 cat ggt ctc ctt gtt gac aat ttt gat tcg tct att gtg gat cct ttt      1296
His Gly Leu Leu Val Asp Asn Phe Asp Ser Ser Ile Val Asp Pro Phe
            420                 425                 430 ggg caa ttg gag gtt agc tat cgg ccg acg cct cga tcg caa tgt tgt      1344
Gly Gln Leu Glu Val Ser Tyr Arg Pro Thr Pro Arg Ser Gln Cys Cys
        435                 440                 445 ttt cta tgg gtt cat gtt aat gag gtg att ctt aat gag tat ttg aaa      1392
Phe Leu Trp Val His Val Asn Glu Val Ile Leu Asn Glu Tyr Leu Lys
    450                 455                 460 cgt cgt gtt gac aac atg gtt gat gct ggg tta gtt gag gaa att gaa      1440
Arg Arg Val Asp Asn Met Val Asp Ala Gly Leu Val Glu Glu Ile Glu
465             470                 475                 480 gaa tat ttt gac aca tta tca gtt aat gga cat gtt cca tat gtg gga      1488
Glu Tyr Phe Asp Thr Leu Ser Val Asn Gly His Val Pro Tyr Val Gly
                485                 490                 495 tta ggg aag gcc att ggt gtt cca gag cta agc gag tat ttt act gga      1536
Leu Gly Lys Ala Ile Gly Val Pro Glu Leu Ser Glu Tyr Phe Thr Gly
            500                 505                 510 cgg gtg agt tgt agt gat gct ctt tct atg atg aag acc aat aca cag      1584
Arg Val Ser Cys Ser Asp Ala Leu Ser Met Met Lys Thr Asn Thr Gln
        515                 520                 525 att ctt gca cga tct caa gtc aca aag att cat cgc atg gtt gat gtg      1632
Ile Leu Ala Arg Ser Gln Val Thr Lys Ile His Arg Met Val Asp Val
    530                 535                 540 tgg gga tgg cat gtt cat gcc ctt gat tgt act gaa act att cta gca      1680
Trp Gly Trp His Val His Ala Leu Asp Cys Thr Glu Thr Ile Leu Ala
545             550                 555                 560 cat ctt act gga tca aat aag tat atg gag gat ttg gtg tgg aaa cgt      1728
His Leu Thr Gly Ser Asn Lys Tyr Met Glu Asp Leu Val Trp Lys Arg
                565                 570                 575 gat gta agt gac cct gga ctt gct gct ata caa gat ttt ctg tga          1773
Asp Val Ser Asp Pro Gly Leu Ala Ala Ile Gln Asp Phe Leu *
            580                 585                 590
```

<210> SEQ ID NO 75

<211> LENGTH: 3280
<212> TYPE: DNA
<213> ORGANISM: Zea mays
<220> FEATURE:
<221> NAME/KEY: promoter
<222> LOCATION: (1)...(3280)
<223> OTHER INFORMATION: ZmIPT2 promoter (from Mo17)

<400> SEQUENCE: 75

```
tagtcagaga ggagccaaca acaatgccct tgaggtggt taaaacctag agggtgaaga      60
agggcttctt tggccatcaa tgaaggatta taaaatcatg gaaccacttg ttactcaatc    120
tctcactatt tgtctattcg atgtgtgatg aagcgttgat gatacattgt gtgttggcac    180
atgggcttgt gttctactca ttacgtaggc catgtgatag gtgagtagtg gctaactcga    240
caagtggtga tcaagtgagg tagggttaca tagtttttat atatatgata ttatttgggc    300
atatattata cctatattat tgggcttatt ttggtcagta tttgaaatgc attctataat    360
gttcgaaggc cctaacgggt aaccaagaag ggtacatagg aaacaggttg attgtaatgt    420
attcgatatc cttctaaaat ttggccataa agcccttat ggggagtgaa acaacccat     480
caatgtctcg taacggagaa atccctatta tttataaggg attgggcccc atttccatgc    540
ctacggaatg cttatattac aagtgcactc tagaaatgta acttgcacat ggatgacatg    600
attaggattg gtggcatgtg atacaattcc ttttttatt ccacatttt atttgacttt     660
ggttttagt attttttgtt tgtcctggac acccggtcac tggagtccac ttccttgtca    720
atgaacctta actacccacc accaaaaaat ccctctttct actttcatta tattggtata    780
attgctacag ctaccttgtt agttgcaaaa gactagtccc attgccttac tagtgacct    840
aatggagggc tacatatcct tggtagatgt ggaggtacca atggttccat cacatccatt    900
agattaggag gacaccatga tagacactag tctcaatatt aaacatagtt cttgttttta    960
ttttaaaatc gaaagcatta ttttgtttta aattctttta gtcgaaataa acttttaaaa   1020
cttcctagtt caatgaagtt tttctaaact tgaaactatg tgtattgttt gtacttgaaa   1080
cttttgactg gagagtttat acttgttggc atttatatga ttgcttttatg cttaggacaa   1140
tatacctatt gggcttattt aacttggtca gcgcatgaaa ctctttgtat aaattccaaa   1200
ggcccttgat gggcactcgc ttttttattcc ttcgggtagc aaaaacaagg caacacaagt   1260
aagaatgatt aaagcttctc cgcttaatag cttctccttc tgaaatctac cgaggagaga   1320
aggtaaagga gaagctttga cagcttctcc cctcgataac ttctccttct aaaatctatc   1380
aaggggagaa ggtaaagaag aagctttgac atctctttaa ttactaatca aggacaaaa   1440
caaaagagat tcttattcaa tacattcccg tctagaatca gctttcattc ttgcaacgca   1500
acaacaatta caaatatacc ttctacctcg gtaataggag aaggtatctt tggaggagga   1560
gcagattagt gttccaagtt cctgctccct ctcaaatgca tggtattgtt gctctattta   1620
tagccacggg gtacagcttt gtatgaaatt acaaacatac ccacaaactt atacaattgg   1680
actaatgaat acataagggg taatgcagtc attttttgttc acttgcctcg ccaatcgggt   1740
ctcttgggtt tctcaccttc ttctcttctt tgatcttcgt tatgtgttgg tcgaagcttc    1800
cttcggcaca taccttcgtg gttggtgctt tgaagcttct ccttcctagt ttttaagatt    1860
ttccaaagga gcttctcctt cctagttttg aagcttctcc gaaggatctt ctcctttcta    1920
gttttaagc ttctccaaag tagcttctc tttgcatagt acttgaaatg tattcaatgt     1980
taaagggttt ttgaggatct tcggtgatag aggccctcca atagccgtca acatgggcca    2040
gtaattggga agggtacaca agaaatggta gcctaacccc atcatatata atataggat    2100
```

-continued

```
aaatttttggc catatagccc ttagtgggga gtgtaacaaa cctatcaagg cccctattcg   2160
gaggaaatcc tctacagaga ttggggcaca ttgtcatacc tattgagatg tttattaaac   2220
acatgcactc ataatgttta tttaaatgta acttgtggat cgatgacgtg atcaagacct   2280 attttttttca cagacctatt tctcctattt tcatccacat tcgtgtaatc tcatttgtct   2340
ctcgtctcta gtcttttctt ttaagttgga acattattt gttttttaaat cctttctagt   2400 caaagttttta gacaagggaa catatcaggt gcaaccatac cccattagtg taaccgtgca   2460
accaagacac aagaatggtg gtgggaggac cattttaaaa aaattctctt ccacctccat   2520
ccttgtcttg gttgcacggt agcaccaaca gatatggttg catctcatat atatgttccc   2580
tttaaacaaa tggttccatt taaaactttc tagttgaatg aagttttttt ctaaactcaa   2640 ctcttttttgt attatttgta agtgaaaatt ttgactttgc gtgtttagac ttcaaactta   2700
attatttcct gctgtgctag aggacaacta gtaccaaaac ccaccaagtt cagtcaggta   2760
gaaatttact caagattatg atatggtcgt ttctttgatt ggagtcaatc gatggagtcc   2820
atgaacccaa acatttccat cggcagtatt gaacgaagat ggcagagtaa agtttggtaa   2880
tctttagtgg ttacaattat agaaatctcg aaacattttt tgaagcaggt aataatgcat   2940
gagctctaaa gaaggaaaaa tataatatct gttaacacat agaatcgagt gctccaatag   3000
atttagatat taacatatat gcattggata tatggaaaaa aaggatactc atgatatgag   3060
cacattaaat ttcctccaag caaacctagt ataaaaaggg aggaatgggt agatgataga   3120
gcagctcgtt ccttaaacca aatacaccac aaatttcttc aaaacaaaca aacacgatac   3180
atactggtct ctgtgcacaa aaaaggcacg gactgcttct ttttctattt ttttgttgtg   3240
tgcacagaat cgagcggcta cgataatcaa gatcaagaca                          3280
```

<210> SEQ ID NO 76
<211> LENGTH: 969
<212> TYPE: DNA
<213> ORGANISM: Zea mays
<220> FEATURE:
<221> NAME/KEY: misc_feature
<222> LOCATION: (0)...(0)
<223> OTHER INFORMATION: Coding sequence for variant of ZmIPT2 (from
      Mo17)
<220> FEATURE:
<221> NAME/KEY: CDS
<222> LOCATION: (1)...(969)

<400> SEQUENCE: 76

```
atg gag cac ggt gcc gtc gcc ggg aag ccc aag gtg gtg ttc gtg ctc        48
Met Glu His Gly Ala Val Ala Gly Lys Pro Lys Val Val Phe Val Leu
 1               5                  10                  15 ggc gcg aca gcg aca ggg aag tcg aag ctc gcc atc gcc ctc gcc gag        96
Gly Ala Thr Ala Thr Gly Lys Ser Lys Leu Ala Ile Ala Leu Ala Glu
             20                  25                  30 cgc ttc aac ggt gag gtt atc aac gct gac aaa atc cag gtc cac gat       144
Arg Phe Asn Gly Glu Val Ile Asn Ala Asp Lys Ile Gln Val His Asp
         35                  40                  45 ggc gtg ccc atc atc acg aac aag gtc aca gag gaa gag cag ggc ggg       192
Gly Val Pro Ile Ile Thr Asn Lys Val Thr Glu Glu Glu Gln Gly Gly
     50                  55                  60 gtg ccc cac cac ctg ctc agc gtc cgc cac ccg gac gcc gac ttc act       240
Val Pro His His Leu Leu Ser Val Arg His Pro Asp Ala Asp Phe Thr
 65                  70                  75                  80 gcg gag gag ttc cga cgt gag gcg gcc agc gcc gtg gcc cgc gtg ctc       288
Ala Glu Glu Phe Arg Arg Glu Ala Ala Ser Ala Val Ala Arg Val Leu
```

|  |  |  |  |  |  |  |  |  |  |  |  |  |  |  |  |
|---|---|---|---|---|---|---|---|---|---|---|---|---|---|---|---|
|  |  |  | 85 |  |  |  |  | 90 |  |  |  |  | 95 |  |  |
| tcg | gcg | ggc | cgc | ctc | ccc | gtc | gtg | gca | ggc | ggg | tcc | aac | acc | tac | atc |
| Ser | Ala | Gly | Arg | Leu | Pro | Val | Val | Ala | Gly | Gly | Ser | Asn | Thr | Tyr | Ile |
|  |  |  | 100 |  |  |  |  | 105 |  |  |  |  | 110 |  |  |

336

| gag | gca | ctg | gtg | gaa | ggc | gac | ggt | gcc | gcc | ttc | cgc | ttg | gcg | cac | gac |
|---|---|---|---|---|---|---|---|---|---|---|---|---|---|---|---|
| Glu | Ala | Leu | Val | Glu | Gly | Asp | Gly | Ala | Ala | Phe | Arg | Leu | Ala | His | Asp |
|  |  |  |  | 115 |  |  |  |  | 120 |  |  |  |  | 125 |  |

384

| ctc | ctc | ttc | gtc | tgg | gtg | gac | gcg | gag | cgg | gag | ctg | ttg | gag | tgg | tac |
|---|---|---|---|---|---|---|---|---|---|---|---|---|---|---|---|
| Leu | Leu | Phe | Val | Trp | Val | Asp | Ala | Glu | Arg | Glu | Leu | Leu | Glu | Trp | Tyr |
|  | 130 |  |  |  |  | 135 |  |  |  |  | 140 |  |  |  |  |

432

| gcc | gcg | ctg | cgc | gtg | gac | gag | atg | gtg | gcc | cgc | ggg | ctg | gtg | agc | gag |
|---|---|---|---|---|---|---|---|---|---|---|---|---|---|---|---|
| Ala | Ala | Leu | Arg | Val | Asp | Glu | Met | Val | Ala | Arg | Gly | Leu | Val | Ser | Glu |
| 145 |  |  |  |  | 150 |  |  |  |  | 155 |  |  |  |  | 160 |

480

| gct | cgc | gcg | gcg | ttt | ggc | ggc | gcc | gga | gtt | gac | tac | aac | cat | ggc | gtg |
|---|---|---|---|---|---|---|---|---|---|---|---|---|---|---|---|
| Ala | Arg | Ala | Ala | Phe | Gly | Gly | Ala | Gly | Val | Asp | Tyr | Asn | His | Gly | Val |
|  |  |  |  | 165 |  |  |  |  | 170 |  |  |  |  | 175 |  |

528

| cgc | cgc | gcc | atc | ggc | ctg | ccg | gag | atg | cac | gcc | tac | ctg | gtg | gcg | gag |
|---|---|---|---|---|---|---|---|---|---|---|---|---|---|---|---|
| Arg | Arg | Ala | Ile | Gly | Leu | Pro | Glu | Met | His | Ala | Tyr | Leu | Val | Ala | Glu |
|  |  |  | 180 |  |  |  |  | 185 |  |  |  |  | 190 |  |  |

576

| cac | gag | ggc | gtc | gcc | ggg | gag | gcc | gag | ctc | gcg | gcc | atg | ctg | gaa | cgc |
|---|---|---|---|---|---|---|---|---|---|---|---|---|---|---|---|
| His | Glu | Gly | Val | Ala | Gly | Glu | Ala | Glu | Leu | Ala | Ala | Met | Leu | Glu | Arg |
|  |  |  | 195 |  |  |  |  | 200 |  |  |  |  | 205 |  |  |

624

| gcg | gtg | cgc | gag | atc | aag | gac | aac | acc | ttc | cgc | ctc | gcg | cgc | acg | cag |
|---|---|---|---|---|---|---|---|---|---|---|---|---|---|---|---|
| Ala | Val | Arg | Glu | Ile | Lys | Asp | Asn | Thr | Phe | Arg | Leu | Ala | Arg | Thr | Gln |
| 210 |  |  |  |  | 215 |  |  |  |  | 220 |  |  |  |  |  |

672

| gcg | gag | aag | atc | cgg | cgc | ctc | agc | acg | ctt | gac | ggc | tgg | gac | gtc | cgc |
|---|---|---|---|---|---|---|---|---|---|---|---|---|---|---|---|
| Ala | Glu | Lys | Ile | Arg | Arg | Leu | Ser | Thr | Leu | Asp | Gly | Trp | Asp | Val | Arg |
| 225 |  |  |  |  | 230 |  |  |  |  | 235 |  |  |  |  | 240 |

720

| cgc | atc | gac | gtg | acc | ccc | gtg | ttc | gcg | cgc | aag | gcc | gat | ggc | act | gag |
|---|---|---|---|---|---|---|---|---|---|---|---|---|---|---|---|
| Arg | Ile | Asp | Val | Thr | Pro | Val | Phe | Ala | Arg | Lys | Ala | Asp | Gly | Thr | Glu |
|  |  |  |  | 245 |  |  |  |  | 250 |  |  |  |  | 255 |  |

768

| tgc | cac | gag | ctg | act | tgg | aag | aag | cag | gtg | tgg | gag | ccg | tgc | gag | gag |
|---|---|---|---|---|---|---|---|---|---|---|---|---|---|---|---|
| Cys | His | Glu | Leu | Thr | Trp | Lys | Lys | Gln | Val | Trp | Glu | Pro | Cys | Glu | Glu |
|  |  |  | 260 |  |  |  |  | 265 |  |  |  |  | 270 |  |  |

816

| atg | gtg | agg | gct | ttc | ctc | gag | ccg | tcc | ctg | act | gcc | gtt | cca | ggt | gtt |
|---|---|---|---|---|---|---|---|---|---|---|---|---|---|---|---|
| Met | Val | Arg | Ala | Phe | Leu | Glu | Pro | Ser | Leu | Thr | Ala | Val | Pro | Gly | Val |
|  |  | 275 |  |  |  |  | 280 |  |  |  |  | 285 |  |  |  |

864

| gca | gta | act | gaa | gaa | ggg | aac | gcc | ggc | gtc | gtc | gct | act | gct | gca | ccc |
|---|---|---|---|---|---|---|---|---|---|---|---|---|---|---|---|
| Ala | Val | Thr | Glu | Glu | Gly | Asn | Ala | Gly | Val | Val | Ala | Thr | Ala | Ala | Pro |
| 290 |  |  |  |  | 295 |  |  |  |  | 300 |  |  |  |  |  |

912

| gct | ggt | gat | gtc | gtc | gtc | cca | act | ggc | gat | gtc | gtc | acc | gcc | gtg | gct |
|---|---|---|---|---|---|---|---|---|---|---|---|---|---|---|---|
| Ala | Gly | Asp | Val | Val | Val | Pro | Thr | Gly | Asp | Val | Val | Thr | Ala | Val | Ala |
| 305 |  |  |  | 310 |  |  |  |  | 315 |  |  |  |  | 320 |  |

960

| gat | gca | taa |
|---|---|---|
| Asp | Ala | * |

969

<210> SEQ ID NO 77
<211> LENGTH: 322
<212> TYPE: PRT
<213> ORGANISM: Zea mays

<400> SEQUENCE: 77

| Met | Glu | His | Gly | Ala | Val | Ala | Gly | Lys | Pro | Lys | Val | Val | Phe | Val | Leu |
|---|---|---|---|---|---|---|---|---|---|---|---|---|---|---|---|
| 1 |  |  |  | 5 |  |  |  |  | 10 |  |  |  |  | 15 |  |

| Gly | Ala | Thr | Ala | Thr | Gly | Lys | Ser | Lys | Leu | Ala | Ile | Ala | Leu | Ala | Glu |
|---|---|---|---|---|---|---|---|---|---|---|---|---|---|---|---|
|  |  |  | 20 |  |  |  |  | 25 |  |  |  |  | 30 |  |  |

| Arg | Phe | Asn | Gly | Glu | Val | Ile | Asn | Ala | Asp | Lys | Ile | Gln | Val | His | Asp |
|---|---|---|---|---|---|---|---|---|---|---|---|---|---|---|---|
|  |  |  | 35 |  |  |  |  | 40 |  |  |  |  | 45 |  |  |

Gly Val Pro Ile Ile Thr Asn Lys Val Thr Glu Glu Glu Gln Gly Gly

```
                50                  55                  60
Val Pro His His Leu Leu Ser Val Arg His Pro Asp Ala Asp Phe Thr
 65                  70                  75                  80

Ala Glu Glu Phe Arg Arg Glu Ala Ala Ser Ala Val Ala Arg Val Leu
                 85                  90                  95

Ser Ala Gly Arg Leu Pro Val Val Ala Gly Ser Asn Thr Tyr Ile
            100                 105                 110

Glu Ala Leu Val Glu Gly Asp Gly Ala Ala Phe Arg Leu Ala His Asp
            115                 120                 125

Leu Leu Phe Val Trp Val Asp Ala Glu Arg Glu Leu Leu Glu Trp Tyr
130                 135                 140

Ala Ala Leu Arg Val Asp Glu Met Val Ala Arg Gly Leu Val Ser Glu
145                 150                 155                 160

Ala Arg Ala Ala Phe Gly Gly Ala Gly Val Asp Tyr Asn His Gly Val
                165                 170                 175

Arg Arg Ala Ile Gly Leu Pro Glu Met His Ala Tyr Leu Val Ala Glu
            180                 185                 190

His Glu Gly Val Ala Gly Glu Ala Glu Leu Ala Ala Met Leu Glu Arg
            195                 200                 205

Ala Val Arg Glu Ile Lys Asp Asn Thr Phe Arg Leu Ala Arg Thr Gln
210                 215                 220

Ala Glu Lys Ile Arg Arg Leu Ser Thr Leu Asp Gly Trp Asp Val Arg
225                 230                 235                 240

Arg Ile Asp Val Thr Pro Val Phe Ala Arg Lys Ala Asp Gly Thr Glu
                245                 250                 255

Cys His Glu Leu Thr Trp Lys Lys Gln Val Trp Glu Pro Cys Glu Glu
            260                 265                 270

Met Val Arg Ala Phe Leu Glu Pro Ser Leu Thr Ala Val Pro Gly Val
            275                 280                 285

Ala Val Thr Glu Glu Gly Asn Ala Gly Val Val Ala Thr Ala Ala Pro
            290                 295                 300

Ala Gly Asp Val Val Val Pro Thr Gly Asp Val Val Thr Ala Val Ala
305                 310                 315                 320

Asp Ala

<210> SEQ ID NO 78
<211> LENGTH: 25
<212> TYPE: DNA
<213> ORGANISM: Artificial Sequence
<220> FEATURE:
<223> OTHER INFORMATION: primer

<400> SEQUENCE: 78
atcatcaaga caatggagca cggtg                                    25

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
cgtccgctag ctacttatgc atcag                                    25

<210> SEQ ID NO 80
<211> LENGTH: 53
```

-continued

```
<210> SEQ ID NO 80
<211> LENGTH: 53
<212> TYPE: DNA
<213> ORGANISM: Artificial Sequence
<220> FEATURE:
<223> OTHER INFORMATION: primer

<400> SEQUENCE: 80
ggggacaagt ttgtacaaaa aagcaggctc aatggagcac ggtgccgtcg ccg       53

<210> SEQ ID NO 81
<211> LENGTH: 52
<212> TYPE: DNA
<213> ORGANISM: Artificial Sequence
<220> FEATURE:
<223> OTHER INFORMATION: primer

<400> SEQUENCE: 81
ggggaccact ttgtacaaga aagctgggtc ttatgcatca gccacggcgg tg        52

<210> SEQ ID NO 82
<211> LENGTH: 24
<212> TYPE: DNA
<213> ORGANISM: Artificial Sequence
<220> FEATURE:
<223> OTHER INFORMATION: ZmIPT2-F primer

<400> SEQUENCE: 82
tgttgtgtgc acagaatcga gcgg                                       24

<210> SEQ ID NO 83
<211> LENGTH: 25
<212> TYPE: DNA
<213> ORGANISM: Artificial Sequence
<220> FEATURE:
<223> OTHER INFORMATION: ZmIPT2-R primer

<400> SEQUENCE: 83
cgtccgctag ctacttatgc atcag                                      25

<210> SEQ ID NO 84
<211> LENGTH: 32
<212> TYPE: DNA
<213> ORGANISM: Artificial Sequence
<220> FEATURE:
<223> OTHER INFORMATION: Mu TIR primer

<400> SEQUENCE: 84
agagaagcca acgccawcgc ctcyatttcg tc                              32

<210> SEQ ID NO 85
<211> LENGTH: 1495
<212> TYPE: DNA
<213> ORGANISM: Zea mays
<220> FEATURE:
<221> NAME/KEY: CDS
<222> LOCATION: (83)...(1048)
<223> OTHER INFORMATION: ZmIPT2 ORF
<220> FEATURE:
<221> NAME/KEY: polyA_signal
<222> LOCATION: (1411)...(1416)
<220> FEATURE:
<221> NAME/KEY: misc_feature
<222> LOCATION: (1214)...(1230)
<223> OTHER INFORMATION: Lynx tag
<220> FEATURE:
<221> NAME/KEY: misc_feature
<222> LOCATION: (624)...(632)
<223> OTHER INFORMATION: transposon

<400> SEQUENCE: 85
```

-continued

```
aaaaggcacg gactgcttct ttttctattt tttgttgtgt gcacagaatc gagcggctac    60
aataatcaag atcatcaaga ca atg gag cac ggt gcc gtc gcc ggg aag ccc   112
                        Met Glu His Gly Ala Val Ala Gly Lys Pro
                          1               5                  10 aag gtg gtg ttc gtg ctc ggc gcc aca gcg aca ggg aag tcg aag ctc    160
Lys Val Val Phe Val Leu Gly Ala Thr Ala Thr Gly Lys Ser Lys Leu
                 15                  20                  25 gcc atc gcc ctc gcc gag cgc ttc aac ggt gag gtt atc aac gct gac    208
Ala Ile Ala Leu Ala Glu Arg Phe Asn Gly Glu Val Ile Asn Ala Asp
             30                  35                  40 aaa atc cag gtc cac gat ggc gtg ccc atc atc acg aac aag gtc aca    256
Lys Ile Gln Val His Asp Gly Val Pro Ile Ile Thr Asn Lys Val Thr
         45                  50                  55 gag gaa gag cag ggc ggg gtg ccc cac cac ctg ctc agc gtc cgc cac    304
Glu Glu Glu Gln Gly Gly Val Pro His His Leu Leu Ser Val Arg His
     60                  65                  70 ccg gac gcc gac ttc act gcg gag gag ttc cga cgt gag gcg gcc agc    352
Pro Asp Ala Asp Phe Thr Ala Glu Glu Phe Arg Arg Glu Ala Ala Ser
 75                  80                  85                  90 gcc gtg gcc cgc gtg ctc tcg gcg ggc cgc ctc ccc gtc gtg gca ggc    400
Ala Val Ala Arg Val Leu Ser Ala Gly Arg Leu Pro Val Val Ala Gly
                 95                 100                 105 ggg tcc aac acc tac atc gag gca ctg gtg gaa ggc gac ggc gcc gcc    448
Gly Ser Asn Thr Tyr Ile Glu Ala Leu Val Glu Gly Asp Gly Ala Ala
            110                 115                 120 ttc cgc gcg gcg cac gac ctc ctc ttc gtc tgg gtg gac gcg gag cag    496
Phe Arg Ala Ala His Asp Leu Leu Phe Val Trp Val Asp Ala Glu Gln
            125                 130                 135 gag ctg ctg gag tgg tac gcc gcg ctg cgc gtg gac gag atg gtg gcc    544
Glu Leu Leu Glu Trp Tyr Ala Ala Leu Arg Val Asp Glu Met Val Ala
        140                 145                 150 cgc ggg ctg gtg agc gag gct cgc gcg gcg ttc ggc ggc gcc ggg gtt    592
Arg Gly Leu Val Ser Glu Ala Arg Ala Ala Phe Gly Gly Ala Gly Val
155                 160                 165                 170 gac tac aac cat ggc gtg cgc cgc gcc atc ggc ctg ccg gag atg cac    640
Asp Tyr Asn His Gly Val Arg Arg Ala Ile Gly Leu Pro Glu Met His
                175                 180                 185 gcc tac ctg gtg gcg gag cgc gag ggc gtc gct ggg gag gcc gag ctc    688
Ala Tyr Leu Val Ala Glu Arg Glu Gly Val Ala Gly Glu Ala Glu Leu
            190                 195                 200 gcg gcc atg ctg gaa cgc gcg gtg cgc gag atc aag gac aac acc ttc    736
Ala Ala Met Leu Glu Arg Ala Val Arg Glu Ile Lys Asp Asn Thr Phe
            205                 210                 215 cgc ctc gcg cgc acg cag gcg gag aag atc cgg cgc ctc agc acg ctc    784
Arg Leu Ala Arg Thr Gln Ala Glu Lys Ile Arg Arg Leu Ser Thr Leu
        220                 225                 230 gac ggc tgg gac gtc cgc cgc atc gac gtg acc ccc gtg ttc gcg cgc    832
Asp Gly Trp Asp Val Arg Arg Ile Asp Val Thr Pro Val Phe Ala Arg
235                 240                 245                 250 aag gcc gat ggc act gag tgc cac gag ctg act tgg aag aag cag gtg    880
Lys Ala Asp Gly Thr Glu Cys His Glu Leu Thr Trp Lys Lys Gln Val
                255                 260                 265 tgg gag ccg tgc gag gag atg gtg agg gct ttc ctc gag ccg tcc ctg    928
Trp Glu Pro Cys Glu Glu Met Val Arg Ala Phe Leu Glu Pro Ser Leu
            270                 275                 280 act gcc gtt cca ggt gtt gca gta act gaa gaa ggg aac gcc ggc gtc    976
Thr Ala Val Pro Gly Val Ala Val Thr Glu Glu Gly Asn Ala Gly Val
            285                 290                 295
```

```
                                                    -continued
gtc gct act gct gca ccc gct ggt gat gtc gtc gtc cca act ggc gat     1024
Val Ala Thr Ala Ala Pro Ala Gly Asp Val Val Val Pro Thr Gly Asp
    300             305                 310 gtc gtc acc gcc gtg gct gat gca taagtagcta gcggacgtag cgcatgcatg    1078
Val Val Thr Ala Val Ala Asp Ala
315             320 caatgcatgc aggctggctg gctggcttaa ttagtgcctc cgacttgctt taaactcatg   1138
tagctgcgtc catgggagag ggtgagatac aagtttatgc gacttatatt tctttctaaa   1198
tttaaatgga tctcggatcc gtagtatctg gtttaatata attataatat ttccttcgaa   1258
ttattatata tatatgctca cactcagtta gggatatata ctccctccat tcactctatg   1318
tatttggatt catatgcaaa agtattttaa aattatacta cctccattct cgaatatttg   1378
ttacccgctt gtttattttc taaaacatga taaataaaaa aacggagaga atagtatttt   1438
attatttgtt gatgatatat tttgtaagat atgaacggtg aaagttttac cataaag     1495

<210> SEQ ID NO 86
<211> LENGTH: 71
<212> TYPE: DNA
<213> ORGANISM: Artificial Sequence
<220> FEATURE:
<223> OTHER INFORMATION: IPT2 TIR L

<400> SEQUENCE: 86
gagataattg ccattataga agaagagaga aggggattcg acgaaataga ggcgatggcg    60
ttggcttctc t                                                         71

<210> SEQ ID NO 87
<211> LENGTH: 67
<212> TYPE: DNA
<213> ORGANISM: Artificial Sequence
<220> FEATURE:
<223> OTHER INFORMATION: IPT2 TIR R

<400> SEQUENCE: 87
aagccaacgc caacgcctct atttcgtcga atcccttct ctcttcttct ataatggcaa    60
ttatctc                                                              67
```